(12) United States Patent
Yokoyama et al.

(10) Patent No.: US 10,505,119 B2
(45) Date of Patent: Dec. 10, 2019

(54) ORGANIC ELECTROLUMINESCENCE DEVICE

(71) Applicants: HODOGAYA CHEMICAL CO., LTD., Tokyo (JP); SFC CO., LTD., Chungcheongbuk-do (KR)

(72) Inventors: Norimasa Yokoyama, Tokyo (JP); Shuichi Hayashi, Tokyo (JP); Takeshi Yamamoto, Tokyo (JP); Naoaki Kabasawa, Tokyo (JP); Daizo Kanda, Tokyo (JP); Shunji Mochiduki, Tokyo (JP); Se-Jin Lee, Chungcheongbuk-do (KR); Oun-gyu Lee, Chungcheongbuk-do (KR); Bong-Ki Shin, Chungcheongbuk-do (KR)

(73) Assignees: HODOGAYA CHEMICAL CO., LTD., Tokyo (JP); SFC CO., LTD., Chungcheongbuk-Do (KR)

( * ) Notice: Subject to any disclaimer, the term of this patent is extended or adjusted under 35 U.S.C. 154(b) by 214 days.

(21) Appl. No.: 15/541,849

(22) PCT Filed: Jan. 5, 2016

(86) PCT No.: PCT/JP2016/050167
§ 371 (c)(1),
(2) Date: Jul. 6, 2017

(87) PCT Pub. No.: WO2016/111301
PCT Pub. Date: Jul. 14, 2016

(65) Prior Publication Data
US 2018/0026198 A1 Jan. 25, 2018

(30) Foreign Application Priority Data
Jan. 8, 2015 (JP) .................. 2015-002095

(51) Int. Cl.
*H01L 51/00* (2006.01)
*C07C 211/54* (2006.01)
(Continued)

(52) U.S. Cl.
CPC ........ *H01L 51/0059* (2013.01); *C07C 211/54* (2013.01); *C07C 211/61* (2013.01);
(Continued)

(58) Field of Classification Search
None
See application file for complete search history.

(56) References Cited

U.S. PATENT DOCUMENTS

| 5,639,914 A | 6/1997 | Tomiyama et al. |
| 5,707,747 A | 1/1998 | Tomiyama et al. |

(Continued)

FOREIGN PATENT DOCUMENTS

| CN | 101005122 A | 7/2007 |
| JP | 8-48656 | 2/1996 |

(Continued)

OTHER PUBLICATIONS

Goodbrand et al. "Ligand-Accelerated Catalysis of the Ullmann Condensation: Applicationto Hole Conducting Triarylamines" J. Org. Chem. 1999, 64, 670-674. (Year: 1999).*

(Continued)

*Primary Examiner* — Robert S Loewe
(74) *Attorney, Agent, or Firm* — Greenblum & Bernstein, P.L.C.

(57) ABSTRACT

The organic EL device of the present invention has an anode, a hole transport layer, a luminous layer, an electron transport layer, and a cathode in the order of description. The hole transport layer includes an arylamine compound represented by the following general formula (1):

(Continued)

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ANODE
1 GLASS SUBSTRATE

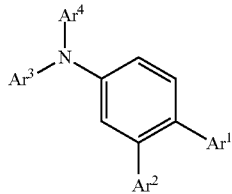 (1)

in the formula,
Ar¹ to Ar⁴ each represent a monovalent aromatic hydrocarbon group or a monovalent aromatic heterocyclic group, and the luminous layer includes an N-aromatic substituted nitrogen-containing heterocyclic compound.

11 Claims, 67 Drawing Sheets

(51) Int. Cl.
$C07C\ 211/61$ (2006.01)
$C09K\ 11/06$ (2006.01)
$H01L\ 51/50$ (2006.01)
$C09B\ 57/00$ (2006.01)

(52) U.S. Cl.
CPC ............ $C09B\ 57/008$ (2013.01); $C09K\ 11/06$ (2013.01); $H01L\ 51/006$ (2013.01); $H01L\ 51/0067$ (2013.01); $H01L\ 51/0071$ (2013.01); $H01L\ 51/0072$ (2013.01); $H01L\ 51/0077$ (2013.01); $H01L\ 51/0085$ (2013.01); $H01L\ 51/50$ (2013.01); $C09K\ 2211/1007$ (2013.01); $C09K\ 2211/1011$ (2013.01); $C09K\ 2211/1018$ (2013.01); $C09K\ 2211/1029$ (2013.01); $C09K\ 2211/1044$ (2013.01); $C09K\ 2211/185$ (2013.01); $H01L\ 51/0052$ (2013.01); $H01L\ 51/0058$ (2013.01); $H01L\ 51/5016$ (2013.01); $H01L\ 51/5024$ (2013.01); $H01L\ 51/5056$ (2013.01); $H01L\ 51/5064$ (2013.01); $H01L\ 51/5072$ (2013.01)

(56) References Cited

U.S. PATENT DOCUMENTS

| | | | |
|---|---|---|---|
| 5,792,557 A | 8/1998 | Nakaya et al. | |
| 7,759,030 B2 | 7/2010 | Abe et al. | |
| 7,799,492 B2 | 9/2010 | Abe et al. | |
| 8,021,764 B2 | 9/2011 | Hwang et al. | |
| 8,021,765 B2 | 9/2011 | Hwang et al. | |
| 8,188,315 B2 | 5/2012 | Hwang et al. | |
| 8,343,637 B2* | 1/2013 | Parham | C07D 209/80 313/504 |
| 8,394,510 B2 | 3/2013 | Mizuki et al. | |
| 8,895,159 B2 | 11/2014 | Mizuki et al. | |
| 8,974,922 B2 | 3/2015 | Hwang et al. | |
| 9,478,754 B2 | 10/2016 | Hwang et al. | |
| 2003/0165715 A1* | 9/2003 | Yoon | C07D 235/08 428/690 |
| 2005/0236976 A1 | 10/2005 | Leung et al. | |
| 2010/0019657 A1* | 1/2010 | Eum | C07C 211/61 313/504 |
| 2010/0244008 A1* | 9/2010 | Lee | C07D 409/10 257/40 |
| 2012/0228598 A1* | 9/2012 | Yokoyama | C07D 471/04 257/40 |
| 2014/0167026 A1* | 6/2014 | Kato | C07D 457/04 257/40 |
| 2014/0203257 A1* | 7/2014 | Hwang | H01L 51/0094 257/40 |
| 2014/0217393 A1* | 8/2014 | Kato | C07D 403/10 257/40 |
| 2015/0041773 A1* | 2/2015 | Park | H01L 51/0058 257/40 |
| 2015/0179940 A1 | 6/2015 | Mujica-Fernaud et al. | |
| 2015/0179953 A1 | 6/2015 | Mujica-Fernaud et al. | |
| 2015/0380657 A1 | 12/2015 | Yokoyama et al. | |
| 2016/0079548 A1 | 3/2016 | Kita et al. | |
| 2016/0126468 A1 | 5/2016 | Nagaoka et al. | |
| 2017/0005273 A1 | 1/2017 | Hwang et al. | |
| 2017/0012212 A1 | 1/2017 | Lee et al. | |
| 2018/0269399 A1* | 9/2018 | Stoessel | H01L 51/0059 |

FOREIGN PATENT DOCUMENTS

| | | |
|---|---|---|
| JP | 3194657 | 6/2001 |
| JP | 2006-151979 | 6/2006 |
| JP | 2006-219393 | 8/2006 |
| JP | 4943840 | 5/2012 |
| KR | 10-2011-0084797 | 7/2011 |
| KR | 10-2015-0007476 | 1/2015 |
| KR | 10-2015-0116337 | 10/2015 |
| WO | 2008/062636 | 5/2008 |
| WO | 2014/015935 | 1/2014 |
| WO | 2014/015937 | 1/2014 |
| WO | 2014/129201 | 8/2014 |
| WO | 2014/129764 | 8/2014 |
| WO | 2014/189072 | 11/2014 |
| WO | 2014196556 A1 | 12/2014 |
| WO | 2015/041428 | 3/2015 |
| WO | 2015/111888 | 7/2015 |
| WO | 2016/006629 | 1/2016 |
| WO | 2016/017594 | 2/2016 |

OTHER PUBLICATIONS

International Search Report issued in WIPO Patent Application No. PCT/JP2016/050167, dated Mar. 22, 2016.
European Search Report issued with respect to Application No. 16735040.4, dated Jul. 3, 2018.
Chinese Office Action issued with respect to Chinese Application No. 201680014456.0, dated Sep. 4, 2018.

* cited by examiner

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ANODE
1 GLASS SUBSTRATE (1-6)

(1-7)

(1-8)

(1-9)

(1-10)

(1-11)

(1-12)

(1-13)

(1-14)

(1-15)

(1-16)

(1-17)

(1-18)

(1-19)

(1-20)

(1-21)

(1-22)

(1-23)

(1-24)

(1-25)

(1-31)

(1-32)

(1-33)

(1-34)

(1-35)

(1-51)

(1-52)

(1-53)

(1-54)

(1-55)

(1-56)

(1-57)

(1-58)

(1-59)

(1-70)

(1-71)

(1-72)

(1-73)

(1-74)

(1-75)

(1-76)

(1-77)

(1-78)

(1-79)

(1-80)

(1-81)

(1-82)

(1-83)

(1-84)

(1-85)

(1-86)

(1-87)

(1-88)

(1-89)

(1-90)

(1-91)

(1-92)

(1-93)

(1-94)

(1-95)

(1-96)

(1-97)

(1-98)

(1-99)

(1-100)

(1-101)

(1-102)

(1-108)

(1-109)

(1-110)

(1-111)

(1-117)

(1-118)

(1-119)

(1-120)

(1-121)

(1-122)

(1-123)

(1-124)

(1-125)

(1-126)

(1-127)

(1-128)

(1-129)

(1-130)

(1-131)

(1-132)

(1-133)

(1-134)

(1-135)

(1-136)

(1-137)

(1-138)

(1-139)

(1-140)

(1-141)

(1-142)

(1-143)

(1-144)

(1-145)

(1-151)

(1-152)

(1-153)

(1-154)

(1-155)

(1-156)

(1-157)

(1-158)

(1-159)

(1-160)

(2-1)

(2-2)

(2-3)

(2-4)

(2-5)

(2-6)

(2-12)

(2-13)

(2-14)

(2-15)

(3-1)

(3-2)

(3-3)

(3-4)

(3-5)

(3-6)

(3-7)

(3-8)

(3-9)

(3-10)

(3-11)

(3-12)

(3-13)

(3-14)

(3-15)

(3-16)

(3-17)

(3-18)

(3-19)

(3-20)

(3-21)

(3-22)

(3-23)

(4a-1)

(4a-2)

(4a-3)

(4a-4)

(4a-5)

(4a-6)

(4a-7)

(4a-8)

(4a-9)

(4a-10)

(4a-11)

(4a-12)

(4a-13)

(4a-14)

(4a-15)

(4a-16)

(4a-17)

(4a-18)

(4a-19)

(4a-20)

(4b-1)

(4b-2)

(4b-3)

(4b-4)

(4b-5)

(4b-6)

(4b-7)

(4b-8)

(4b-9)

(4b-10)

(4b-11)

(4b-12)

(4b-13)

(4b-14)

(4b-15)

(4b-16)

(4c-1)

(4c-2)

(4c-3)

(4c-4)

(4c-5)

(4c-6)

(4c-7)

(4c-8)

(4c-9)

(4c-10)

(4c-11)

(4c-12)

(4c-13)

(4c-14)

(4c-15)

(4c-16)

(4c-17)

(4c-18)

(4c-19)

(4c-20)

(4c-21)

(4c-22)

(4c-23)

(4c-24)

(4c-25)

(4c-26)

(4c-27)

(4c-28)

(4c-29)

(4c-30)

(5-21)

(5-22)

(5-23)

(5'-1)

(5'-2)

(6-1)

(6-2)

(6-3)

(6-4)

(6-5)

(6-6)

(6-7)

(6-8)

(6-9)

(6-10)

ORGANIC ELECTROLUMINESCENCE DEVICE

TECHNICAL FIELD

The present invention relates to an organic electroluminescence device (organic EL device), which is a self light-emitting device suitable for various display devices, and more particularly to an organic EL device including an arylamine compound having a specific molecular structure in a hole transport layer.

BACKGROUND ART

An organic EL device is a self light-emitting device, and is thus brighter, better in visibility, and capable of clearer display, than a liquid crystal device. Hence, active researches have been conducted on organic EL devices.

In 1987, C. W. Tang et al. of Eastman Kodak Company developed a laminated structure device sharing various roles for light emission among different materials, thereby imparting practical applicability to organic EL devices. The developed organic EL device is configured by laminating a layer of a fluorescent body capable of transporting electrons, and a layer of an organic substance capable of transporting holes. As a result of injecting positive charges and negative charges into the layer of the fluorescent body to perform light emission, it is possible to obtain a high luminance of 1000 $cd/m^2$ or higher at a voltage of 10 V or less.

Many improvements have been heretofore made to put the organic EL devices to practical use. For example, it is generally well known that high efficiency and durability can be achieved by further segmenting the roles to be played by respective layers of the laminated structure and providing a laminated structure in which an anode, a hole injection layer, a hole transport layer, a luminous layer, an electron transport layer, an electron injection layer, and a cathode on a substrate.

For further increase in the luminous efficiency, it has been attempted to utilize triplet excitons, and the utilization of phosphorescent luminous compounds has been investigated.

Furthermore, devices utilizing light emission by thermally activated delayed fluorescence (TADF) have been developed. For example, in 2011, Adachi et al. from Kyushu University have realized an external quantum efficiency of 5.3% with a device using a thermally activated delayed fluorescence material.

The luminous layer can also be prepared by doping a charge transport compound, generally called a host material, with a fluorescent compound, a phosphorescent luminous compound, or a material radiating delayed fluorescence. The selection of the organic material in the organic EL device greatly affects the characteristics of the device, such as efficiency and durability.

With the organic EL device, the charges injected from both electrodes recombine in the luminous layer, thereby producing light emission, and how efficiently the charges of the holes and the electrons are passed on to the luminous layer is of importance, and a device that exhibits excellent carrier balance is required. Further, by enhancing hole injection property or increasing electron blocking property, that is, property to block electrons injected from the cathode, it is possible to increase the probability of holes and electrons recombining. Besides, excitons generated in the luminous layer are confined. By so doing, it is possible to obtain a high luminous efficiency. Therefore, the role of the hole transport material is important, and a demand has been created for a hole transport material having high hole injection property, high hole mobility, high electron blocking property, and high durability to electrons.

Further, from the viewpoint of device life, heat resistance and amorphousness of the materials are also important. A material with a low heat resistance is thermally decomposed even at a low temperature by heat produced during device driving, and the material deteriorates. In a material with low amorphousness, crystallization of a thin film occurs even in a short time, and the device deteriorates. Thus, high heat resistance and satisfactory amorphousness are required of the materials to be used.

N,N'-diphenyl-N,N'-di(α-naphthyl)benzidine (NPD) and various aromatic amine derivatives are known as hole transport materials which have been heretofore used in organic EL devices (see, for example, PTL 1 and PTL 2). NPD has satisfactory hole transport capability, but the glass transition temperature (Tg), which is an indicator of heat resistance, is as low as 96° C. and device characteristics degrade due to crystallization under high-temperature conditions.

Further, among the aromatic amine derivatives described in PTL 1 and 2, there are also compounds with an excellent hole mobility of $10^{-3}$ $cm^2/Vs$ or higher. Since electron blocking property of the compounds is insufficient, however, some of electrons pass through the luminous layer, and no increase in luminous efficiency can be expected. Thus, materials with better electron blocking property, higher stability of a thin film, and high heat resistance are needed to increase further the efficiency.

An aromatic amine derivative with high durability has also been reported (see, for example, PTL 3), but this derivative is used as a charge transport material for use in an electrophotographic photosensitive body and there is no example of application to an organic EL device.

Arylamine compounds having a substituted carbazole structure have been suggested as compounds with improved properties such as heat resistance and hole injection property (see, for example, PTL 4 and 5). Although heat resistance, luminous efficiency, and the like of devices using these compounds for a hole injection layer or hole transport layer have been improved, the results are still insufficient and further decrease in a driving voltage and increase in luminous efficiency are needed.

Devices in which holes and electrons can recombine with a high efficiency and which have a high luminous efficiency, a low driving voltage, and a long life need to be provided by combining materials with excellent hole and electron injection-transport performance and stability and durability of a thin film so as to improve device characteristics of organic EL devices and increase the yield in device production.

Further, devices which have carrier balance, a high efficiency, a low driving voltage, and a long life need to be provided by combining materials with excellent hole and electron injection-transport performance and stability and durability of a thin film so as to improve device characteristics of organic EL devices.

CITATION LIST

Patent Literature

PTL 1: Japanese Patent Application Publication No. H8-048656
PTL 2: Japanese Patent No. 3194657
PTL 3: Japanese Patent No. 4943840
PTL 4: Japanese Patent Application Publication No. 2006-151979
PTL 5: WO 2008/62636

SUMMARY OF INVENTION

Technical Problem

It is an object of the present invention to provide an organic EL device in which a hole transport layer is formed from a hole transport material that excels in hole injection-transport performance, electron blocking capability, and stability and durability of a thin film and in which other layers are combined so as to demonstrate sufficiently the excellent characteristics of the hole transport material, thereby ensuring a high efficiency, a low driving voltage, and a long life.

Solution to Problem

The inventors of the present invention found that an arylamine compound having a specific molecular structure demonstrates excellent characteristics as a hole transport material and that an organic EL device in which excellent carrier balance is ensured and which excels in various characteristics can be obtained when such an arylamine compound is used to form a hole transport layer, and at the same time when a luminous layer includes an N-aromatic substituted nitrogen-containing heterocyclic compound. As a result, the inventors have accomplished the present invention.

According to the present invention, there is provided an organic electroluminescence device having an anode, a hole transport layer, a luminous layer, an electron transport layer, and a cathode in the order of description, wherein the hole transport layer includes an arylamine compound represented by the following general formula (1), and the luminous layer includes an N-aromatic substituted nitrogen-containing heterocyclic compound.

The Arylamine Compound;

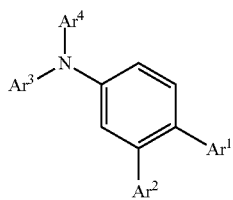

(1)

In this formula, $Ar^1$ to $Ar^4$ each represent a monovalent aromatic hydrocarbon group or a monovalent aromatic heterocyclic group.

In the organic EL device of the present invention, it is preferred that an indenoindole compound represented by the following general formula (2) or a carbazole compound represented by a general formula (3) be used as the N-aromatic substituted nitrogen-containing heterocyclic compound which is used for the luminous layer.

The Indenoindole Compound;

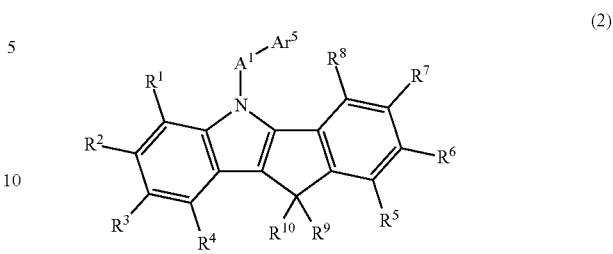

(2)

In this formula, $A^1$ represents a divalent aromatic hydrocarbon group, a divalent aromatic heterocyclic group, or a single bond;

$Ar^5$ represents a monovalent aromatic hydrocarbon group or a monovalent aromatic heterocyclic group;

$R^1$ to $R^8$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a di-aromatic substituted amino group;

these $R^1$ to $R^8$ may be bonded to each other via a single bond, an optionally substituted methylene group, an oxygen atom, or a sulfur atom to form a ring; further, some of $R^1$ to $R^4$ or some of $R^5$ to $R^8$ may be detached from the benzene ring, and the remaining groups of $R^1$ to $R^4$ or the remaining groups of $R^5$ to $R^8$ may be bonded to vacancies in the benzene ring generated by the detachment via an optionally substituted methylene group, an oxygen atom, a sulfur atom, or a monoarylamino group to form a ring; and $R^9$ and $R^{10}$ are each an alkyl group having 1 to 6 carbon atoms, a monovalent aromatic hydrocarbon group, or a monovalent aromatic heterocyclic group and may be bonded to each other via a single bond, an optionally substituted methylene group, an oxygen atom, or a sulfur atom to form a ring.

The Carbazole Compound;

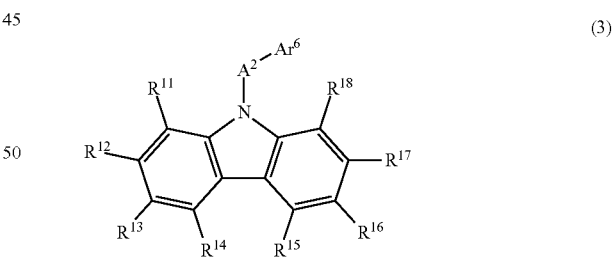

(3)

In this formula, $A^2$ represents a divalent aromatic hydrocarbon group, a divalent aromatic heterocyclic group, or a single bond;

$Ar^6$ represents a monovalent aromatic hydrocarbon group or a monovalent aromatic heterocyclic group;

$R^{11}$ to $R^{18}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a di-aromatic substituted amino group; and these $R^{11}$ to $R^{18}$ may be bonded to each other via a single bond, an optionally substituted methylene group, an oxygen atom, or a sulfur atom to form a ring; further, some of $R^{11}$ to $R^{14}$ or some of $R^{15}$ to $R^{18}$ may be detached from the benzene ring, and the remaining groups of $R^{11}$ to $R^{14}$ or the remaining groups of $R^{15}$ to $R^{18}$ may be bonded to vacancies in the benzene ring generated by the detachment via an optionally substituted methylene group, an oxygen atom, a sulfur atom, or a monoarylamino group to form a ring.

Further, in the organic EL device of the present invention, it is preferred that the arylamine compound used for the hole transport layer be represented by the following general formula (1a) or (1b).

The Arylamine Compound of the General Formula (1a);

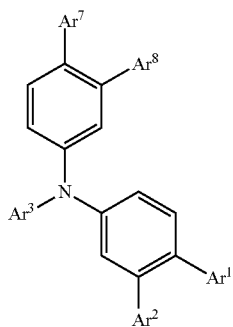

(1a)

In this formula, $Ar^1$ to $Ar^3$ are as defined in the general formula (1); and $Ar^7$ and $Ar^8$ each represent a monovalent aromatic hydrocarbon group or a monovalent aromatic heterocyclic group.

The Arylamine Compound of the General Formula (1b);

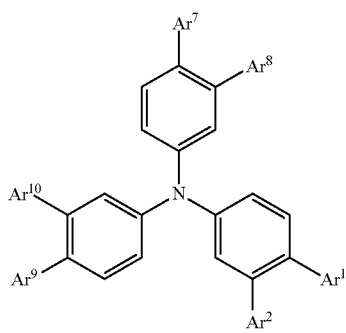

(1b)

In this formula, $Ar^1$, $Ar^2$, $Ar^7$, and $Ar^8$ are as defined in the general formula (1) or the general formula (1a); and $Ar^9$ and $Ar^{10}$ each represent a monovalent aromatic hydrocarbon group or a monovalent aromatic heterocyclic group.

Furthermore, in the organic EL device of the present invention, it is more preferred that the electron transport layer include an anthracene derivative represented by the following general formula (4).

The Anthracene Derivative;

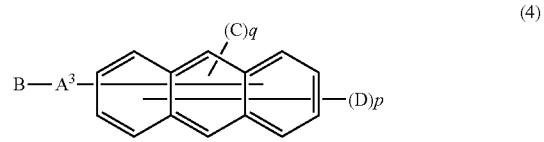

(4)

In this formula, $A^3$ represents a divalent aromatic hydrocarbon group, a divalent aromatic heterocyclic group, or a single bond;

B represents a monovalent aromatic heterocyclic group;

C represents a monovalent aromatic hydrocarbon group or a monovalent aromatic heterocyclic group;

D represents a hydrogen atom, a deuterium atom, a fluorine atom, a chlorine atom, a cyano group, an alkyl group having 1 to 6 carbon atoms, a monovalent aromatic hydrocarbon group, or a monovalent aromatic heterocyclic group; and in p and q, p is an integer of 7 or 8 and q is an integer of 1 or 2 provided that a sum of p and q is 9.

It is preferred that an anthracene derivative having a molecular structure represented by the following general formula (4a), (4b), or (4c) be used as the abovementioned anthracene derivative.

The Anthracene Derivative of the General Formula (4a);

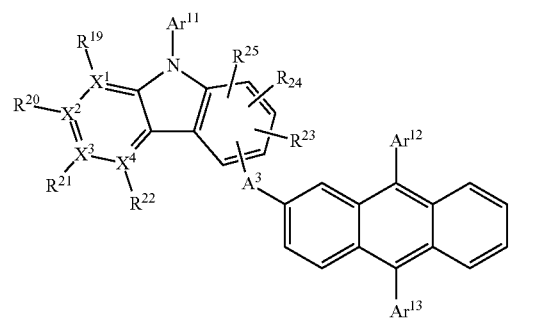

(4a)

In this formula, $A^3$ is as defined in the general formula (4);

$Ar^{11}$, $Ar^{12}$, and $Ar^{13}$ each represent a monovalent aromatic hydrocarbon group or a monovalent aromatic heterocyclic group;

$R^{19}$ to $R^{25}$ are each a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, or an aryloxy group and may be bonded to each other via a single bond, an optionally substituted methylene group, an oxygen atom, or a sulfur atom to form a ring; and $X^1$, $X^2$, $X^3$, and $X^4$ each represent a carbon atom or a nitrogen atom, provided that only any one thereof is a nitrogen atom, and none of $R^{19}$ to $R^{25}$, including a hydrogen atom, is bonded to the nitrogen atom.

The Anthracene Derivative of the General Formula (4b);

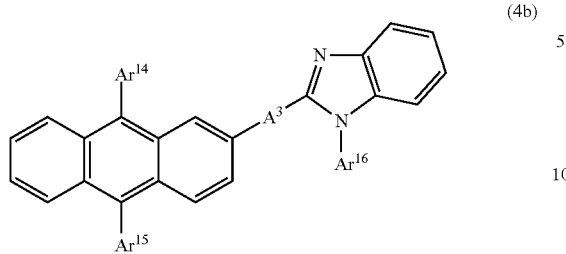

(4b)

In this formula,
$A^3$ is as defined in the general formula (4); and
$Ar^{14}$, $Ar^{15}$, and $Ar^{16}$ each represent a monovalent aromatic hydrocarbon group or a monovalent aromatic heterocyclic group.

The Anthracene Derivative of the General Formula (4c);

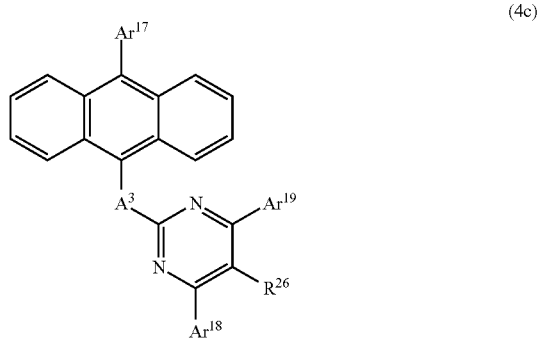

(4c)

In this formula,
$A^3$ is as defined in the aforementioned general formula (4);
$Ar^{17}$, $Ar^{18}$, and $Ar^{19}$ each represent a monovalent aromatic hydrocarbon group or a monovalent aromatic heterocyclic group; and
$R^{26}$ represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, or an aryloxy group.

Further, in the organic EL device of the present invention, it is more preferable that:
(A) the hole transport layer have a two-layer structure including a first hole transport layer and a second hole transport layer, and the second hole transport layer be positioned on the luminous layer side and include the arylamine compound represented by the general formula (1);
(B) the luminous layer include a red luminous material;
(C) the luminous layer include a phosphorescence luminous material; and
(D) the phosphorescence luminous material be a metal complex including iridium or platinum.

Advantageous Effects of Invention

As shown in the below-described Examples, the arylamine compound represented by the general formula (1) and included in the hole transport layer in the organic EL device of the present invention has the following specific features:
(1) satisfactory hole injection-transport characteristic;
(2) excellent electron blocking capability;
(3) stability in a thin-film state; and
(4) excellent heat resistance.

Further, in the organic EL device of the present invention, in addition to including such an arylamine compound into the hole transport layer, an N-aromatic substituted nitrogen-containing heterocyclic compound (for example, an N-aromatic substituted indenoindole compound or an N-aromatic substituted carbazole compound) is included in the luminous layer. As a result, excellent characteristics of the arylamine compound are fully demonstrated, holes can be injected and transported in the luminous layer with satisfactory efficiency, light emission is realized with a high efficiency at a low driving voltage, and the service life of the device is extended.

Further, in the present invention, an electron transport layer formed from the aforementioned anthracene derivative represented by the general formula (4) is provided in combination with the above-described hole transport layer and luminous layer. As a result, holes and electrons can be injected and transported in the luminous layer with satisfactory efficiency, a high carrier balance can be ensured, and higher characteristics can be realized.

Furthermore, in the present invention, the hole transport layer has a two-layer structure including a first hole transport layer and a second hole transport layer, and the second hole transport layer positioned on the side adjacent to the luminous layer is formed by the aforementioned arylamine compound represented by the general formula (1). As a result, it is possible to maximize the electron blocking performance of the arylamine compound and realize an organic EL device with higher efficiency and longer life (high endurance).

DESCRIPTION OF EMBODIMENTS

Figure 1:
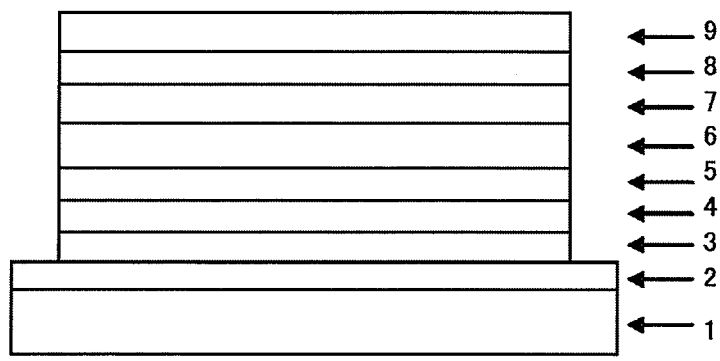
FIG. 1 is a view showing the preferred layer configuration of the organic EL device of the present invention.
Figure 2:
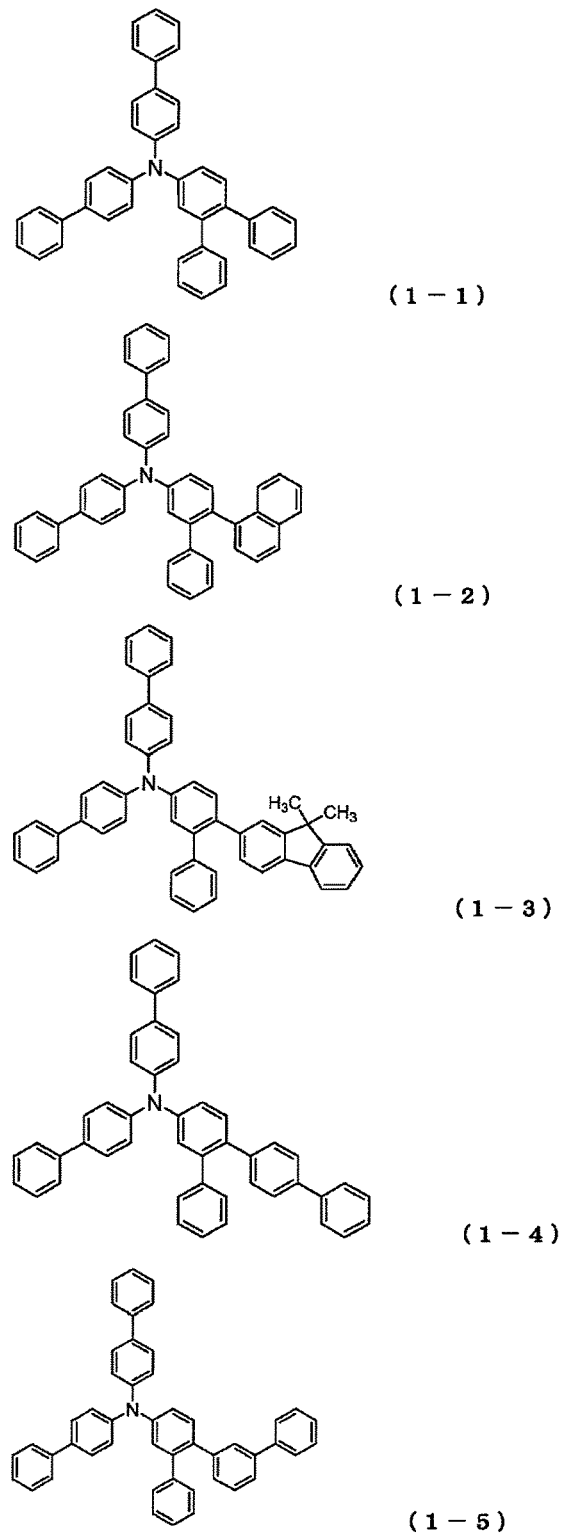
FIG. 2 is a view showing the structural formulas of Compounds No. (1-1) to (1-5) in the arylamine compound of a general formula (1).
Figure 3:
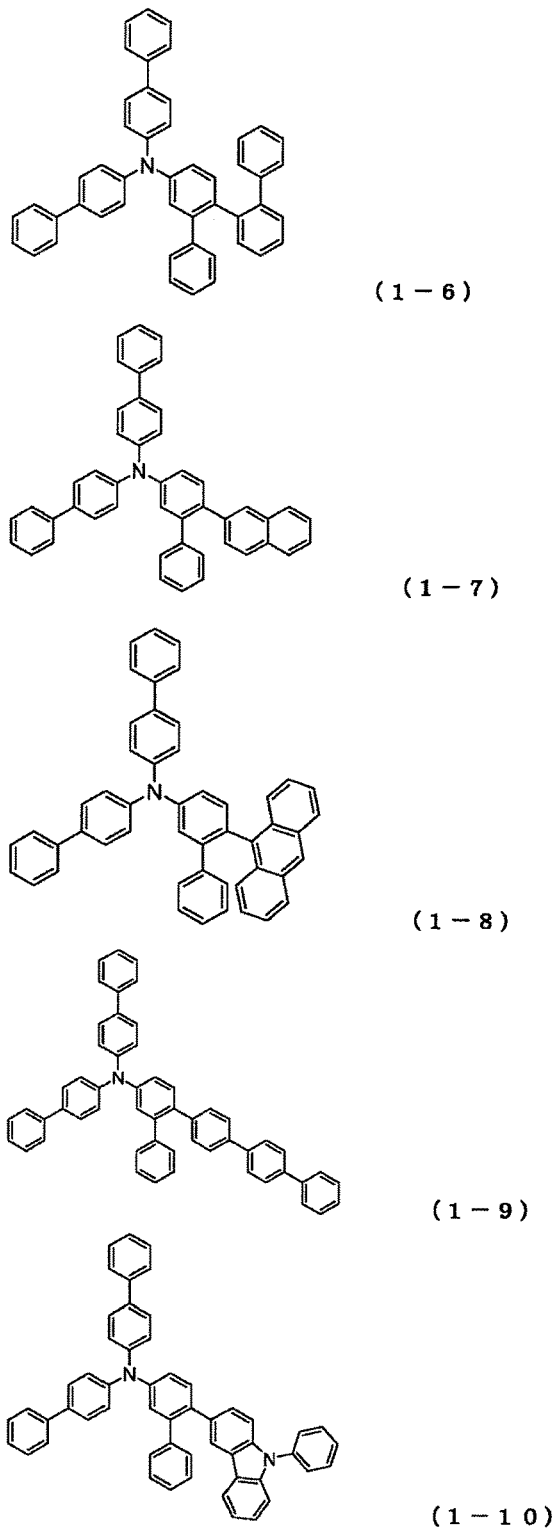
FIG. 3 is a view showing the structural formulas of Compounds No. (1-6) to (1-10) in the arylamine compound of the general formula (1).
Figure 4:
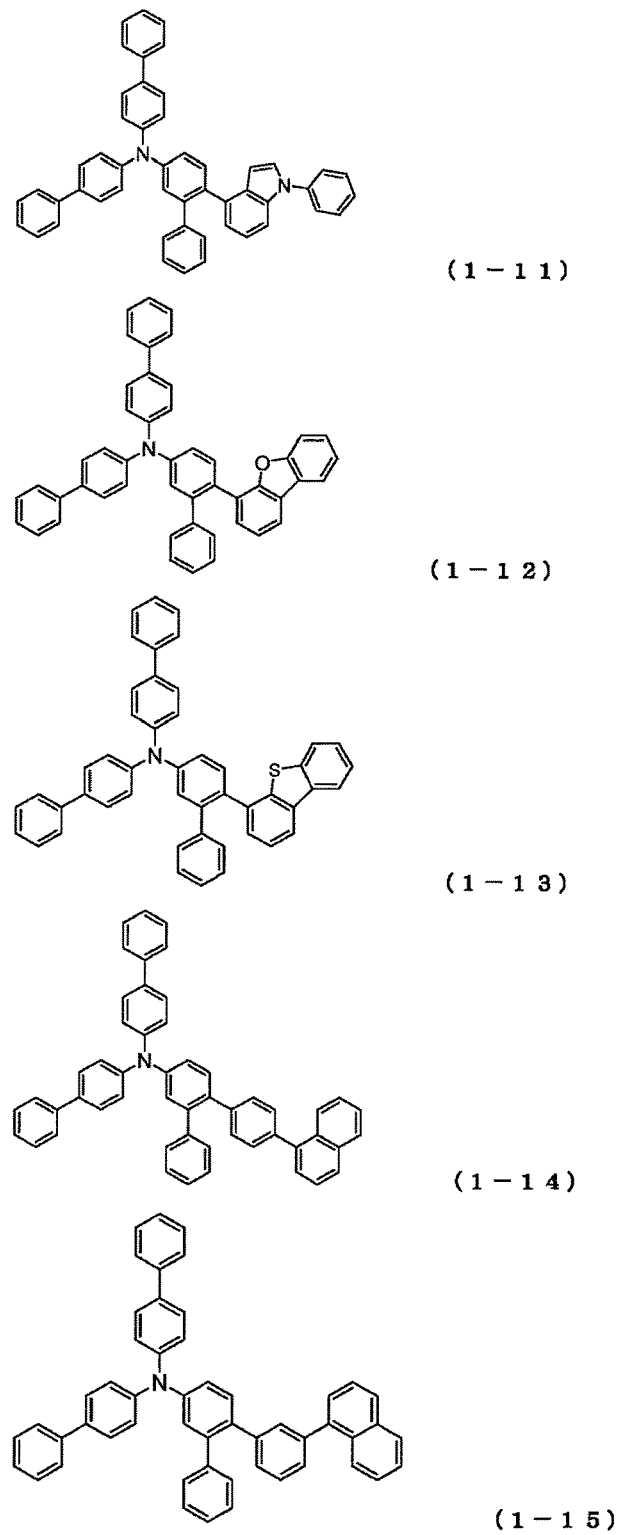
FIG. 4 is a view showing the structural formulas of Compounds No. (1-11) to (1-15) in the arylamine compound of the general formula (1).
Figure 5:
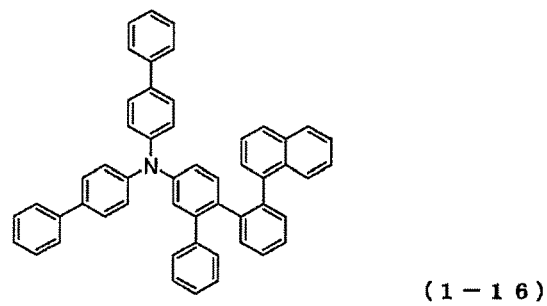
FIG. 5 is a view showing the structural formulas of Compounds No. (1-16) to (1-20) in the arylamine compound of the general formula (1).
Figure 5:
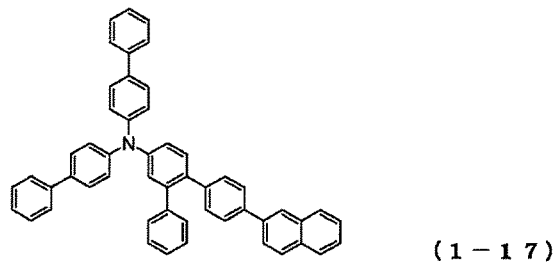
Figure 5:
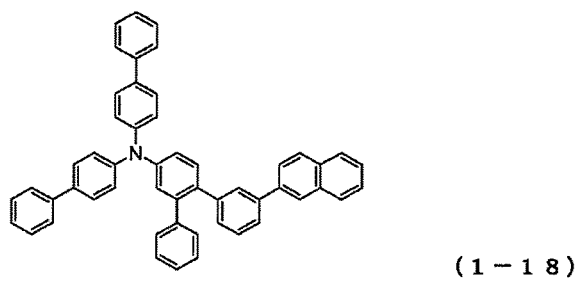
Figure 5:
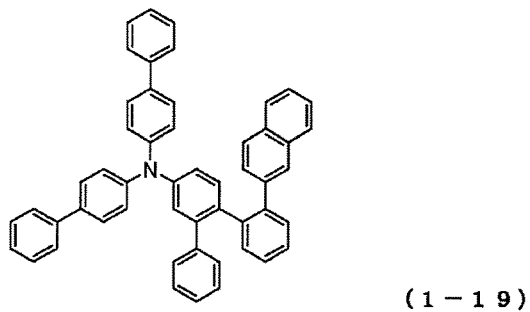
Figure 5:
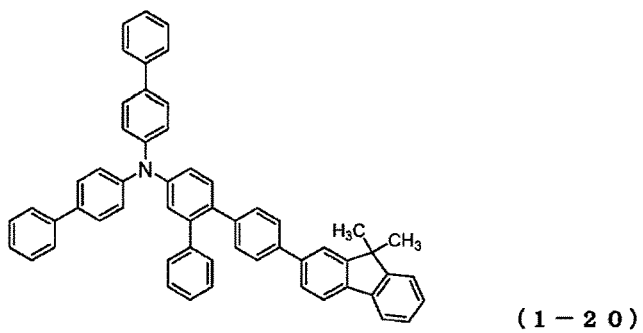
Figure 6:
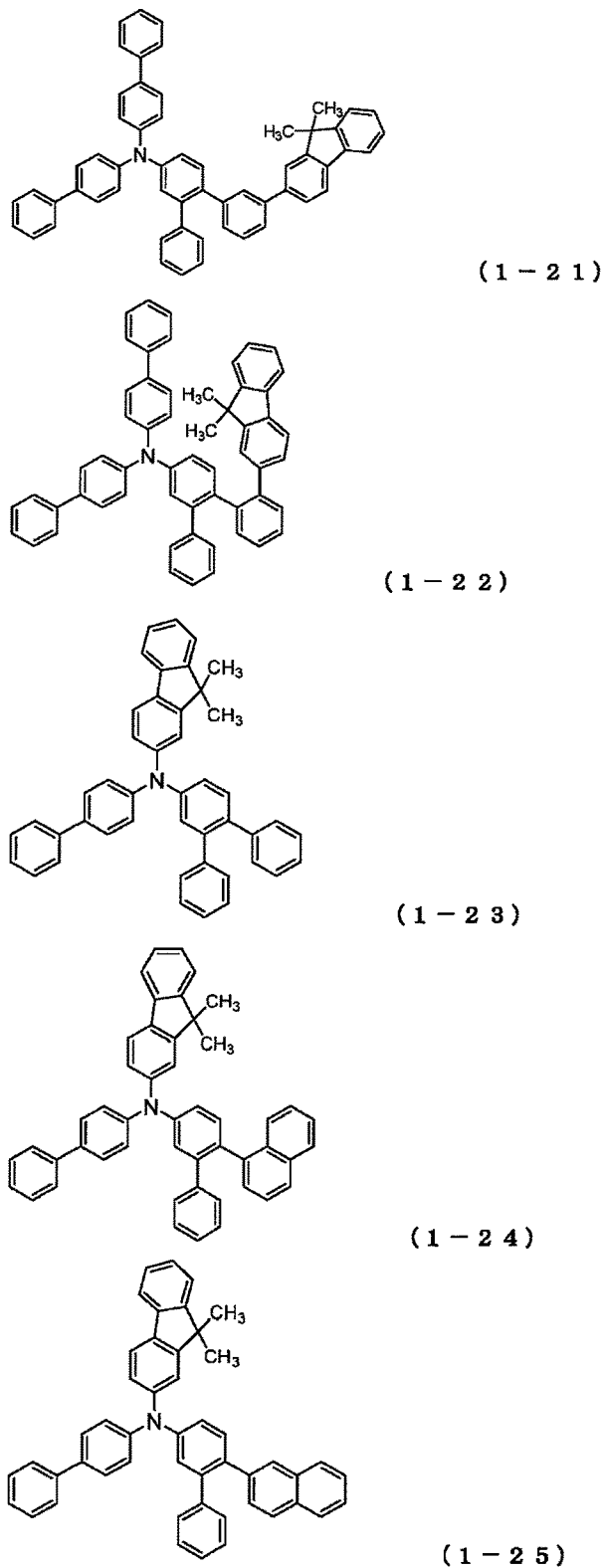
FIG. 6 is a view showing the structural formulas of Compounds No. (1-21) to (1-25) in the arylamine compound of the general formula (1).
Figure 7:
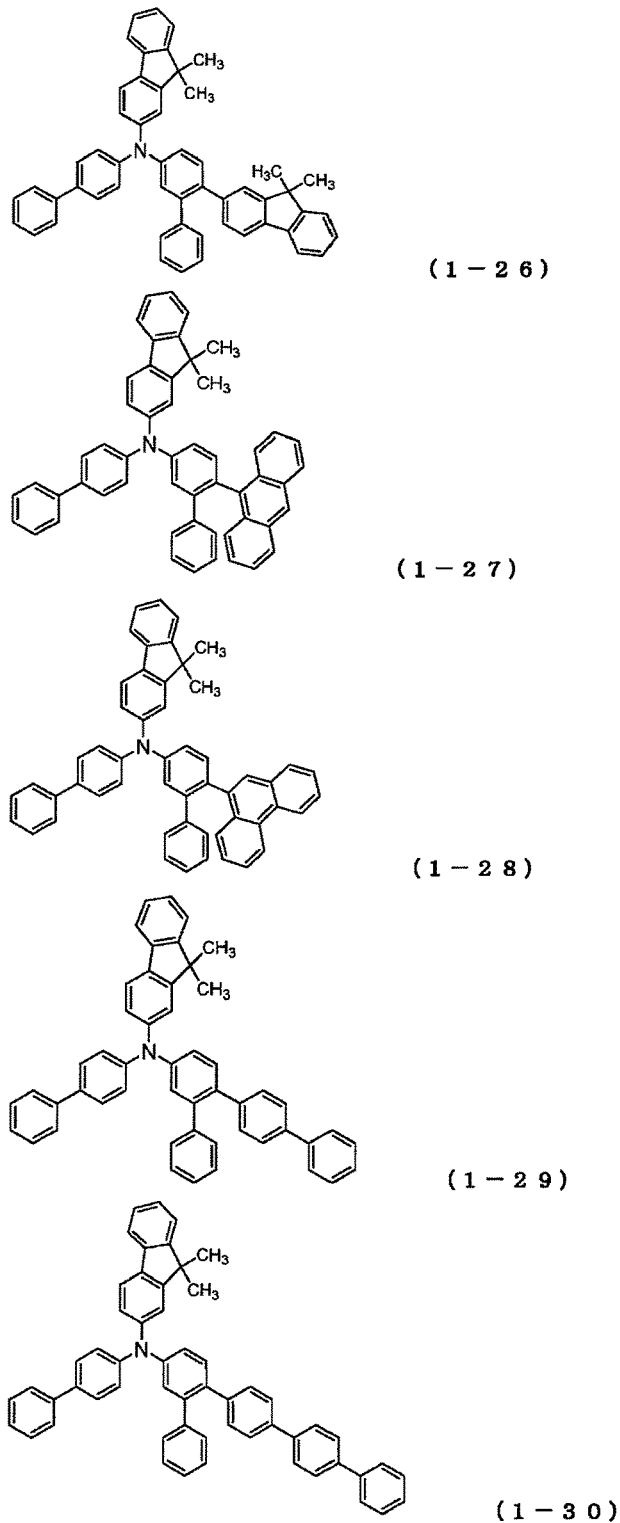
FIG. 7 is a view showing the structural formulas of Compounds No. (1-26) to (1-30) in the arylamine compound of the general formula (1).
Figure 8:
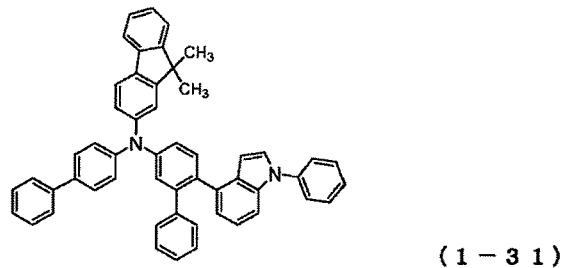
FIG. 8 is a view showing the structural formulas of Compounds No. (1-31) to (1-35) in the arylamine compound of the general formula (1).
Figure 8:
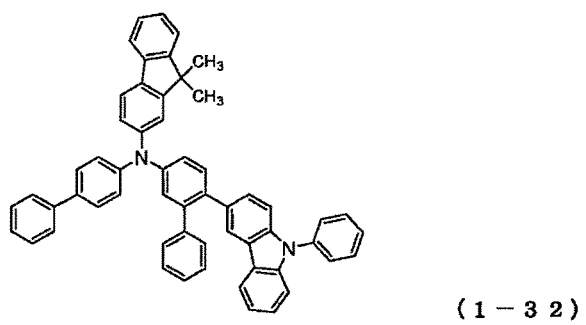
Figure 8:
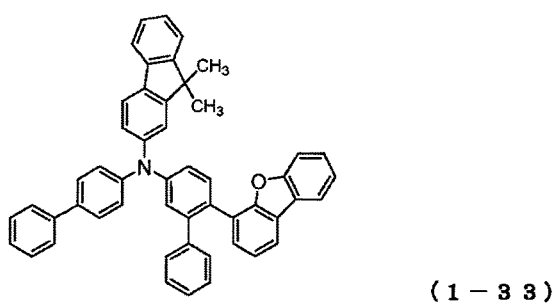
Figure 8:
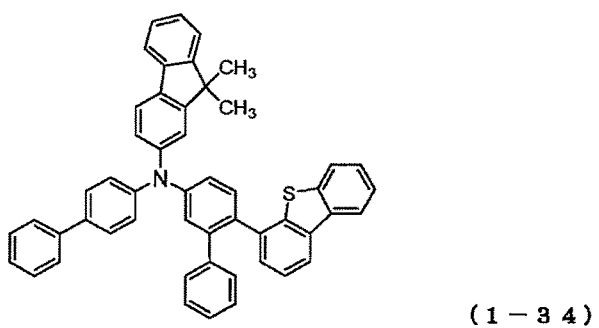
Figure 8:
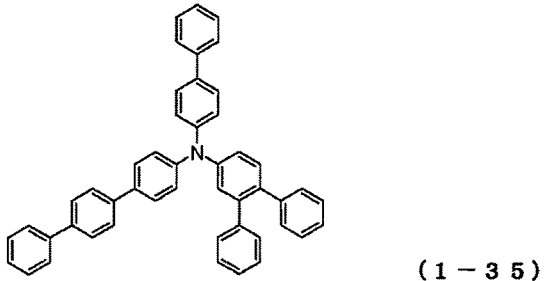
Figure 9:
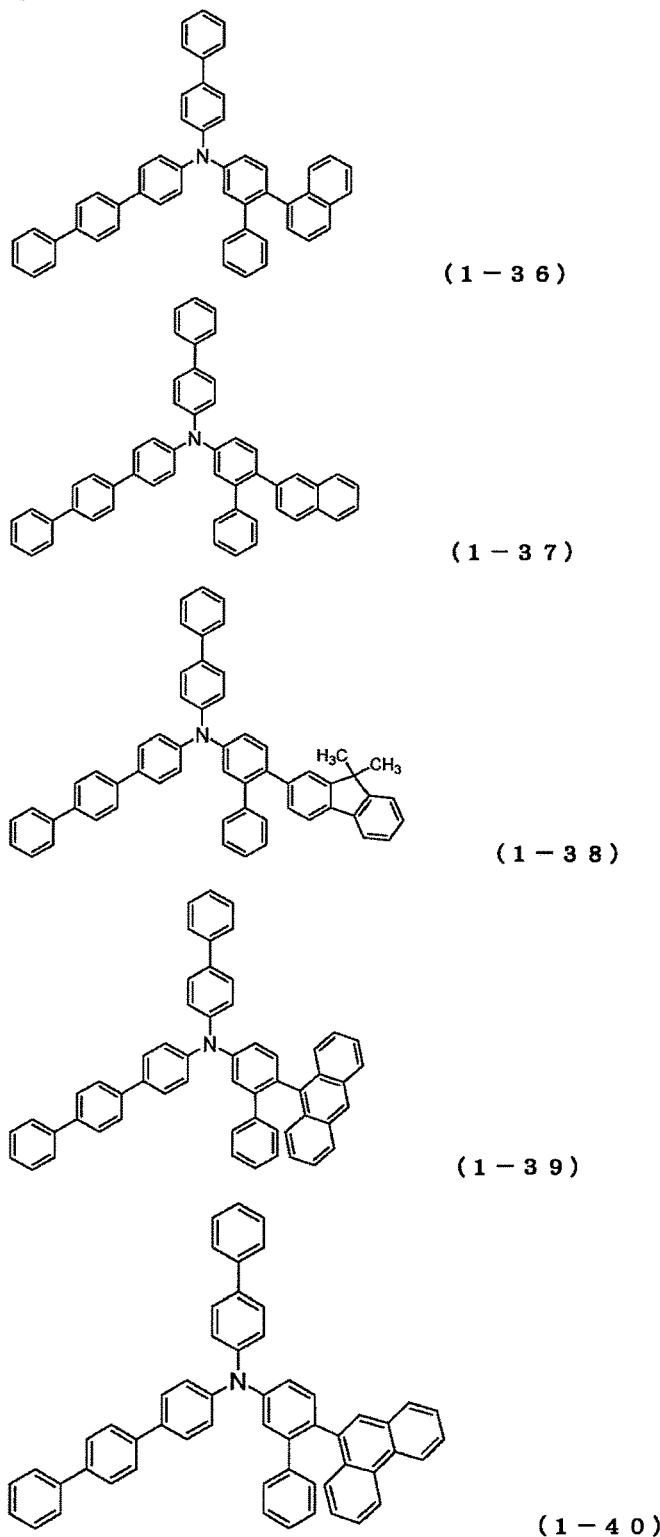
FIG. 9 is a view showing the structural formulas of Compounds No. (1-36) to (1-40) in the arylamine compound of the general formula (1).
Figure 10:
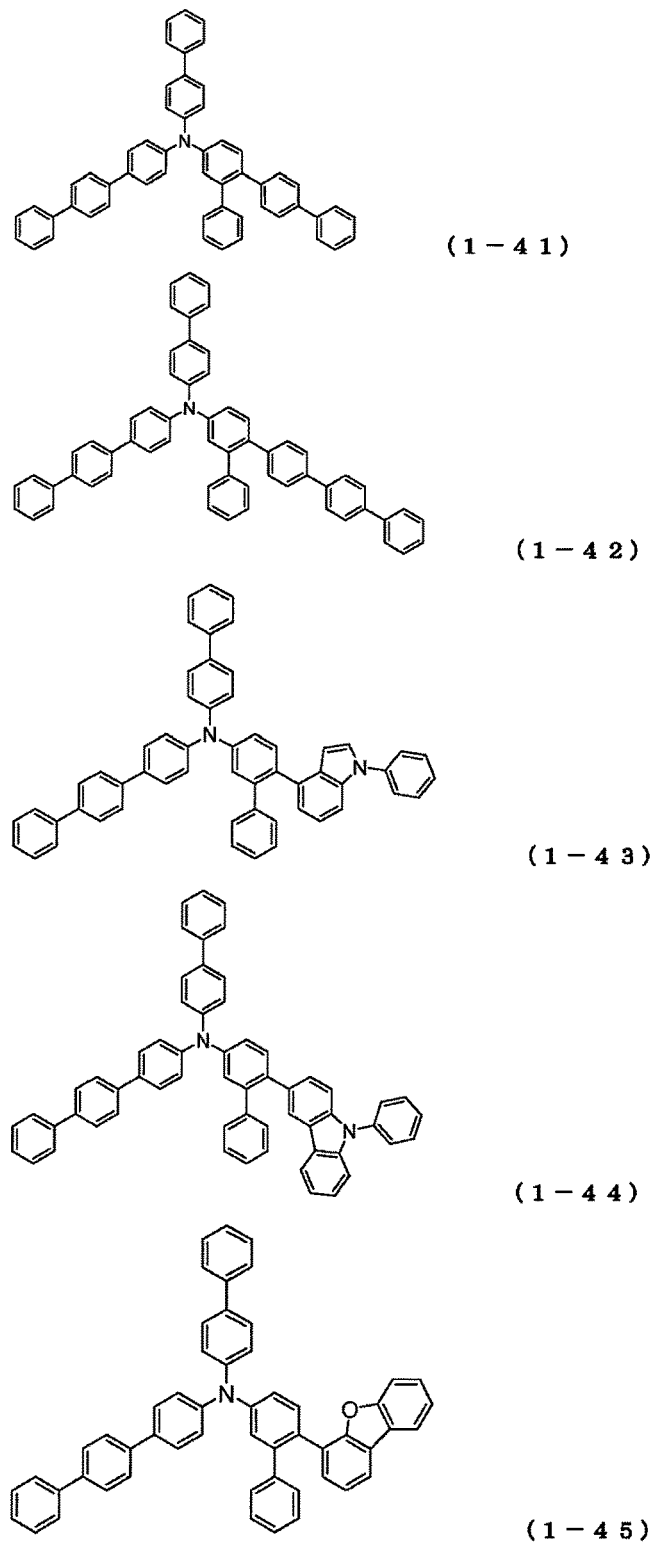
FIG. 10 is a view showing the structural formulas of Compounds No. (1-41) to (1-45) in the arylamine compound of the general formula (1).
Figure 11:
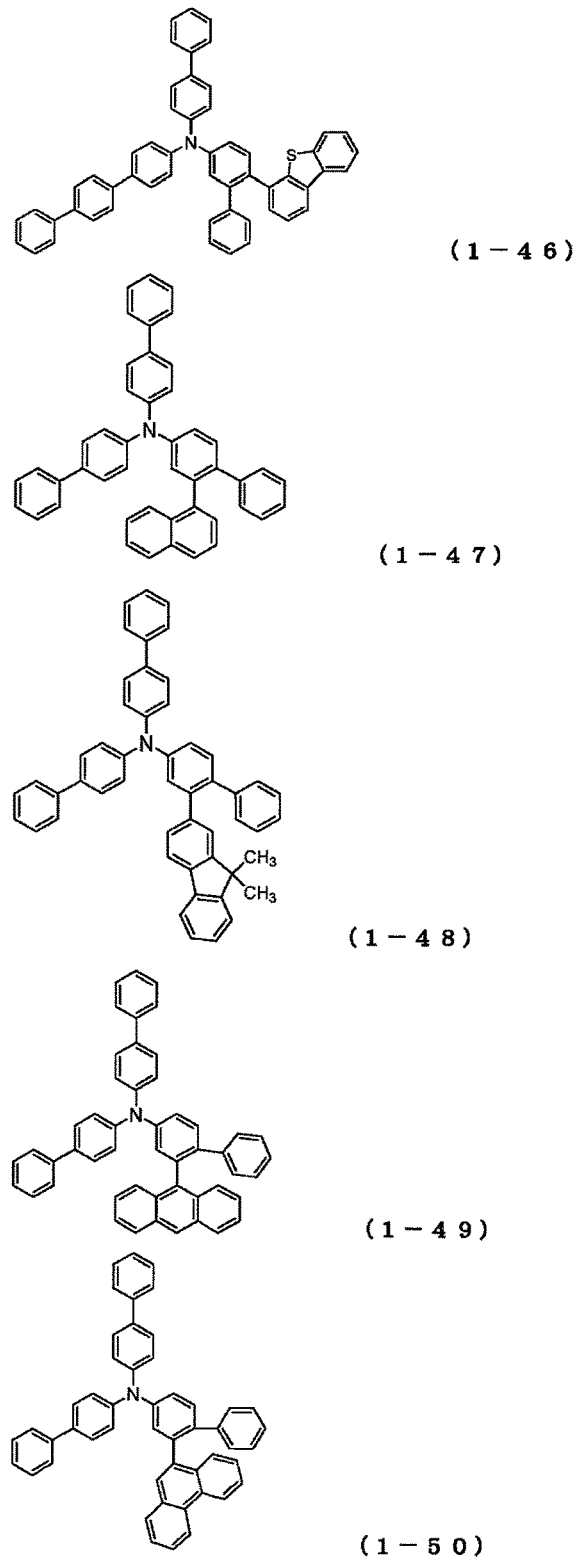
FIG. 11 is a view showing the structural formulas of Compounds No. (1-46) to (1-50) in the arylamine compound of the general formula (1).
Figure 12:
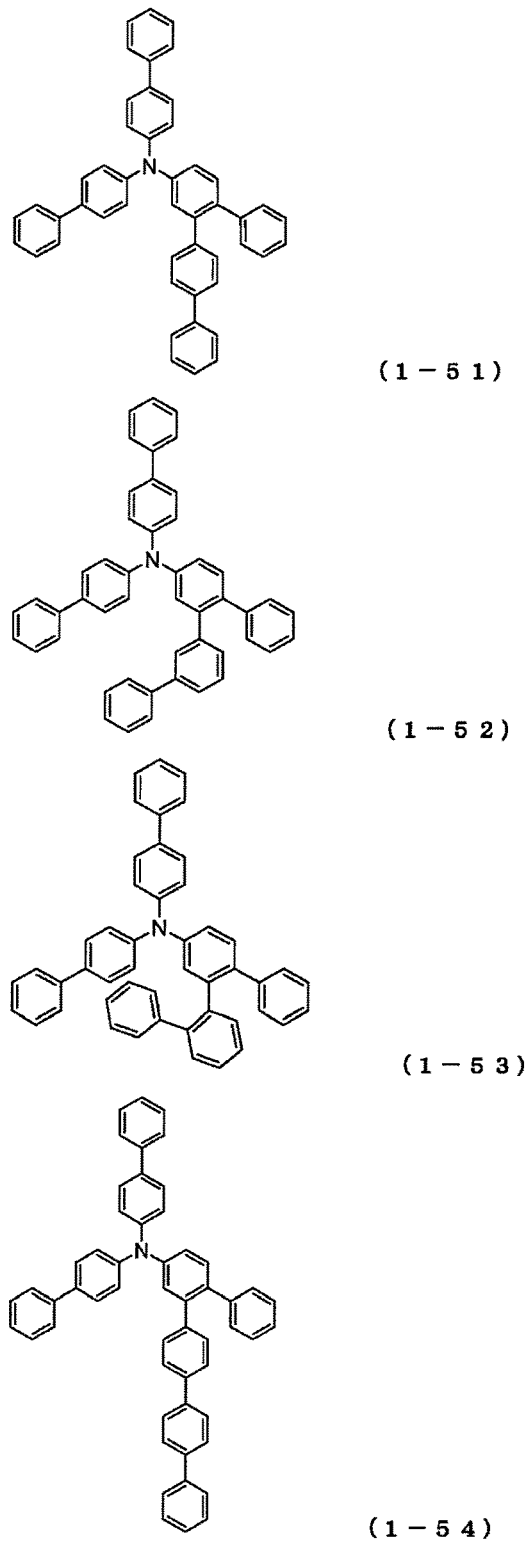
FIG. 12 is a view showing the structural formulas of Compounds No. (1-51) to (1-54) in the arylamine compound of the general formula (1).
Figure 13:
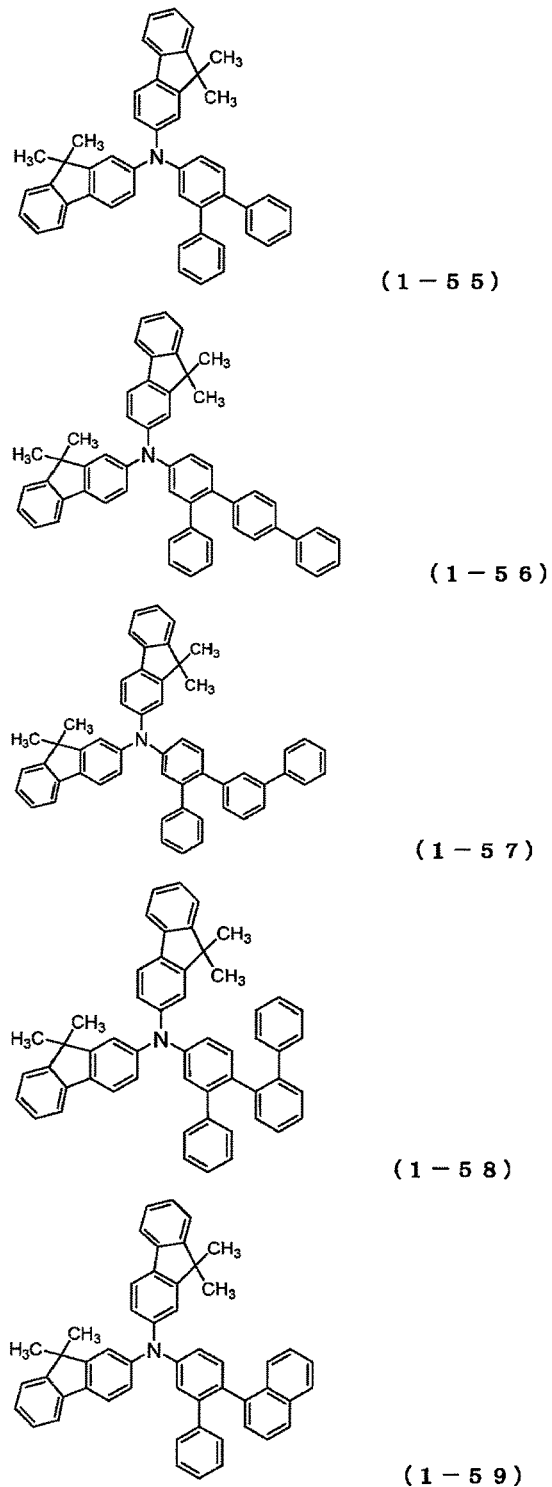
FIG. 13 is a view showing the structural formulas of Compounds No. (1-55) to (1-59) in the arylamine compound of the general formula (1).
Figure 14:
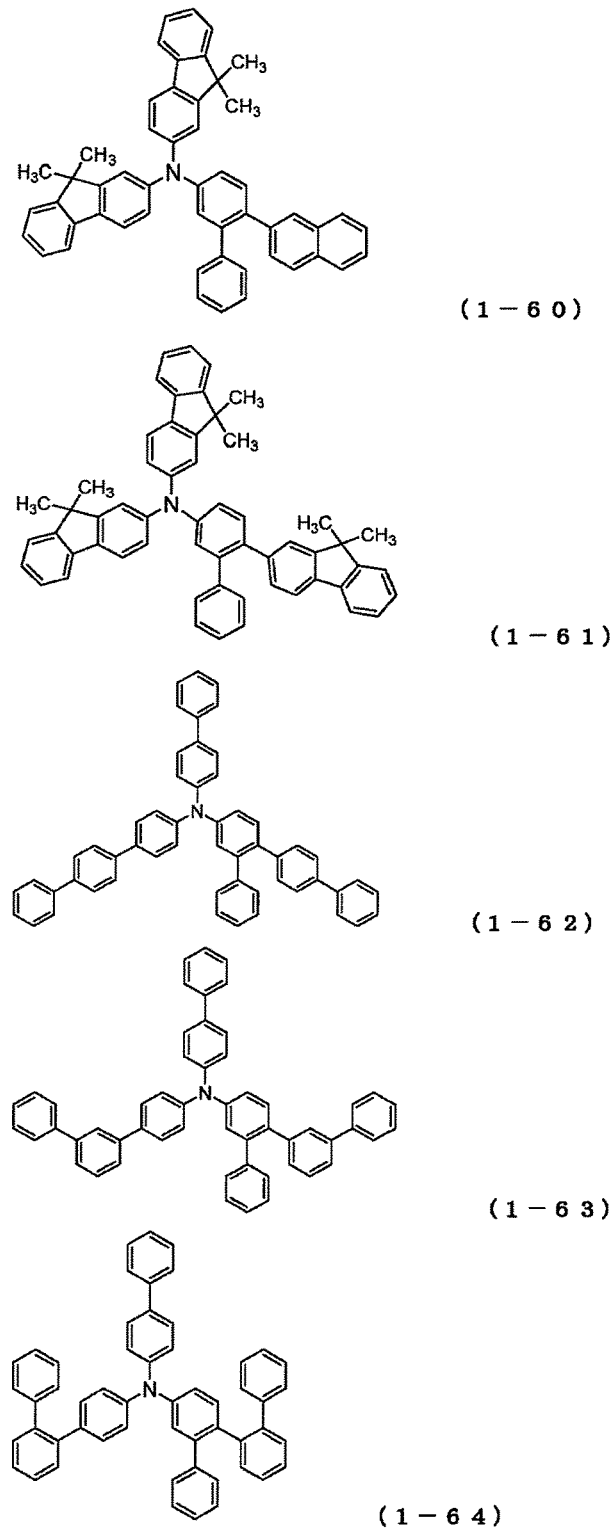
FIG. 14 is a view showing the structural formulas of Compounds No. (1-60) to (1-64) in the arylamine compound of the general formula (1).
Figure 15:
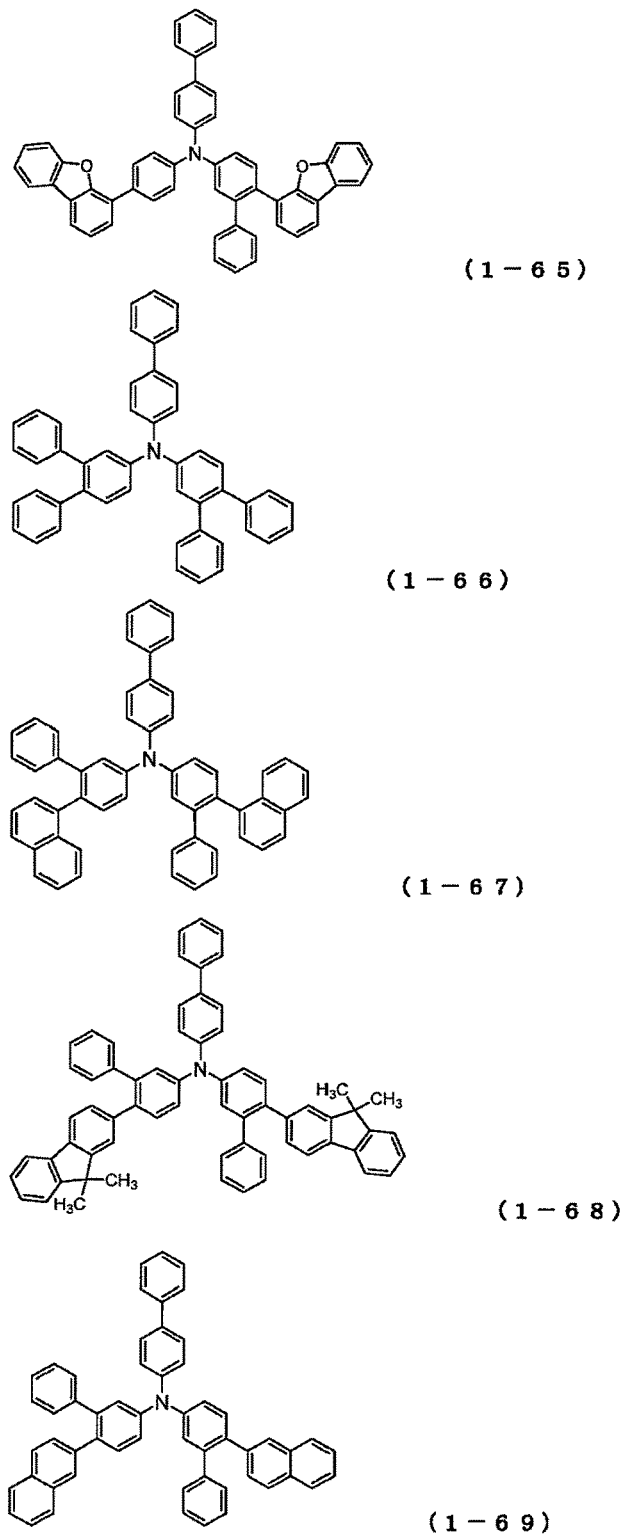
FIG. 15 is a view showing the structural formulas of Compounds No. (1-65) to (1-69) in the arylamine compound of the general formula (1).
Figure 16:
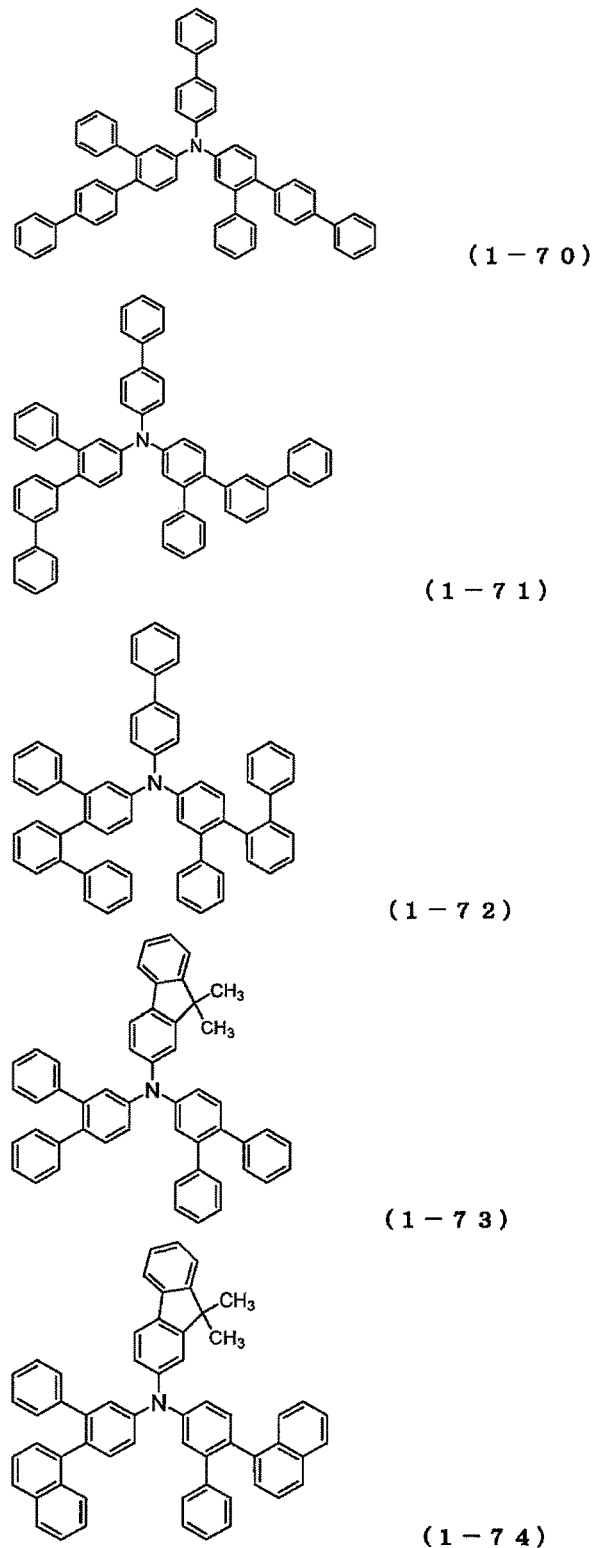
FIG. 16 is a view showing the structural formulas of Compounds No. (1-70) to (1-74) in the arylamine compound of the general formula (1).
Figure 17:
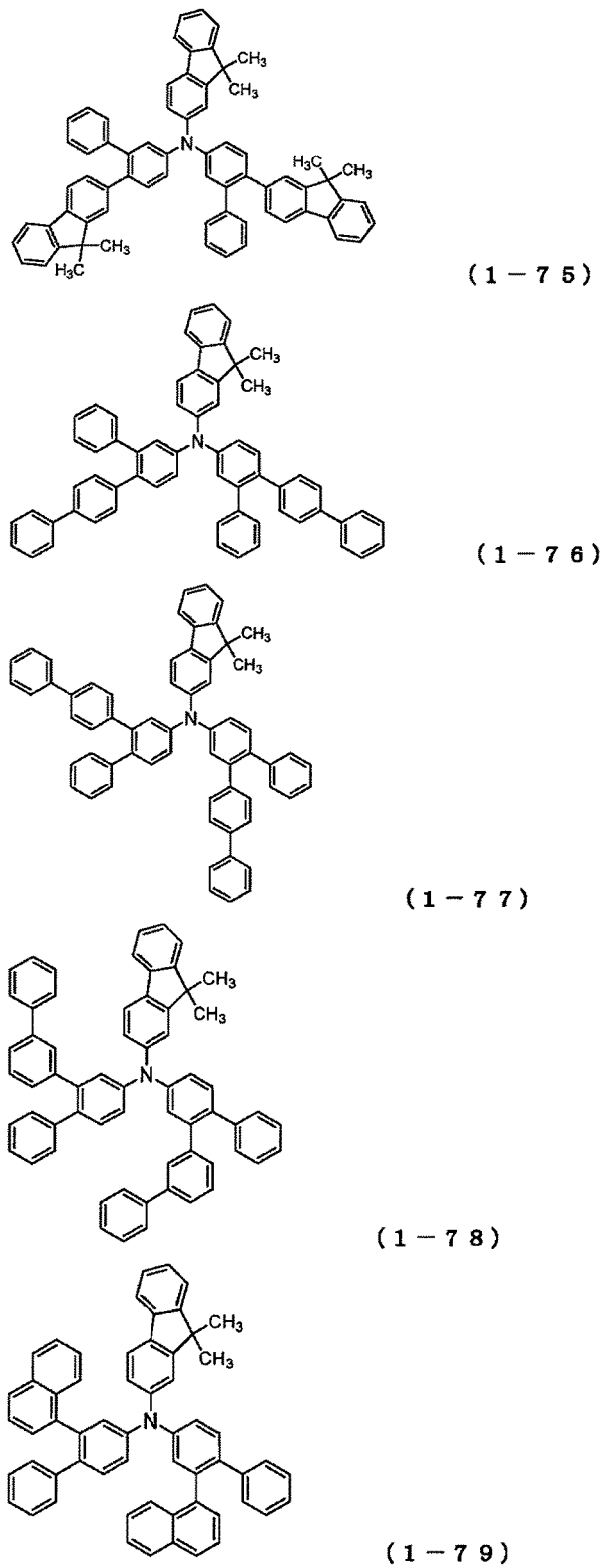
FIG. 17 is a view showing the structural formulas of Compounds No. (1-75) to (1-79) in the arylamine compound of the general formula (1).
Figure 18:
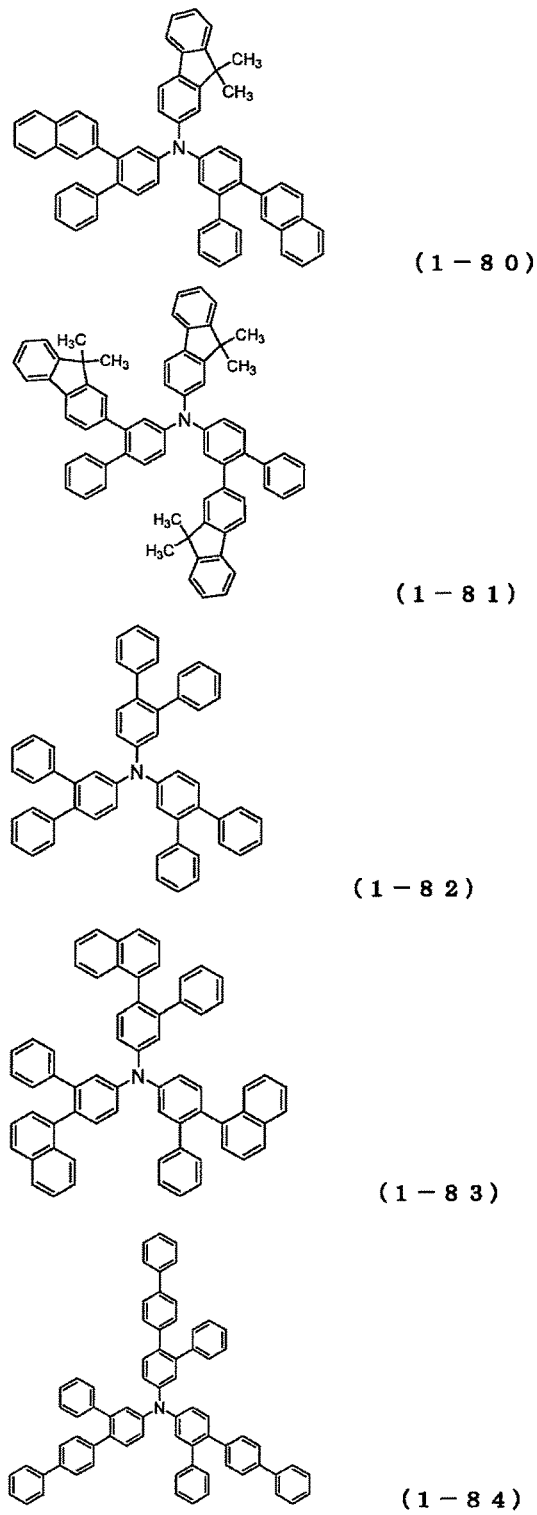
FIG. 18 is a view showing the structural formulas of Compounds No. (1-80) to (1-84) in the arylamine compound of the general formula (1).
Figure 19:
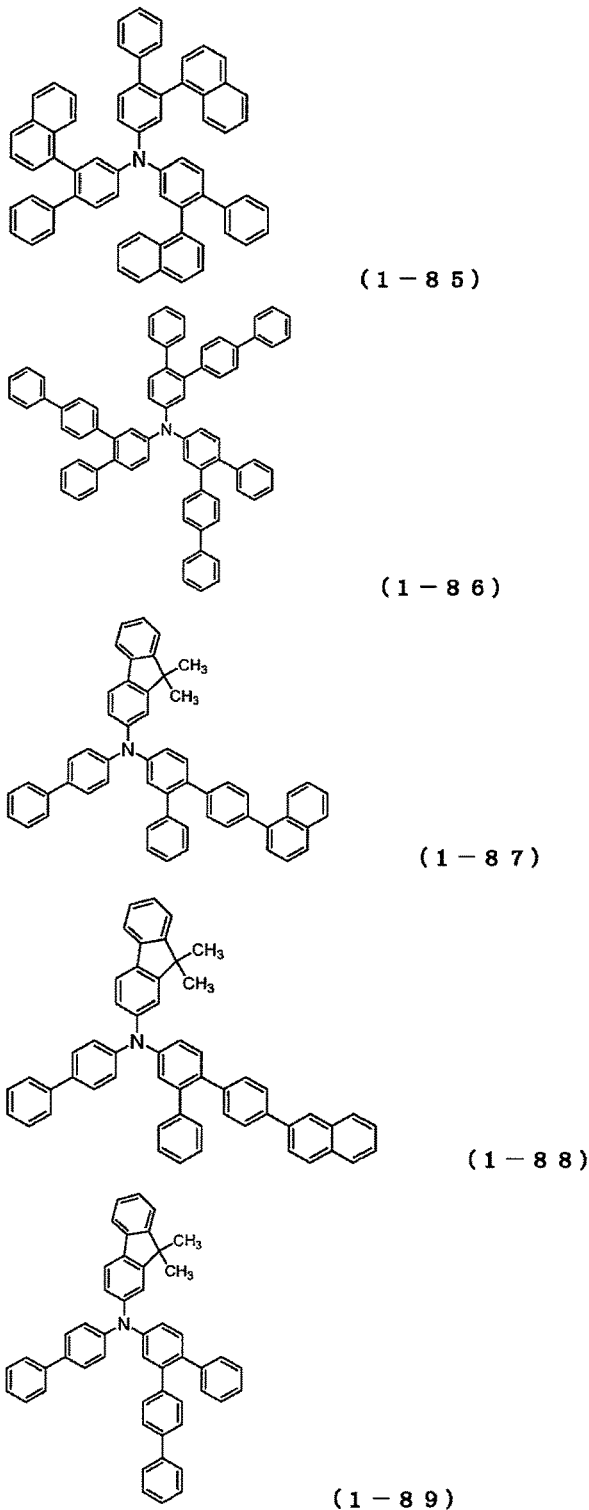
FIG. 19 is a view showing the structural formulas of Compounds No. (1-85) to (1-89) in the arylamine compound of the general formula (1).
Figure 20:
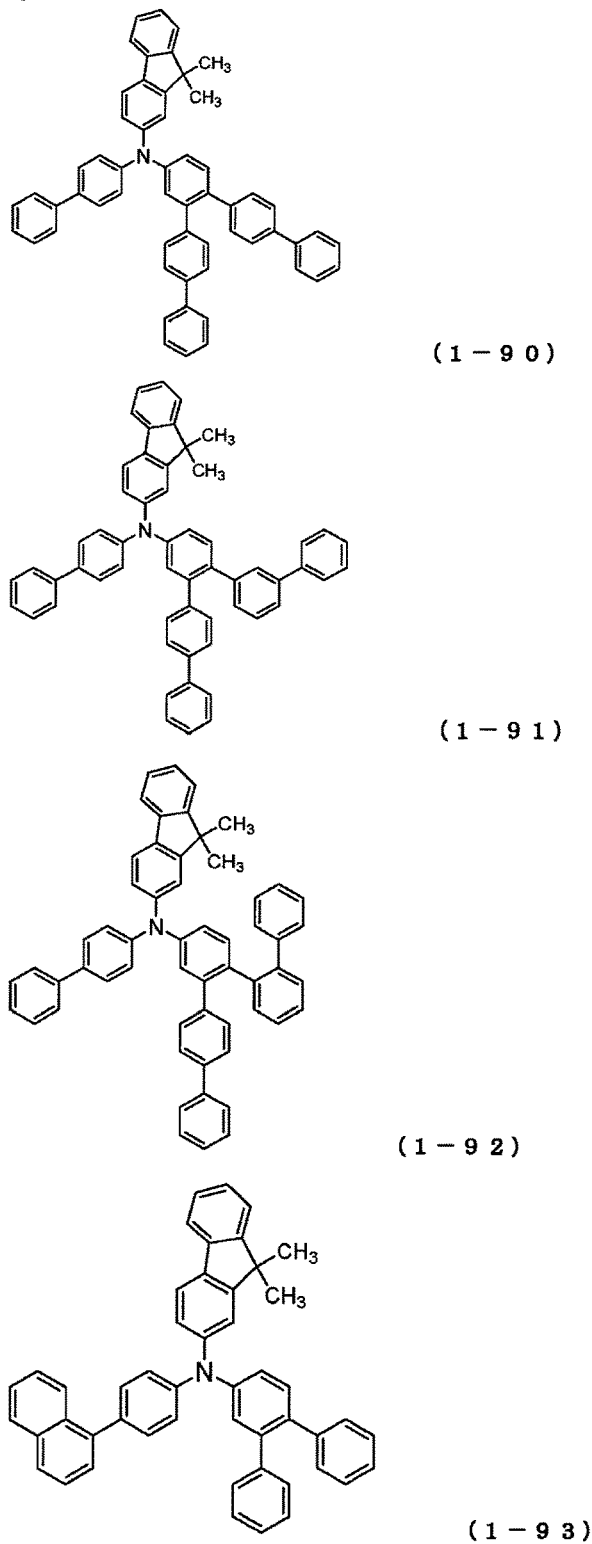
FIG. 20 is a view showing the structural formulas of Compounds No. (1-90) to (1-93) in the arylamine compound of the general formula (1).
Figure 21:
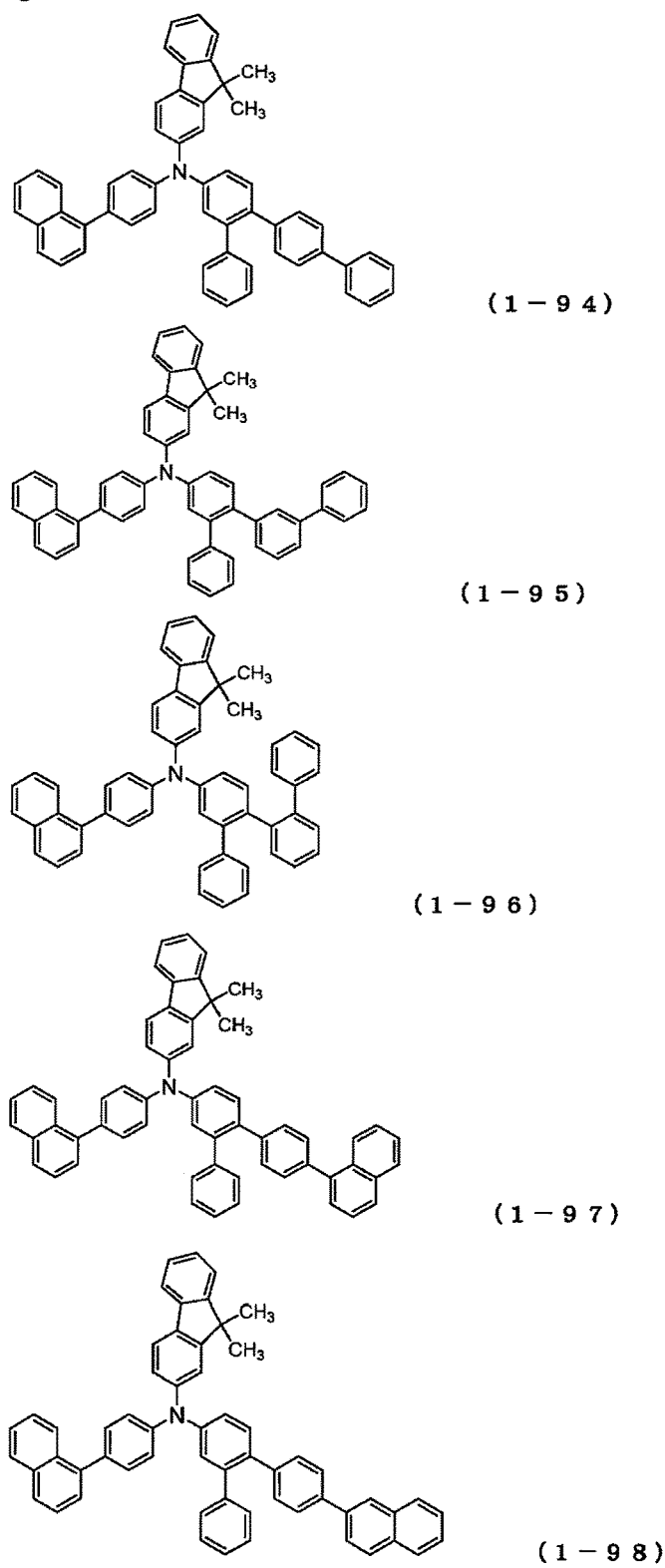
FIG. 21 is a view showing the structural formulas of Compounds No. (1-94) to (1-98) in the arylamine compound of the general formula (1).
Figure 22:
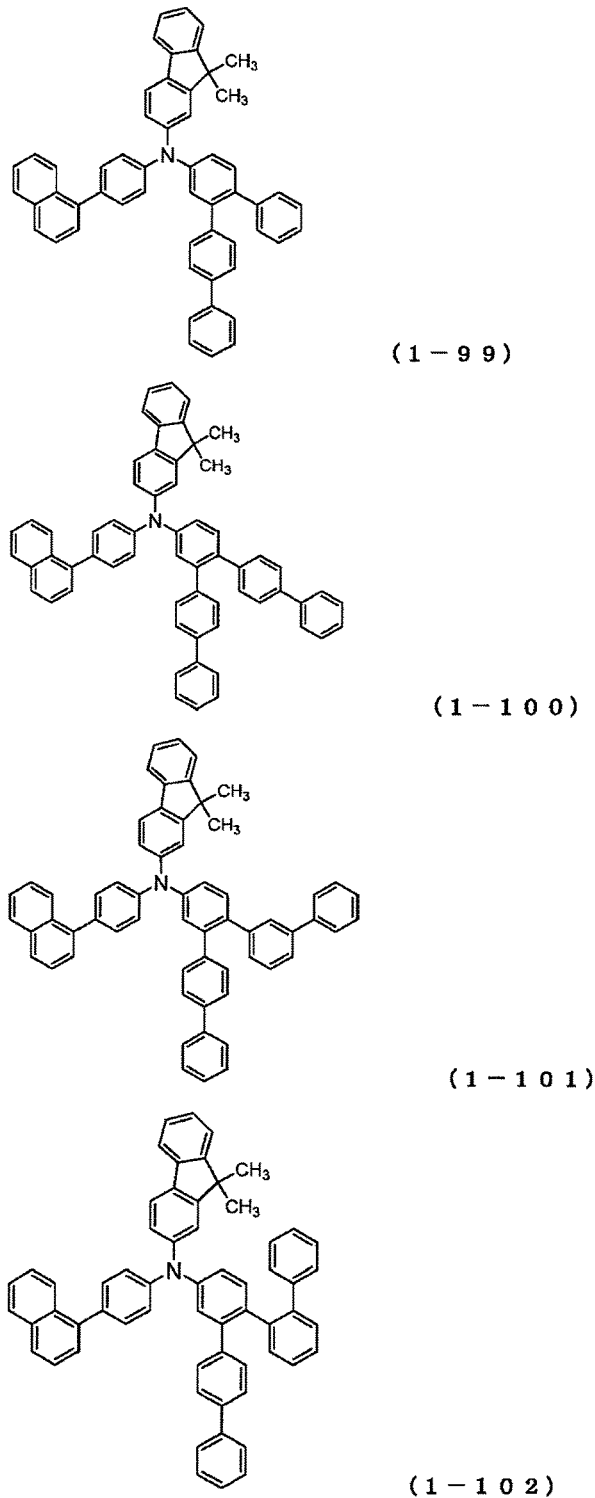
FIG. 22 is a view showing the structural formulas of Compounds No. (1-99) to (1-102) in the arylamine compound of the general formula (1).
Figure 23:
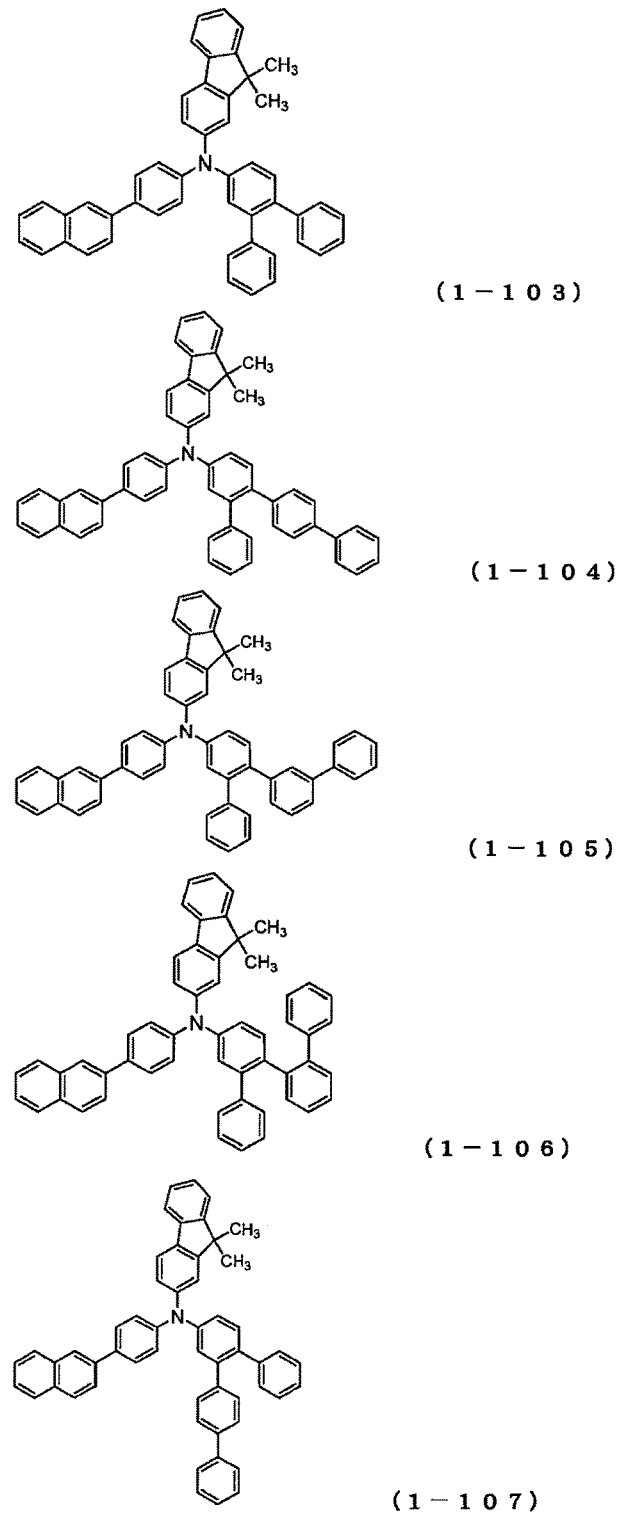
FIG. 23 is a view showing the structural formulas of Compounds No. (1-103) to (1-107) in the arylamine compound of the general formula (1).
Figure 24:
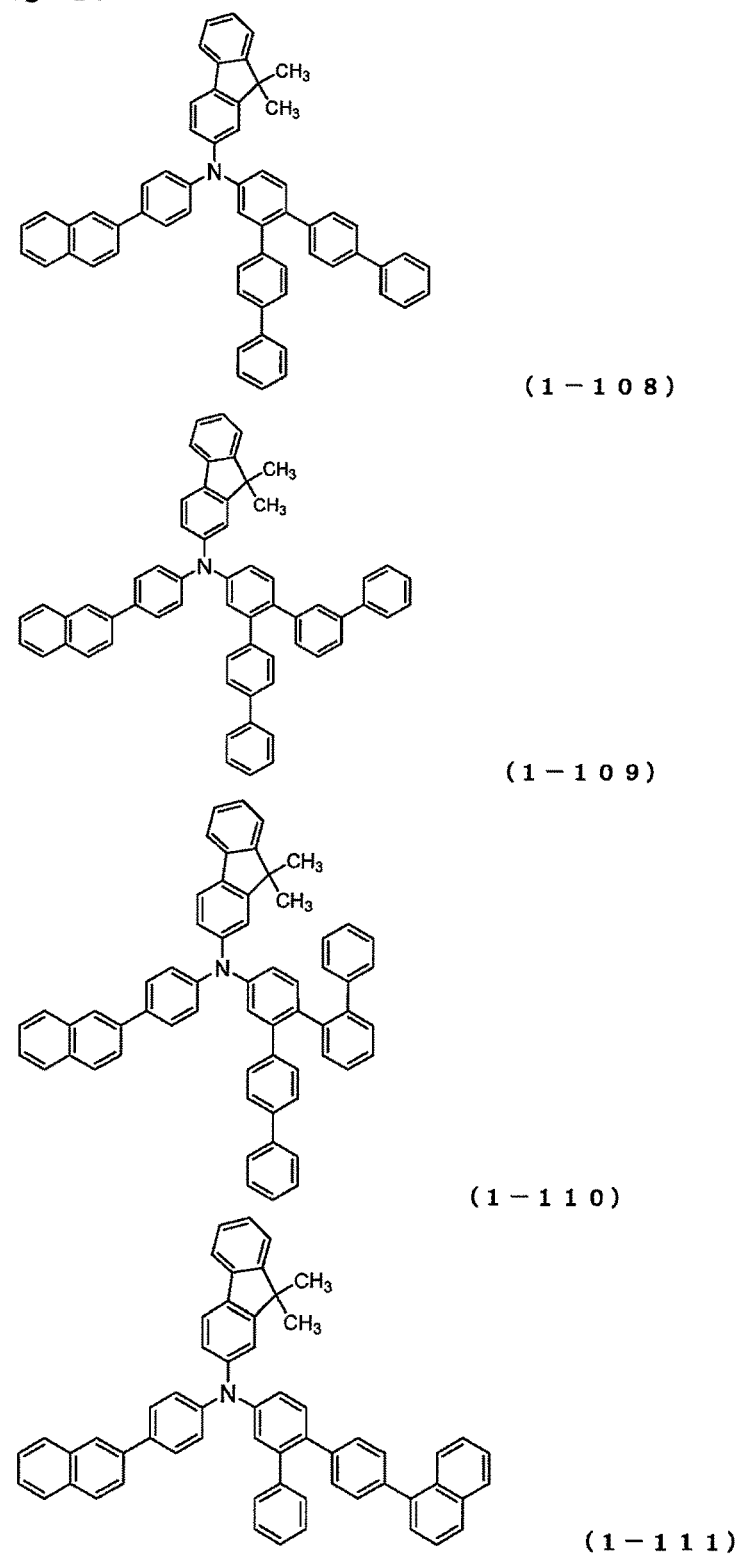
FIG. 24 is a view showing the structural formulas of Compounds No. (1-108) to (1-111) in the arylamine compound of the general formula (1).
Figure 25:
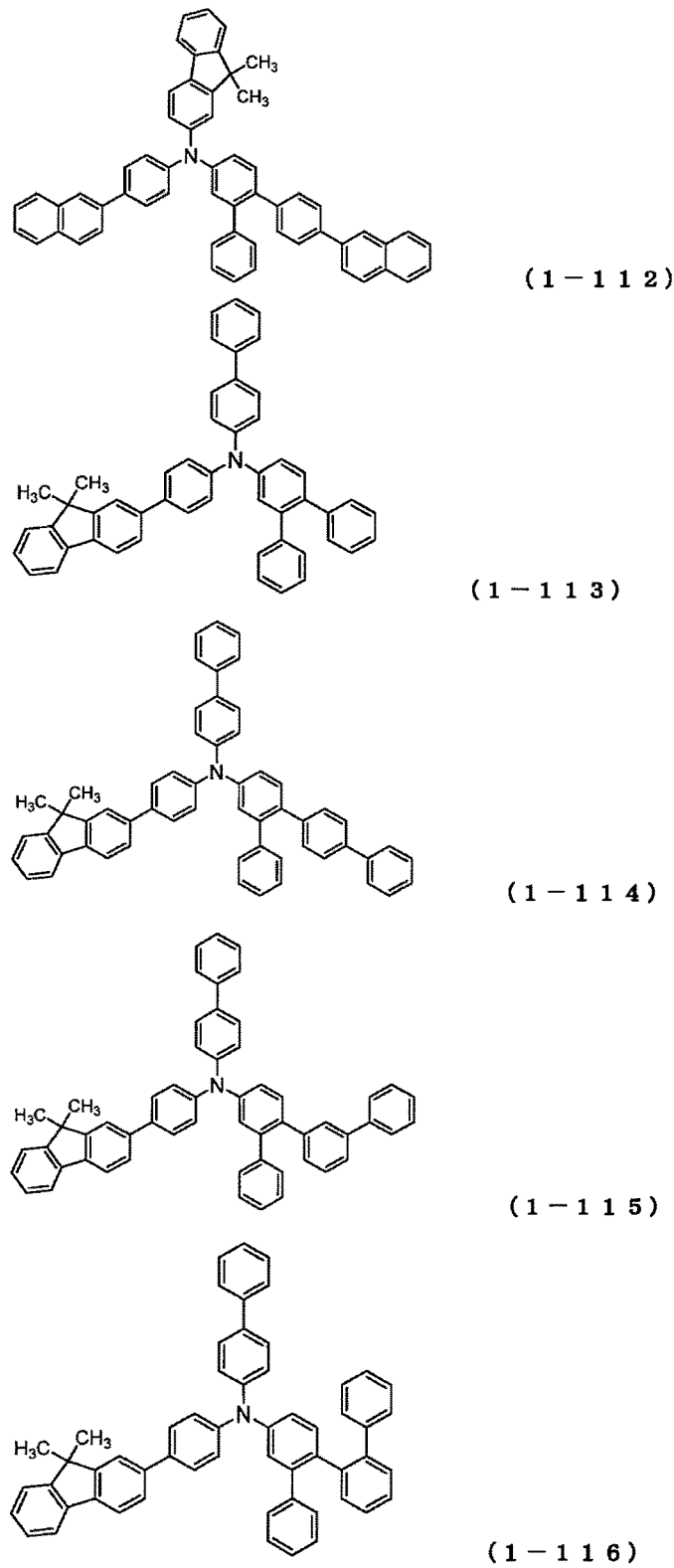
FIG. 25 is a view showing the structural formulas of Compounds No. (1-112) to (1-116) in the arylamine compound of the general formula (1).
Figure 26:
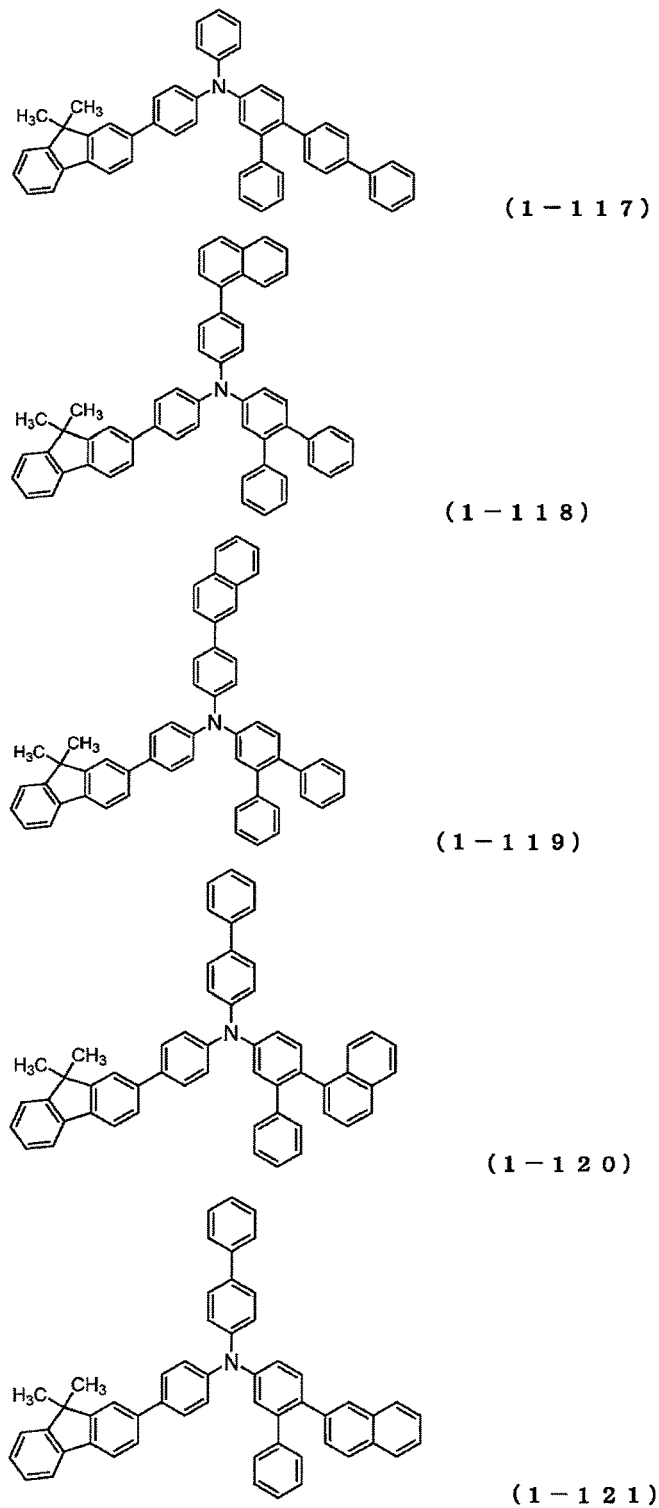
FIG. 26 is a view showing the structural formulas of Compounds No. (1-117) to (1-121) in the arylamine compound of the general formula (1).
Figure 27:
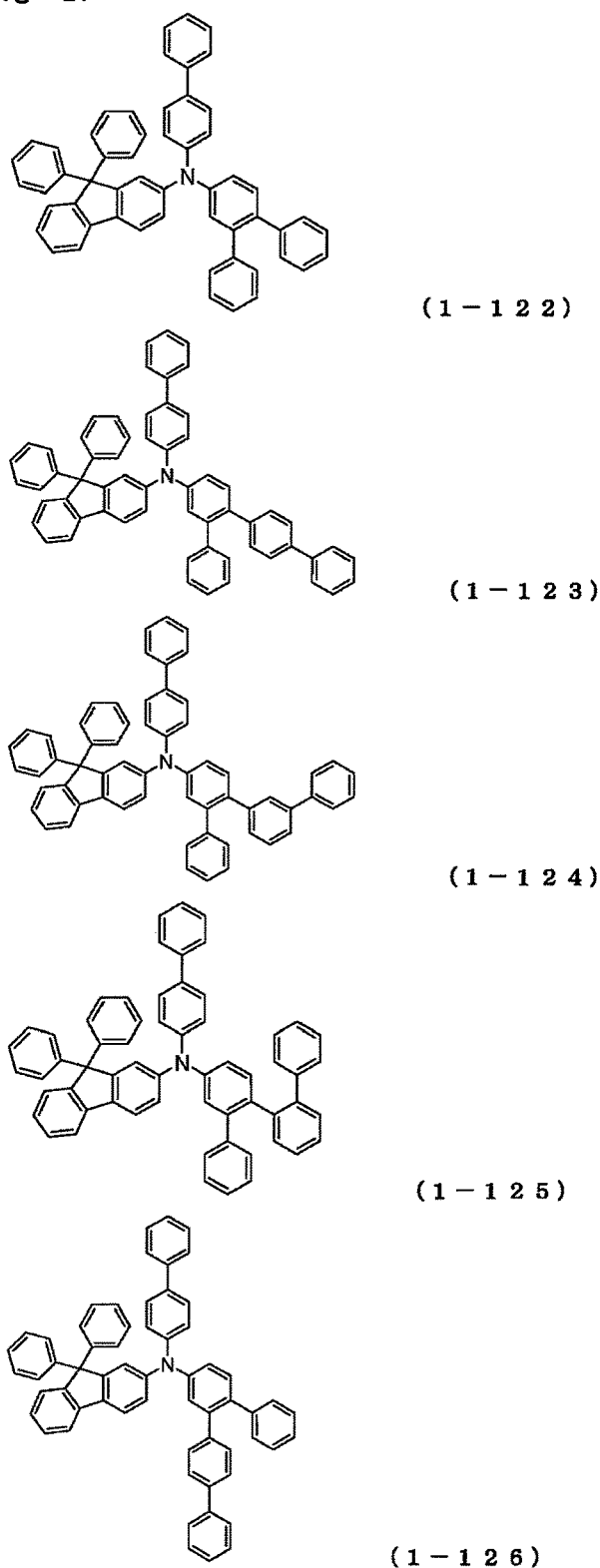
FIG. 27 is a view showing the structural formulas of Compounds No. (1-122) to (1-126) in the arylamine compound of the general formula (1).
Figure 28:
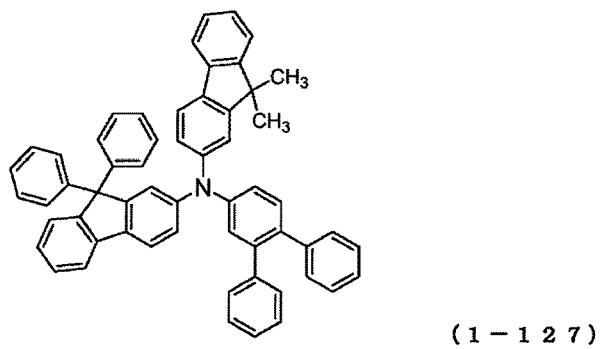
FIG. 28 is a view showing the structural formulas of Compounds No. (1-127) to (1-131) in the arylamine compound of the general formula (1).
Figure 28:
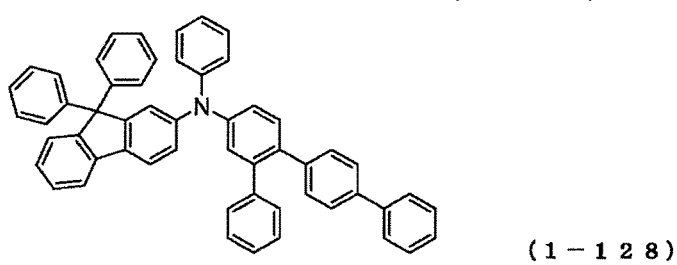
Figure 28:
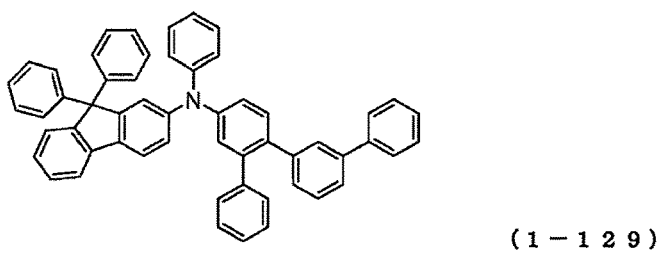
Figure 28:
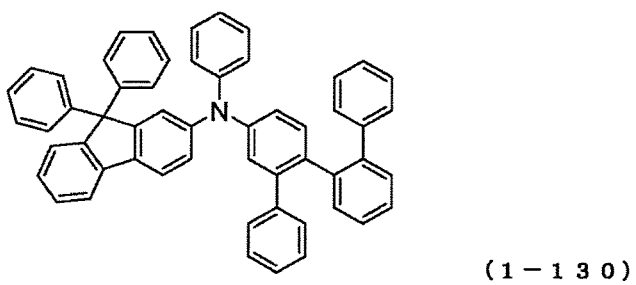
Figure 28:
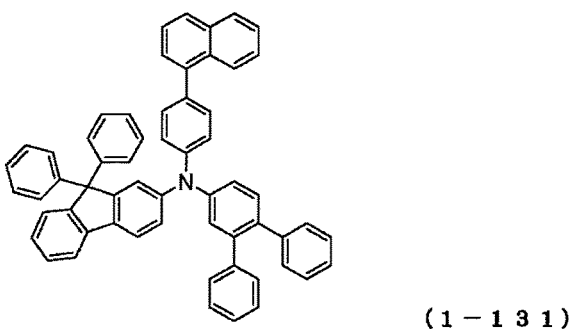
Figure 29:
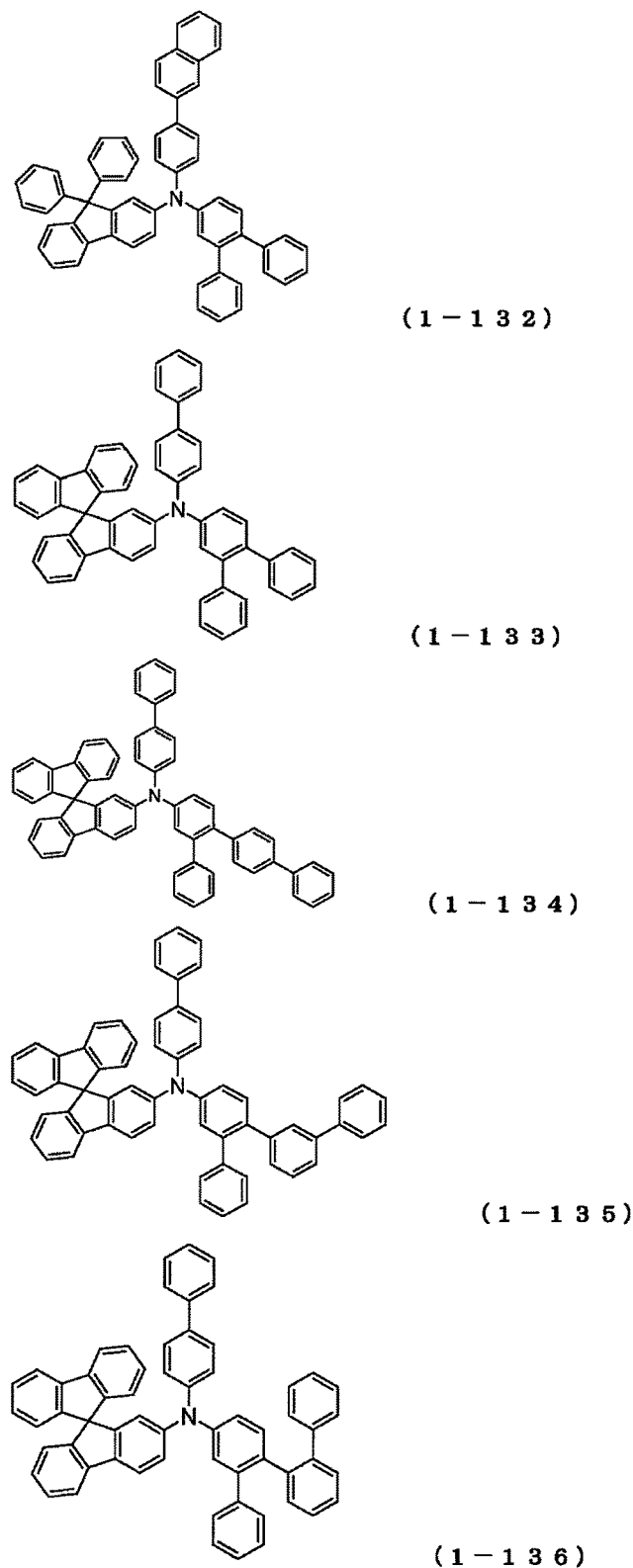
FIG. 29 is a view showing the structural formulas of Compounds No. (1-132) to (1-136) in the arylamine compound of the general formula (1).
Figure 30:
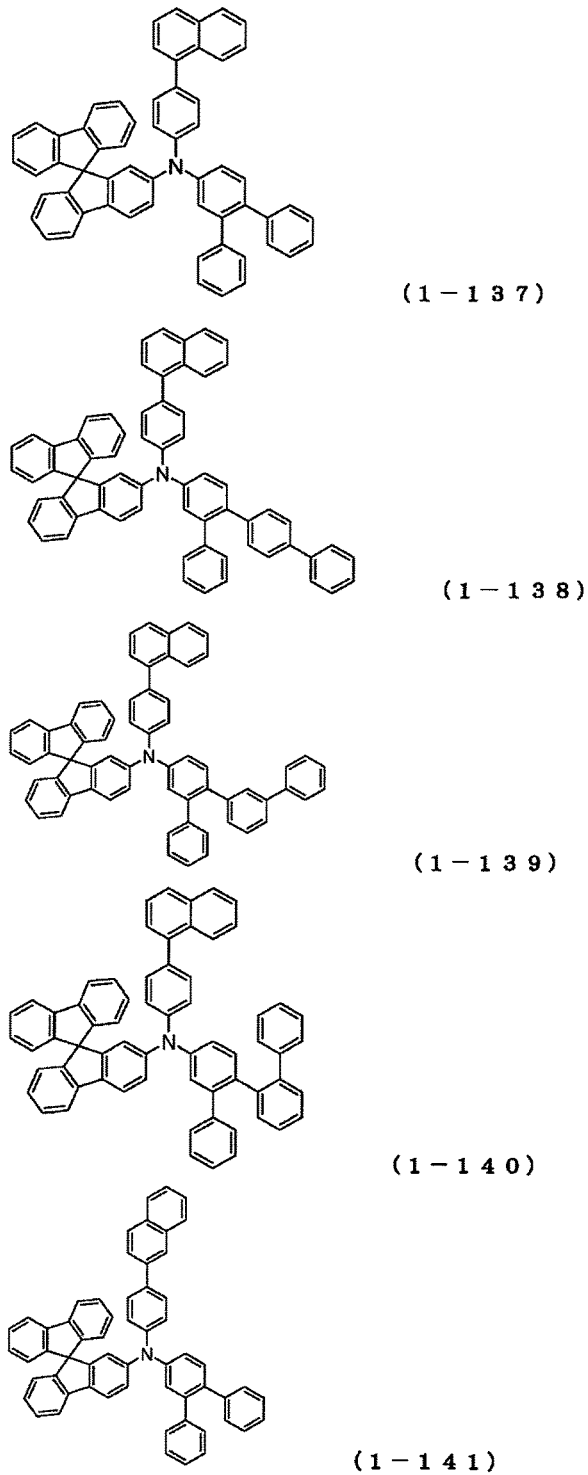
FIG. 30 is a view showing the structural formulas of Compounds No. (1-137) to (1-141) in the arylamine compound of the general formula (1).
Figure 31:
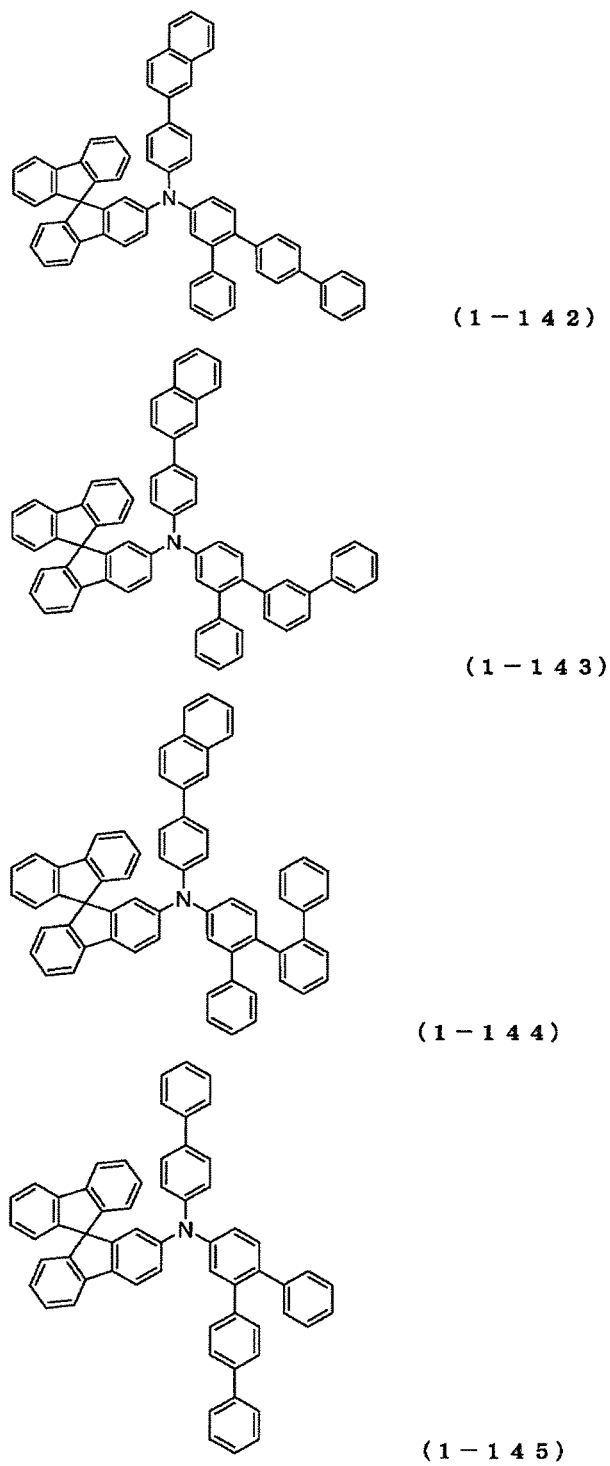
FIG. 31 is a view showing the structural formulas of Compounds No. (1-142) to (1-145) in the arylamine compound of the general formula (1).
Figure 32:
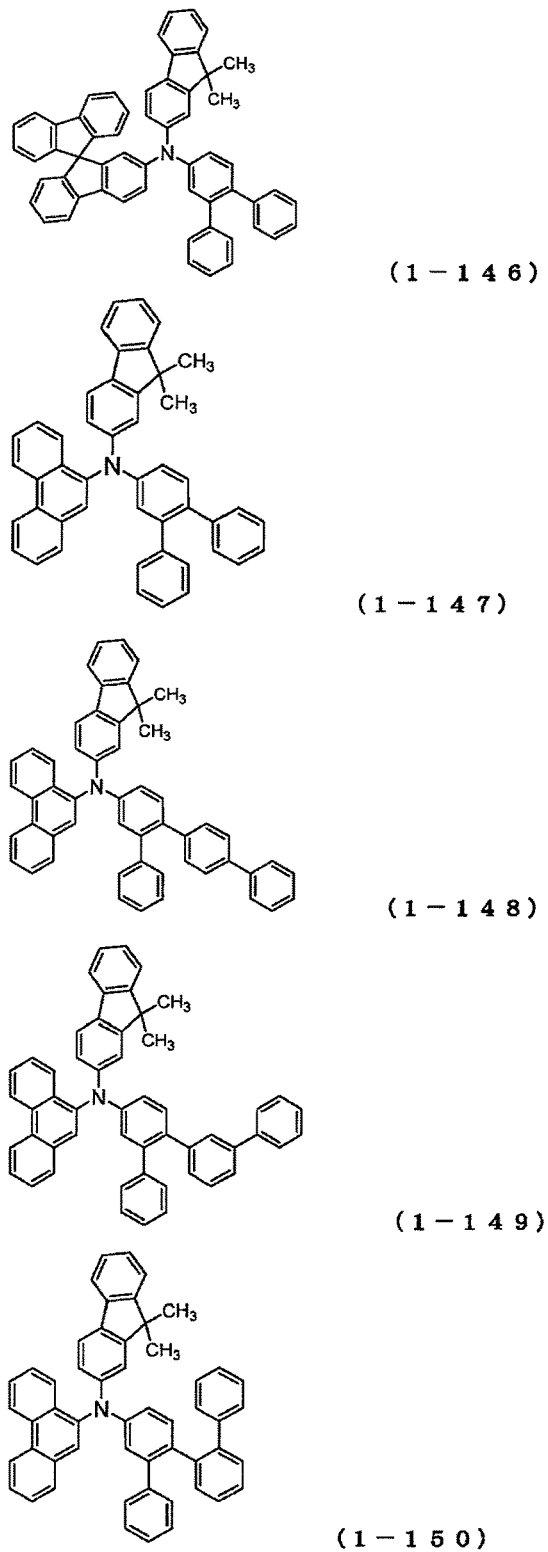
FIG. 32 is a view showing the structural formulas of Compounds No. (1-146) to (1-150) in the arylamine compound of the general formula (1).
Figure 33:
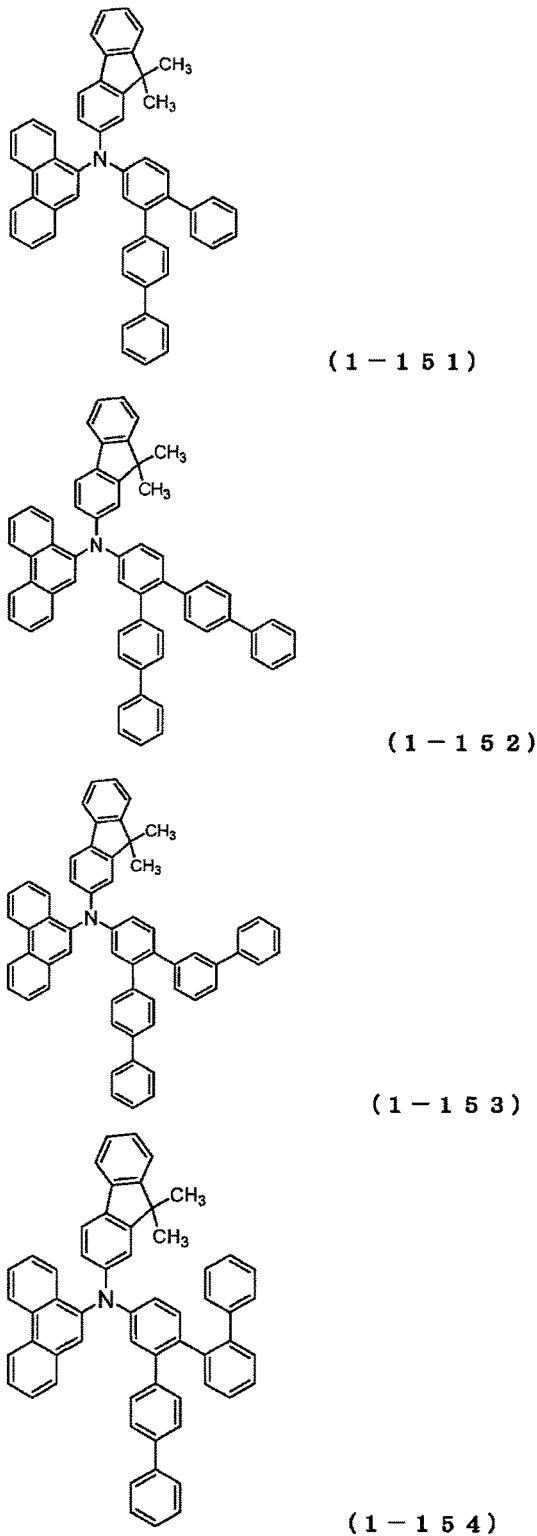
FIG. 33 is a view showing the structural formulas of Compounds No. (1-151) to (1-154) in the arylamine compound of the general formula (1).
Figure 34:
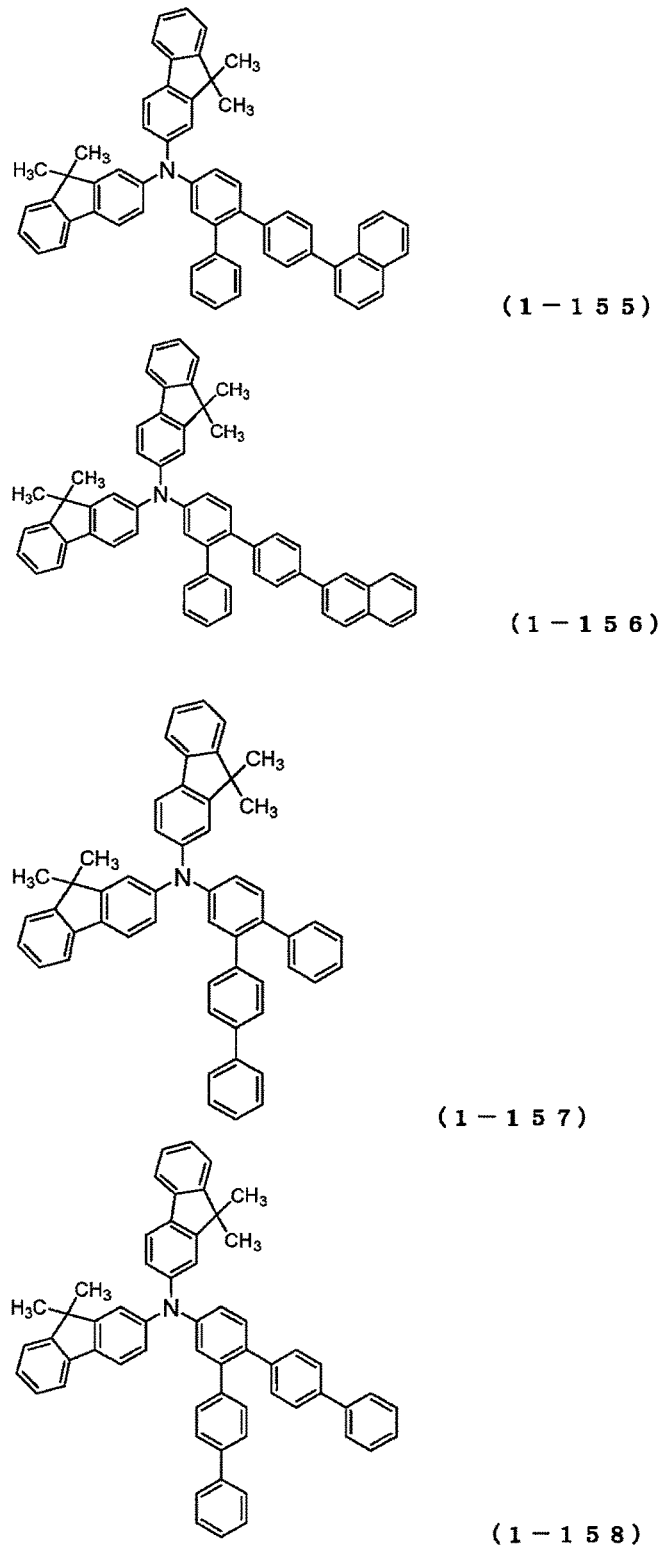
FIG. 34 is a view showing the structural formulas of Compounds No. (1-155) to (1-158) in the arylamine compound of the general formula (1).
Figure 35:
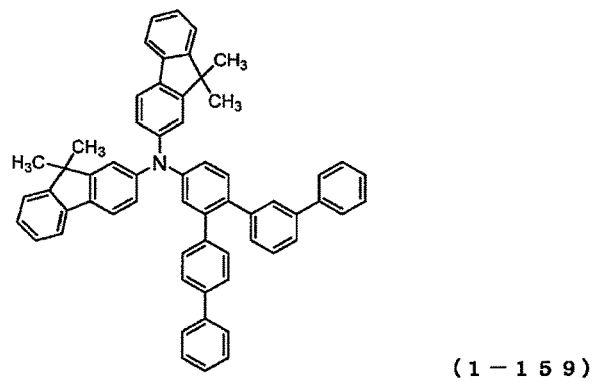
FIG. 35 is a view showing the structural formulas of Compounds No. (1-159) and (1-160) in the arylamine compound of the general formula (1).
Figure 35:
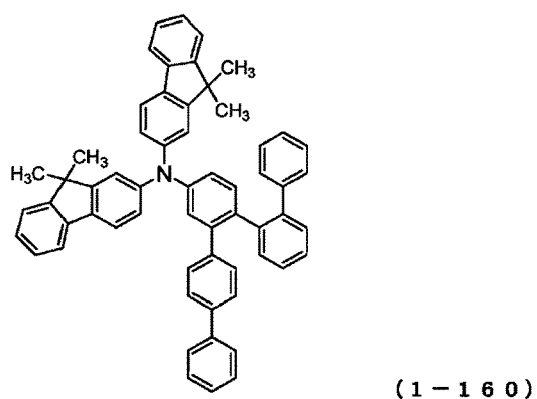
Figure 36:
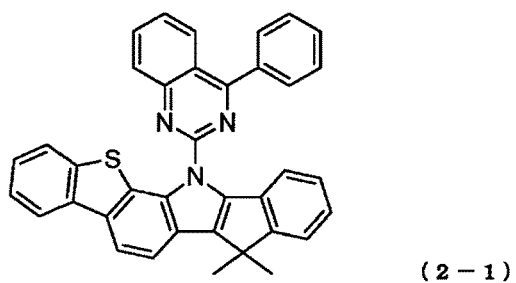
FIG. 36 is a view showing the structural formulas of Compounds No. (2-1) and (2-2) in the indenoindole compounds of a general formula (2).
Figure 36:
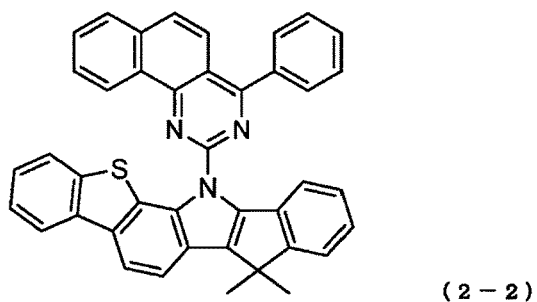
Figure 37:
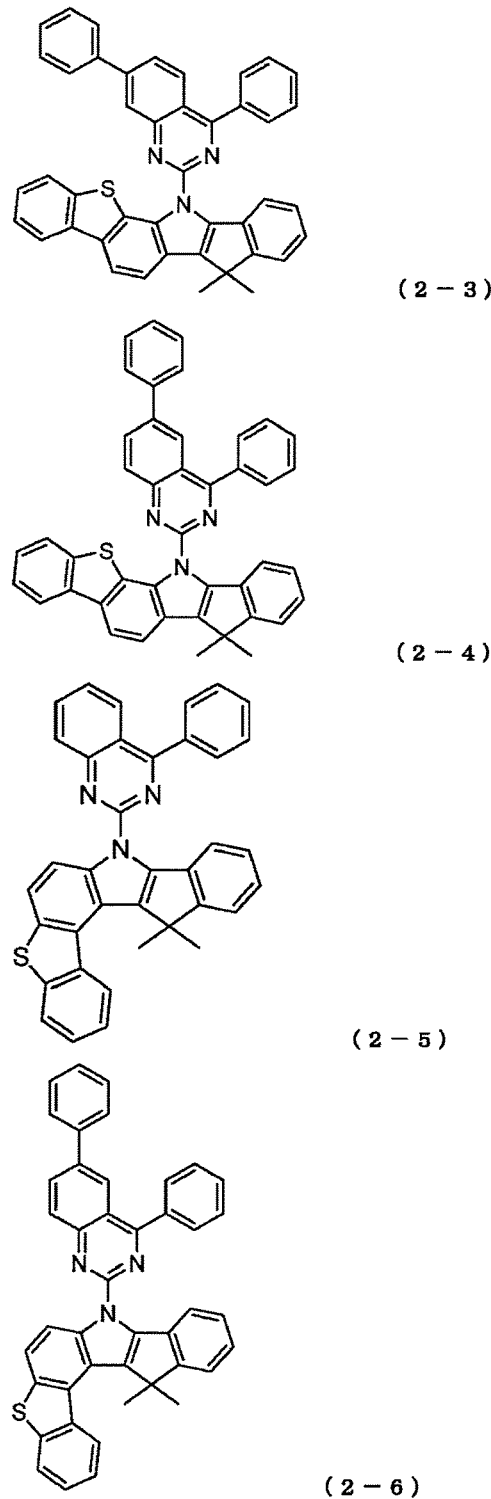
FIG. 37 is a view showing the structural formulas of Compounds No. (2-3) to (2-6) in the indenoindole compounds of the general formula (2).
Figure 38:
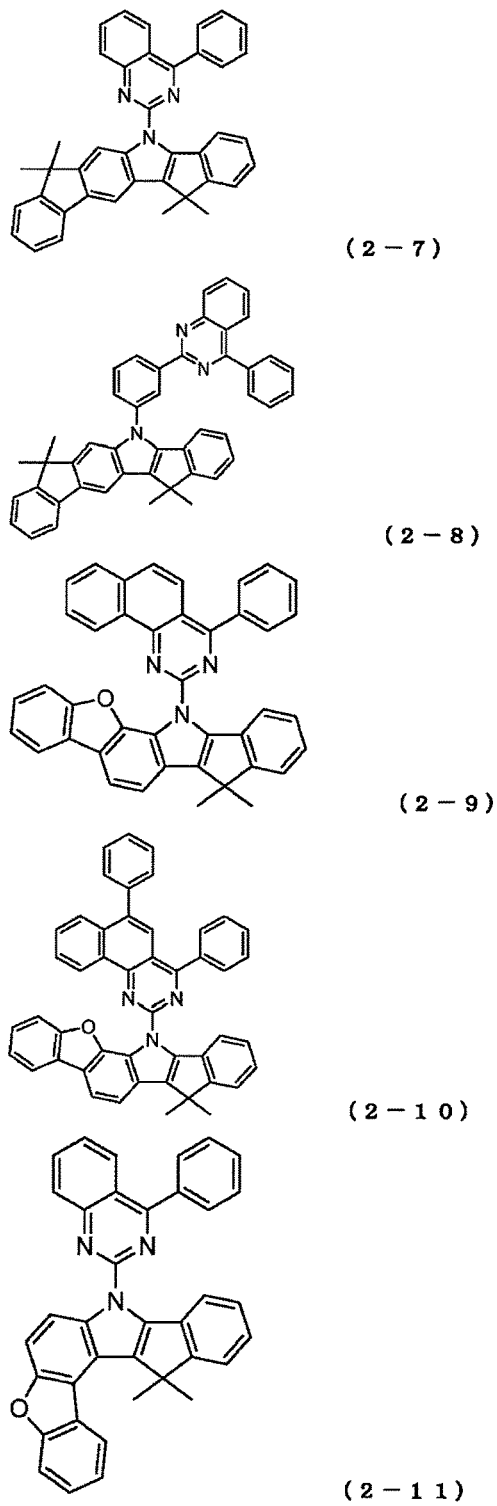
FIG. 38 is a view showing the structural formulas of Compounds No. (2-7) to (2-11) in the indenoindole compounds of the general formula (2).
Figure 39:
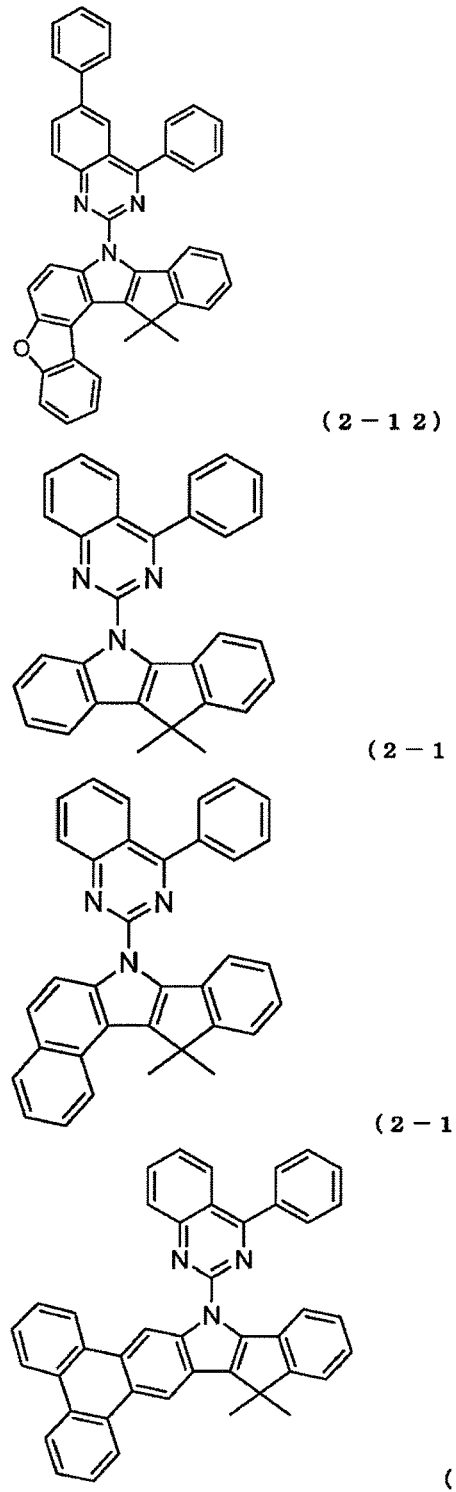
FIG. 39 is a view showing the structural formulas of Compounds No. (2-12) to (2-15) in the indenoindole compounds of the general formula (2).
Figure 40:
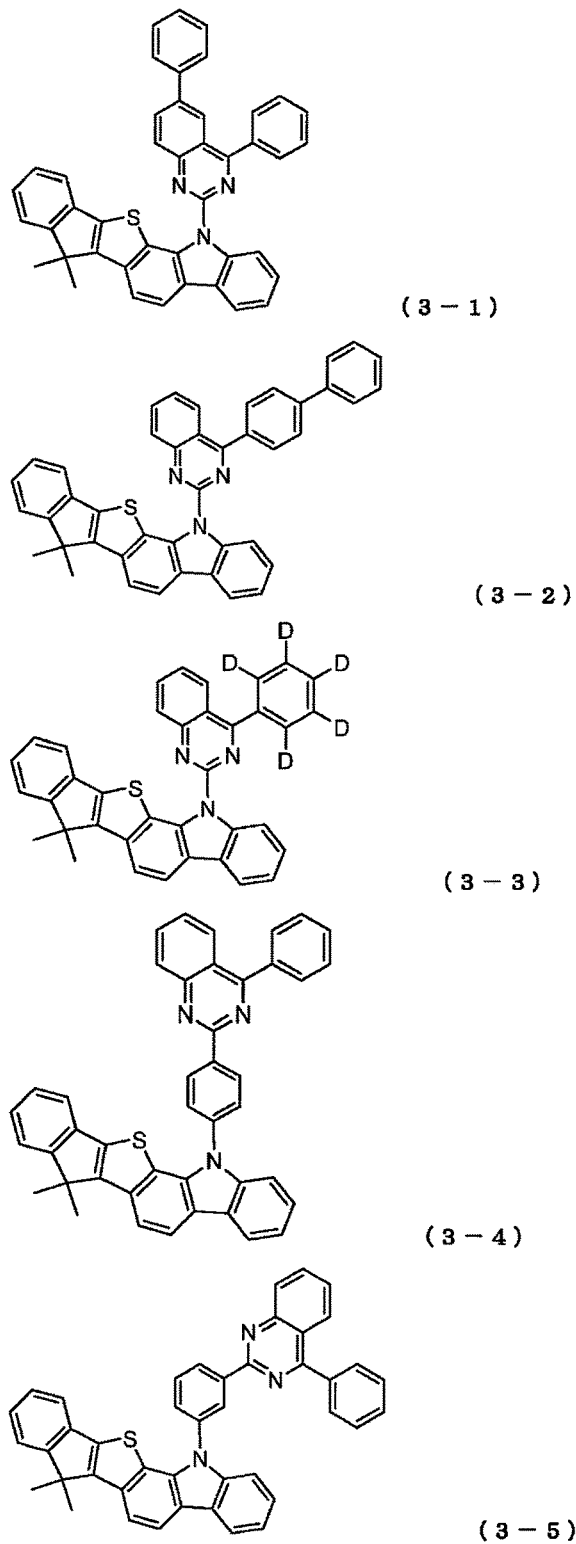
FIG. 40 is a view showing the structural formulas of Compounds No. (3-1) to (3-5) in the carbazole compounds of a general formula (3).
Figure 41:
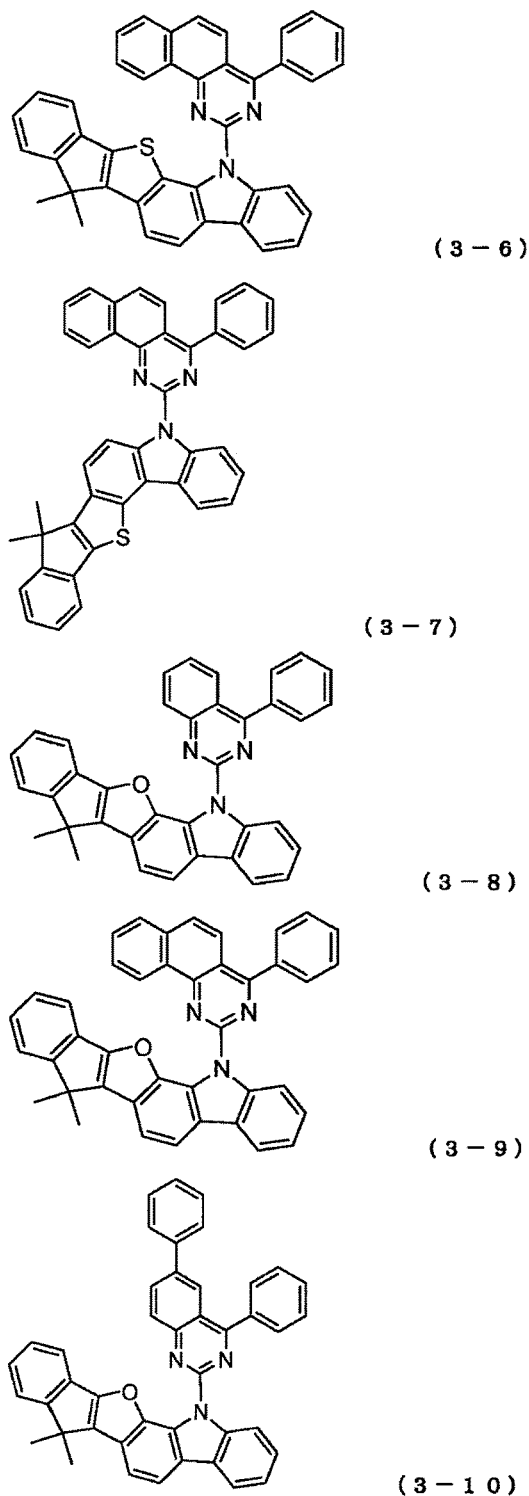
FIG. 41 is a view showing the structural formulas of Compounds No. (3-6) to (3-10) in the carbazole compounds of the general formula (3).
Figure 42:
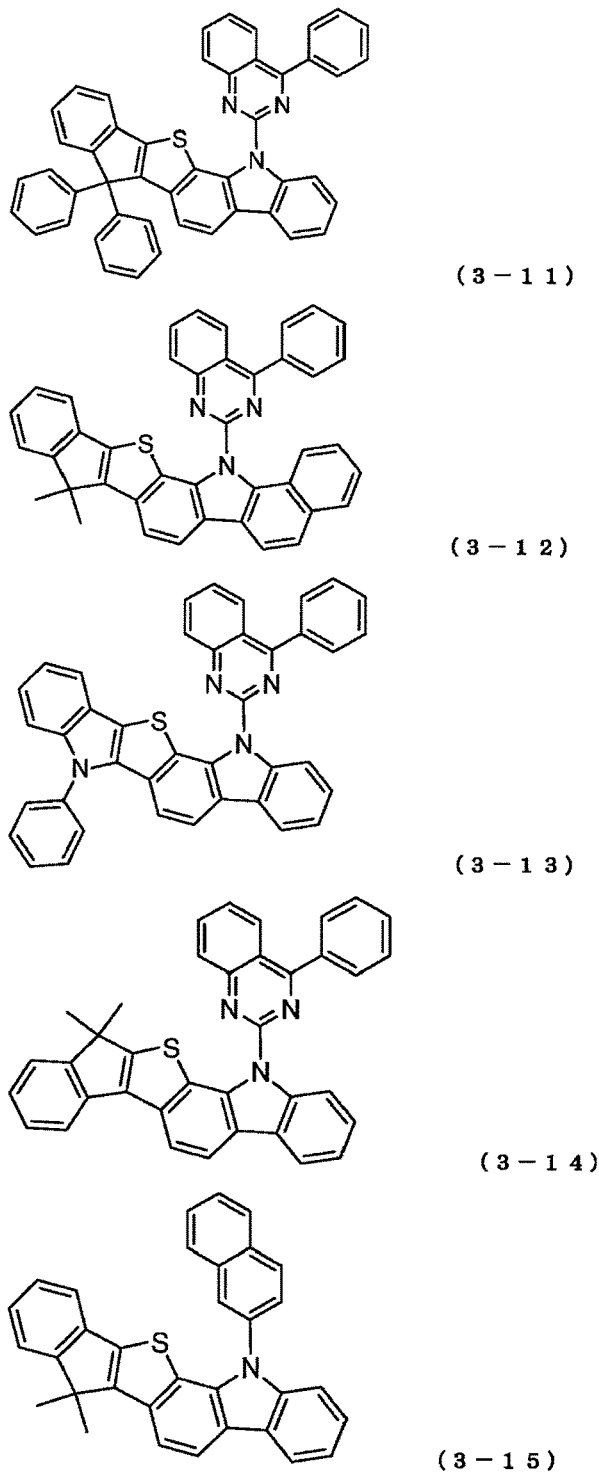
FIG. 42 is a view showing the structural formulas of Compounds No. (3-11) to (3-15) in the carbazole compounds of the general formula (3).
Figure 43:
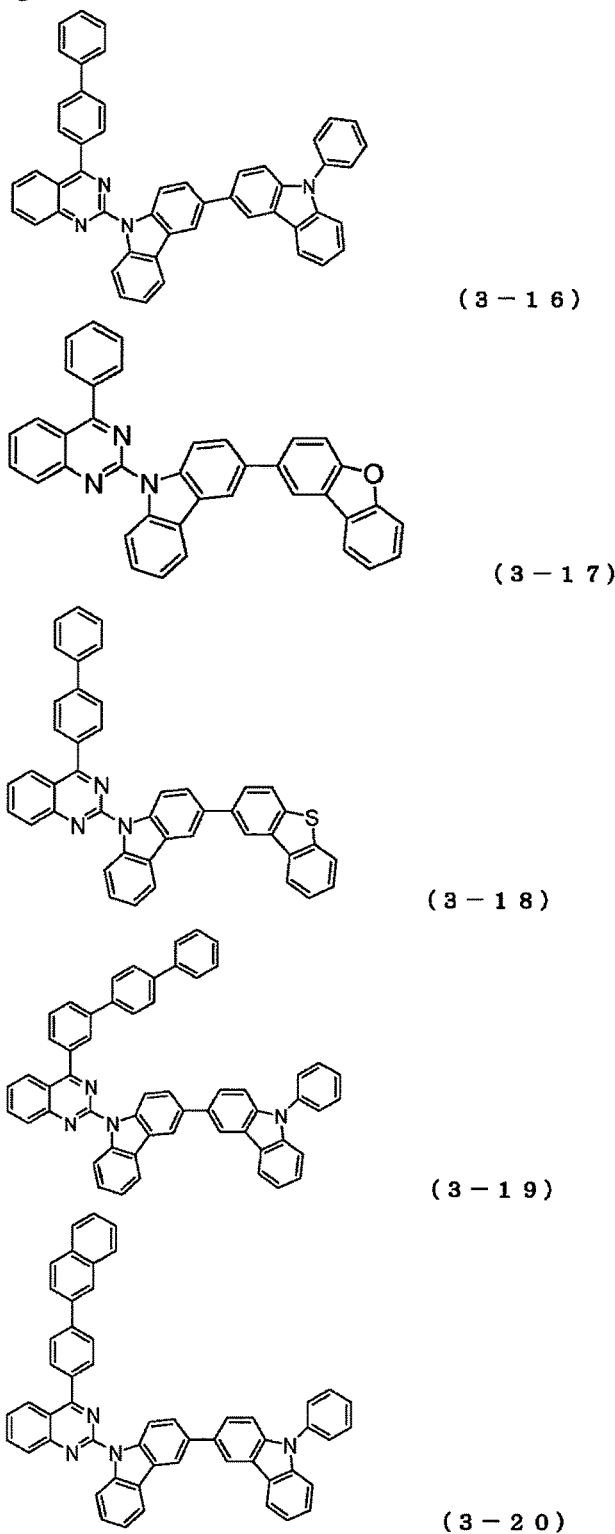
FIG. 43 is a view showing the structural formulas of Compounds No. (3-16) to (3-20) in the carbazole compounds of the general formula (3).
Figure 44:
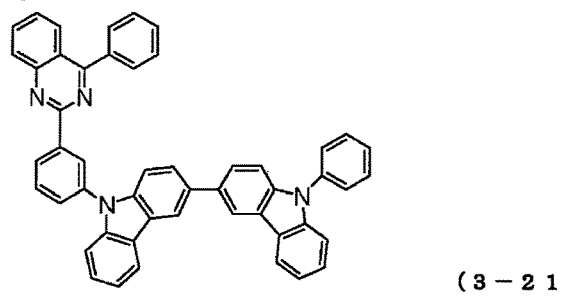
FIG. 44 is a view showing the structural formulas of Compounds No. (3-21) to (3-23) in the carbazole compounds of the general formula (3).
Figure 44:
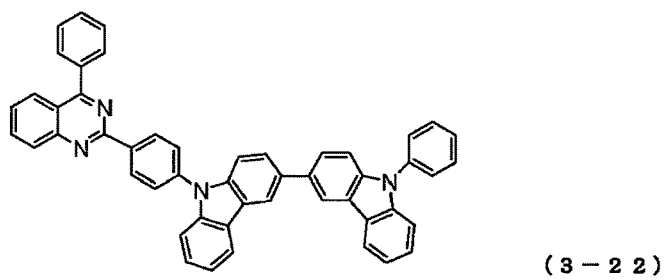
Figure 44:
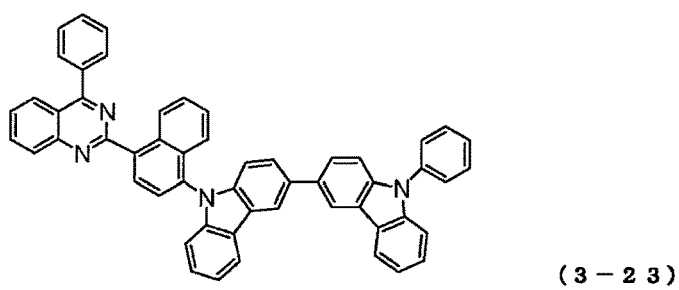
Figure 45:
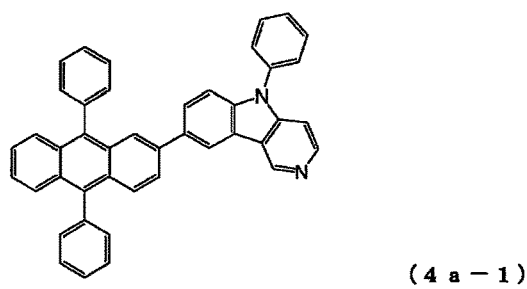
FIG. 45 is a view showing the structural formulas of Compounds No. (4a-1) and (4a-2) in the anthracene derivative of a general formula (4a).
Figure 45:
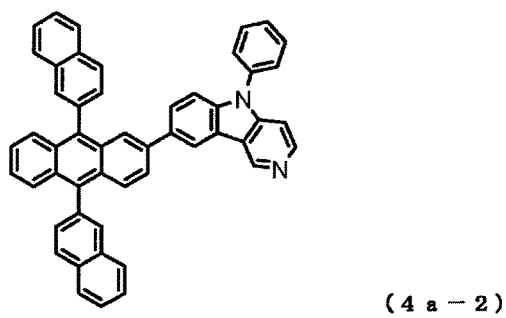
Figure 46:
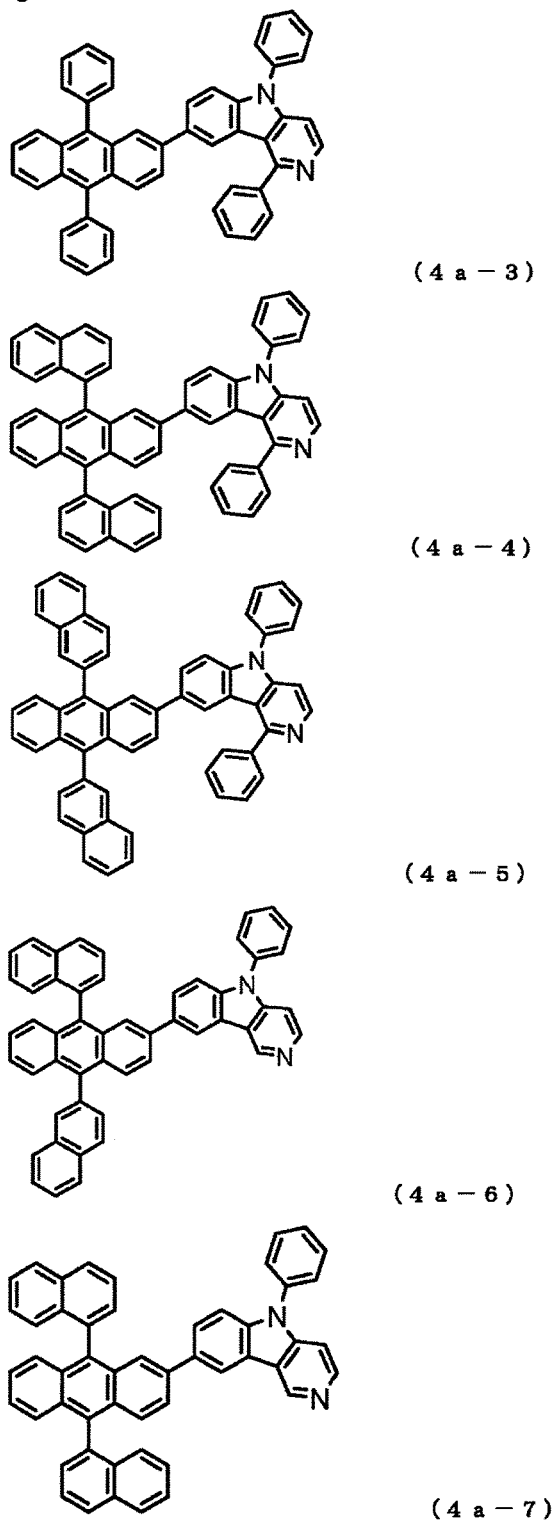
FIG. 46 is a view showing the structural formulas of Compounds No. (4a-3) to (4a-7) in the anthracene derivative of the general formula (4a).
Figure 47:
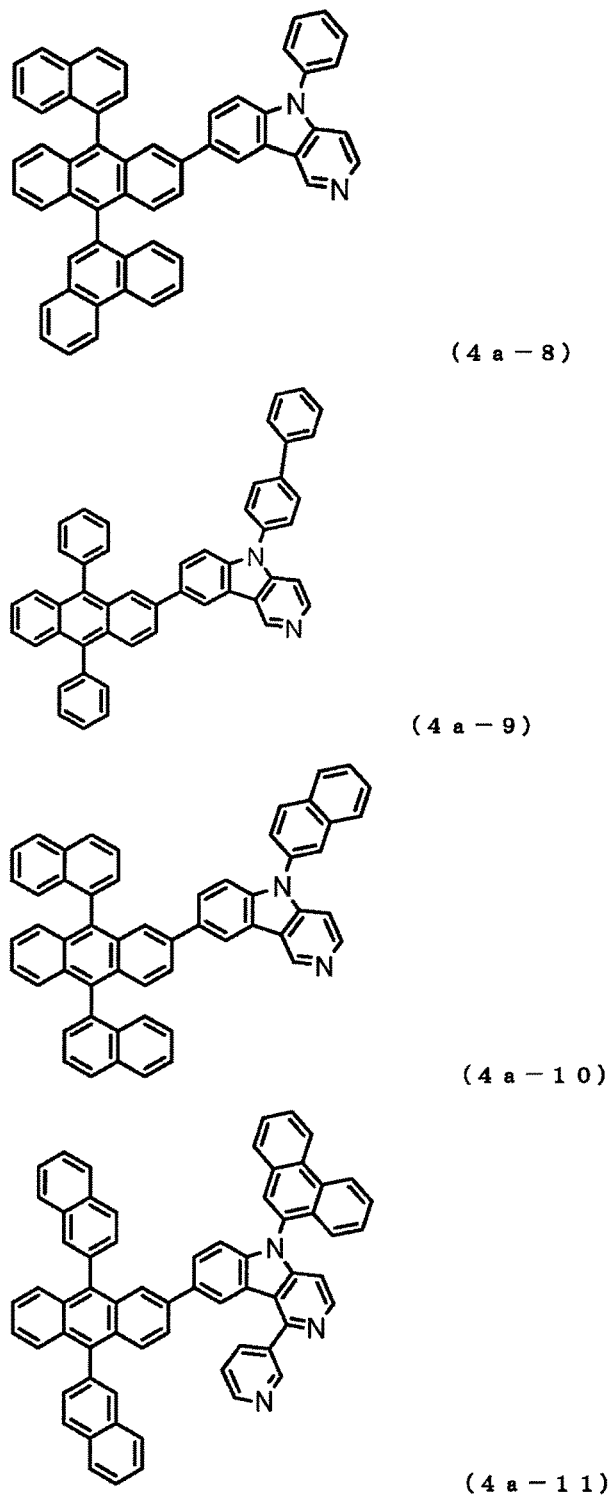
FIG. 47 is a view showing the structural formulas of Compounds No. (4a-8) to (4a-11) in the anthracene derivative of the general formula (4a).
Figure 48:
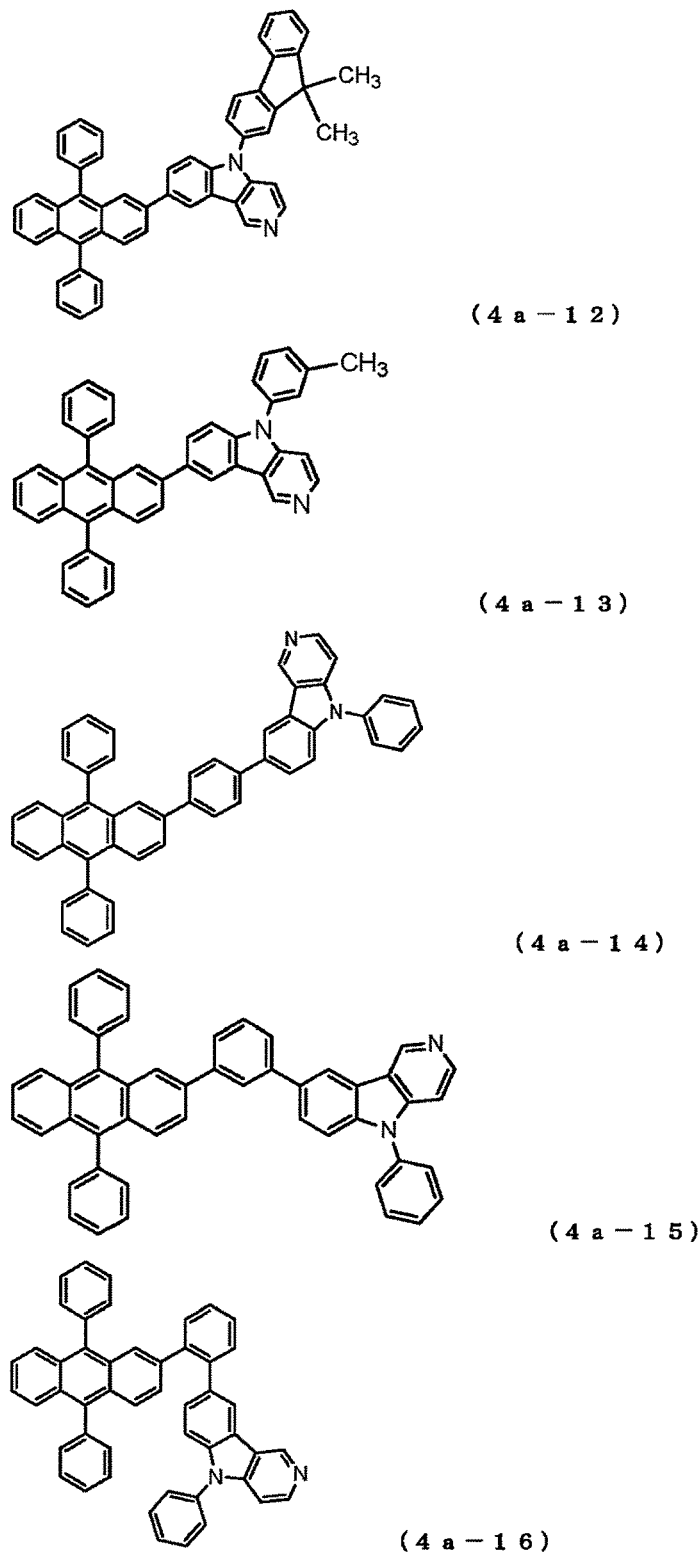
FIG. 48 is a view showing the structural formulas of Compounds No. (4a-12) to (4a-16) in the anthracene derivative of the general formula (4a).
Figure 49:
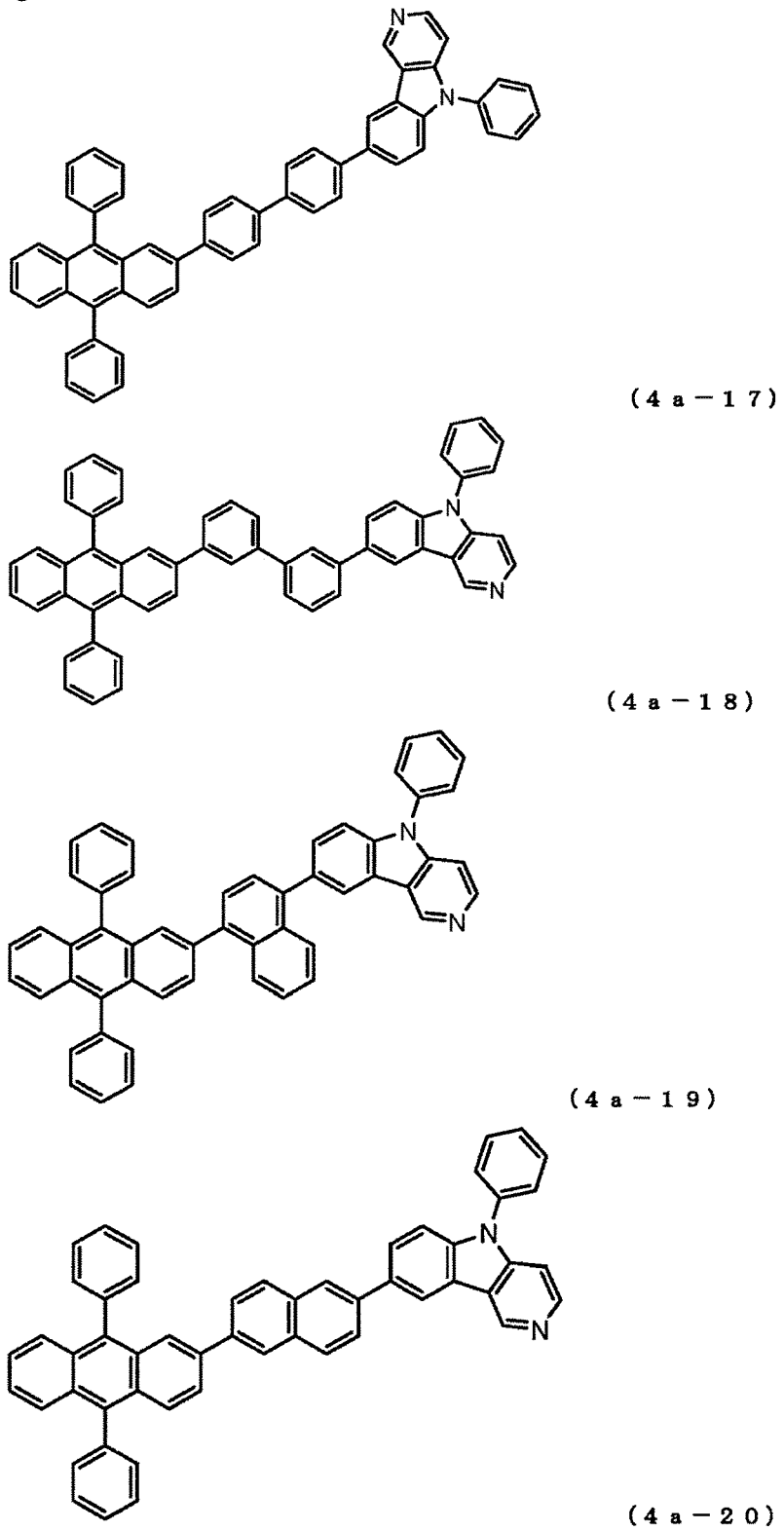
FIG. 49 is a view showing the structural formulas of Compounds No. (4a-17) to (4a-20) in the anthracene derivative of the general formula (4a).
Figure 50:
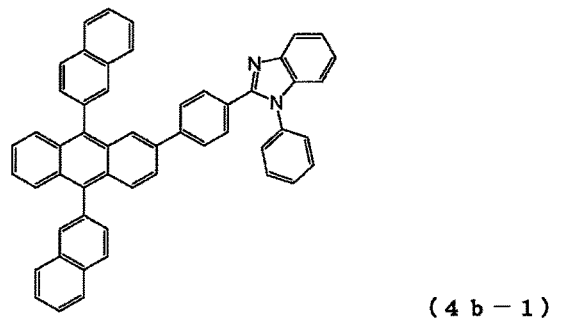
FIG. 50 is a view showing the structural formulas of Compounds No. (4b-1) to (4b-5) in the anthracene derivative of a general formula (4b).
Figure 50:
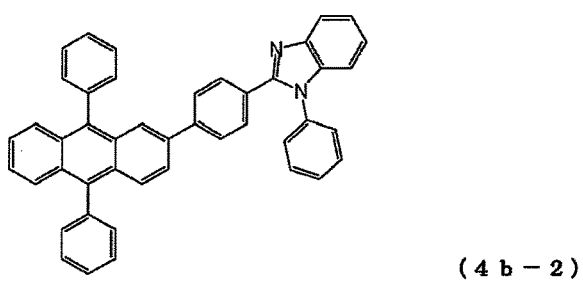
Figure 50:
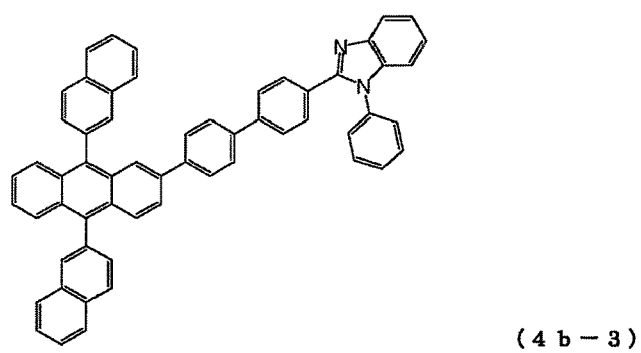
Figure 50:
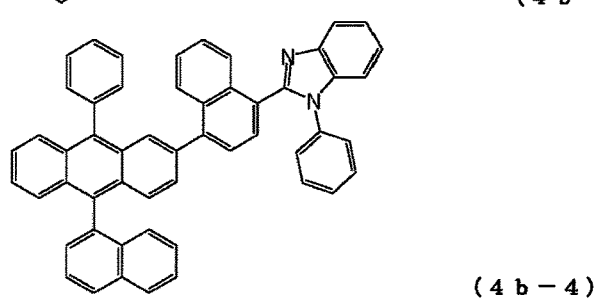
Figure 50:
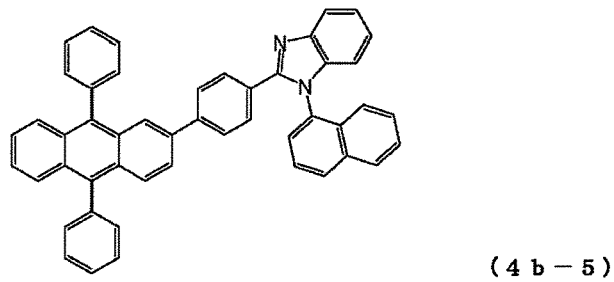
Figure 51:
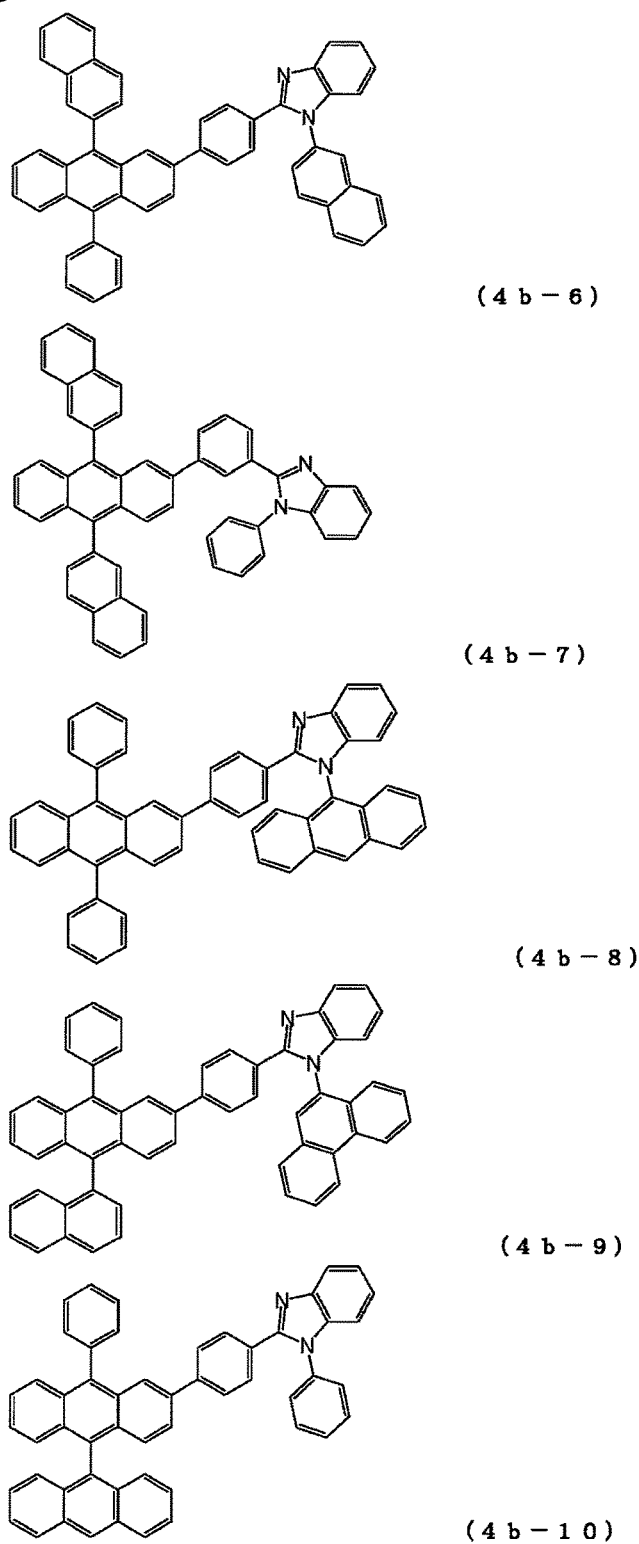
FIG. 51 is a view showing the structural formulas of Compounds No. (4b-6) to (4b-10) in the anthracene derivative of the general formula (4b).
Figure 52:
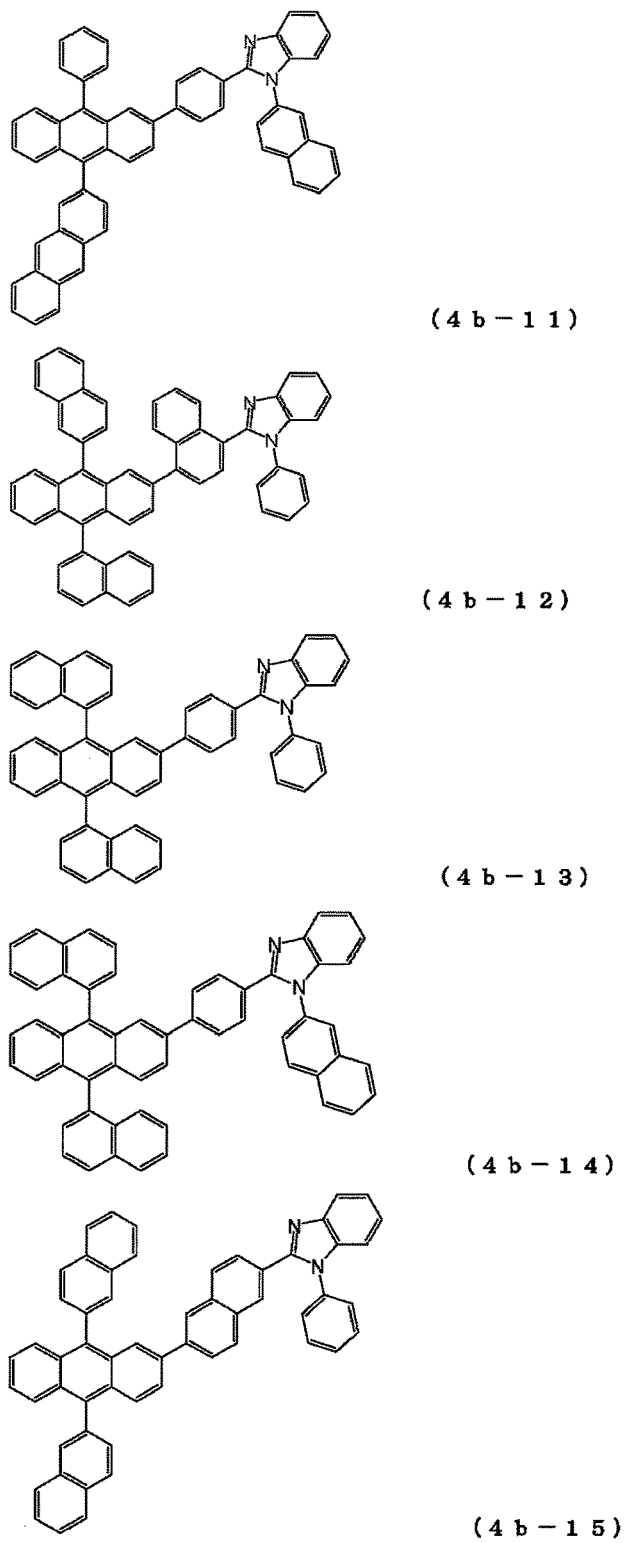
FIG. 52 is a view showing the structural formulas of Compounds No. (4b-11) to (4b-15) in the anthracene derivative of the general formula (4b).
Figure 53:
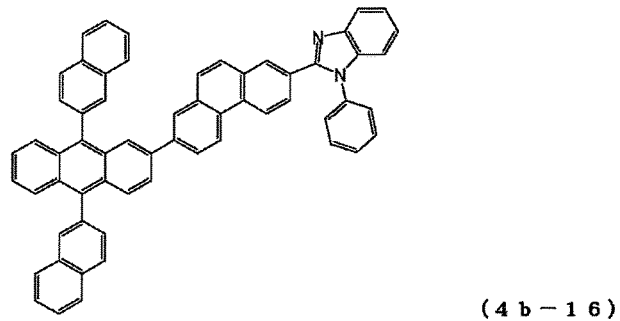
FIG. 53 is a view showing the structural formula of Compound No. (4b-16) in the anthracene derivative of the general formula (4b).
Figure 54:
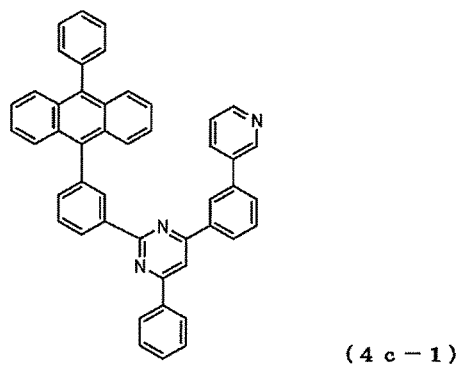
FIG. 54 is a view showing the structural formulas of Compounds No. (4c-1) to (4c-3) in the anthracene derivative of a general formula (4c).
Figure 54:
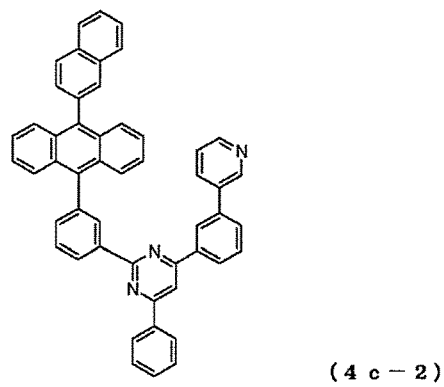
Figure 54:
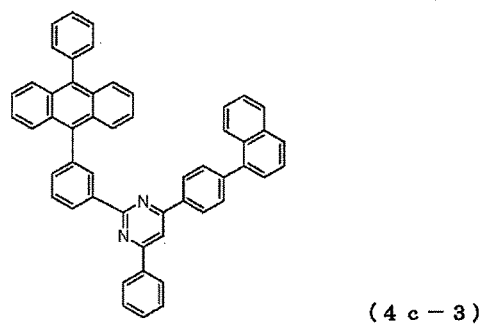
Figure 55:
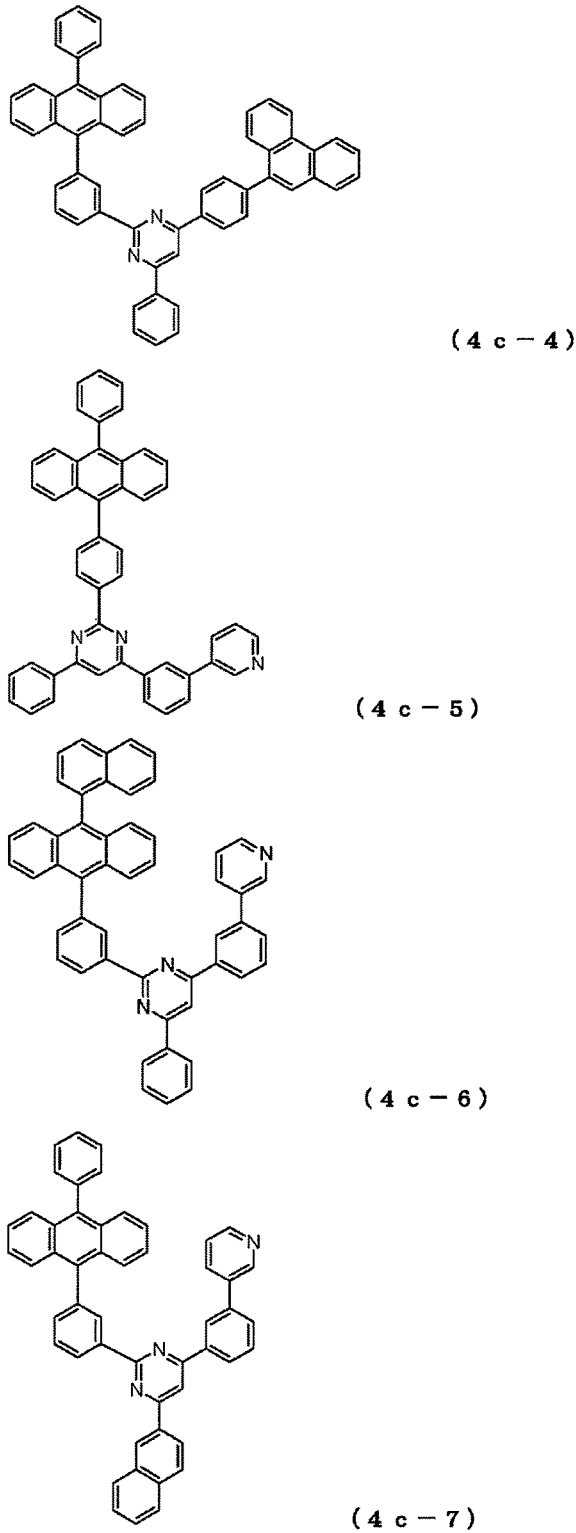
FIG. 55 is a view showing the structural formulas of Compounds No. (4c-4) to (4c-7) in the anthracene derivative of the general formula (4c).
Figure 56:
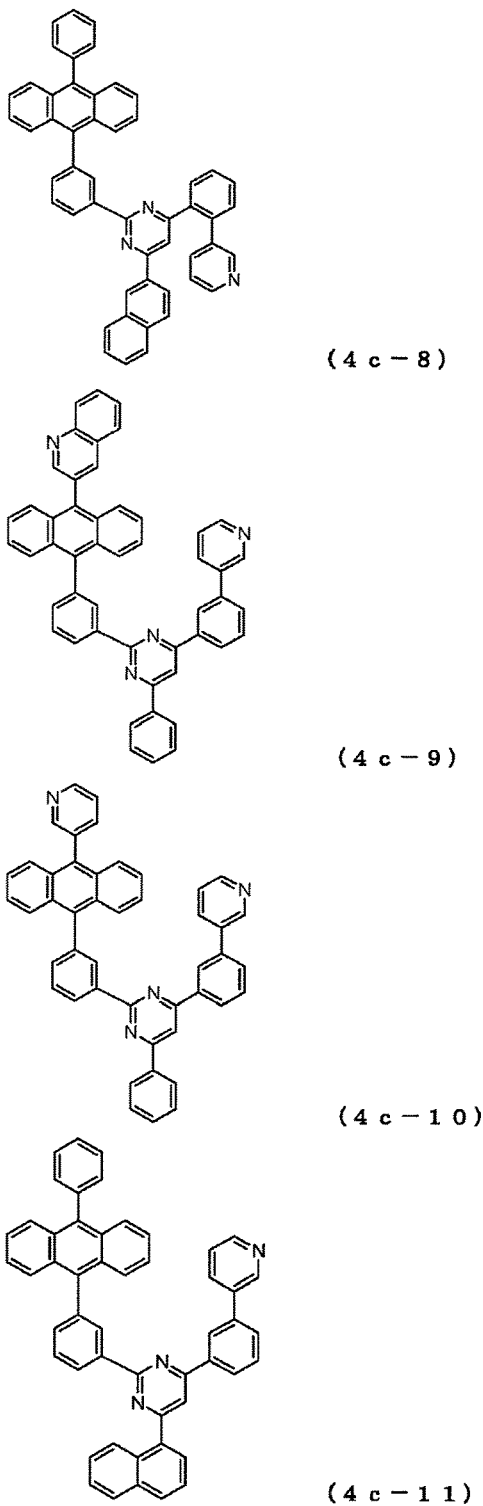
FIG. 56 is a view showing the structural formulas of Compounds No. (4c-8) to (4c-11) in the anthracene derivative of the general formula (4c).
Figure 57:
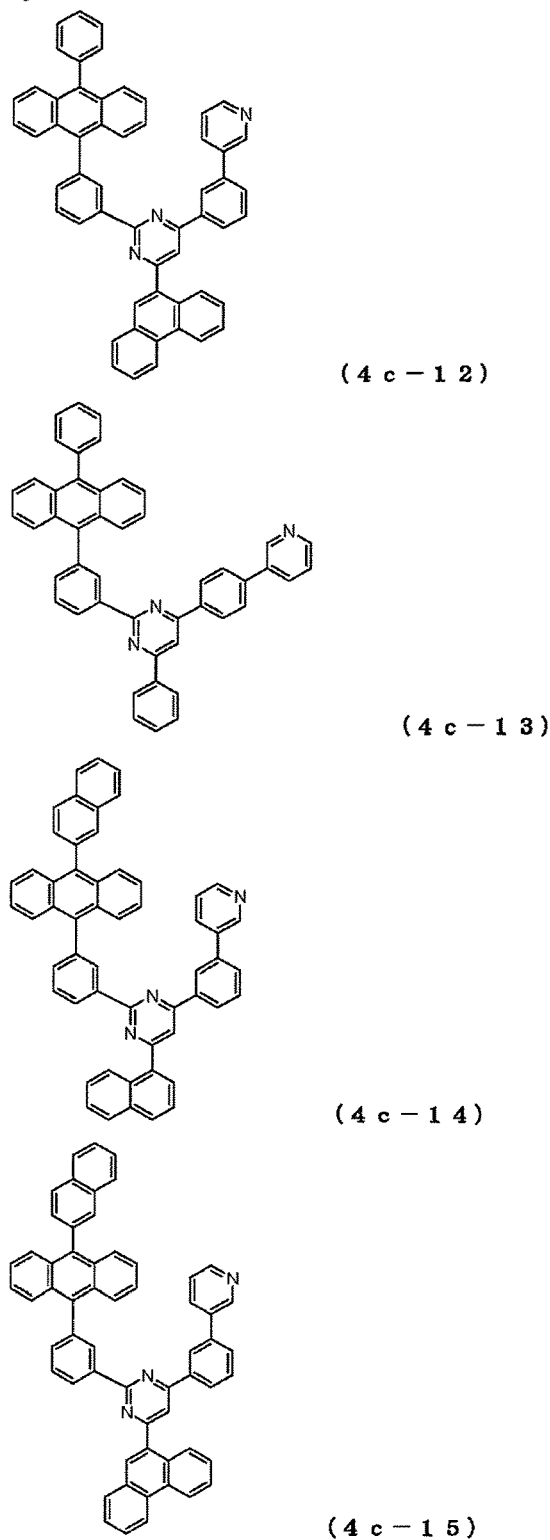
FIG. 57 is a view showing the structural formulas of Compounds No. (4c-12) to (4c-15) in the anthracene derivative of the general formula (4c).
Figure 58:
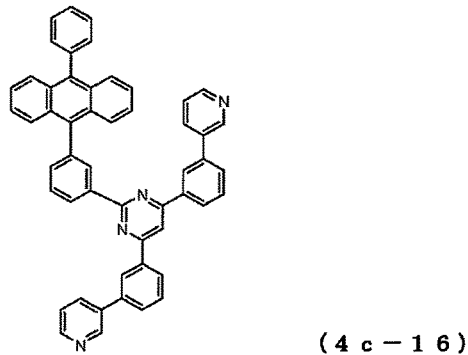
FIG. 58 is a view showing the structural formulas of Compounds No. (4c-16) to (4c-19) in the anthracene derivative of the general formula (4c).
Figure 58:
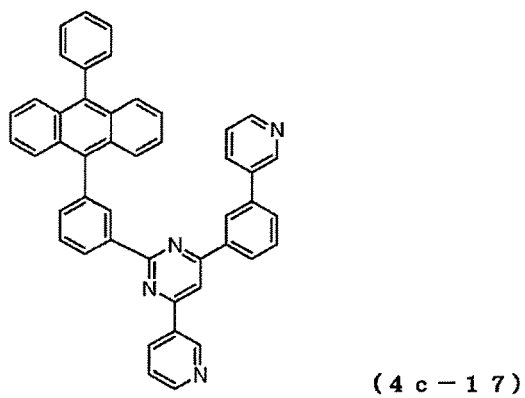
Figure 58:
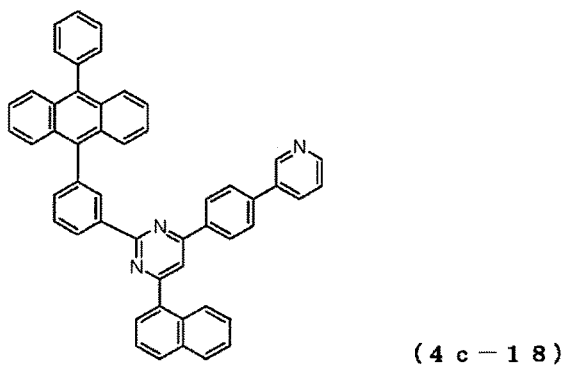
Figure 58:
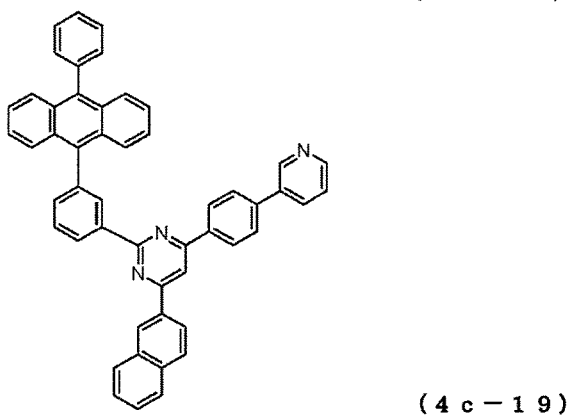
Figure 59:
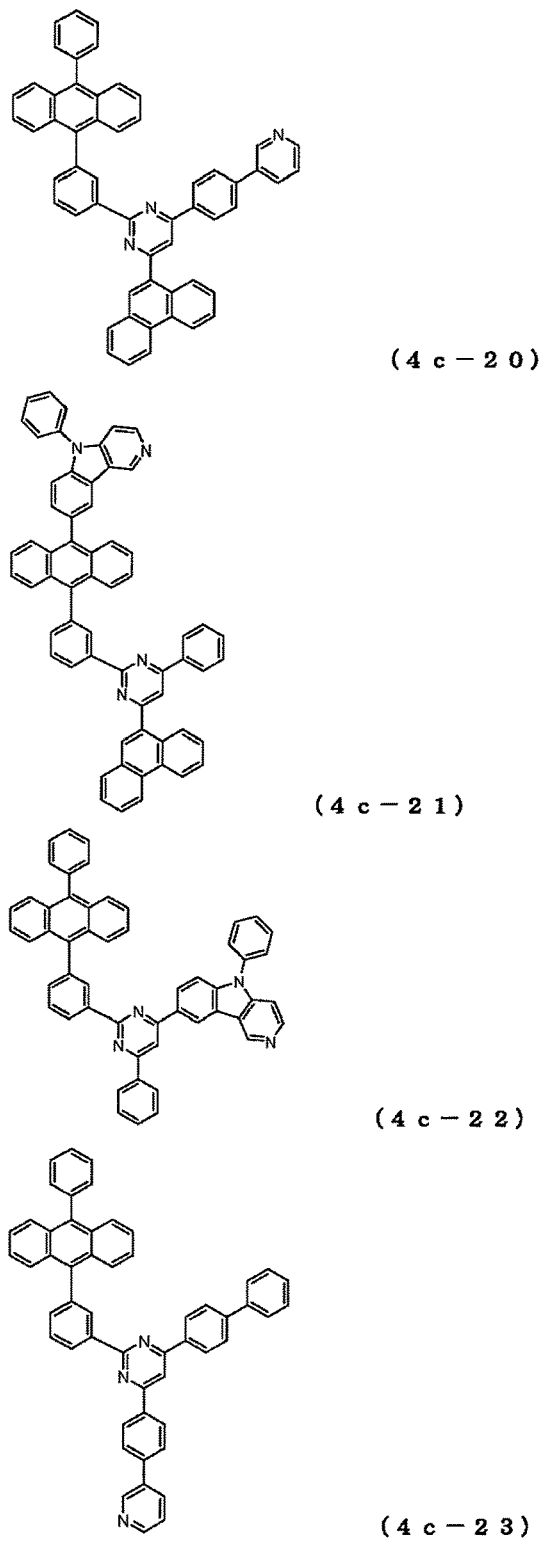
FIG. 59 is a view showing the structural formulas of Compounds No. (4c-20) to (4c-23) in the anthracene derivative of the general formula (4c).
Figure 60:
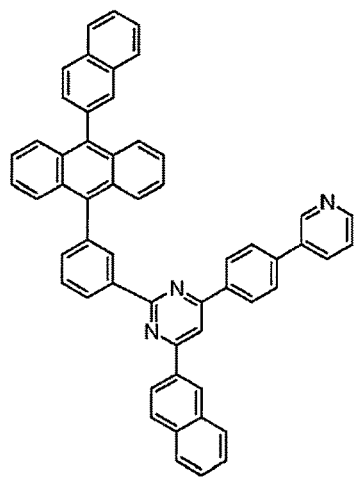
FIG. 60 is a view showing the structural formulas of Compounds No. (4c-24) to (4c-26) in the anthracene derivative of the general formula (4c).
Figure 60:
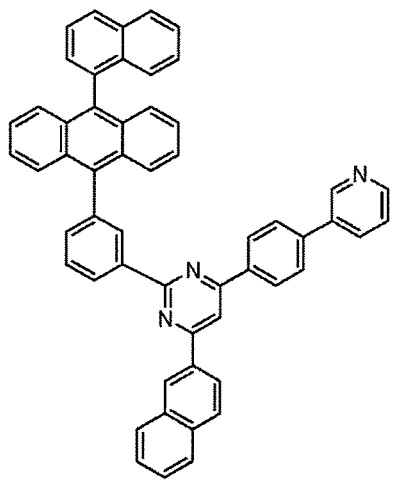
Figure 60:
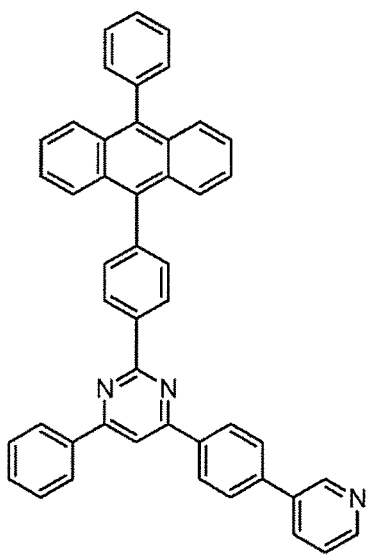
Figure 61:
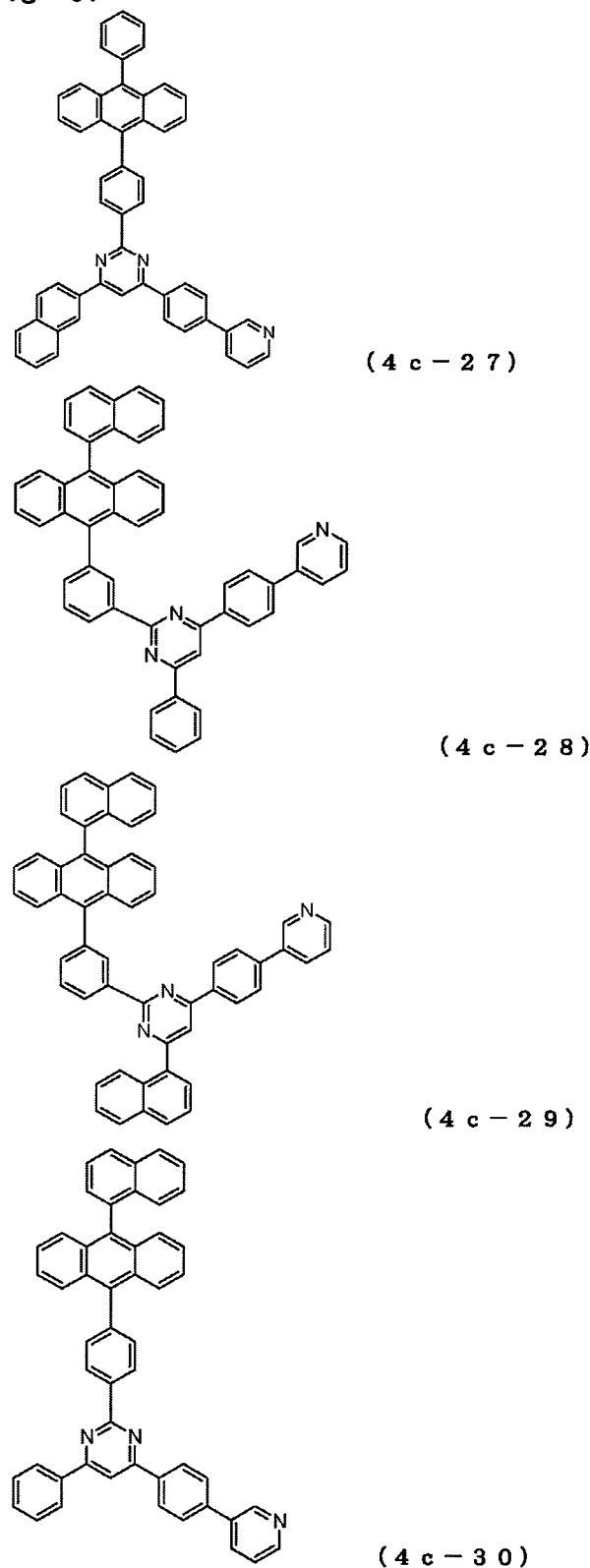
FIG. 61 is a view showing the structural formulas of Compounds No. (4c-27) to (4c-30) in the anthracene derivative of the general formula (4c).
Figure 62:
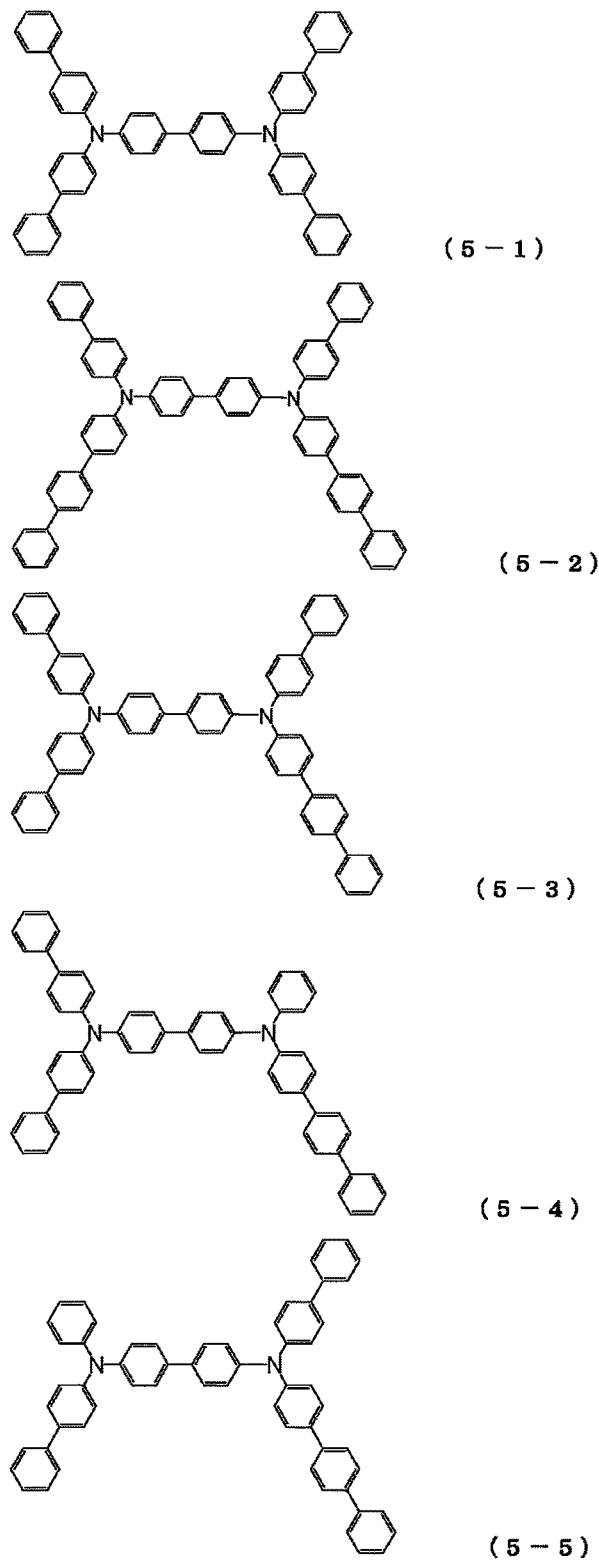
FIG. 62 is a view showing the structural formulas of Compounds No. (5-1) to (5-5) in the triarylamine derivative of a general formula (5).
Figure 63:
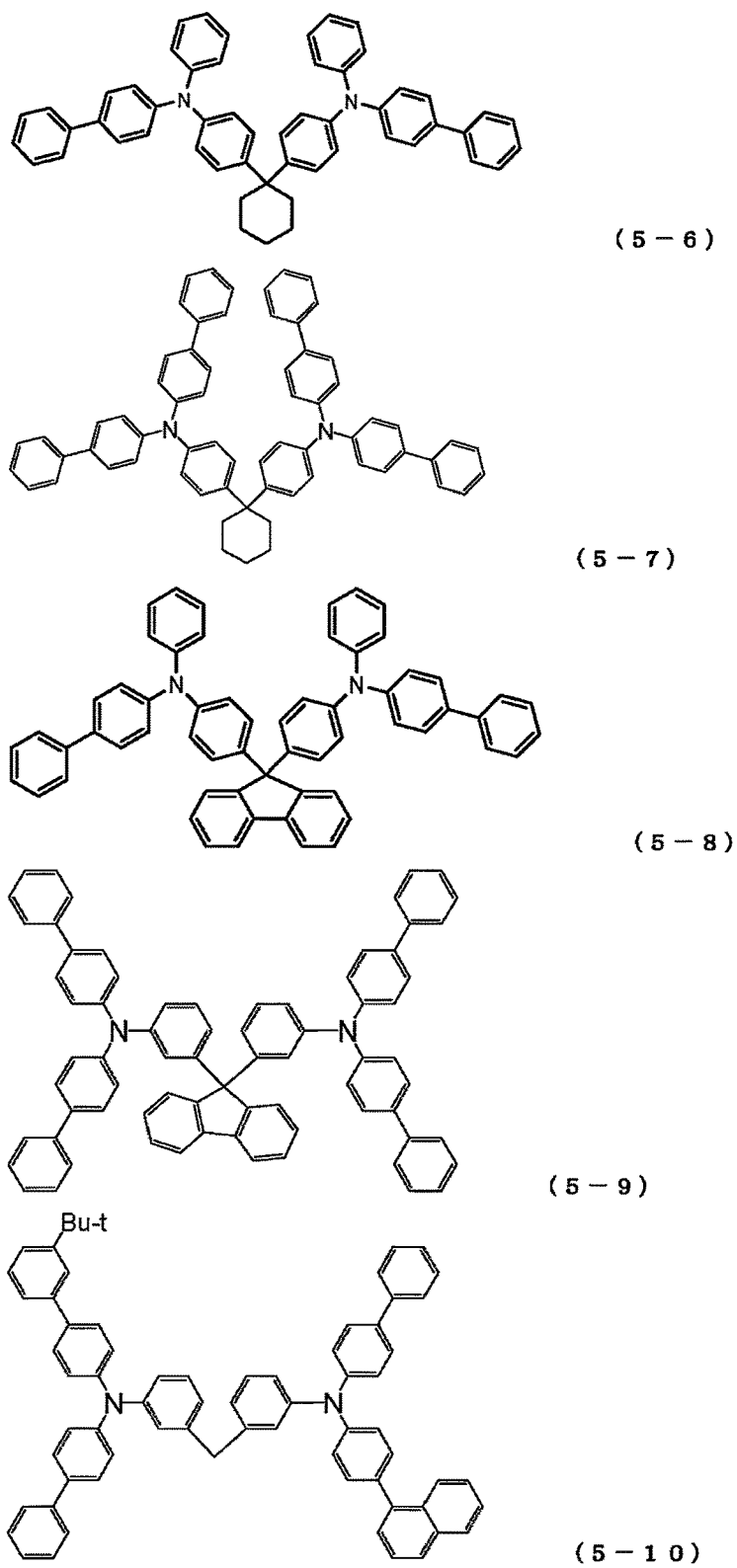
FIG. 63 is a view showing the structural formulas of Compounds No. (5-6) to (5-10) in the triarylamine derivative of the general formula (5).
Figure 64:
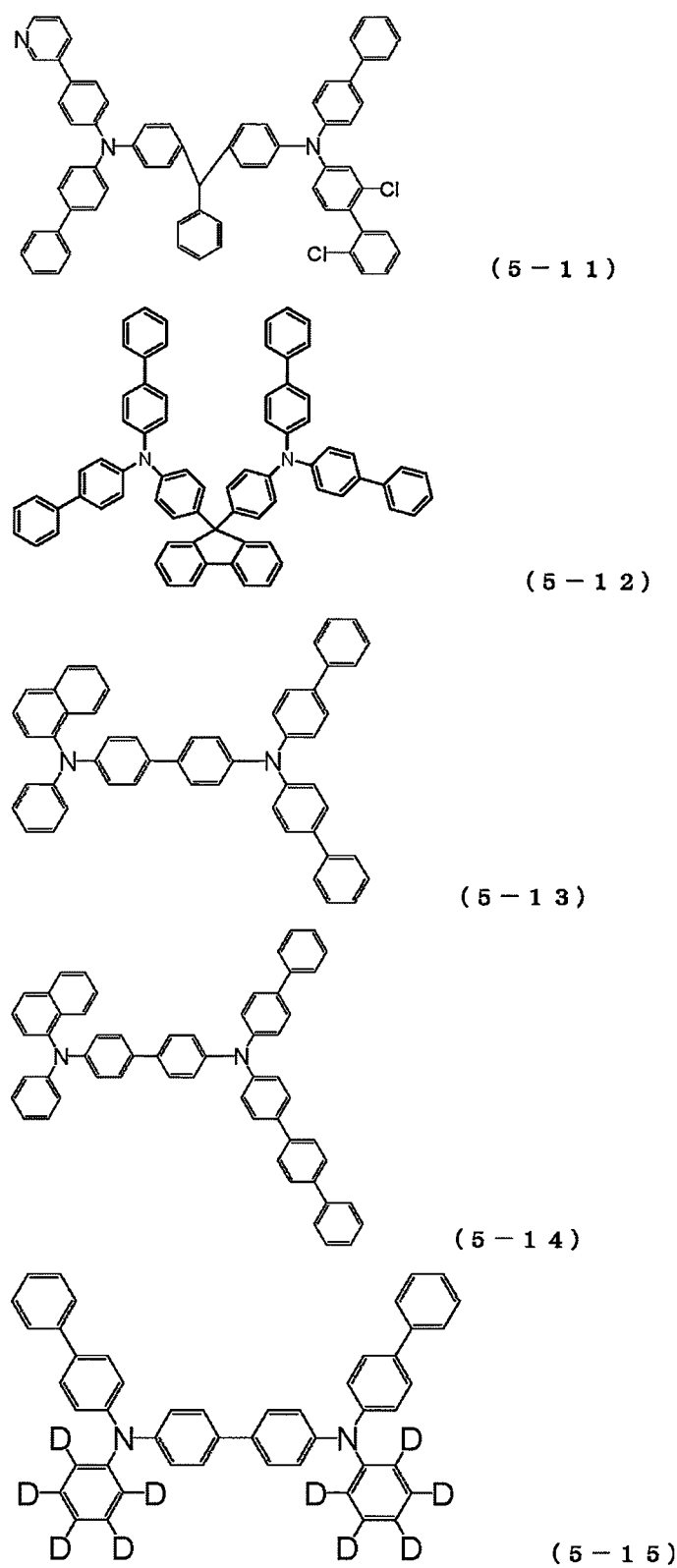
FIG. 64 is a view showing the structural formulas of Compounds No. (5-11) to (5-15) in the triarylamine derivative of the general formula (5).
Figure 65:
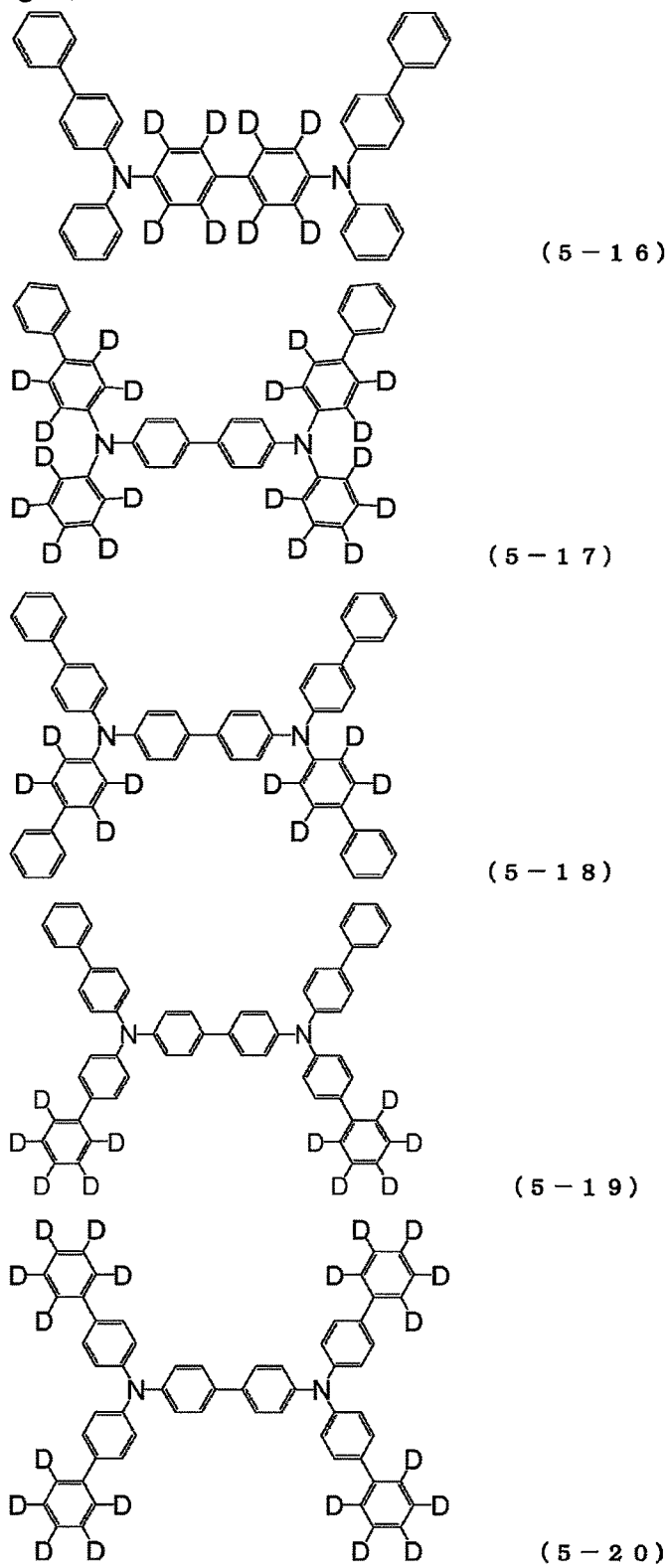
FIG. 65 is a view showing the structural formula of Compounds No. (5-16) to (5-20) in the triarylamine derivative of the general formula (5).
Figure 66:
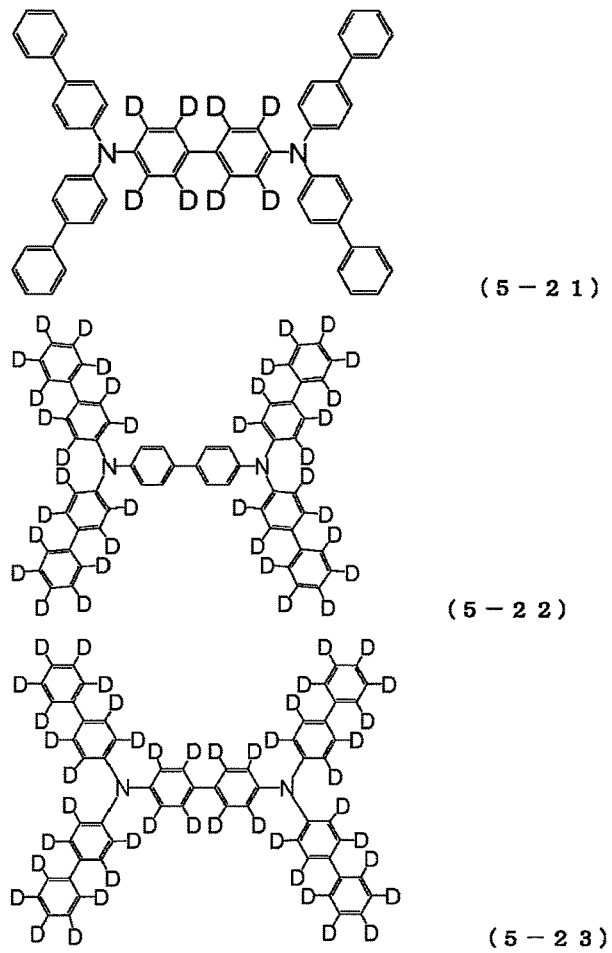
FIG. 66 is a view showing the structural formula of Compounds No. (5-21) to (5-23) in the triarylamine derivative of the general formula (5).

The organic EL device of the present invention has a basic structure in which an anode, a hole transport layer, a luminous layer, an electron transport layer, and a cathode are formed, in the order of description, on a transparent substrate such as a glass substrate or a transparent plastic substrate (for example, a polyethylene terephthalate substrate). The layered structure can be in various forms, provided that it has such a basic structure. For example, the hole transport layer can have a two-layer structure including a first hole transport layer positioned on the anode side and a second hole transport layer adjacent to the luminous layer, a hole injection layer can be provided between the transparent electrode and the hole transport layer, and an electron injection layer can be provided between the electron transport layer and the cathode. For example, FIG. 1 illustrates a layered structure used in the below-described Examples. In this example, an anode 2, a hole injection layer 3, a first hole transport layer 4, a second hole transport layer 5, a luminous layer 6, an electron transport layer 7, an electron injection layer 8, and a cathode 9 are formed, in the order of description, on a transparent substrate 1.

Each layer constituting the organic EL device of the present invention will be explained hereinbelow.

<Anode>

The anode 2 is formed on the transparent substrate 1 by vapor deposition of an electrode material with a large work function, such as ITO or gold.

<Hole Transport Layer>

The hole transport layer is provided between the anode 2 and the luminous layer 6. In the present invention, the hole transport layer includes the arylamine compound represented by the following general formula (1).

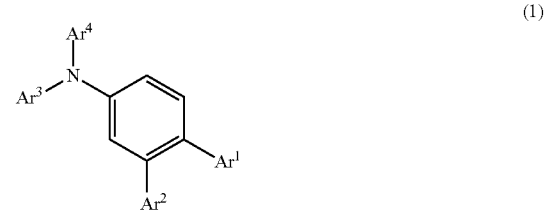

(1)

In this formula, $Ar^1$ to $Ar^4$ each represent a monovalent aromatic hydrocarbon group or a monovalent aromatic heterocyclic group.

This arylamine compound is a triarylamine compound in which three hydrogen atoms are all substituted with aromatic groups, and in particular has a structure such that has at least one benzene ring (can be abbreviated hereinbelow as pm-substituted benzene ring) to which monovalent aromatic hydrocarbon groups or monovalent aromatic heterocyclic groups are bonded as substituents (for example, $Ar^1$ and $Ar^2$ in the formula (1)) at a p-position and an m-position with respect to the nitrogen atom of the amino group.

As will be understood from the below-described Examples, the arylamine compound having such a structure has a high glass transition temperature Tg (for example, 100° C. or higher) and, therefore, has stability in a thin-film state and also excellent heat resistance. Further, such a compound has a high work function as compared with the work function (about 5.4 eV) of a general hole transport material, and therefore excels in hole transport property, has a high hole mobility, and also has a satisfactory hole injection characteristic. Such a compound also excels in electron blocking property.

In the general formula (1), $Ar^1$ to $Ar^4$ may be the same or different. Monovalent aromatic hydrocarbon groups or monovalent aromatic heterocyclic groups represented by these groups $Ar^1$ to $Ar^4$ can be exemplified by the following groups.

Monovalent Aromatic Hydrocarbon Groups;

a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a spirobifluorenyl group, etc.

Monovalent Aromatic Heterocyclic Groups;

a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a benzoquinazolinyl group, a pyridopyrimidinyl group, a pyrazolyl group, a naphthopyrimidinyl group, a dibenzofuranyl group, a dibenzothienyl group, a naphthyridinyl group, a phenanthrolinyl group, an acridinyl group, a carbolinyl group, etc.

The monovalent aromatic hydrocarbon groups and monovalent aromatic heterocyclic groups may have a substituent.

The following groups, in addition to a deuterium atom, a cyano group, and a nitro group, can exemplify the substituents.

A halogen atom, for example, a fluorine atom, a chlorine atom, a bromine atom, and an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, and an n-hexyl group;

an alkyloxy group having 1 to 6 carbon atoms, for example, a methyloxy group, an ethyloxy group, and a propyloxy group;

an alkenyl group, for example, a vinyl group and an allyl group;

an aryl group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, and a spirobifluorenyl group;

an aryloxy group, for example, a phenyloxy group and a tolyloxy group;

an arylalkyloxy group, for example, a benzyloxy group and a phenethyloxy group;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, dibenzothienyl group, and a carbolinyl group; an arylvinyl group, for example, a styryl group and a naphthylvinyl group;

an acyl group, for example, an acetyl group and a benzoyl group;

These substituents may further have the substituents exemplified hereinabove.

In the above-described general formula (1), the group $Ar^1$ is preferably a phenyl group, a biphenylyl group, a terphenylyl group, a naphthyl group, a phenanthrenyl group, an anthracenyl group, a fluorenyl group, a carbazolyl group, an indolyl group, a dibenzofuranyl group, and dibenzothienyl group. Among these groups, aromatic hydrocarbon groups, for example, a phenyl group, a biphenylyl group, a terphenylyl group, a naphthyl group, a phenanthrenyl group, and a fluorenyl group are particularly preferred. It goes without saying that these groups may have a substituent.

Further, the group $Ar^2$ is preferably an aromatic hydrocarbon group. Among the aromatic hydrocarbon groups, a phenyl group, a biphenylyl group, a terphenylyl group, a naphthyl group, a phenanthrenyl group, an anthracenyl group, and a fluorenyl group are more preferred, and a phenyl group and a biphenylyl group are much more preferred. These groups may have a substituent, but an unsubstituted phenyl group and an unsubstituted biphenylyl group are most preferred.

Furthermore, the groups $Ar^3$ and $Ar^4$ each are preferably an aromatic hydrocarbon group. Among them, a phenyl group, a biphenylyl group, a terphenylyl group, and a fluorenyl group are more preferred. These groups may have a substituent. The particularly preferred groups $Ar^3$ and $Ar^4$ are an unsubstituted biphenylyl group, an unsubstituted terphenylyl group, a phenyl group having a substituent, and a fluorenyl group having a substituent. A naphthyl group or a fluorenyl group is a preferred substituent for the phenyl group, and a methyl group and a phenyl group are the preferred substituents for the fluorenyl group.

In the present invention, a specific structural feature of the arylamine compound represented by the above-described general formula (1) is that, as described hereinabove, the arylamine compound has at least one pm-substituted benzene ring.

For example, the arylamine compound represented by the following general formula (1a) indicated below has at least two pm-substituted benzene rings, and the arylamine compound represented by the following general formula (1b) indicated below has three pm-substituted benzene rings.

The Arylamine Compound of the General Formula (1a);

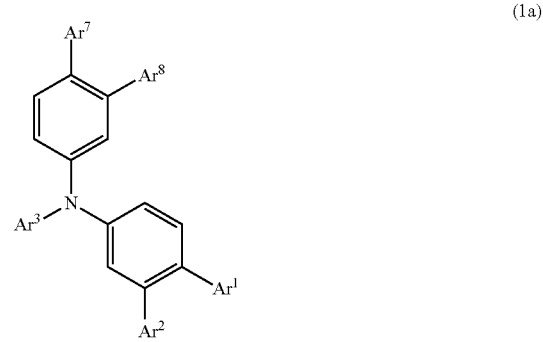

(1a)

The Arylamine Compound of the General Formula (1b);

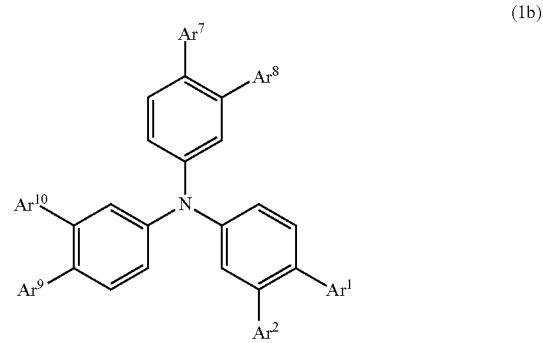

(1b)

In the general formulas (1a) and (1b), $Ar^1$ to $Ar^3$ are as defined in the general formula (1); and $Ar^7$, $Ar^8$, $Ar^9$, and $Ar^{10}$ each are also a monovalent aromatic hydrocarbon group or a monovalent aromatic heterocyclic group.

In the compound of the general formula (1a), the group $Ar^4$ in the general formula (1) is a group having the aforementioned pm-substituted benzene ring, and $Ar^7$ and $Ar^8$ in the formula (1a) correspond to two substituents possessed by the pm-substituted benzene ring.

In this general formula (1a), from the viewpoint of synthesis, it is preferred that the groups $Ar^1$ and $Ar^7$ (the two groups bonded at the p-position of the benzene ring with respect to the nitrogen atom) be the same group and that the groups $Ar^2$ and $Ar^8$ (the two groups bonded at the m-position of the benzene ring with respect to the nitrogen atom) be the same group.

In the compound of the general formula (1b), the groups $Ar^3$ and $Ar^4$ in the general formula (1) are groups having the aforementioned pm-substituted benzene ring, and $Ar^7$ and $Ar^8$, and $Ar^9$ and $Ar^{10}$ in the formula (1b) each correspond to two substituents possessed by the pm-substituted benzene ring.

In this general formula (1b), from the viewpoint of synthesis, it is preferred that the groups $Ar^1$, $Ar^7$ and $Ar^9$ be the same group and $Ar^2$, $Ar^8$ and $Ar^{10}$ be the same group, as in the abovementioned general formula (1a).

The arylamine compound represented by the above-described general formula (1) (or the general formula (1a) or the general formula (1b)) can be specifically exemplified by Compounds (1-1) to (1-160) having the structural formulas shown in FIGS. 2 to 35.

Further, the compound represented by the general formula (1) can be synthesized by a publicly known method such as Suzuki coupling, as shown in the below-described Examples. The synthesized compound can be purified by column chromatography purification, adsorption purification with silica gel, activated carbon, activated clay, and the like, recrystallization or crystallization with a solvent, a sublimation purification method, or the like.

The compound used in the organic EL device of the present invention is finally purified by the sublimation purification method and supplied for use.

For example, an arylamine compound having one pm-substituted benzene ring can be produced in the following manner.

Thus, an N,N-bisarylamine (disubstituted aromatic amine) in which two hydrogen atoms are substituted with aromatic groups is used as a starting raw material, and reacts with an m-substituted halogenated aromatic compound having a halogen atom such as a bromine atom at the m-position, thereby introducing an m-substituted benzene ring group in the nitrogen atom of the disubstituted aromatic amine. The obtained aromatic amine reacts with a brominating agent such as N-bromosuccinimide to introduce a halogen group at the p-position of the m-substituted benzene ring group, then reacts with a corresponding boronic acid and a coupling agent such as tetrakis(triphenylphosphine) palladium to introduce an aromatic group at the p-position of the m-substituted benzene ring group. Then, a target arylamine compound having one pm-substituted benzene ring can be produced.

Further, an arylamine compound having two pm-substituted benzene rings can be produced in the following manner.

Thus, an N,N-bis (m-substituted aromatic) amine having m-substituted aromatic groups (substituted at the m-position with an aromatic group) is synthesized and a halogenated aromatic compound is reacted with the synthesized disubstituted amine to synthesize an N-aryl-N, N-bis (m-substituted aromatic) amine. The obtained aromatic amine reacts with brominating agent such as N-bromosuccinimide to introduce halogen groups at the p-positions of the m-substituted benzene rings, then reacts with a corresponding boronic acid and a phenyl coupling agent such as tetrakis (triphenylphosphine)palladium to introduce aromatic groups at the p-positions of the m-substituted benzene ring groups. Then, a target arylamine compound having two pm-substituted benzene rings can be produced.

Further, an arylamine compound having three pm-substituted benzene rings can be produced in the following manner.

Thus, a target arylamine compound having three pm-substituted benzene rings can be produced by using a tris (m-substituted aromatic) amine having an m-substituted aromatic group (substituted at the m-position with an aromatic group) and introducing aromatic groups, in the same manner as described hereinabove, at the p-positions of the three m-substituted aromatic groups possessed by the triarylamine.

In the present invention, the arylamine compound represented by the above-described general formula (1) can be used singly, or two or more such compounds can be used in a mixture. Furthermore, the hole transport layer can be also formed by using this compound together with a publicly known hole transport agent taken within a range in which the excellent properties of the arylamine compound are not impaired.

Examples of the publicly known hole transport agents include benzidine derivatives such as N,N'-diphenyl-N,N'-di(m-tolyl)benzidine (TPD), N,N$^1$-diphenyl-N,N'-di($\alpha$-naphthyl)benzidine (NPD), and N,N,N',N'-tetrabiphenylyl-benzidine; 1,1-bis[4-(di-4-tolylamino)phenyl]cyclohexane (TAPC); triarylamine derivatives represented by the below-described general formula (3) or general formula (4); various triphenylamine trimers; and the like.

Further, a material P-doped with trisbromophenylamine hexachloroantimony, a radialene derivative (see, for example, WO 2014/009310) or the like, or a polymer compound having the molecular structure of a benzidine derivative such as TPD can be also used for the hole transport layer.

The above-described hole transport layer is preferably formed by vapor deposition or co-deposition from a gas including the arylamine compound of the general formula (1), but the hole transport layer can be also formed by a publicly known method such as a spin coat method or an ink jet method.

The thickness of the hole transport layer is usually about 25 to 60 nm, but since light emission can be performed under a low driving voltage, the increase in the driving voltage can be suppressed even when the thickness is increased, for example, to 100 nm or more. Thus, there is a high degree of freedom in selecting the thickness of the hole transport layer. For example, a practical driving voltage can be maintained at a thickness of 20 to 300 nm, in particular 20 to 200 nm.

Further, in the present invention, it is preferred that the hole transport layer including the abovementioned arylamine compound has, for example, as shown in FIG. 1, a two-layer structure including a first hole transport layer 4 positioned on the side of the anode and a second hole transport layer 5 positioned on the side of the luminous layer 6.

The hole transport layer having such a two-layer structure will be described hereinbelow.

<Luminous Layer>

The luminous layer in the organic EL device of the present invention includes an N-aromatic substituted nitrogen-containing heterocyclic compound and is formed by a publicly known method such as a vapor deposition method, a spin coat method, and an ink jet method.

Thus, as a result of an N-aromatic substituted nitrogen-containing heterocyclic compound being present together with a luminous material in the luminous layer 6, the hole transport-injection property of the arylamine compound contained in the aforementioned hole transport layer 5 is maximized, holes can be injected with satisfactory efficiency into the luminous layer 6, and high-efficiency emission at a low driving voltage can be realized.

In the present invention, it is particularly preferred that an indenoindole compound or a carbazole compound be used as the abovementioned N-aromatic substituted nitrogen-containing heterocyclic compound.

The Indenoindole Compound;

The indenoindole compound has an indenoindole ring as a nitrogen-containing heterocycle, and an aromatic group is introduced as a substituent at the nitrogen atom of the indenoindole ring. Such a compound is represented, for example, by the following general formula (2).

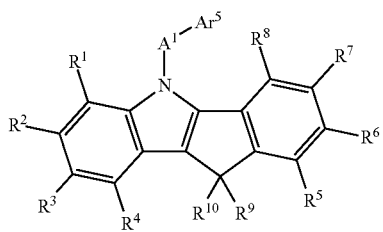

(2)

In the general formula (2), $A^1$ bonded to the nitrogen atom represents a divalent aromatic hydrocarbon group, a divalent aromatic heterocyclic group, or a single bond, and the group $Ar^5$ bonded to the $A^1$ represents a monovalent aromatic hydrocarbon group or a monovalent aromatic heterocyclic group.

Here, the divalent aromatic hydrocarbon group is formed from an aromatic hydrocarbon ring having two bonding hands, and such an aromatic hydrocarbon ring can be exemplified by benzene, biphenyl, terphenyl, tetrakisphenyl, styrene, naphthalene, anthracene, acenaphthalene, fluorene, phenanthrene, indan, pyrene, triphenylene, fluoranthene, etc.

Further, the divalent aromatic heterocyclic group is formed from an aromatic heterocycle having two bonding hands, and such an aromatic heterocycle can be exemplified by pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, acridin, quinazoline, benzoquinazoline, etc.

Further, the monovalent aromatic hydrocarbon group and the monovalent aromatic heterocyclic group, which are represented by $Ar^5$, can be exemplified by the same groups as those illustrated with respect to $Ar^1$ to $Ar^4$ in the aforementioned general formula (1).

The abovementioned divalent group $A^1$ and the monovalent group $Ar^5$ may also have substituents, as the aforementioned $Ar^1$ to $Ar^4$, and the substituents may be bonded to each other via a single bond, a substituted or unsubstituted methylene group, an oxygen atom, or a sulfur atom to form a ring.

$R^1$ to $R^8$ in the general formula (2) each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a di-aromatic substituted amino group.

The abovementioned di-aromatic substituted amino group is a group in which two aromatic groups (that is, a monovalent aromatic hydrocarbon group and/or a monovalent aromatic heterocyclic group) are bonded as substituents to the nitrogen atom of the amino group.

The monovalent aromatic hydrocarbon group and the monovalent aromatic heterocyclic group in the abovementioned $R^1$ to $R^8$ or the di-aromatic substituted amino group can be exemplified by the same groups as those illustrated with respect to $Ar^1$ to $Ar^4$ in the aforementioned general formula (1).

Further, the abovementioned alkyl group, cycloalkyl group, alkenyl group, alkyloxy group, cycloalkyloxy group, aralkyl group, and aryloxy group represented by $R^1$ to $R^8$ can be exemplified by the following groups.

The Alkyl Group (1 to 6 Carbon Atoms):
a methyl group, an ethyl group, an n-propyl group, an isopropyl group, an n-butyl group, an isobutyl group, a tert-butyl group, an n-pentyl group, an isopentyl group, a neopentyl group, an n-hexyl group, etc.

The Alkenyl Group (2 to 6 Carbon Atoms):
a vinyl group, an allyl group, etc.

The Alkyloxy Group (1 to 6 Carbon Atoms):
a methyloxy group, an ethyloxy group, a propyloxy group, etc.

The Cycloalkyloxy Group (5 to 10 Carbon Atoms):
a methyloxy group, an ethyloxy group, a propyloxy group, etc.

The Aralkyl Group:
a benzyl group, a phenethyl group, etc.

The Aryloxy Group:
a phenyloxy group, a tolyloxy group, etc.

Further, the groups represented by the above-described $R^1$ to $R^8$ may be bonded to each other via a single bond, a substituted or unsubstituted methylene group, an oxygen atom, or a sulfur atom to form a ring (that is, a condensed ring) (for example, see the below-described general formulas (2d) and (2e)).

Further, some of $R^1$ to $R^4$ or some of $R^5$ to $R^8$ may be detached from the benzene ring and the remaining groups of $R^1$ to $R^4$ or the remaining groups of $R^5$ to $R^8$ (these remaining groups are the groups mentioned hereinabove) may be bonded to vacancies in the benzene ring generated by the detachment via an optionally substituted methylene group, an oxygen atom, a sulfur atom, or a monoarylamino group to form a ring (that is, a condensed ring) (for example, see the below-described general formulas (2a) to (2c)).

$R^9$ and $R^{10}$ in the general formula (2) are each an alkyl group having 1 to 6 carbon atoms, a monovalent aromatic hydrocarbon group, or a monovalent aromatic heterocyclic group. These groups can be specifically exemplified by the alkyl groups having 1 to 6 carbon atoms which are represented by $R^1$ to $R^8$ in the general formula (2) and $Ar^1$ to $Ar^4$ in the general formula (1). These groups may be also bonded to each other via a single bond, an optionally substituted methylene group, an oxygen atom, or a sulfur atom to form a ring.

In the indenoindole compound represented by the above-described general formula (2), it is preferred that a ring be formed by $R^1$ to $R^8$.

For example, the indenoindole compounds represented by the following general formulas (2a) to (2e) exemplify the compounds in which a ring is formed by some groups of $R^1$ to $R^8$.

Further, in the following general formulas (2a) to (2e), $A^1$, $Ar^5$, and $R^1$ to $R^{10}$ have the same meaning as that defined in the aforementioned general formula (2). X is a divalent linking group and represents an optionally substituted methylene group, an oxygen atom, a sulfur atom, or a monoarylamino group.

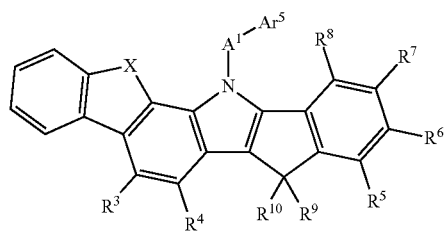

(2a)

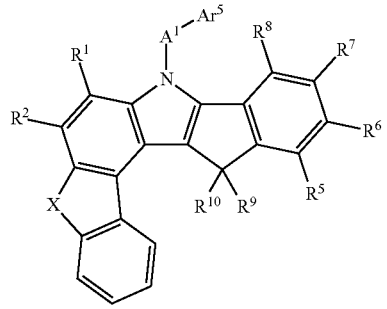

(2b)

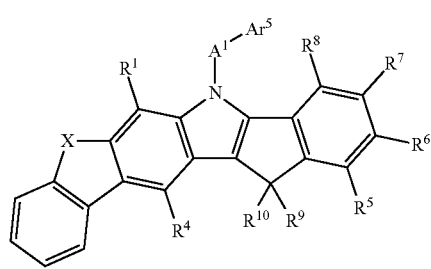

(2c)

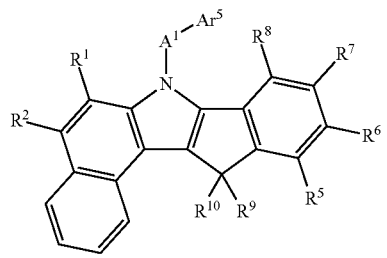

(2d)

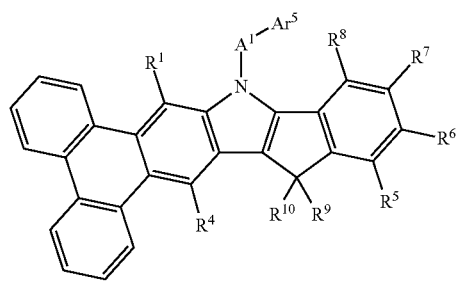

(2e)

The general formula (2a) has a structure in which $R^2$ adjacent to $R^1$ is bonded via the linking group X to the benzene ring at a position where a vacancy has been generated by the detachment of $R^1$ in the general formula (2), thereby forming a condensed ring.

The general formula (2b) has a structure in which $R^4$ adjacent to $R^3$ is bonded via the linking group X to the benzene ring at a position where a vacancy has been generated by the detachment of $R^3$ in the general formula (2), thereby forming a condensed ring.

The general formula (2c) has a structure in which $R^3$ adjacent to $R^2$ is bonded via the linking group X to the benzene ring at a position where a vacancy has been generated by the detachment of $R^2$ in the general formula (2), thereby forming a condensed ring.

The condensed ring formed by bonding to the benzene ring via the linking group X in the general formulas (2a) to (2c) can be exemplified by a fluorene ring (X=methylene), a carbazole ring (X=monoarylamino group), a dibenzofuran ring (X=oxygen atom), and a dibenzothiophene ring (X=sulfur atom).

Further, the general formula (2d) has a structure in which $R^3$ (vinyl group) and $R^4$ (vinyl group) in the general formula (2) are bonded to form a benzene ring.

Furthermore, the general formula (2e) has a structure in which $R^3$ (phenyl group) and $R^4$ (phenyl group) in the general formula (2) are bonded to form a phenanthrene ring.

In the general formulas (2a) to (2e), structures are shown in which some of $R^1$ to $R^4$ form a ring, but in a structure in which $R^5$ to $R^8$ form a ring, the ring is formed by condensation on a benzene ring to which $R^5$ to $R^8$ are bonded.

In the present invention, the indenoindole compound represented by the above-described general formula (2) (or the general formulas (2a) to (2e)) can be specifically exemplified by Compounds (2-1) to (2-15) having the structural formulas shown in FIGS. 36 to 39.

The Carbazole Compound;

in the present invention, the carbazole compound used to form the luminous layer 6 has a carbazole ring as a nitrogen-containing heterocycle, and an aromatic group is introduced as a substituent at the nitrogen atom in the carbazole ring. Such a compound is represented, for example, by the following general formula (3).

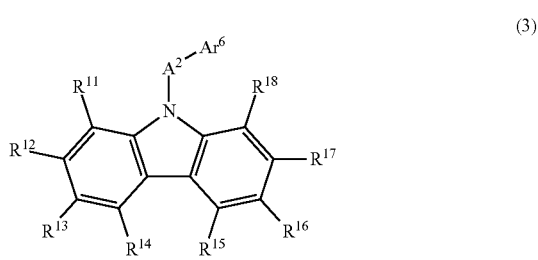

(3)

In the general formula (3), $A^2$, $Ar^6$, and $R^{11}$ to $R^{18}$ are the same groups as $A^1$, $Ar^5$, and $R^1$ to $R^8$ in the aforementioned general formula (2).

Thus, in the general formula (3), $A^2$ bonded to the nitrogen atom represents a divalent aromatic hydrocarbon group, a divalent aromatic heterocyclic group, or a single bond, similarly to $A^1$ in the general formula (2).

These divalent aromatic hydrocarbon group and divalent aromatic heterocyclic group can be exemplified by the same groups as those illustrated with respect to $A^1$ in the general formula (2). These groups may have the same substituents as those illustrated with respect to $A^1$. Further, these substituents may be bonded to each other via a single bond, a substituted or unsubstituted methylene group, an oxygen atom, or a sulfur atom to form a ring.

Further, $Ar^6$ in the general formula (3) represents a monovalent aromatic hydrocarbon group or a monovalent aromatic heterocyclic group. These monovalent aromatic hydrocarbon group and monovalent aromatic heterocyclic group can be exemplified by the same groups as those illustrated with respect to $Ar^8$ in the general formula (2) (or $Ar^1$ to $Ar^4$ in the general formula (1)), and similarly to $Ar^5$ may have a substituent. These substituents may be bonded to each other via a single bond, a substituted or unsubstituted methylene group, an oxygen atom, or a sulfur atom to form a ring.

Similarly to $R^1$ to $R^8$ of the general formula (2), to $R^{18}$ in the general formula (3) each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a di-aromatic substituted amino group. Specific examples of these groups are the same ones as those illustrated with respect to $R^1$ to $R^{18}$ of the general formula (2). These groups also may be bonded to each other via a single bond, an optionally substituted methylene group, an oxygen atom, or a sulfur atom to form a ring (that is, a condensed ring).

Further, some of $R^{11}$ to $R^{14}$ or some of $R^{15}$ to $R^{18}$ may be detached from the benzene ring, and the remaining groups (in particular, groups adjacent to the detached groups) which are bonded to the benzene ring may be bonded to the vacancies in the benzene ring generated by the detachment via an optionally substituted methylene group, an oxygen atom, a sulfur atom, or a monoarylamino group to form a ring (that is, a condensed ring).

In such a carbazole compound, it is preferred that a ring be formed by some of $R^{11}$ to $R^{18}$. Thus, a structure is preferred in which a ring is condensed on the benzene ring possessed by the carbazole ring. In particular, as shown in the general formulas (3a-1) to (3a-4) and (3b-1) indicated below, it is preferred that the remaining adjacent groups be bonded to the vacancies generated by the detachment by some of $R^{11}$ to $R^{18}$ via an optionally substituted methylene group, an oxygen atom, a sulfur atom, or a monoarylamino group to form a ring.

In the general formulas (3a-1) to (3a-4) and (3b-1) indicated below, $A^2$, $Ar^6$, and $R^{11}$ to $R^{18}$ have the same meaning as that defined in the general formula (3); X is a divalent linking group and represents an optionally substituted methylene group, an oxygen atom, a sulfur atom, or a monoarylamino group.

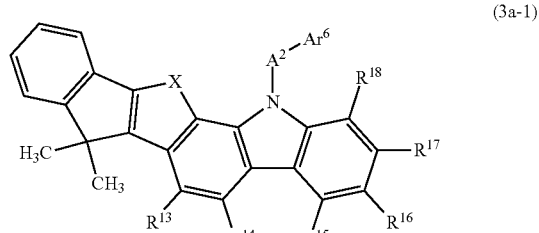

(3a-1)

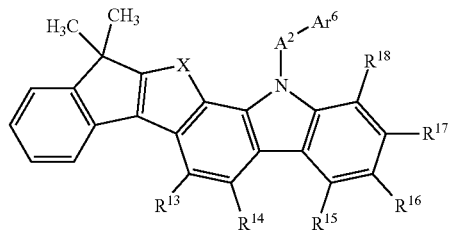

(3a-2)

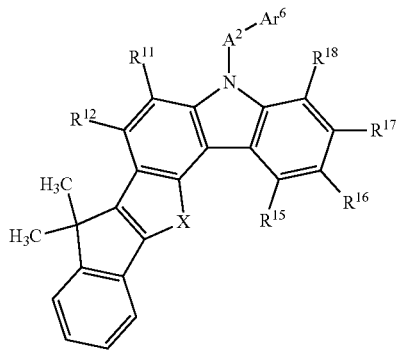

(3a-3)

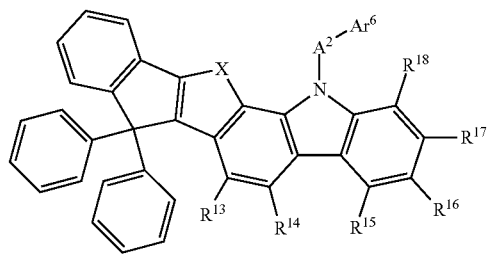

(3a-4)

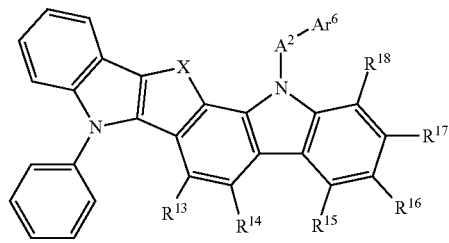

(3b-1)

The general formula (3a-1) has a structure in which $R^{12}$ (an indenyl group having two methyl groups as substituents) adjacent to $R^{11}$ is bonded via the linking group X to the benzene ring at a position where a vacancy has been generated by the detachment of $R^{11}$ in the general formula (3), thereby forming a condensed ring.

Similarly to the general formula (3a-1), the general formula (3a-2) also has a structure in which $R^{12}$ (an indenyl group having two methyl groups as substituents) adjacent to $R^{11}$ is bonded via the linking group X to the benzene ring at a position where a vacancy has been generated by the detachment of $R^{11}$ in the general formula (3), thereby forming a condensed ring.

The general formula (3a-3) has a structure in which $R^{13}$ (an indenyl group having two methyl groups as substituents) adjacent to $R^{11}$ is bonded via the linking group X to the benzene ring at a position where a vacancy has been generated by the detachment of $R^{14}$ in the general formula (3), thereby forming a condensed ring.

The general formula (3a-4) has a structure in which $R^{12}$ (an indenyl group having two phenyl groups as substituents)

adjacent to $R^{11}$ is bonded via the linking group X to the benzene ring at a position where a vacancy has been generated by the detachment of $R^{11}$ in the general formula (3), thereby forming a condensed ring.

The general formula (3b-1) has a structure in which $R^{12}$ (an N-phenyl-substituted indolyl group) adjacent to $R^{11}$ is bonded via the linking group X at a position where a vacancy has been generated by the detachment of $R^{11}$ in the general formula (3), thereby forming a condensed ring.

The condensed ring formed by bonding to the benzene ring via the linking group X in the general formulas (3a-1) to (3a-4) can be exemplified by an indenoindan ring (X=methylene), an indenoindole ring (X=monoarylamino group), an indenobenzofuran ring (X=oxygen atom), an indenobenzothiophene ring (X=sulfur atom) and the like.

In the above-described general formulas (3a-1) to (3a-4) and (3b-1), a structure is shown in which $R^{11}$ to $R^{14}$ form a ring, but it goes without saying that $R^{15}$ to $R^{18}$ also may form a ring in the same manner as in these formulas.

In the present invention, the carbazole compound represented by the above-descried general formula (3) (or general formulas (3a-1) to (3a-4) and (3b-1)) can be specifically exemplified by Compounds (3-1) to (3-23) having the structural formulas shown in FIGS. 40 to 44.

As the abovementioned carbazole compounds, the compounds represented by the aforementioned general formula (3) are preferred. However, in addition to the carbazole compounds represented by the general formula (3), carbazole derivatives, for example, 4,4'-di(N-carbazolyl)biphenyl (CBP), TCTA, mCP and the like can be used.

The above-described N-aromatic substituted nitrogen-containing compound, in particular, the indenoindole compound and the carbazole compound, has excellent characteristics as a host material for the luminous layer. These compounds can be used singly or in combination of two or more thereof. By using such compounds in combination with a luminous material to form the luminous layer 6, it is possible to maximize the hole transport-injection properties of the arylamine compound included in the aforementioned hole transport layer and achieve a high luminous efficiency.

Further, compounds that have been conventionally used together with luminous materials, for example, metal complexes of a quinolinol derivative such as $Alq_3$, various metal complexes, anthracene derivatives, bis-styrylbenzene derivatives, pyrene derivatives, oxazole derivatives, poly-paraphenylene vinylene derivatives, thiazole derivatives, benzimidazole derivatives, polydialkylfluorene derivatives, quinazoline derivatives and the like can be used in combination with the indenoindole compound and the carbazole compound within a range in which the excellent properties of the indenoindole compound and the carbazole compound are not impaired. Furthermore, compounds having electron transport property, for example, p-bis(triphenylsilyl)benzene (UGH2) and 2,2'2"-(1,3,5-phenylene)-tris(1-phenyl-1H-benzimidazole) (TPBI) can also be used in combination with the indenoindole compound and the carbazole compound.

The luminous material is not particularly limited, and publicly known luminous materials can be used. However, in the present invention, it is particularly preferred that a phosphorescent luminous body be used.

Metal complexes including iridium, platinum, or the like are typical representatives of such phosphorescent luminous bodies, and phosphorescent luminous bodies of such metal complexes are exemplified by red phosphorescent luminous bodies such as bis(3-methyl-2-phenylquinoline)iridium (III) acetyl acetonate ($Ir(3'-Mepq)_2(acac)$), $Ir(piq)_3$, and $Btp_2Ir$ (acac), green phosphorescent luminous bodies such as $Ir(ppy)_3$, blue phosphorescent luminous bodies such as FIrpic and FIr6 and the like.

In the present invention, among the abovementioned phosphorescent luminous bodies, a red phosphorescent luminous body is particularly preferred.

A material which emits delayed fluorescence, such as a CDCB derivative, for example, PIC-TRZ, CC2TA, PXZ-TRZ, and 4CzIPN, can be used as the luminous material (see, for example, Appl. Phys. Let., 98, 0833302).

In the present invention, the abovementioned luminous material can be used as a dopant, and the aforementioned N-aromatic substituted nitrogen-containing heterocyclic compound and other materials can be used as a host material.

The host material is preferably doped with the phosphorescent luminous material in an amount in a range of 1% to 30% by weight relative to the whole luminous layer 6 by co-deposition to avoid concentration quenching.

In the present invention, the most preferred luminous layer 6 uses a red luminous material (that is, a red phosphorescent luminous body) as a dopant.

When the luminous layer 6 is formed from the host material and dopant such that are mentioned hereinabove, quinacridone, coumarin, rubrene, perylene, and derivatives thereof; benzopyran derivatives; rhodamine derivatives; aminostyrene derivatives; and the like can be also used as the dopant.

<Electron Transport Layer>

In the present invention, the electron transport layer 7 provided on the above-described luminous layer 6 can be formed by a publicly known method such as a vapor deposition method, a spin coat method, and an ink jet method by using a publicly known electron transporting material.

The electron transport layer may be formed from a publicly known electron transporting material, and metal complexes of quinolinol derivatives such as $Alq_3$, various metal complexes including zinc, beryllium, and aluminum, triazole derivatives, triazine derivatives, oxadiazole derivatives, thiadiazole derivatives, carbodiimido derivatives, quinoxaline derivatives, phenanthroline derivatives, silole derivatives and the like can be used therefor.

Further, in the present invention, it is preferred that the electron transport layer be formed using the anthracene derivative represented by the following general formula (4) as the electron transporting material. Such an anthracene derivative excels in electron injection and transport capability and also stability and durability of a thin film. By combining the electron transport layer formed from such an anthracene derivative with the hole transport layer including the arylamine compound of the aforementioned general formula (1), it is possible to inject holes and electrons in the luminous layer 6 with satisfactory efficiency. As a result, it is possible to ensure optimum carrier balance and greatly improve the characteristics of the organic EL device.

The Anthracene Derivative;

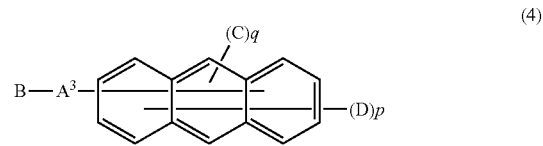

(4)

$A^3$ represents a divalent aromatic hydrocarbon group, a divalent aromatic heterocyclic group, or a single bond;

B represents a monovalent aromatic heterocyclic group;

C represents a monovalent aromatic hydrocarbon group or a monovalent aromatic heterocyclic group;

D represents a hydrogen atom, a deuterium atom, a fluorine atom, a chlorine atom, a cyano group, an alkyl group having 1 to 6 carbon atoms, a monovalent aromatic hydrocarbon group, or a monovalent aromatic heterocyclic group; and in p and q, p is an integer of 7 or 8 and q is an integer of 1 or 2, provided that a sum of p and q is 9.

As can be understood from the general formula (4), the anthracene derivative has a molecular structure in which the anthracene ring and the group B are connected by the group $A^3$ (a divalent group or a single bond). One or two monovalent aromatic hydrocarbon groups or monovalent aromatic heterocyclic groups (group C) is bonded as a substituent to the anthracene ring to which the group B is connected.

In the general formula (4), $A^3$ represents a single bond or a divalent group, and the divalent group is a divalent aromatic hydrocarbon group or a divalent aromatic heterocyclic group. Specific examples thereof are, as described below, the same ones as those illustrated with respect to $A^1$ in the general formula (2).

The divalent aromatic hydrocarbon group is formed from an aromatic hydrocarbon ring having two bonding hands. Such an aromatic hydrocarbon ring can be exemplified by benzene, biphenyl, terphenyl, tetrakisphenyl, styrene, naphthalene, anthracene, acenaphthalene, fluorene, phenanthrene, indan, pyrene, and triphenylene.

Further, the divalent aromatic heterocyclic group is formed from an aromatic heterocycle having two bonding hands. Such an aromatic heterocycle ring can be exemplified by pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, acridinine, etc.

These aromatic hydrocarbon rings and aromatic heterocycles may have a substituent that can be introduced, provided that excellent properties of the anthracene derivative are not impaired.

The substituents are the same ones as those illustrated as the substituents optionally possessed by the monovalent aromatic hydrocarbon group or the monovalent aromatic heterocyclic group represented by the groups $Ar^1$ to $Ar^4$ in the general formula (1).

In the present invention, the particularly preferred divalent group is derived from a substituted or unsubstituted benzene ring, biphenyl ring, naphthalene ring, and phenathrene ring.

Further, the group B in the general formula (4) is a monovalent aromatic heterocyclic group. Such a heterocyclic group can be exemplified by a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, a carbolinyl group, etc.

The monovalent aromatic heterocyclic group in the abovementioned group B also may have a substituent, provided that excellent properties of the anthracene derivative are not impaired. The following groups, in addition to a deuterium atom, a cyano group, and a nitro group, can exemplify the substituents.

A halogen atom, for example, a fluorine atom, a chlorine atom, a bromine atom, an iodine atom, etc.;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, and an n-hexyl group;

a cycloalkyl group having 5 to 10 carbon atoms, for example, a cyclopentyl group, a cyclohexyl group, a 1-adamantyl group, and a 2-adamantyl group;

an alkyloxy group having 1 to 6 carbon atoms, for example, a methyloxy group, an ethyloxy group, and a propyloxy group;

a cycloalkyloxy group having 5 to 10 carbon atoms, for example, a cyclopentyloxy group, a cyclohexyloxy group, a 1-adamantyloxy group, and a 2-adamantyloxy group;

an alkenyl group, for example, a vinyl group and an allyl group;

an aryloxy group, for example, a phenyloxy group, a tolyloxy group, a biphenylyloxy group, a naphthyloxy group, an anthracenyloxy group, and a phenanthrenyloxy group;

an arylalkyloxy group, for example, a benzyloxy group and a phenethyloxy group;

an aromatic hydrocarbon group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, and a spirobifluorenyl group;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group;

an arylvinyl group, for example, a styryl group and a naphthylvinyl group; and an acyl group, for example, an acetyl group and a benzoyl group.

The substituents exemplified hereinabove may be present independently of each other, or these substituents may be bonded to each other via a single bond, an optionally substituted methylene group, an oxygen atom, or a sulfur atom to form a ring.

In the present invention, as a monovalent aromatic heterocyclic group which is preferred as the abovementioned group B, nitrogen-containing aromatic heterocyclic groups, for example, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzimidazolyl group, a pyrazolyl group, a carbolinyl group, etc., are preferred, and among them, a pyridyl group, a pyrimidinyl group, a quinolyl group, an isoquinolyl group, an indolyl group, a pyrazolyl group, a benzimidazolyl group, and a carbolinyl group are more preferred.

Further, C in the general formula (4) represents a monovalent aromatic hydrocarbon group or a monovalent aromatic heterocyclic group. This group can be exemplified by the same ones as those illustrated in relation to $Ar^1$ to $Ar^4$ in the general formula (1). Further, these monovalent aromatic hydrocarbon group and monovalent aromatic heterocyclic group may have a substituent similarly to the aromatic groups represented by the aforementioned $Ar^1$ to $Ar^4$.

When two such groups C are present in the molecule (when q=2 in the formula (4)), the two groups C may be the same or different.

Furthermore, D in the general formula (4) is a hydrogen atom, a deuterium atom, a fluorine atom, a chlorine atom, a cyano group, or an alkyl group having 1 to 6 carbon atoms. Among them, the alkyl group having 1 to 6 carbon atoms can be exemplified by a methyl group, an ethyl group, an n-propyl group, an isopropyl group, an n-butyl group, an isobutyl group, a tert-butyl group, an n-pentyl group, an isopentyl group, a neopentyl group, an n-hexyl group, etc.

These alkyl groups may have a substituent, for example, a deuterium atom, a fluorine atom, a chlorine atom, a cyano group, etc.

A plurality of present D may be the same or different.

In the present invention, the most preferred D is a hydrogen atom.

In the anthracene derivative of the above-described general formula (4), it is preferred that B be a nitrogen-containing aromatic heterocyclic group and D be a hydrogen atom, and such preferred anthracene derivatives are particularly represented by the following general formulas (4a), (4b), or (4c).

The anthracene Derivative Represented by the General Formula (4a);

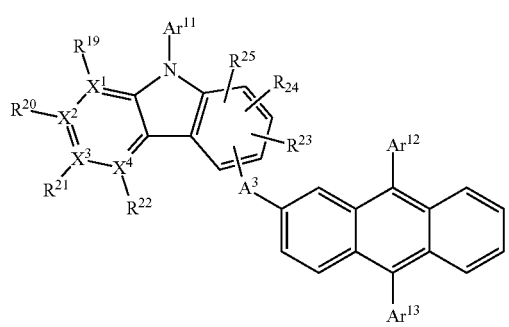

(4a)

In the general formula (4a), $A^3$ is as defined in the aforementioned formula (4) and is a divalent aromatic hydrocarbon group, a divalent aromatic heterocyclic group, or a single bond.

Further, the nitrogen-containing heterocycle of a three-ring structure to which the $A^3$ is bonded corresponds to the group B in the general formula (4).

$X^1$, $X^2$, $X^3$ and $X^4$ in the formula (4a) are ring elements constituting part of the abovementioned nitrogen-containing heterocycle and each represent a carbon atom or a nitrogen atom, provided that only any one of them is a nitrogen atom.

Further, $R^{19}$ to $R^{25}$ and $Ar^{11}$ represent substituents bonded to the nitrogen-containing heterocycle.

Thus, $R^{19}$ to $R^{22}$ are shown as substituents in the ring formed by $X^1$, $X^2$, $X^3$ and $X^4$, and when the ring element is a nitrogen atom, it is assumed that none of $R^{19}$ to $R^{22}$ (including a hydrogen atom) is bonded to the nitrogen atom. For example, when $X^1$ is a nitrogen atom, $R^{3-9}$ is not present; when $X^2$ is a nitrogen atom, $R^{20}$ is not present; when $X^3$ is a nitrogen atom, $R^{21}$ is not present; and when $X^4$ is a nitrogen atom, $R^{22}$ is not present.

Further, $R^{19}$ to $R^{25}$ which are bonded to the abovementioned nitrogen-containing heterocycle are each a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

The alkyl group having 1 to 6 carbon atoms can be exemplified by the same ones as those illustrated in relation to D in the general formula (4).

The cycloalkyloxy group having 5 to 10 carbon atoms can be exemplified by a cyclopentyl group, a cyclohexyl group, a 1-adamantyl group, and a 2-adamantyl group.

The alkenyl group having 2 to 6 carbon atoms can be exemplified by a vinyl group, an allyl group, an isopropenyl group, a 2-butenyl group, etc.

The alkyloxy group having 1 to 6 carbon atoms can be exemplified by a methyloxy group, an ethyloxy group, an n-propyloxy group, an isopropyloxy group, an n-butyloxy group, a tert-butyloxy group, an n-pentyloxy group, and an n-hexyloxy group.

The cycloalkyloxy group having 5 to 10 carbon atoms can be exemplified by a cyclopentyloxy group, a cyclohexyloxy group, a cycloheptyloxy group, a cyclooctyloxy group, a 1-adamantyloxy group, and a 2-adamantyloxy group.

Further, the monovalent aromatic hydrocarbon group and the monovalent aromatic heterocyclic group can be exemplified by the same ones as those illustrated in relation to the groups $Ar^1$ to $Ar^4$ in the general formula (1).

The aryloxy group can be exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, a perylenyloxy group, etc.

Each group represented by the above-described $R^{19}$ to $R^{25}$ may have a substituent, and these substituents can be exemplified by the same ones as those illustrated as the substituents possessed by the groups $Ar^1$ to $Ar^4$ in the general formula (1) within a range in which the condition relating to the number of carbon atoms is satisfied.

Further, these substituents may be present independently of each other, or these substituents may be bonded to each other via a single bond, an optionally substituted methylene group, an oxygen atom, or a sulfur atom to form a ring.

Furthermore, $Ar^{11}$ in the general formula (4a) is a substituent bonded to the nitrogen-containing aromatic ring. $Ar^{12}$ and $Ar^{13}$ correspond to C in the general formula (4) (that is, q=2).

These $Ar^{11}$ to $Ar^{13}$ each represent a monovalent aromatic hydrocarbon group or a monovalent aromatic heterocyclic group. These groups can be exemplified by the same ones as those illustrated in relation to $Ar^1$ to $Ar^4$ in the general formula (1). Further, these monovalent aromatic hydrocarbon group and monovalent aromatic heterocyclic group may have a substituent similarly to the aromatic groups represented by the aforementioned $Ar^1$ to $Ar^4$.

The anthracene derivative represented by the above-described general formula (4a) can be specifically exemplified by Compounds (4a-1) to (4a-20) having the structural formulas shown in FIGS. 45 to 49.

Among the anthracene derivatives represented by the above-described general formula (4a), the anthracene derivative represented by the following general formula (4a') is most preferred.

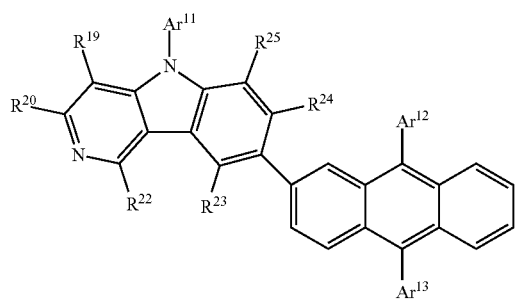

(4a')

In the general formula (4a'), $R^{19}$ to $R^{25}$ and $Ar^{11}$ to $Ar^{13}$ have the same meaning as that defined in the general formula (4a).

The Anthracene Derivative Represented by the General Formula (4b);

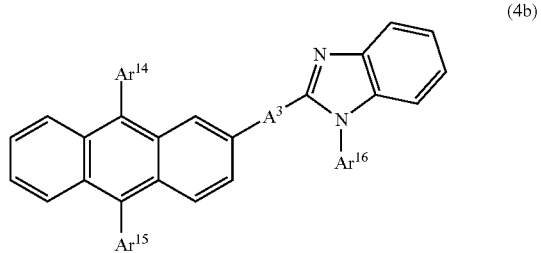

(4b)

In the general formula (4b), $A^3$ is as defined in the aforementioned formula (4) and is a divalent aromatic hydrocarbon group, a divalent aromatic heterocyclic group, or a single bond.

Further, the nitrogen-containing heterocycle to which the $A^3$ is bonded corresponds to the group B in the general formula (4).

Furthermore, $Ar^{14}$ and $Ar^{15}$ in the general formula (4b) correspond to C in the general formula (4) (that is, q=2), and $Ar^{16}$ is a substituent bonded to the nitrogen-containing aromatic ring.

These $Ar^{14}$ to $Ar^{16}$ each represent a monovalent aromatic hydrocarbon group or a monovalent aromatic heterocyclic group. These groups can be specifically exemplified by the same ones as those illustrated as the monovalent aromatic hydrocarbon group and the monovalent aromatic heterocyclic group represented by $Ar^1$ to $Ar^4$ in the general formula (1). Further, these monovalent aromatic hydrocarbon group and monovalent aromatic heterocyclic group may have a substituent similarly to the groups represented by $Ar^1$ to $Ar^4$ in the general formula (1).

The anthracene derivative represented by the above-described general formula (4b) can be specifically exemplified by Compounds (4b-1) to (4b-16) having the structural formulas shown in FIGS. 50 to 53.

The Anthracene Derivative Represented by the General Formula (4c);

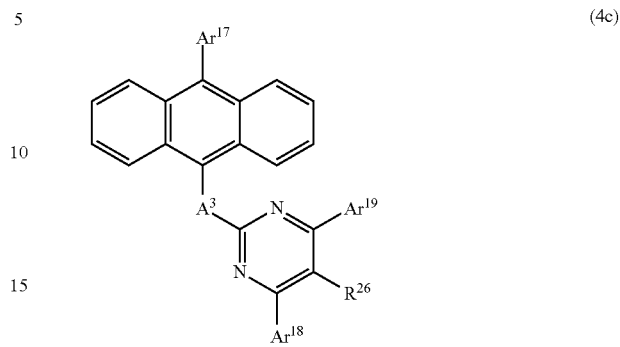

(4c)

In the general formula (4c), $A^3$ is as defined in the aforementioned formula (4) and is a divalent aromatic hydrocarbon group, a divalent aromatic heterocyclic group, or a single bond.

Further, the nitrogen-containing heterocycle to which the $A^3$ is bonded corresponds to the group B in the general formula (4).

Furthermore, $Ar^{17}$ in the general formula (4c) corresponds to C in the general formula (4) (that is, q=1), and $Ar^{18}$, $Ar^{19}$, and $R^{26}$ are substituents bonded to the nitrogen-containing aromatic ring.

The abovementioned $Ar^{17}$ to $Ar^{19}$ each represent a monovalent aromatic hydrocarbon group or a monovalent aromatic heterocyclic group. Similarly to $Ar^{11}$ to $Ar^{13}$, these groups can be specifically exemplified by the same groups as those illustrated in relation to $Ar^1$ to $Ar^4$ in the general formula (1). Further, similarly to $Ar^{11}$ to $Ar^{13}$, these monovalent aromatic hydrocarbon group and monovalent aromatic heterocyclic group may have a substituent.

Further, $R^{26}$ which is bonded to the abovementioned nitrogen-containing heterocycle is the same as $R^{19}$ to $R^{25}$ in the aforementioned general formula (4a) and represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, or an aryloxy group.

Each of the abovementioned groups represented by $R^{26}$ may have the same substituents as the groups represented by $Ar^1$ to $Ar^4$ in the general formula (1), and when a plurality of the substituents is present, it is preferred that the plurality of the substituents be present independently of each other, but the plurality of the substituents may be bonded to each other via a single bond, an optionally substituted methylene group, an oxygen atom, or a sulfur atom to form a ring.

The anthracene derivative represented by the above-described general formula (4c) can be specifically exemplified by Compounds (4c-1) to (4c-30) having the structural formulas shown in FIGS. 54 to 61.

In the present invention, it is desirable that the electron transport layer be formed by the above-described anthracene derivative, and various anthracene derivatives exemplified hereinabove can be synthesized by publicly known methods (see, for example, WO 2011/0593000, WO 2003/060956, and Korean Patent Publication No. 2013-060956).

These anthracene derivatives may be used single or in a mixture of a plurality of kinds thereof to form the electron transport layer.

<Electron Injection Layer>

The electron injection layer 8 is appropriately provided between the cathode 9 and the electron transport layer 7. The electron injection layer 8 can be formed using an alkali metal salt such as lithium fluoride and cesium fluoride, an alkaline earth metal salt such as magnesium fluoride, a metal oxide such as aluminum oxide, etc.

<Cathode>

A metal with a low work function, such as aluminum, and alloys with a lower work function such as a magnesium-silver alloy, a magnesium-indium alloy, and an aluminum-magnesium alloy can be used as the electrode material for the cathode 9 in the organic EL device of the present invention.

<Other layers>

The organic EL device of the present invention may have other layers, if necessary. For example, an electron blocking layer can be provided between the hole transport layer and the luminous layer, and a hole blocking layer can be provided between the luminous layer and the electron transport layer (these configurations are not shown in FIG. 1).

These appropriately provided layers may be formed from publicly known materials by a publicly known method such as a vapor deposition method, a spin coat method, and an ink jet method selected according to the type of the material to be used.

The Electron Blocking Layer;

The electron blocking layer, which is not shown in FIG. 1, is provided between the hole transport layer and the luminous layer and is formed to block the transmission of electrons from the luminous layer and increase the luminous efficiency. Various compounds having electron blocking property can be used as the material for forming the electron blocking layer, the following carbazole derivatives being typical such compounds.

4,4',4"-tri(N-carbazolyl)triphenylamine (TCTA);
9,9-bis[4-(carbazol-9-yl)phenyl]fluorene;
1,3-bis(carbazol-9-yl)benzene (mCP); and
2,2-bis(4-carbazol-9-ylphenyl)adamantane (Ad-Cz).

In addition to the abovementioned carbazole derivatives, compounds having a triphenylsilyl group and a triarylamine skeleton in a molecule, for example, 9-[4-(carbazol-9-yl)phenyl]-9-[4-(triphenylsilyl)phenyl]-9H-fluorene, can be also used as materials for forming the electron blocking layer.

The Hole Blocking Layer;

The hole blocking layer, which is not shown in FIG. 1, is appropriately provided between the electron transport layer and the luminous layer and is formed to prevent the transmission of holes from the luminous layer and increase the luminous efficiency. The following compounds demonstrating the hole blocking action can be used as materials for forming the hole blocking layer: phenanthroline derivatives such as bathocuproine (BCP), metal complexes of quinolinol derivatives such as aluminum(III) bis(2-methyl-8-quinolinato)-4-phenylphenolate (BAlq), various rare earth complexes, triazole derivatives, triazine derivatives, oxadiazole derivatives, etc.

In the organic EL device of the present invention, each layer constituting the device may have a monolayer structure formed by the aforementioned various materials, or each layer can have a multilayer structure obtained by appropriately combining various materials.

In particular, in the present invention, in order to demonstrate excellent properties of the arylamine compound of the aforementioned general formula (1), it is preferred that the hole transport layer have a two-layer structure including the first hole transport layer 4 and the second hole transport layer 5, as shown in FIG. 1.

The hole transport layer having a two-layer structure will be described below.

<Hole Transport Layer having a Two-layer Structure>

In the organic EL device of the present invention, the arylamine compound represented by the general formula (1) is used to form the hole transport layer, but it is preferred that the hole transport layer including such an arylamine compound have a two-layer structure.

Thus, it is preferred that the hole transport layer have a two-layer structure in which the hole transport layer is divided, as shown in FIG. 1, into the first hole transport layer 4 positioned on the side of the anode 2 and the second hole transport layer 5 positioned on the side of the luminous layer 6 and that the arylamine compound represented by the general formula (1) be included in the second hole transport layer 5. In this case, a hole transport material different from that of the arylamine compound used in the second hole transport layer 5 is used to form the first hole transport layer 4.

When the hole transport layer is thus divided into two layers, the second hole transport layer 5 on the side of the luminous layer 6 demonstrates hole transport property and also very high electron blocking property. This is because the arylamine compound represented by the aforementioned general formula (1) has high electron blocking property in addition to hole transport property. Therefore, by placing the second hole transport layer 5 adjacently to the luminous layer 6, in particular, as shown in FIG. 1, it is possible to maintain a higher carrier balance in the luminous layer 6, and this is also very advantageous in terms of improving the characteristics of the organic EL device.

In such a two-layer structure, the second hole transport layer 5 is formed by the arylamine compound represented by the general formula (1), but the first hole transport layer 4 is formed using a hole transport material which is different from the arylamine compound used to form the second hole transport layer 5.

This hole transport material may be the arylamine compound represented by the general formula (1), as long as it is different from the compound used to form the second hole transport layer 5, but it is generally desirable that the first hole transport layer 4 be formed using a triarylamine derivative. This is because from the viewpoint of the electron blocking property, such a triarylamine compound is inferior to the abovementioned arylamine compound, but from the viewpoint of the hole transport property, the triarylamine derivative exhibits performance equal to or higher than that of the arylamine compounds and also because the electron blocking property is not so required for the first hole transport layer 4 which is not in direct contact with the luminous layer 6.

From the viewpoint of hole transport property, stability of a thin film and heat resistance and also easiness of synthesis, it is preferable that such a triarylamine derivative be:

(1) a di(triarylamine) compound having a structure which has two triarylamine skeletons in a molecule, the triarylamine skeletons being linked to each other via a single bond or a divalent group having no heteroatom, or (2) a poly(triarylamine) compound having a structure which has three to six triarylamine skeletons, the triarylamine skeletons being linked to each other via a single bond or a divalent group having no heteroatom.

Such triarylamine compounds can be used singly or in a mixture of two or more thereof, and also in combination with publicly known hole transport materials, as in the aforementioned second hole transport layer 5.

The Di(triarylamine Compounds);

The di(triarylamine) compounds have two triarylamine skeletons in a molecule and are represented, for example, by a general formula (5).

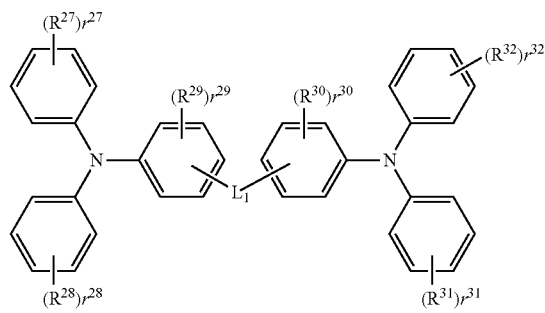

(5)

In the general formula (5), $r^{27}$ to $r^{32}$ each are an integer representing the number of substituents $R^{27}$ to $R^{32}$ bonded to the aromatic ring. $r^{27}$, $r^{28}$, $r^{31}$, and $r^{32}$ each represent an integer of 0 to 5, and $r^{29}$ and $r^{30}$ each represent an integer of 0 to 4.

These $r^{27}$ to $r^{32}$ are preferably integers of 0 to 3, and more preferably integers of 0 to 2.

Further, $L^1$ is a bridging group that bonds the triarylamine skeletons and represents a single bond or a divalent organic group represented by the following formulas (B) to (G).

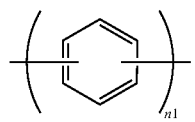

(B)

(n1 represents an integer of 1 to 4)

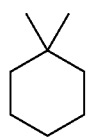

(C)

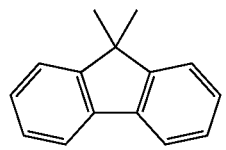

(D)

—CH$_2$—  (E)

—CH—  (F)

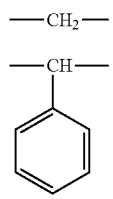

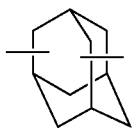

(G)

The $L^1$ is preferably a single bond or a divalent organic group represented by the formula (B), (D), or (G), and more preferably a single bond or a divalent organic group represented by the formula (B) or (D). Further, n1 in the formula (B) is preferably 2 or 3.

Further, in the general formula (5), $R^{27}$ to $R^{32}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aralkyl group, or an aryloxy group. When a plurality of $R^{27}$ to $R^{32}$ is bonded to the same benzene ring, the plurality of present groups may be bonded to each other via a single bond, an oxygen atom, a sulfur atom, or an optionally substituted methylene group to form a ring.

The alkyl group, cycloalkyl group, alkenyl group, alkyloxy group, cycloalkyloxy group, aromatic hydrocarbon group, aromatic heterocyclic group, aralkyl group, and aryloxy group can be specifically exemplified by the same groups as those illustrated in relation to groups $R^1$ to $R^8$ in the aforementioned general formula (2).

The groups represented by the above-described $R^{27}$ to $R^{32}$ may have a substituent. The substituents can be exemplified by the same ones as those illustrated in relation to the aforementioned groups $R^1$ to $R^8$. These substituents may be present independently of each other, or these substituents may be bonded to each other via a single bond, an optionally substituted methylene group, an oxygen atom, or a sulfur atom to form a ring.

The preferred groups represented by the above-described $R^{27}$ to $R^{32}$ are a deuterium atom, an alkyl group, an alkenyl group, and an aromatic hydrocarbon group, and the more preferred groups are a deuterium atom, a phenyl group, and a biphenyl group. It is also preferred that these groups be bonded to each other via a single bond to form a condensed aromatic ring.

The di(triarylamine) compound represented by the above-described general formula (5) can be specifically exemplified by Compounds (5-1) to (5-23) having structural formulas shown in FIGS. 62 to 66.

Figure 67:
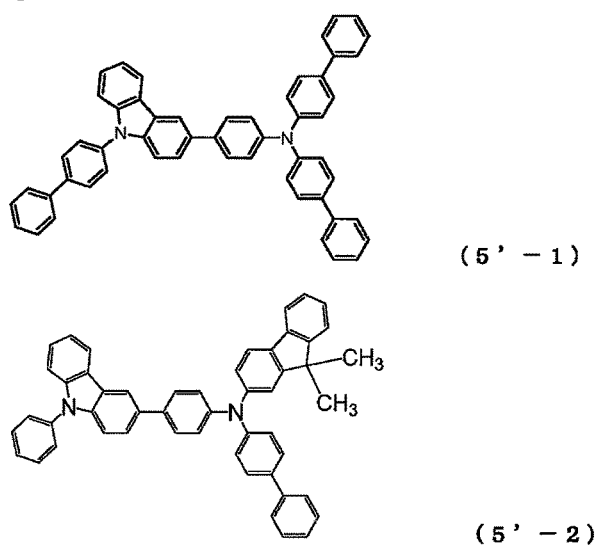
FIG. 67 is a view showing the structural formulas of triarylamine derivatives No. (5'-1) and (5'-2).
Figure 68:
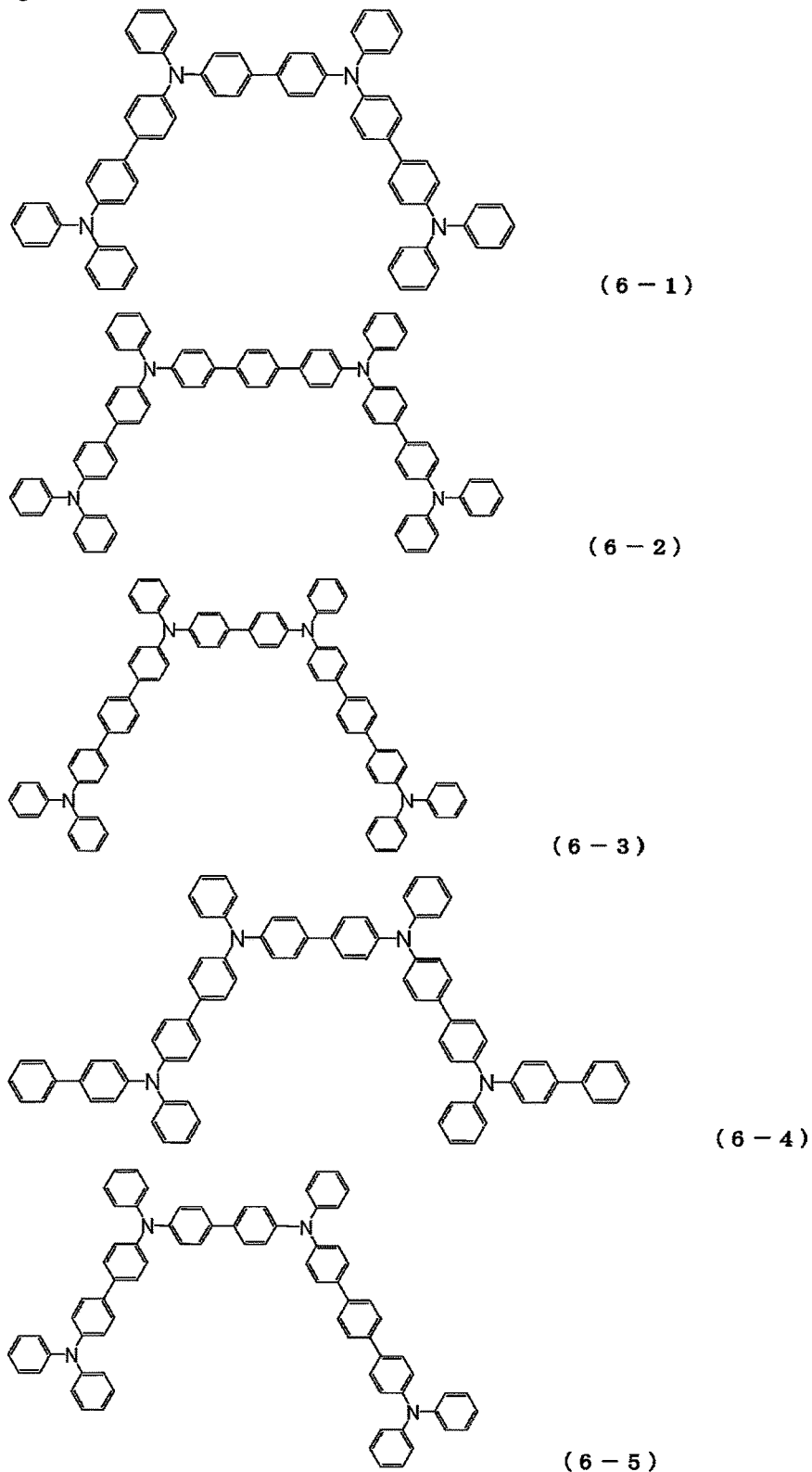
FIG. 68 is a view showing the structural formulas of Compounds No. (6-1) to (6-5) in the triarylamine derivative of a general formula (6).
Figure 69:
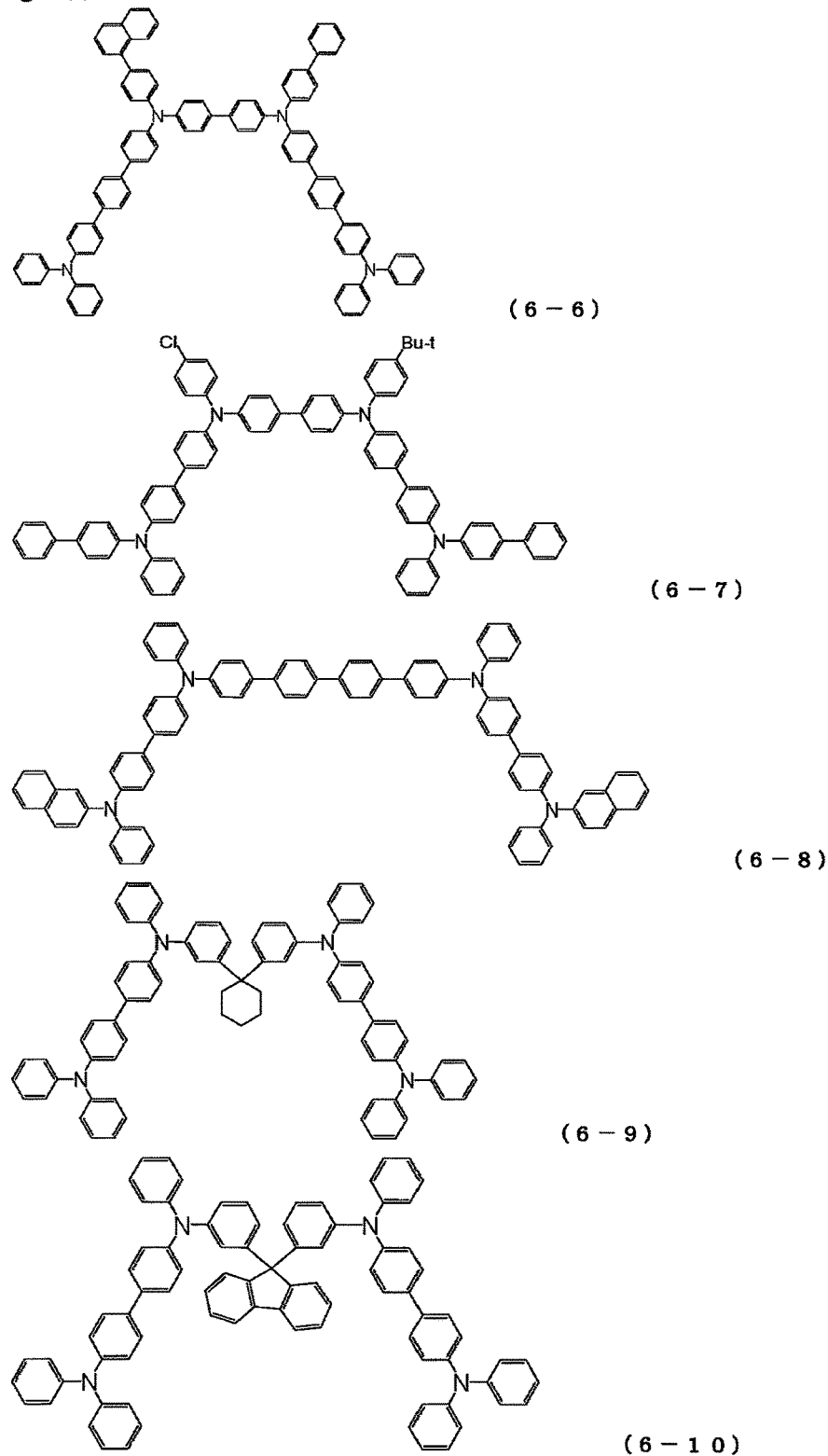
FIG. 69 is a view showing the structural formulas of Compounds No. (6-6) to (6-10) in the triarylamine derivative of the general formula (6).
Figure 70:
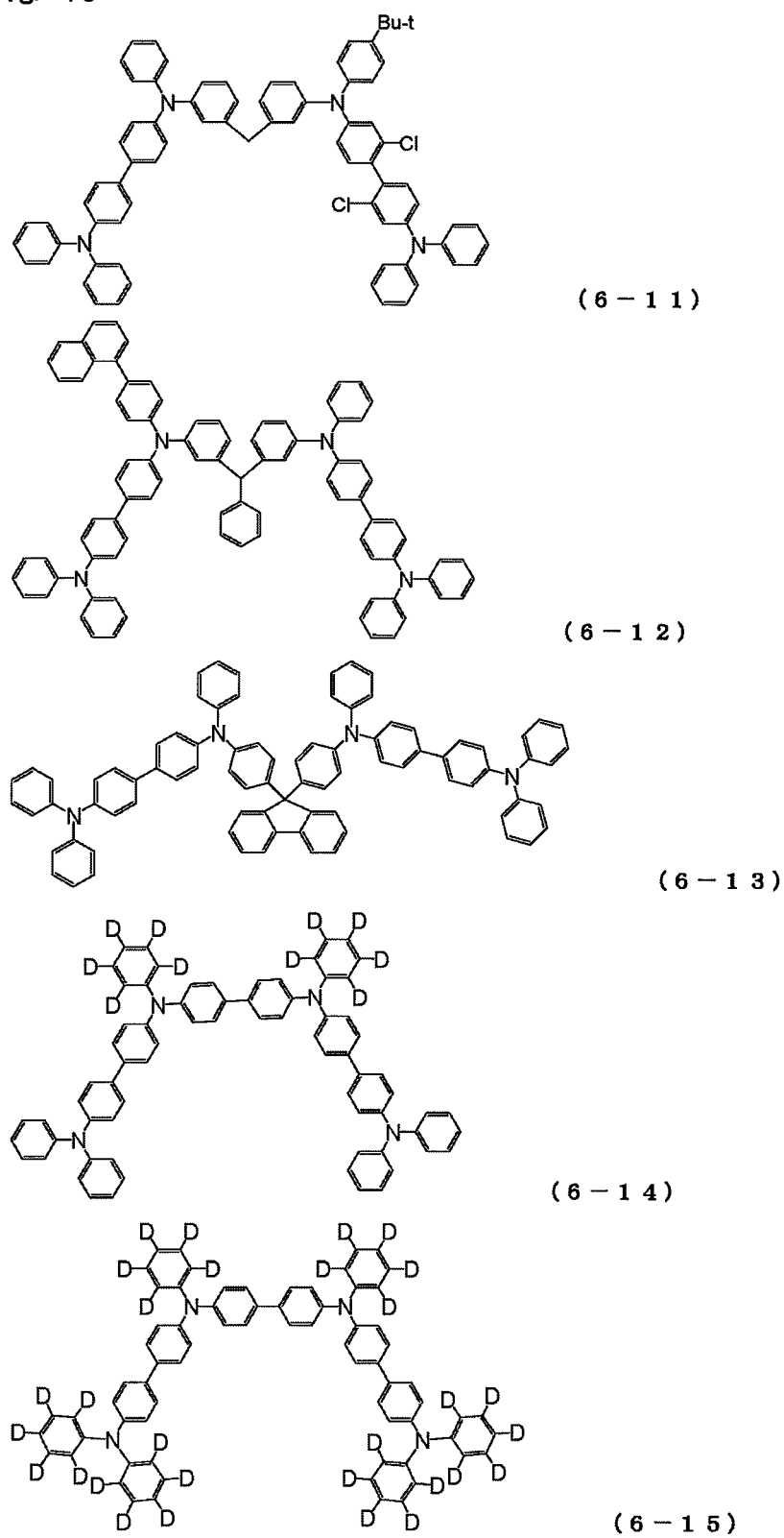
FIG. 70 is a view showing the structural formulas of Compounds No. (6-11) to (6-15) in the triarylamine derivative of the general formula (6).
Figure 71:
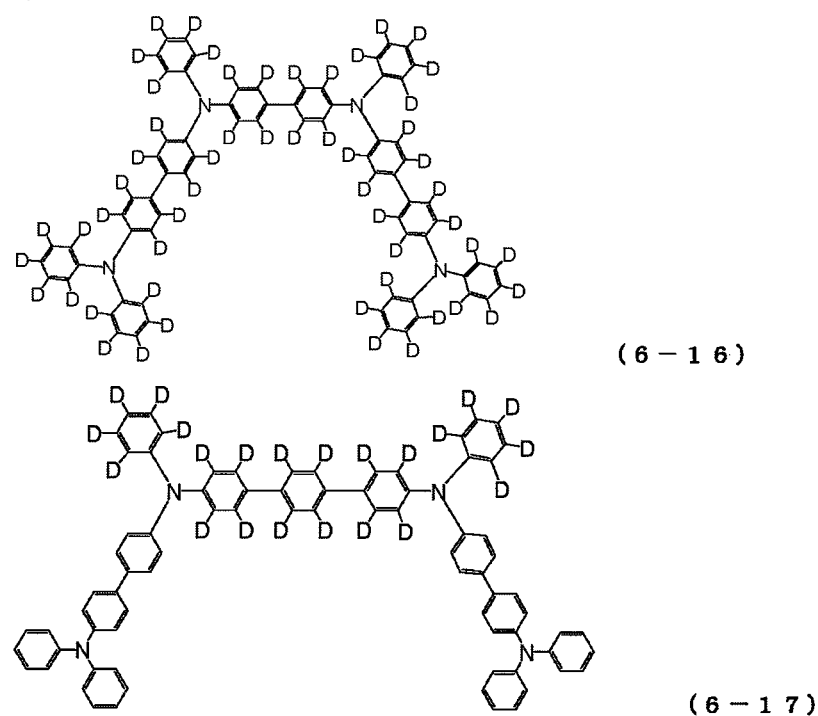
FIG. 71 is a view showing the structural formulas of Compounds No. (6-16) and (6-17) in the triarylamine derivative of the general formula (6).

Further, Compounds (5'-1) and (5'-2) which have the structural formulas shown in FIG. 67 and are not the di(triarylamine) compounds represented by the general formula (5) have two triarylamine skeletons and can also be advantageously used for forming the first hole transport layer 4.

The Poly(triarylamine) Compounds;

The abovementioned poly(triarylamine) compound is represented, for example, by a general formula (6).

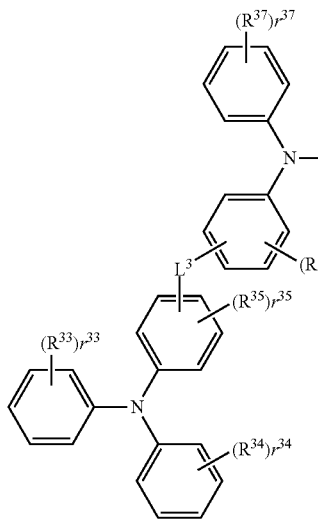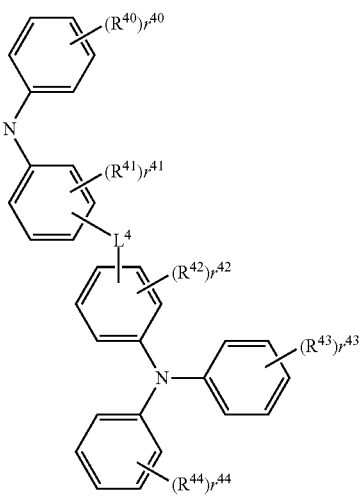

(6)

The poly(triarylamine) compound represented by the general formula (6) has four triarylamine skeletons.

In the general formula (6), $r^{33}$ to $r^{44}$ each represent an integer indicating the number of substituents $R^{33}$ to $R^{44}$ bonded to the aromatic ring. $r^{33}$, $r^{34}$, $r^{37}$, $r^{40}$, $r^{43}$ and $r^{44}$ each represent an integer of 0 to 5. Further, $r^{35}$, $r^{36}$, $r^{38}$, $r^{39}$, $r^{41}$, and $r^{42}$ each represent an integer of 0 to 4.

These $r^{33}$ to $r^{44}$ are preferably integers of 0 to 3, and more preferably integers of 0 to 2.

Further, $L^1$, $L^2$, and $L^3$ are bridging groups that bond the triarylamine skeletons, and each represents a single bond or a divalent organic group represented by the following formula (B') or the same as those represented by formulas (C) to (G) in the aforementioned general formula (5).

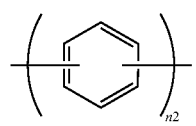

(B')

(n2 represents an integer of 1 to 3)

The $L^1$, $L^2$, and $L^3$ are each preferably a single bond and a divalent organic group represented by the formula (B') or the formula (D), and more preferably a single bond and a divalent organic group represented by the formula (B'). Further, n2 in the formula (B') is preferably 1 or 2, and more preferably 1.

Further, in the general formula (6), substituents $R^{33}$ to $R^{44}$ bonded to the aromatic ring each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aralkyl group, or an aryloxy group.

When a plurality of $R^{33}$ to $R^{44}$ is bonded to the same benzene ring, the plurality of present groups may be bonded to each other via a single bond, an oxygen atom, a sulfur atom, or an optionally substituted methylene group to form a ring.

The alkyl group having 1 to 6 carbon atoms can be exemplified by a methyl group, an ethyl group, an n-propyl group, an isopropyl group, an n-butyl group, an isobutyl group, a tert-butyl group, an n-pentyl group, an isopentyl group, a neopentyl group, and an n-hexyl group.

The cycloalkyl group having 5 to 10 carbon atoms can be exemplified by a cyclopentyl group, a cyclohexyl group, a 1-adamantyl group, and a 2-adamantyl group.

The alkenyl group having 2 to 6 carbon atoms can be exemplified by a vinyl group, an allyl group, an isopropenyl group, and a 2-butenyl group.

The alkyloxy group having 1 to 6 carbon atoms can be exemplified by a methyloxy group, an ethyloxy group, an n-propyloxy group, an isopropyloxy group, an n-butyloxy group, a tert-butyloxy group, an n-pentyloxy group, and an n-hexyloxy group.

The cycloalkyloxy group having 5 to 10 carbon atoms can be exemplified by a cyclopentyloxy group, a cyclohexyloxy group, a cycloheptyloxy group, a cyclooctyloxy group, a 1-adamantyloxy group, and a 2-adamantyloxy group.

The aromatic hydrocarbon group and the aromatic heterocyclic group can be exemplified by the same ones as those illustrated in relation to groups $Ar^1$ to $Ar^4$ in the general formula (1).

The aralkyl group can be exemplified by a benzyl group and a phenethyl group.

The aryloxy group can be exemplified by a phenyloxy group, a biphenyloxy group, a terphenyloxy group, a naphthyloxy group, an anthracenyloxy group, a phenanthrenyloxy group, a fluorenyloxy group, an indenyloxy group, a pyrenyloxy group, and a perylenyloxy group.

Groups represented by the above-described $R^{33}$ to $R^{44}$ may have a substituent. The substituents can be exemplified by the same ones as those illustrated as the substituents possessed by the aromatic hydrocarbon group and the aromatic heterocyclic group represented by groups $Ar^1$ to $Ar^4$ in the general formula (1), within ranges in which the conditions relating to the number of carbon atoms are satisfied.

Further, these substituents may be present independently of each other, or these substituents may be bonded to each other via a single bond, an optionally substituted methylene group, an oxygen atom, or a sulfur atom to form a ring.

The preferred groups represented by the above-described $R^{33}$ to $R^{44}$ are a deuterium atom, an alkyl group, an alkenyl group, and an aromatic hydrocarbon group, and the particularly preferred examples are a deuterium atom, a phenyl group, a biphenyl group, a naphthyl group, and a vinyl group. It is also preferred that these groups be bonded to each other via a single bond to form a condensed aromatic ring.

The poly(triarylamine) compound represented by the above-described general formula (6) can be specifically exemplified by Compounds (6-1) to (6-17) having structural formulas shown in FIGS. 68 to 71.

The thickness of the second hole transport layer 5 formed using the arylamine compound of the above-described general formula (1) and the thickness of the first hole transport layer 4 formed using another triarylamine derivative are not particularly limited, but in order to maximize the characteristics of these layers, the total thickness (t1+t2) of the thickness t1 of the first hole transport layer 4 and the thickness t2 of the second hole transport layer 5 is usually within a range of 20 to 300 nm, preferably within a range of 50 to 200 nm, and particularly within a range of 50 to 150 nm, these ranges being advantageous in terms of ensuring light emission at a low driving voltage.

In the present invention, various triarylamine compounds exemplified hereinabove can be synthesized by publicly known methods (see, for example, Japanese Patent Application Publication No. H7-126615, Japanese Patent Application Publication No. H08-048656, and Japanese Patent Application Publication No. 2005-108804).

Further, the above-described first hole transport layer 4 and second hole transport layer 5 are preferably formed by vapor deposition or vapor co-deposition of a gas including a predetermined triarylamine derivative or arylamine compound, but they can be also formed by a publicly known method such as a spin coat method and an ink jet method.

In the organic EL device of the present invention which has the above-described structure, materials for an organic EL device which excels in hole and electron injection-transport performance and stability and endurance of a thin film are combined with consideration for carrier balance. Therefore, the efficiency of hole transport from the hole transport layer into the luminous layer is increased and the efficiency of electron transport from the electron transport layer into the luminous layer is also increased as compared with the conventional organic EL devices. Further, when the hole transport layer has a two-layer structure including a first hole transport layer and a second transport layer, the carrier balance is further improved, the luminous efficiency is further increased, the driving voltage is further lowered, and the durability of the organic EL device is further increased.

In accordance with the present invention, it is possible to realize an organic EL device with a high efficiency, a low diving voltage, and a long life.

EXAMPLES

The present invention will be described by way of the following Examples.

Synthesis Example 1

Synthesis of an Arylamine Compound (1-1);
(First Step)

| | |
|---|---|
| A nitrogen-purged reaction vessel was charged with bis(biphenyl-4-yl)amine | 40.5 g, |
| 3-bromobiphenyl | 28.0 g, |
| t-butoxysodium and | 13.7 g, |
| toluene | 400 mL. |

A nitrogen gas was passed through the mixture for 30 min under ultrasonic irradiation.
Then,

| | |
|---|---|
| palladium acetate and | 0.54 g |
| 50% (w/v) toluene solution of t-butylphopshine | 1.46 g | were added, followed by heating and stirring for 4 h at 95° C.

The insolubles were removed by filtration, followed by adsorption purification using silica gel at 100° C., and hot filtration. The filtrate was cooled to room temperature under stirring, and the precipitated solid matter was collected by filtration. As a result,

| | |
|---|---|
| a green white solid body of bis(biphenyl-4-yl)-(biphenyl-3-yl)amine | 50.2 g (yield 88%) | was obtained.
(Second Step)

| | |
|---|---|
| A nitrogen-purged reaction vessel was charged with the resulting bis(biphenyl-4-yl)-(biphenyl-3-yl)amine and | 50.0 g |
| dimethylformamide | 500 mL, | followed by cooling in an ice bath.
Then,

| | |
|---|---|
| N-bromosuccinimide | 22.1 g | was gradually added, followed by stirring for 4 h. Methanol was then added and the precipitated crude product was collected by filtration.

Then, reflux washing using ethyl acetate was performed to obtain

| | |
|---|---|
| Then, reflux washing using ethyl acetate was performed to obtain a pink powder of N,N-bis(biphenyl-4-yl)-(6-bromobiphenyl-3-yl)amine | 40.2 g (yield 69%). |

(Third Step)
Then, a nitrogen-purged reaction vessel was charged with

| | |
|---|---|
| Then, a nitrogen-purged reaction vessel was charged with the resulting bis(biphenyl-4-yl)-(6-bromobiphenyl-3-yl)amine | 11.8 g, |
| toluene | 94 mL, |
| phenylboronic acid | 2.7 g, | and an aqueous solution obtained by dissolving 5.9 g of potassium carbonate in 36 mL of water, and a nitrogen gas was passed through the mixture for 30 min under ultrasonic irradiation.

Then,

| | |
|---|---|
| tetrakis(triphenylphosphine)palladium | 0.74 g | was added, followed by heating and stirring for 18 h at 72° C. After cooling to room temperature, the organic layer was collected by liquid separation. Washing with water and washing with saturated brine were performed in sequence, followed by drying with magnesium sulfate anhydrous and concentrating to obtain a crude product.

| | |
|---|---|
| Subsequent purification using column chromatography produced a white powder of bis(biphenyl-4-yl)-{(1,1':2',1''-terpheny1)-4'-yl}amine. | 8.4 g (yield 72%) |

This arylamine compound is Compound (1-1) having the structural formula represented by the following formula.

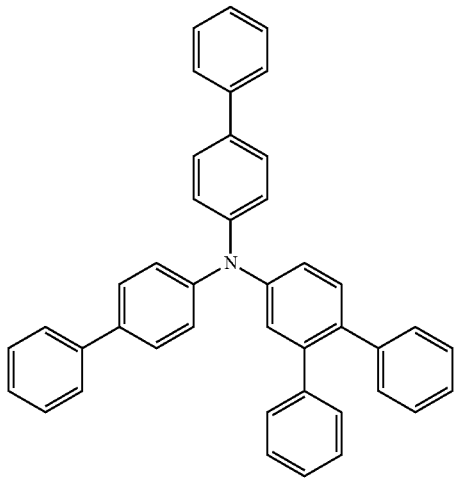

(1-1)

The structure of the resulting white powder was identified using NMR.

In $^1$H-NMR (CDCl$_3$), the following signals of 31 hydrogens were detected.

$\delta$(ppm) = 7.56 – 7.68 (7H)

7.45 – 7.52 (4H)

7.14 – 7.41 (20H).

Synthesis Example 2

Synthesis of an Arylamine Compound (1-9);

the reaction was conducted under the same conditions as in Synthesis Example 1, except that 4-terphenylboronic acid was used instead of phenylboronic acid that was used in the third step of Synthesis Example 1. As a result,

| | |
|---|---|
| a white powder of bis(biphenyl-4-y1)-{(1,1':2',1'':4'':1''':1''':4''',1''''-quinquepheny1)-5'''-yl}amine | 4.5 g (yield 40%) | was obtained.

This arylamine compound is Compound (1-9) having the structural formula represented by the following formula.

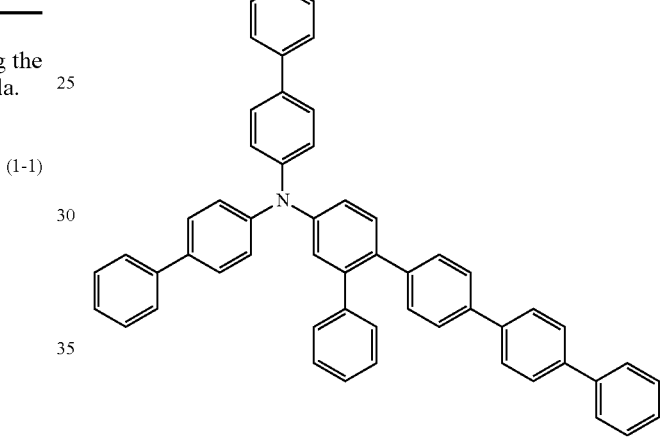

(1-9)

The structure of the resulting white powder was identified using NMR.

In $^1$H-NMR (CDCl$_3$), the following signals of 39 hydrogens were detected.

$\delta$ (ppm)=7.19-7.53 (39H)

Synthesis Example 3

Synthesis of an Arylamine Compound (1-20);

the reaction was conducted under the same conditions as in Synthesis Example 1, except that 4-(9,9-dimethylfluoren-2-yl)phenylboronic acid was used instead of phenylboronic acid that was used in the third step of Synthesis Example 1. As a result,

| | |
|---|---|
| a white powder of bis(biphenyl-4-yl)-[{4-(9,9-dimethylfluoren-2-yl)-1,1':2',1''-terphenyl}-4'-yl]amine | 13.1 g (yield 81%) | was obtained.

This arylamine compound is Compound (1-20) having the structural formula represented by the following formula.

(1-20)

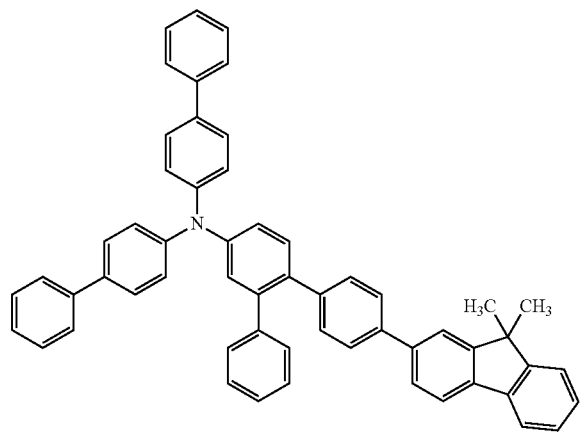

The structure of the resulting white powder was identified using NMR.

In $^1$H-NMR (CDCl$_3$), the following signals of 43 hydrogens were detected.

$\delta$ (ppm) = 7.72 – 7.77 (2H)

7.55 – 7.67 (10H)

7.18 – 7.49 (25H)

1.55 (6H)

Synthesis Example 4

Synthesis of an Arylamine Compound (1-29);

(First Step)

| A nitrogen-purged reaction vessel was charged with (biphenyl-4-yl)-(9,9-dimethylfluoren-2-yl)amine | 100 g, |
| 3-bromobiphenyl | 70.9 g, |
| t-butoxysodium | 32.5 g, |
| and toluene | 990 mL. |

A nitrogen gas was passed through the mixture for 30 min under ultrasonic irradiation.

Then,

| tris(dibenzylideneacetone)dipalladium and | 2.5 g |
| 50% (w/v) toluene solution of t-butylphopshine | 3.9 mL | were added, followed by heating and stirring for 2 h at 82° C. Then, 100 g of silica gel was added and removed together with insolubles by filtration, and adsorption purification using silica gel and activated clay was performed at room temperature. The filtrate was then concentrated, ethyl acetate and methanol were added to the precipitated solid matter, and dispersion washing was performed. The solid matter was collected by filtration.

| As a result, a brown powder of (biphenyl-3-yl)-(biphenyl-4-yl)-(9,9-dimethylfluoren-2-yl)amine | 119 g (yield 83%) | was obtained.

(Second Step)

| A nitrogen-purged reaction vessel was charged with the resulting (biphenyl-3-yl)-(biphenyl-4-yl)-(9,9-dimethylfluoren-2-yl)amine and | 119 g |
| dichloromethane | 1200 mL, | followed by heating and dissolving once and then cooling in an ice bath.

Then,

| N-bromosuccinimide | 41.3 g | was gradually added, followed by stirring for 3 h. Water was then added and the organic layer was collected by liquid separation. Washing with water was then performed, followed by drying with magnesium sulfate anhydrous and two cycles of adsorption purification using silica gel. The filtrate was concentrated to obtain a crude product, and crystallization using acetone and heptane was then performed to obtain

| a white powder of (6-bromobiphenyl-3-yl)-(biphenyl-4-yl)-(9,9-dimethylfluoren-2-yl)amine | 121 g (yield 88%). |

(Third Step)

| Then, a nitrogen-purged reaction vessel was charged with the resulting (6-bromobiphenyl-3-yl)-(biphenyl-4-yl)-(9,9-dimethylfluoren-2-yl)amine | 20.1 g, |
| toluene | 200 mL, |
| ethanol | 50 mL, |
| 4-biphenylboronic acid | 4.7 g, | and an aqueous solution obtained by dissolving 5.4 g of potassium carbonate in 20 mL of water, and a nitrogen gas was passed through the mixture for 30 min under ultrasonic irradiation.

Then,

| tetrakis(triphenylphosphine)palladium | 0.54 g | was added, followed by heating and stirring for 19 h at 72° C. After cooling to room temperature, the organic layer was collected by liquid separation. Washing with water was performed twice, followed by drying with magnesium sulfate anhydrous and concentrating to obtain a crude product. Subsequent purification using column chromatography produced

| a white powder of (biphenyl-4-yl)-(1,1':2',1'':4'',1'''-quaterphenyl-5'-yl)-(9,9-dimethylfluoren-2-yl)amine | 17.8 g (yield 89%). |

This arylamine compound is Compound (1-29) having the structural formula represented by the following formula.

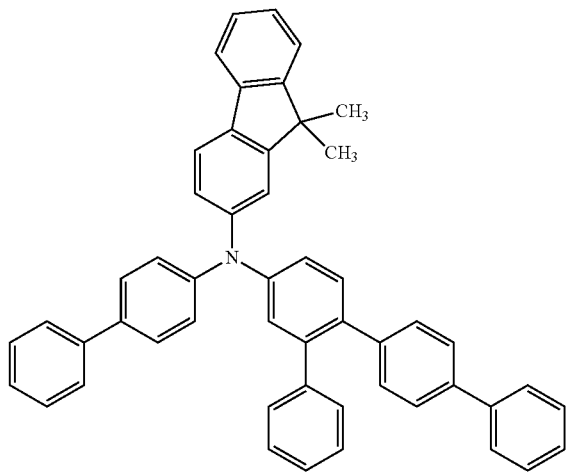

(1-29)

The structure of the resulting white powder was identified using NMR.

In $^1$H-NMR (CDCl$_3$), the following signals of 39 hydrogens were detected.

$\delta$ (ppm) = 7.57 – 7.70 (7H)

7.18 – 7.52 (26H)

1.52 (6H)

Synthesis Example 5

Synthesis of an Arylamine Compound (1-55);
(First Step)

| | |
|---|---|
| A nitrogen-purged reaction vessel was charged with bis(9,9-dimethylfluoren-2-yl)amine | 100 g, |
| 3-bromobiphenyl | 63.9 g, |
| t-butoxysodium | 29.0 g, |
| and | |
| toluene | 965 mL. |

A nitrogen gas was passed through the mixture for 30 min under ultrasonic irradiation.
Then,

| | |
|---|---|
| tris(dibenzylideneacetone)dipalladium | 2.3 g |
| and | |
| 50% (w/v) toluene solution of t-butylphopshine | 3.5 mL | were added, followed by heating and stirring for 3 h at 98° C. Then, Celite (registered trademark) was added and removed together with insolubles by filtration. Adsorption purification using silica gel and activated clay was performed at room temperature. The filtrate was then concentrated, ethyl acetate and acetone were added to the precipitated solid matter, and crystallization was performed. Crystallization was then performed with toluene, methanol, and acetone, and the solid matter was collected by filtration. As a result,

| | |
|---|---|
| a white powder of (biphenyl-3-yl)-bis(9,9-dimethylfluoren-2-yl)amine | 123 g (yield 89%) | was obtained.
(Second Step)

| | |
|---|---|
| A nitrogen-purged reaction vessel was charged with the resulting (biphenyl-3-yl)-bis(9,9-dimethylfluoren-2-yl)amine and | 123 g |
| dichloromethane | 1000 mL, | followed by cooling in an ice bath.
Then,

| | |
|---|---|
| N-bromosuccinimide | 38.5 g | was gradually added, followed by stirring for 2 h. Water was then added and the organic layer was collected by liquid separation. Washing with water was then performed, followed by drying with magnesium sulfate anhydrous and adsorption purification using silica gel and activated clay. The filtrate was concentrated to obtain a crude product. Crystallization using acetone and heptane was then performed to obtain

| | |
|---|---|
| a white powder of (6-bromobiphenyl-3-yl)-bis(9,9-dimethylfluoren-2-yl)amine | 111 g (yield 79%). |

(Third Step)

| | |
|---|---|
| Then, a nitrogen-purged reaction vessel was charged with the resulting (6-bromobiphenyl-3-yl)-bis(9,9-dimethylfluoren-2-yl)amine | 20.1 g, |
| toluene | 200 mL, |
| ethanol | 50 mL, |
| phenylboronic acid | 4.7 g, | and
an aqueous solution obtained by dissolving 5.7 g of pottassium carbonate in 21 mL of water,
and a nitrogen gas was passed through the mixture for 30 min under ultrasonic irradiation.
Then,

| | |
|---|---|
| tetrakis(triphenylphosphine)palladium | 0.56 g | was added, followed by heating and stirring for 19 h at 72° C. After cooling to room temperature, the organic layer was collected by liquid separation. Washing with water was performed twice, followed by drying with magnesium sulfate anhydrous and concentrating to obtain a crude product. Subsequent purification using column chromatography produced

| | |
|---|---|
| a white powder of bis(9,9-dimethylfluoren-2-yl)-{(1,1':2',1''-terphenyl)-4'-yl}amine | 11.5 g (yield 57%). |

This arylamine compound is Compound (1-55) having the structural formula represented by the following formula.

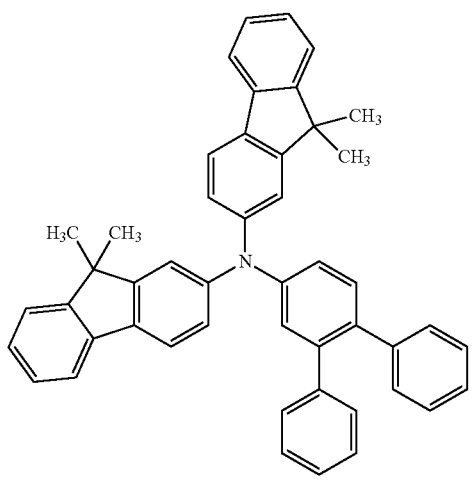

(1-55)

The structure of the resulting white powder was identified using NMR.

In $^1$H-NMR (CDCl$_3$), the following signals of 39 hydrogens were detected.

$\delta$ (ppm) = 7.65 – 7.71 (4H)

7.10 – 7.45 (23H)

1.49 (12H)

Synthesis Example 6

Synthesis of an Arylamine Compound (1-56);

the reaction was conducted under the same conditions as in Synthesis Example 5, except that 4-biphenylboronic acid was used instead of phenylboronic acid that was used in the third step of Synthesis Example 5. As a result,

| | |
|---|---|
| a white powder of bis(9,9-dimethylfluoren-2-yl)-{(1,1':2',1'':4'',1'''-quaterphenyl-5'-yl)amine | 16.7 g (yield 92%) | was obtained.

This arylamine compound is Compound (1-56) having the structural formula represented by the following formula.

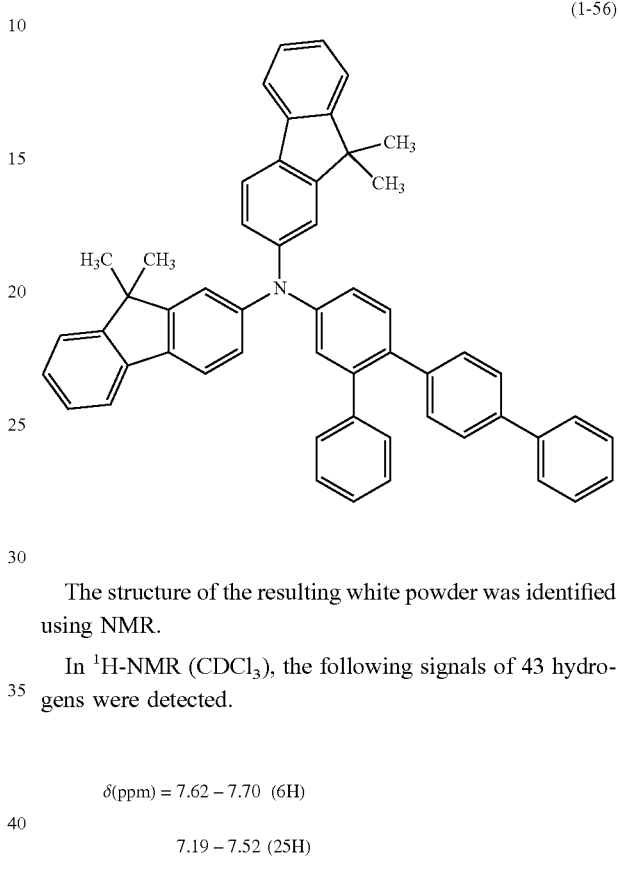

(1-56)

The structure of the resulting white powder was identified using NMR.

In $^1$H-NMR (CDCl$_3$), the following signals of 43 hydrogens were detected.

$\delta$(ppm) = 7.62 – 7.70 (6H)

7.19 – 7.52 (25H)

1.50 (12H)

Synthesis Example 7

Synthesis of an Arylamine Compound (1-60);

the reaction was conducted under the same conditions as in Synthesis Example 5, except that 4-biphenylboronic acid was used instead of phenylboronic acid that was used in the third step of Synthesis Example 5. As a result,

| | |
|---|---|
| a white powder of bis(9,9-dimethylfluoren-2-yl)-[{2-(naphthalen-2-yl)-1,1-'biphenyl}-5-yl]amine | 12.1 g (yield 67%) | was obtained.

This arylamine compound is Compound (1-60) having the structural formula represented by the following formula.

(1-60)

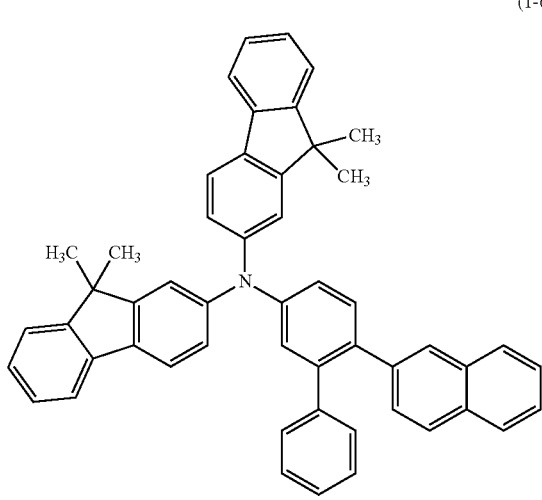

The structure of the resulting white powder was identified using NMR.

In ¹H-NMR (CDCl₃), the following signals of 41 hydrogens were detected.

δ(ppm) = 7.62 – 7.82 (8H)

7.16 – 7.51 (21H)

1.51 (12H)

Synthesis Example 8

Synthesis of an Arylamine Compound (1-87);

the reaction was conducted under the same conditions as in Synthesis Example 4, except that 4-(naphthalen-1-yl)biphenylboronic acid was used instead of 4-biphenylboronic acid that was used in the third step of Synthesis Example 4. As a result,

| | |
|---|---|
| a white powder of (biphenyl-4-yl)-{4-(naphthalen-1-yl)-{(1,1':2',1''-terphenyl)-4-yl}-9,9-dimethylfluoren-2-yl}amine | 17.8 g (yield 89%) | was obtained.

This arylamine compound is Compound (1-87) having the structural formula represented by the following formula.

(1-87)

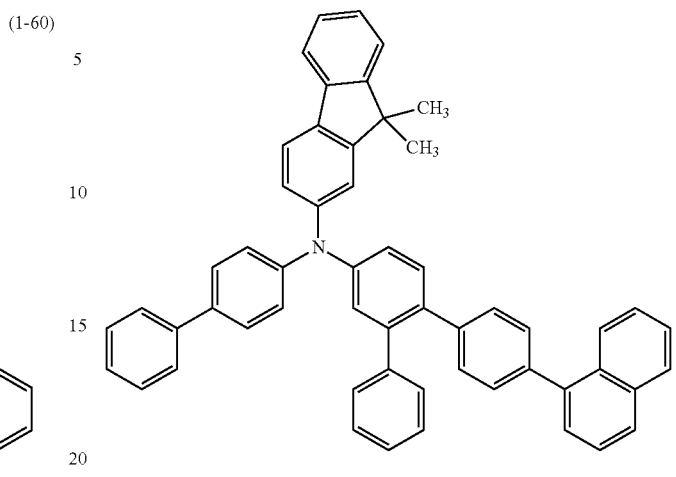

The structure of the resulting white powder was identified using NMR.

In ¹H-NMR (CDCl₃), the following signals of 41 hydrogens were detected.

δ(ppm) = 7.85 – 7.96 (3H)

= 7.18 – 74 (32H)

= 1.53 (6H)

Synthesis Example 9

Synthesis of an Arylamine Compound (1-89);

(First Step)

| | |
|---|---|
| A nitrogen-purged reaction vessel was charged with (biphenyl-4-yl)-(9,9-dimethylfluoren-2-yl)amine | 20 g, |
| 3-bromoterphenyl | 18.8 g, |
| t-butoxysodium | 6.4 g, |
| and | |
| toluene | 250 mL. |
| Then, | |
| palladium acetate | 0.12 g |
| and | |
| 50% (w/v) toluene solution of t-butylphophsine | 0.39 mL | were added, followed by heating and stirring for 13 h at 98° C. Then, Celite (registered trademark) was added, followed by the removal of insolubles by filtration. Acetone was added to the filtrate, and the precipitated solid matter was removed by filtration, followed by the concentration of the filtrate. Heptane was added to the concentrate, and the precipitate was collected by filtration. As a result,

| | |
|---|---|
| a yellow white powder of (biphenyl-4-yl)-(1,1':4',1''-terphenyl-3-yl)-(9,9-dimethylfluoren-2-yl)amine | 28.9 g (yield 88%) | was obtained.

(Second Step)

| A nitrogen-purged reaction vessel was charged with the resulting (biphenyl-4-yl)-(1,1':4',1''-terphenyl-3-yl)-(9,9-dimethylfluoren-2-yl)amine and | 28.8 g |
| --- | --- |
| dichloromethane | 500 mL, | followed by cooling in an ice bath.

Then,

| N-bromosuccinimide | 8.3 g |
| --- | --- | was gradually added, followed by stirring for 3 h. Water was then added and the organic layer was collected by liquid separation. Washing with water was then performed, followed by drying with magnesium sulfate anhydrous and adsorption purification using silica gel. The filtrate was concentrated to obtain

| a white amorphous (biphenyl-4-yl)-(6-bromo-1,1':4',1''-terphenyl-3-yl)-(9,9-dimethylfluoren-2-yl)amine | 31.2 g (yield 96%). |
| --- | --- |

(Third Step)

| Then, a nitrogen-purged reaction vessel was charged with the resulting (biphenyl-4-yl)-(6-bromo-1,1':4',1''-terphenyl-3-yl)-(9,9-dimethylfluoren-2-yl)amine | 31.1 g, |
| --- | --- |
| toluene | 310 mL, |
| ethanol | 310 mL, |
| phenylboronic acid | 5.9 g, | and an aqueous solution obtained by dissolving 8.4 g of potassium carbonate in 30 mL of water.

and a nitrogen gas was passed through the mixture for 30 min under ultrasonic irradiation.

Then,

| tetrakis(triphenylphosphine)palladium | 1.1 g |
| --- | --- | was added, followed by heating and stirring for 13 h at 72° C. After cooling to room temperature, 200 mL of water was added and the organic layer was then collected by liquid separation. Washing with water was performed twice, followed by drying with magnesium sulfate anhydrous and concentrating to obtain a crude product. The crude product was crystallization purified using acetone and then crystallization purified using heptane to obtain

| a white powder of (biphenyl-4-yl)-(1,1':2',1'':4'',1'''-quaterphenyl-4'-yl)-(9,9-dimethylfluoren-2-yl)amine | 22.0 g (yield 71%). |
| --- | --- |

This arylamine compound is Compound (1-89) having the structural formula represented by the following formula.

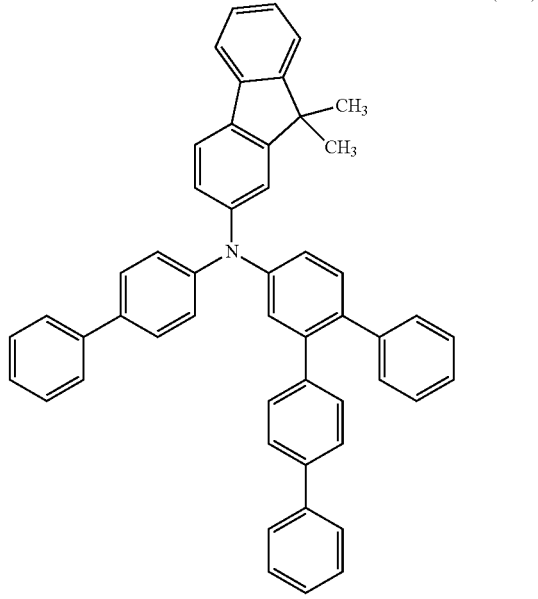

(1-89)

The structure of the resulting white powder was identified using NMR.

In $^1$H-NMR (CDCl$_3$), the following signals of 39 hydrogens were detected.

$\delta$(ppm) = 7.51 – 7.76 (7H)

7.20 – 7.48 (26H)

1.53 (6H)

Synthesis Example 10

Synthesis of an Arylamine Compound (1-92);

the reaction was conducted under the same conditions as in Synthesis Example 9, except that 2-biphenylboronic acid was used instead of phenylboronic acid that was used in the third step of Synthesis Example 9. As a result,

| a white powder of (biphenyl-4-yl)-(1,1':2',1'':2'',1''':4''',1''''-quinquephenyl-4''-yl)-(9,9-dimethylfluoren-2-yl)amine | 6.8 g (yield 30%) |
| --- | --- | was obtained.

51

This arylamine compound is Compound (1-92) having the structural formula represented by the following formula.

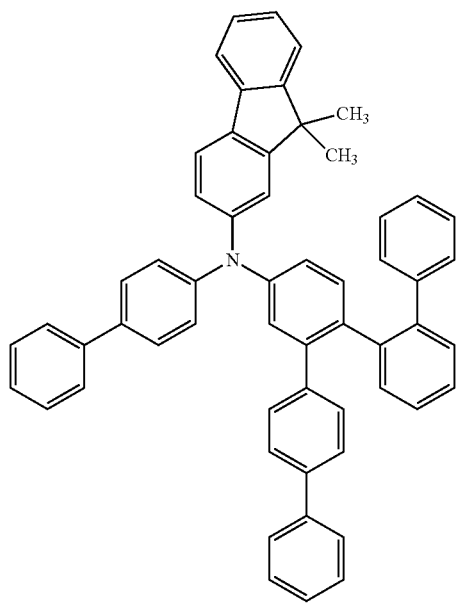

(1-92)

The structure of the resulting white powder was identified using NMR.

In $^1$H-NMR (CDCl$_3$), the following signals of 43 hydrogens were detected.

$\delta$(ppm) = 7.15 – 7.59 (31H)

= 6.64 – 6.78 (4H)

= 1.54 (6H)

Synthesis Example 11

Synthesis of an Arylamine Compound (1-94);

the reaction was conducted under the same conditions as in Synthesis Example 9, except that {4-(naphthalen-1-yl)phenyl}-(6-bromobiphenyl-3-yl)-(9,9-dimethylfluoren-2-yl)amine and 4-biphenylboronic acid were used instead of (biphenyl-4-yl)-(6-bromo-1,1': 4',1"-terphenyl-3-yl)-(9,9dimethylfluoren-2-yl)amine and phenylboronic acid that were used in the third step of Synthesis Example 9. As a result,

| a white powder of {4-(naphthalen-1-yl)phenyl}-(1,1':2',1":4",1'"-quaterphenyl-5'-yl)-(9,9dimethylfluoren-2-yl)amine | 19.9 g (yield 89%) |
|---|---| was obtained.

52

This arylamine compound is Compound (1-94) having the structural formula represented by the following formula.

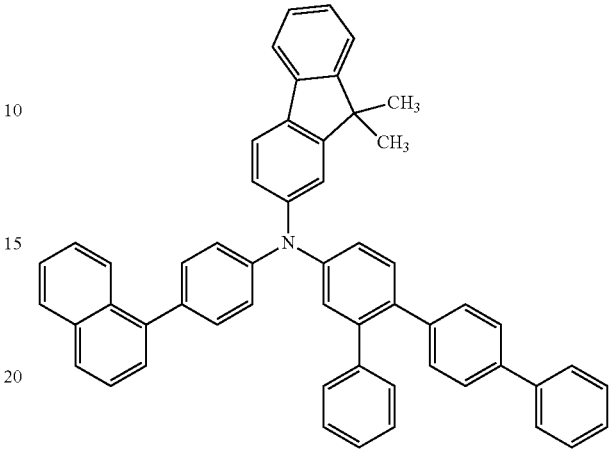

(1-94)

The structure of the resulting white powder was identified using NMR.

In $^1$H-NMR (CDCl$_3$), the following signals of 41 hydrogens were detected.

$\delta$(ppm) = 8.07 – 8.13 (1H)

7.88 – 7.96 (2H)

7.16 – 7.72 (32H)

1.54 (6H)

Synthesis Example 12

Synthesis of an Arylamine Compound (1-113);
(First Step)

| A nitrogen-purged reaction vessel was charged with | |
|---|---|
| (biphenyl-3-yl)-(biphenyl-4-yl)amine | 41.4 g, |
| 2-(4-bromophenyl)-9,9-dimethylfluorene | 47.2 g, |
| t-butoxysodium and | 14.9 g, |
| toluene | 760 mL. |

A nitrogen gas was passed through the mixture for 30 min under ultrasonic irradiation.
Then,

| palladium acetate and | 0.58 g |
|---|---|
| 50% (w/v) toluene solution of t-butylphosphine | 2.1 g | were added, followed by heating and stirring for 2 h at 102° C. Then, Celite (registered trademark) was added, followed by the removal of insolubles by filtration. The filtrate was concentrated and purified using column chromatography to obtain

| | |
|---|---|
| a white powder of (biphenyl-3-yl)-(biphenyl-4-yl)-{4-(9,9-dimethylfluoren-2-yl)plhenyl}amine | 69.0 g (yield 91%). |

(Second Step)

| | |
|---|---|
| A nitrogen-purged reaction vessel was charged with the resulting (biphenyl-3-yl)-(biphenyl-4-yl)-{4-(9,9-dimethylfluoren-2-yl)plhenyl}amine and | 68.8 g |
| dimethylformamide | 680 mL, | followed by cooling in an ice bath.
Then,

| | |
|---|---|
| N-bromosuccinimide | 21.8 g | was gradually added, followed by stirring for 5 h. The reaction liquid was poured into water and stirred for 1 h, and the precipitated crude product was then collected by filtration. Methanol was added to the resulting crude product, and purification by dispersion washing under refluxing was performed to obtain

| | |
|---|---|
| a white powder of (6-bromobiphenyl-3-yl)-(biphenyl-4-yl)-{4-(9,9-dimethylfluoren-2-yl)phenyl}amine | 75.3 g (yield 97%). |

(Third Step)

| | |
|---|---|
| Then, a nitrogen-purged reaction vessel was charged with the resulting (6-bromobiphenyl-3-yl)-(biphenyl-4-yl)-{4-(9,9-dimethylfluoren-2-yl)phenyl}amine | 17.5 g, |
| toluene | 140 mL, |
| ethanol | 35 mL, |
| phenylboronic acid | 3.5 g, | and
an aqueous solution obtained by dissolving 4.3 g of potassium carbonate in 31 mL of water,
and a nitrogen gas was passed through the mixture for 30 min under ultrasonic irradiation.
Then,

| | |
|---|---|
| tetrakis(triphenylphosphine)palladium | 0.60 g | was added, followed by heating and stirring for 20 h at 72° C. After cooling to room temperature, the organic layer was collected by liquid separation. Washing with water was performed twice, followed by drying with magnesium sulfate anhydrous and concentrating to obtain a crude product. The crude product was then purified using column chromatography to obtain

| | |
|---|---|
| a white powder of (biphenyl-4-yl)-{4-(9,9-dimethylfluoren-2-yl)phenyl}-(1,1':2',1'''-terphenyl-4'-yl)amine | 8.3 g (yield 48%). |

This arylamine compound is Compound (1-113) having the structural formula represented by the following formula.

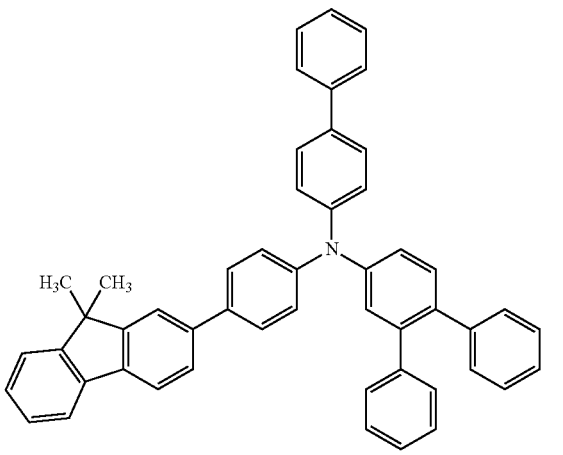

(1-113)

The structure of the resulting white powder was identified using NMR.

In $^1$H-NMR (CDCl$_3$), the following signals of 39 hydrogens were detected.

$\delta$(ppm) = 7.77 – 82 (2H)

7.57 – 7.70 (9H)

7.18 – 7.50 (22H)

1.55 (6H)

Synthesis Example 13

Synthesis of an Arylamine Compound (1-115);
the reaction was conducted under the same conditions as in Synthesis Example 12, except that 3-biphenylboronic acid was used instead of phenylboronic acid that were used in the third step of Synthesis Example 12. As a result,

| | |
|---|---|
| a white powder of (biphenyl-4-yl)-{4-(9,9-dimethylfluoren-2-yl)phenyl}-{(1,1':2',1'':3'', 1'''-quaterphenyl)-5'-yl}amine | 8.7 g (yield 49%) | was obtained.

This arylamine compound is Compound (1-115) having the structural formula represented by the following formula.

(1-115)

The structure of the resulting white powder was identified using NMR.

In $^1$H-NMR (CDCl$_3$), the following signals of 43 hydrogens were detected.

$\delta$(ppm) = 7.72 – 7.86 (2H)

7.46 – 7.64 (7H)

7.17 – 7.44 (28H)

1.53 (6H)

Synthesis Example 14

Synthesis of an Arylamine Compound (1-122);

the reaction was conducted under the same conditions as in Synthesis Example 4, except that (6-bromobiphenyl-3-yl)-(biphenyl-4-yl)-(9,9-diphenylfluoren-2-yl)amine and phenylboronic acid were used instead of (6-bromobiphenyl-3-yl)-(biphenyl-4-yl)-(9,9-dimethylfluoren-2-yl)amine and 4-biphenylboronic acid that were used in the third step of Synthesis Example 4. As a result,

| | |
|---|---|
| a white powder of (biphenyl-4-yl)-(1,1':2',1''-terphenyl-4'-yl)-(9,9-diphenylfluoren-2-yl)amine | 11.0 g (yield 61%) | was obtained.

This arylamine compound is Compound (1-122) having the structural formula represented by the following formula.

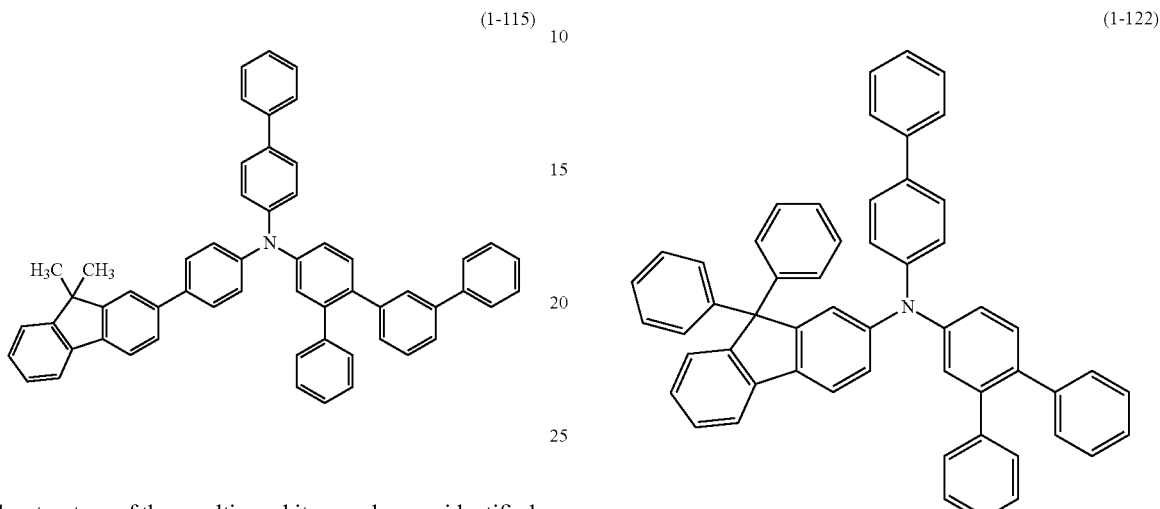

(1-122)

The structure of the resulting white powder was identified using NMR.

In $^1$H-NMR (CDCl$_3$), the following signals of 39 hydrogens were detected.

$\delta$(ppm) = 7.60 – 7.74 (4H)

7.14 – 7.52 (33H)

7.00 – 7.03 (2H)

Synthesis Example 15

Synthesis of an Arylamine Compound (1-123);

the reaction was conducted under the same conditions as in Synthesis Example 4, except that (6-bromobiphenyl-3-yl)-(biphenyl-4-yl)-(9,9-diphenylfluoren-2-yl)amine was used instead of (6-bromobiphenyl-3-yl)-(biphenyl-4-yl)-(9,9-dimethylfluoren-2-yl)amine that was used in the third step of Synthesis Example 4. As a result,

| | |
|---|---|
| a white powder of (biphenyl-4-yl)-(1,1':2',1'':4'',1'''-quaterphenyl-5'-yl)-(9,9-diphenylfluoren-2-yl)amine | 6.5 g (yield 71%) | was obtained.

This arylamine compound is Compound (1-123) having the structural formula represented by the following formula.

(1-123)

The structure of the resulting white powder was identified using NMR.

In ¹H-NMR (CDCl$_3$), the following signals of 43 hydrogens were detected.

δ(ppm) = 7.61 – 7.77 (6H)

7.20 – 7.51 (34H)

7.06 – 7.11 (3H)

Synthesis Example 16

Synthesis of an Arylamine Compound (1-124);

the reaction was conducted under the same conditions as in Synthesis Example 4, except that (6-bromobiphenyl-3-yl)-(biphenyl-4-yl)-(9,9-diphenylfluoren-2-yl)amine and 4-biphenylboronic acid were used instead of (6-bromobiphenyl-3-yl)-(biphenyl-4-yl)-(9,9-dimethylfluoren-2-yl)amine and 4-biphenylboronic acid that were used in the third step of Synthesis Example 4. As a result,

| | |
|---|---|
| a white powder of (biphenyl-4-yl)-(1,1':2',1'':3'',1'''-quaterphenyl-5'-yl)-(9,9-diphenylfluoren-2-yl)amine | 8.0 g (yield 87%) | was obtained.

This arylamine compound is Compound (1-124) having the structural formula represented by the following formula.

(1-124)

The structure of the resulting white powder was identified using NMR.

In ¹H-NMR (CDCl$_3$), the following signals of 43 hydrogens were detected.

δ(ppm) = 7.70 – 7.76 (2H)

7.63 – 7.65 (2H)

7.18 – 7.54 (36H)

7.08 – 7.12 (3H)

Synthesis Example 17

Synthesis of an Arylamine Compound (1-128);
(First Step)

| | |
|---|---|
| A nitrogen-purged reaction vessel was charged with (9,9-diphenylfluoren-2-yl)-amine | 51.5 g, |
| 3-bromobiphenyl | 30.0 g, |
| t-butoxysodium | 24.7 g, |
| and | |
| toluene | 300 mL. |
| Then, | |
| tris(dibenzylideneacetone)dipalladium | 2.4 g and |
| 2,2'-bis(diphenylphosphino)-1,1-binaphthyl | 1.6 g | were added, followed by heating and stirring for 24 h at 75° C. Then, methanol was added and solids were collected by filtration, followed by the addition of toluene, heating and dissolving, and removal of insolubles by filtration. The filtrate was concentrated and purified by recrystallization using toluene and then purified by recrystallization using heptane to obtain

| | |
|---|---|
| a yellow white powder of (biphenyl-3-yl)-(9,9-diphenylfluoren-2-yl)amine | 45.0 g (yield 72%). |

(Second Step)

| | |
|---|---|
| A nitrogen-purged reaction vessel was charged with the resulting (biphenyl-3-yl)-(9,9-diphenylfluoren-2-yl)amine | 43.0 g |
| and | |
| dimethylformamide | 430 mL, | followed by cooling in an ice bath.

Then,

| N-bromosuccinimide | 16.5 g | was gradually added, followed by stirring for 6 h. The reaction liquid was poured into water and stirred for 1 h, and the precipitated crude product was then collected by filtration. Methanol was added to the resulting crude product, and purification by dispersion washing under refluxing was performed to obtain

| a white powder of (6-bromobiphenyl-3-yl)-(9,9-diphenylfluoren-2-yl)amine | 41.0 g (yield 82%). |

(Third Step)

| Then, a nitrogen-purged reaction vessel was charged with | |
|---|---|
| the resulting (6-bromobiphenyl-3-yl)-(9,9-diphenylfluoren-2-yl)amine | 10.2 g, |
| toluene | 82 mL, |
| ethanol | 40 mL, |
| 4-biphenylboronic acid | 4.3 g, | and
an aqueous solution obtained by dissolving 5.0 g of potassium carbonate in 30 mL of water,
and a nitrogen gas was passed through the mixture for 30 min under ultrasonic irradiation.
Then,

| tetrakis(triphenylphosphine)palladium | 0.5 g | was added, followed by heating and stirring for 13 h at 72° C. After cooling to room temperature, 200 mL of water was added and the organic layer was collected by liquid separation. Washing with water was performed twice, followed by drying with magnesium sulfate anhydrous and concentrating to obtain a crude product. The crude product was then purified using column chromatography to obtain

| a white powder of (1,1':2',1'':4'',1'''-quaterphenyl-5'-yl)-(9,9-diphenylfluoren-2-yl)amine | 10.2 g (yield 88%). |

(Fourth Step)

| A nitrogen-purged reaction vessel was charged with | 10.1 g, |
|---|---|
| the resulting (1,1':2',1'':4'',1'''-quaterphenyl-5'-yl)-(9,9-diphenylfluoren-2-yl)amine | |
| bromobenzene | 2.7 g, |
| t-butoxysodium | 1.8 g, |
| and | |
| toluene | 100 mL. |

A nitrogen gas was passed through the mixture for 30 min under ultrasonic irradiation.
Then,

| palladium acetate | 0.07 g |
| and | |
| 50% (w/v) toluene solution of t-butylphopshine | 0.1 mL | were added, followed by heating and stirring for 3 h at 100° C. After cooling to 60° C., Celite (registered trademark) and silica gel were added and insolubles were removed by filtration. The filtrate was then concentrated and purified by column chromatography. As a result,

| a white powder of phenyl-(1,1':2',1'':4'',1'''-quaterphenyl-5'-yl)-(9,9-diphenylfluoren-2-yl)amine | 4.2 g (yield 37%) | was obtained.

This arylamine compound is Compound (1-128) having the structural formula represented by the following formula.

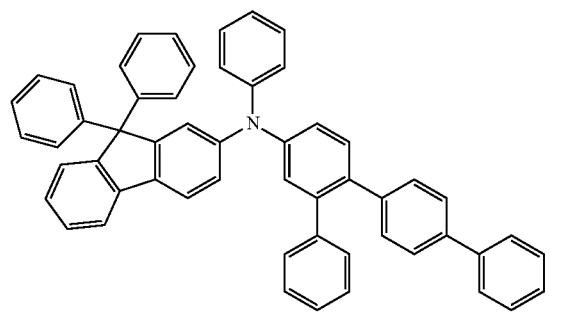

(1-128)

The structure of the resulting white powder was identified using NMR.

In $^1$H-NMR (CDCl$_3$), the following signals of 39 hydrogens were detected.

$\delta$ (ppm) = 7.55 – 7.79 (4H)

7.06 – 7.52 (35H)

Synthesis Example 18

Synthesis of an Arylamine Compound (1-130);
the reaction was conducted under the same conditions as in Synthesis Example 17, except that 2-biphenylboronic acid was used instead of 4-biphenylboronic acid that was used in the third step of Synthesis Example 17. As a result,

| a white powder of phenyl-(1,1':2',1'':2'',1'''-quaterphenyl-5'-yl)-(9,9-diphenylfluoren-2-yl)amine | 9.5 g (yield 82%) |

This arylamine compound is Compound (1-130) having the structural formula represented by the following formula.

(1-130)

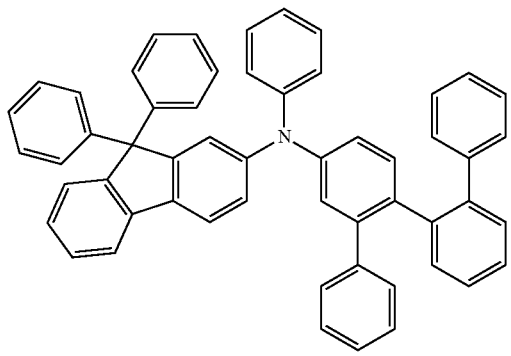

The structure of the resulting white powder was identified using NMR.

In $^1$H-NMR (CDCl$_3$), the following signals of 39 hydrogens were detected.

$\delta$(ppm) = 7.62 – 7.76 (2H)

6.95 – 7.49 (33H)

6.68 – 6.70 (2H)

6.53 – 6.55 (2H)

Synthesis Example 19

Synthesis of an Arylamine Compound (1-133);

(First Step)

| | |
|---|---|
| a nitrogen-purged reaction vessel was charged with (biphenyl-3-yl)-(biphenyl-4-yl)amine and | 40.0 g |
| dimethylformamide | 320 mL, | followed by cooling in an ice bath.

Then,

| | |
|---|---|
| N-bromosuccinimide | 23.3 g | was gradually added, followed by stirring for 6 h. The reaction liquid was poured into water and extracted with dichloromethane, and the organic layer was washed with water, followed by drying using magnesium sulfate anhydrous and concentrating to obtain a crude product. The crude product was purified by recrystallization using dichloromethane and purified by recrystallization using heptane to obtain

| | | |
|---|---|---|
| a white powder of (6-bromobiphenyl-3-yl)-(biphenyl-4-yl)amine | 32 g | (yield 64%). |

(Second Step)

| | |
|---|---|
| A nitrogen-purged reaction vessel was charged with the resulting (6-bromobiphenyl-3-yl)-(biphenyl-4-yl)amine | 10.0 g, |
| toluene | 80 mL, |
| ethanol | 40 mL, |
| phenylboronic acid | 3.7 g, | and an aqueous solution obtained by dissolving 6.9 g of potassium carbonate in 30 mL of water, and a nitrogen gas was passed through the mixture for 30 min under ultrasonic irradiation.

Then,

| | |
|---|---|
| tetrakis(triphenylphosphine)palladium | 0.60 g | was added, followed by heating and stirring for 6 h at 70° C. After cooling to room temperature, the organic layer was collected by liquid separation. Washing with water was performed twice, followed by drying with magnesium sulfate anhydrous and concentrating to obtain a crude product. The crude product was then purified using column chromatography to obtain

| | |
|---|---|
| a white powder of (biphenyl-4-yl)-(1,1':2',1''-terphenyl-4'-yl)amine | 6.5 g (yield 65%). |

(Third Step)

| | |
|---|---|
| A nitrogen-purged reaction vessel was charged with the resulting (biphenyl-4-yl)-(1,1':2',1''-terphenyl-4'-yl)amine | 6.5 g, |
| 2-bromo-9,9-spirobifluorene | 7.8 g, |
| t-butoxysodium and | 1.9 g, |
| toluene | 65 mL. |

A nitrogen gas was passed through the mixture for 30 min under ultrasonic irradiation.

Then,

| | |
|---|---|
| palladium acetate and | 0.1 g |
| 50% (w/v) toluene solution of t-butylphopshine | 0.3 mL | were added, followed by heating and stirring for 3 h at 100° C. After cooling to 60° C., Celite (registered trademark) and silica gel were added and insolubles were removed by filtration. The filtrate was then concentrated and purified using column chromatography. As a result,

| | |
|---|---|
| a white powder of (biphenyl-4-yl)-(1,1':2',1''-terphenyl-4'-yl)-(9,9'-spirobifluoren-2-yl)amine | 6.0 g (yield 52%) | was obtained.

This arylamine compound is Compound (1-133) having the structural formula represented by the following formula.

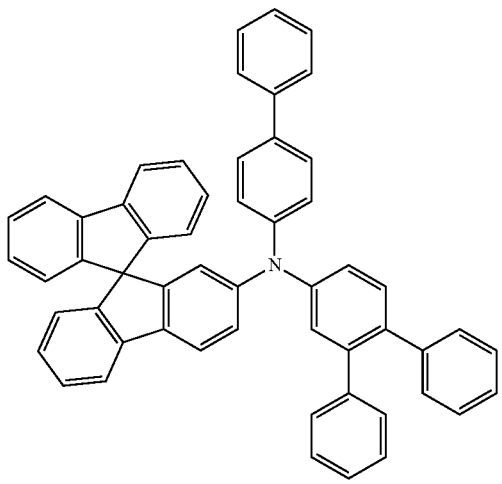
(1-133)

The structure of the resulting white powder was identified using NMR.

In $^1$H-NMR (CDCl$_3$), the following signals of 37 hydrogens were detected.

$\delta$(ppm) = 7.81 – 7.88 (4H)

7.59 – 7.62 (2H)

7.34 – 7.50 (8H)

7.03 – 7.28 (15H)

6.73 – 6.92 (8H)

Synthesis Example 20

Synthesis of an Arylamine Compound (1-136);

the reaction was conducted under the same conditions as in Synthesis Example 19, except that 2-biphenylboronic acid was used instead of phenylboronic acid that was used in the second step of Synthesis Example 19. As a result,

| a white powder of (biphenyl-4-yl)-(1,1':2',1'':4'',1'''-quaterphenyl-5'-yl)-(9,9'-spirobifluoren-2-yl)amine | 6.1 g (yield 42%) |
|---|---| was obtained.

This arylamine compound is Compound (1-136) having the structural formula represented by the following formula.

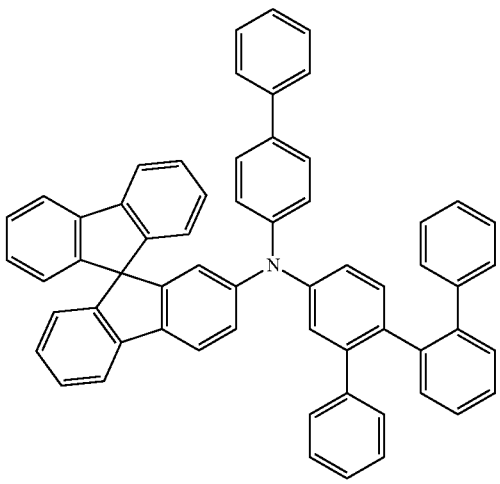
(1-136)

The structure of the resulting white powder was identified using NMR.

In $^1$H-NMR (CDCl$_3$), the following signals of 41 hydrogens were detected.

$\delta$(ppm) = 7.75 – 7.86 (4H)

7.34 – 7.58 (14H)

6.85 – 20 (17H)

6.70 – 6.72 (2H)

6.59 – 6.62 (2H)

6.40 – 6.42 (2H)

Synthesis Example 21

Synthesis of an Arylamine Compound (1-147);
(First Step)

| A nitrogen-purged reaction vessel was charged with (1,1':2',1''-terphenyl-4'-yl)amine | 14.5 g, |
|---|---|
| 9-bromophenanthrene | 18.0 g, |
| t-butoxysodium and | 10.8 g, |
| toluene | 145 mL, | followed by degassing under reduced pressure and then purging with nitrogen.
Then,

| tris(dibenzylideneacetone)dipalladium and | 1.0 g |
|---|---|
| 2,2'-bis(diphenylphosphino)-1,1-binaphthyl | 1.7 g | were added, followed by heating and stirring for 13 h at 100° C. Then, water and dichloromethane were added and the organic layer was collected by performing an extraction operation, followed by drying with magnesium sulfate anhydrous and concentrating to obtain a crude product. The crude product was purified using column chromatography to obtain

| a yellow white powder of (phenanthren-9-yl)-(1,1':2',1''-terphenyl-4'-yl)amine | 18.4 g (yield 77%). |
|---|---|

(Second Step)

| A nitrogen-purged reaction vessel was charged with the resulting (phenanthren-9-yl)-(1,1':2',1''-terphenyl-4'-yl)amine | 8.0 g, |
|---|---|
| 2-bromo-9,9-dimethylfluorene | 5.7 g, |
| t-butoxysodium | 2.2 g, |
| and | |
| toluene | 80 mL. |

A nitrogen gas was passed through the mixture for 30 min under ultrasonic irradiation.
Then,

| palladium acetate | 0.1 g |
|---|---|
| and | |
| 50% (w/v) toluene solution of t-butylphopshine | 0.15 mL | were added, followed by heating and stirring for 13 h at 100° C. Celite (registered trademark) and silica gel were added and insolubles were removed by filtration. The filtrate was then concentrated and purified using column chromatography. As a result,

| a white powder of (phenanthren-9-yl)-(1,1':2',1''-terphenyl-4'-yl)-(9,9-dimethylfluoren-2-yl)amine | 3.2 g (yield 28%) |
|---|---| was obtained.
This arylamine compound is Compound (1-147) having the structural formula represented by the following formula.

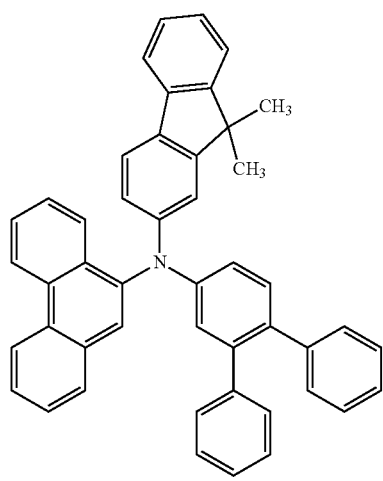

(1-147)

The structure of the resulting white powder was identified using NMR.

In $^1$H-NMR (CDCl$_3$), the following signals of 35 hydrogens were detected.

$\delta$(ppm) = 8.75 – 8.82 (2H)

8.19 – 8.22 (1H)

7.09 – 7.86 (26H)

1.48 (6H)

<Evaluation Test 1>

The glass transition temperature of the arylamine compounds synthesized in the aforementioned synthesis examples was determined with a high-sensitivity differential scanning calorimeter (DSC3100SA, manufactured by Bruker AXS K.K.). The results are presented below.

| | Glass transition temperature |
|---|---|
| Compound (1-9) of Synthesis Example 2 | 116° C. |
| Compound (1-20) of Synthesis Example 3 | 127° C. |
| Compound (1-29) of Synthesis Example 4 | 116° C. |
| Compound (1-55) of Synthesis Example 5 | 119° C. |
| Compound (1-56) of Synthesis Example 6 | 132° C. |
| Compound (1-60) of Synthesis Example 7 | 128° C. |
| Compound (1-87) of Synthesis Example 8 | 119° C. |
| Compound (1-89) of Synthesis Example 9 | 119° C. |
| Compound (1-92) of Synthesis Example 10 | 123° C. |
| Compound (1-94) of Synthesis Example 11 | 121° C. |
| Compound (1-113) of Synthesis Example 12 | 112° C. |
| Compound (1-115) of Synthesis Example 13 | 112° C. |
| Compound (1-122) of Synthesis Example 14 | 125° C. |
| Compound (1-123) of Synthesis Example 15 | 136° C. |
| Compound (1-124) of Synthesis Example 16 | 124° C. |
| Compound (1-128) of Synthesis Example 17 | 125° C. |
| Compound (1-130) of Synthesis Example 18 | 114° C. |
| Compound (1-133) of Synthesis Example 19 | 128° C. |
| Compound (1-136) of Synthesis Example 20 | 133° C. |
| Compound (1-147) of Synthesis Example 21 | 128° C. |

It follows from the results presented hereinabove that the arylamine compound represented by the general formula (1) has a glass transition temperature of 100° C. or higher, in particular 110° C. or higher, which indicates a stable thin-film state.

<Evaluation Test 2>

A vapor-deposited film with a thickness of 100 nm was fabricated on an ITO substrate by using the arylamine compounds produced in the synthesis examples, and the work function was measured with an ionization potential measuring device (PYS-202, manufactured by Sumitomo Heavy Industries, Ltd.).
The results are presented below.

| | Work function |
|---|---|
| Compound (1-1) of Synthesis Example 1 | 5.68 eV |
| Compound (1-9) of Synthesis Example 2 | 5.70 eV |
| Compound (1-20) of Synthesis Example 3 | 5.66 eV |
| Compound (1-29) of Synthesis Example 4 | 5.62 eV |
| Compound (1-55) of Synthesis Example 5 | 5.55 eV |
| Compound (1-56) of Synthesis Example 6 | 5.55 eV |
| Compound (1-60) of Synthesis Example 7 | 5.62 eV |
| Compound (1-87) of Synthesis Example 8 | 5.63 eV |
| Compound (1-89) of Synthesis Example 9 | 5.63 eV |
| Compound (1-92) of Synthesis Example 10 | 5.65 eV |
| Compound (1-94) of Synthesis Example 11 | 5.63 eV |
| Compound (1-113) of Synthesis Example 12 | 5.63 eV |

| | Work function |
|---|---|
| Compound (1-115) of Synthesis Example 13 | 5.64 eV |
| Compound (1-122) of Synthesis Example 14 | 5.66 eV |
| Compound (1-123) of Synthesis Example 15 | 5.67 eV |
| Compound (1-124) of Synthesis Example 16 | 5.68 eV |
| Compound (1-128) of Synthesis Example 17 | 5.71 eV |
| Compound (1-130) of Synthesis Example 18 | 5.73 eV |
| Compound (1-133) of Synthesis Example 19 | 5.64 eV |
| Compound (1-136) of Synthesis Example 20 | 5.65 eV |
| Compound (1-147) of Synthesis Example 21 | 5.70 eV |

It follows from the results presented hereinabove that the arylamine compound represented by the general formula (1) shows an advantageous energy level and has a satisfactory hole transport capability when compared with the work function of 5.4 eV of the typical hole transport materials such as NPD and TPD.

Synthesis Example 24

Synthesis of N-aromatic Substituted Nitrogen-containing Heterocyclic Compound (2-1);

| | |
|---|---|
| a nitrogen-purged reaction vessel was charged with 7,7-dimethyl-7,12-dihydrobenzo[4,5]thieno[3,2-g]indeno[1,2-b]indole | 4.9 g, |
| 2-chloro-4-phenylquinazoline | 5.7 g, |
| tris(dibenzylideneacetone)dipalladium | 0.3 g, |
| tri-tert-butylphosphonium tetrafluoroborate | 0.4 g, |
| tert-butoxysodium and | 4.0 g, |
| xylene | 74 ml. |

The mixture was heated and stirred for 12 h under refluxing. After cooling to room temperature, ethyl acetate and water were added and the organic layer was collected by liquid separation. The organic layer was concentrated and purified by column chromatography. As a result,

| | |
|---|---|
| a powder of 7,7-dimethyl-12-(4-phenylquinazolin-2-yl)-7,12-dihydrobenzo[4,5]thieno[3,2-g]indeno[1,2-b]indole | 3.0 g (yield 38%) | was obtained.
The resulting N-aromatic substituted nitrogen-containing heterocyclic compound is the indenoindole compound (2-1) represented by the following structural formula.

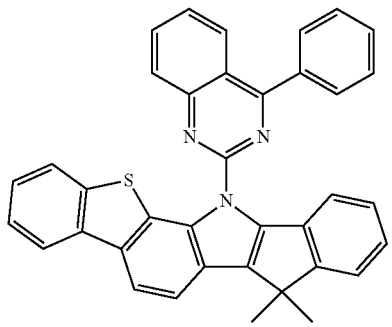

(2-1)

Synthesis Example 25

Synthesis of N-aromatic Substituted Nitrogen-containing Heterocyclic Compound (2-2);

the reaction was conducted under the same conditions as in Synthesis Example 24, except that 2-chloro-4-phenylbenzo[h]quinazoline was used instead of 2-chloro-4-phenylquinazoline used in Synthesis Example 24. As a result,

| | |
|---|---|
| a powder of 7,7-dimethyl-12-(4-phenylbenzo[h]quinazolin-2-yl)-7,12-dihydrobenzo[4,5]thieno[3,2-g]indeno[1,2-b]indole | 3.2 g (yield 38%) | was obtained.
The resulting N-aromatic substituted nitrogen-containing heterocyclic compound is the indenoindole compound (2-2) represented by the following structural formula.

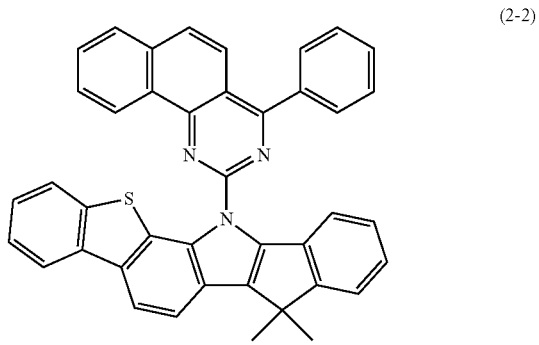 [SMILES: CC1(C)c2ccccc2-c2c1c1ccc3c4ccccc4sc3c1n2-c1nc(-c2ccccc2)c2ccc3ccccc3c2n1]

(2-2)

Synthesis Example 26

Synthesis of N-aromatic Substituted Nitrogen-containing Heterocyclic Compound (2-3);

the reaction was conducted under the same conditions as in Synthesis Example 24, except that 2-chloro-4,7-diphenylquinazoline was used instead of 2-chloro-4-phenylquinazoline used in Synthesis Example 24. As a result,

| | |
|---|---|
| a powder of 12-(4,7- diphenylquinazolin-2-yl)-7,7-dimethyl-7,12-dihydrobenzo[4,5]thieno[3,2-g]indeno[1,2-b]indole | 3.3 g (yield 38%) | was obtained.
The resulting N-aromatic substituted nitrogen-containing heterocyclic compound is the indenoindole compound (2-3) represented by the following structural formula.

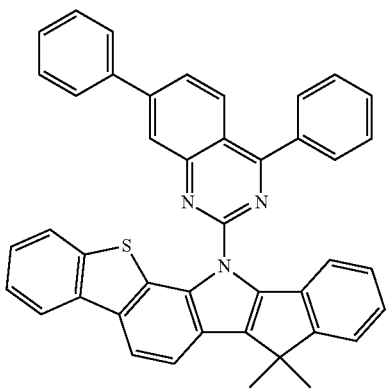

(2-3)

Synthesis Example 27

Synthesis of N-aromatic Substituted Nitrogen-containing Heterocyclic Compound (2-4);

the reaction was conducted under the same conditions as in Synthesis Example 24, except that 2-chloro-4,6-diphenylquinazoline was used instead of 2-chloro-4-phenylquinazoline used in Synthesis Example 24. As a result,

| | |
|---|---|
| a powder of 12-(4,6- diphenylquinazolin-2-yl)-7,7-dimethyl-7,12-dihydrobenzo[4,5]thieno[3,2-g]indeno[1,2-b]indole | 3.3 g (yield 38%) | was obtained.

The resulting N-aromatic substituted nitrogen-containing heterocyclic compound is the indenoindole compound (2-4) represented by the following structural formula.

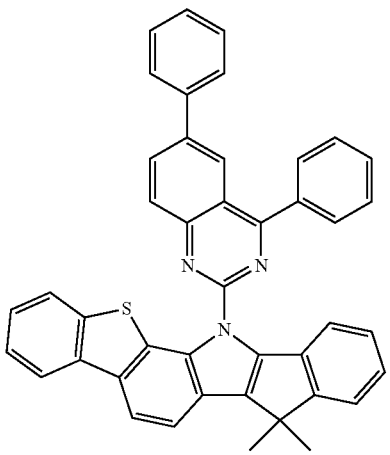

(2-4)

Synthesis Example 28

Synthesis of N-aromatic Substituted Nitrogen-containing Heterocyclic Compound (2-5);

the reaction was conducted under the same conditions as in Synthesis Example 24, except that 13,13-dimethyl-8,13-dihydrobenzo[4,5]thieno[3,2-e]indeno[1,2-b]indole was used instead of 7,7-dimethyl-7,12-dihydrobenzo[4,5]thieno[3,2-g]indeno[1,2-b]indole used in Synthesis Example 24. As a result,

| | |
|---|---|
| a powder of 13,13-dimethyl-8-(4-phenylquinazolin-2-yl)-8,13-dihydrobenzo[4,5]thieno[3,2-e]indeno[1,2-b]indole | 3.0 g (yield 38%) | was obtained.

The resulting N-aromatic substituted nitrogen-containing heterocyclic compound is the indenoindole compound (2-5) represented by the following structural formula.

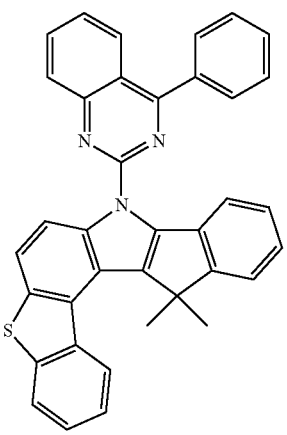

(2-5)

Synthesis Example 29

Synthesis of N-aromatic Substituted Nitrogen-containing Heterocyclic Compound (2-6);

the reaction was conducted under the same conditions as in Synthesis Example 28, except that 2-chloro-4,6-diphenylquinazoline was used instead of 2-chloro-4-phenylquinazoline used in Synthesis Example 28. As a result,

| | |
|---|---|
| a powder of 8-(4,6- diphenylquinazolin-2-yl)-13,13-dimethyl-8,13-dihydrobenzo[4,5]thieno[3,2-e]indeno[1,2-b]indole | 3.3 g (yield 38%) | was obtained.

The resulting N-aromatic substituted nitrogen-containing heterocyclic compound is the indenoindole compound (2-6) represented by the following structural formula.

(2-6)

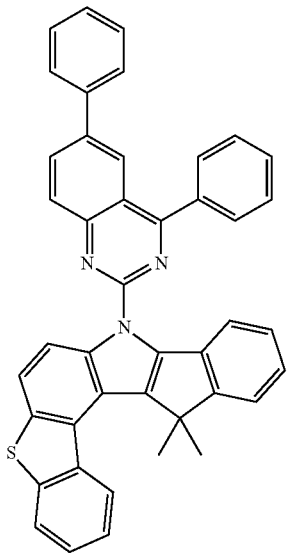

Synthesis Example 30

Synthesis of N-aromatic Substituted Nitrogen-containing Heterocyclic Compound (2-7);

the reaction was conducted under the same conditions as in Synthesis Example 24, except that 7,7,13,13-tetramethyl-7,13-dihydro-5H-diindeno[1,2-b:1',2'-f]indole was used instead of 7,7-dimethyl-7,12-dihydrobenzo[4,5]thieno[3,2-g]indeno[1,2-b]indole used in Synthesis Example 24. As a result,

| a powder of 7,7,13,13-tetramethyl-5-(4-phenylquinazolin-2-yl)-7,13-dihydro-5H-diindeno[1,2-b:1',2'-f]indole | 3.0 g (yield 38%) |
|---|---| was obtained.

The resulting N-aromatic substituted nitrogen-containing heterocyclic compound is the indenoindole compound (2-7) represented by the following structural formula.

(2-7)

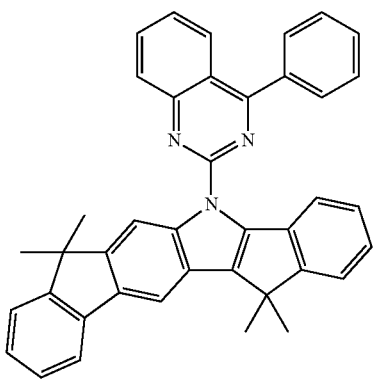

Synthesis Example 31

Synthesis of N-aromatic Substituted Nitrogen-containing Heterocyclic Compound (2-8);

the reaction was conducted under the same conditions as in Synthesis Example 30, except that 2-(3-bromophenyl)-4-phenylquinazoline was used instead of 2-chloro-4-phenylquinazoline used in Synthesis Example 30. As a result,

| a powder of 7,7,13,13-tetramethyl-5-[3-(4-phenylquinazolin-2-yl)plhenyl]-7,13-dihydro-5H-diindeno[1,2-b:1',2'-f]indole | 3.4 g (yield 38%) |
|---|---| was obtained.

The resulting N-aromatic substituted nitrogen-containing heterocyclic compound is the indenoindole compound (2-8) represented by the following structural formula.

(2-8)

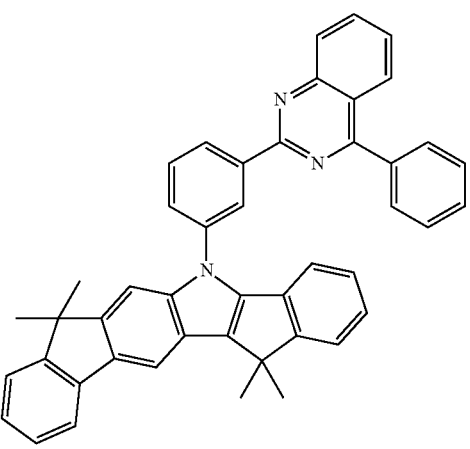

Synthesis Example 32

Synthesis of N-aromatic Substituted Nitrogen-containing Heterocyclic Compound (2-9);

the reaction was conducted under the same conditions as in Synthesis Example 25, except that 7,7-dimethyl-7,12-dihydrobenzofuro[3,2-g]indeno[1,2-b]indole was used instead of 7,7-dimethyl-7,12-dihydrobenzo[4,5]thieno[3,2-g]indeno[1,2-b]indole used in Synthesis Example 25. As a result,

| a powder of 7,7-dimethyl-12-(4-phenylbenzo[h]quinazolin-2-yl)-7,12-dihydrobenzofuro[3,2-g]indeno[1,2-b]indole | 3.0 g (yield 38%) |
|---|---| was obtained.

The resulting N-aromatic substituted nitrogen-containing heterocyclic compound is the indenoindole compound (2-9) represented by the following structural formula.

(2-9)

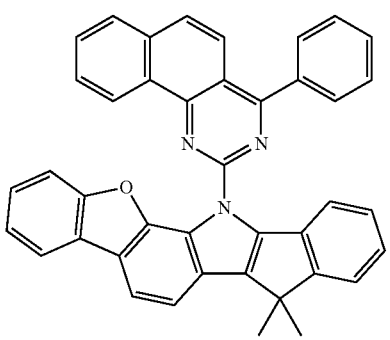

Synthesis Example 33

Synthesis of N-aromatic Substituted Nitrogen-containing Heterocyclic Compound (2-10);

the reaction was conducted under the same conditions as in Synthesis Example 32, except that 2-chloro-4,6-diphenylbenzo[h]quinazoline was used instead of 2-chloro-4-phenylbenzo[h]quinazoline used in Synthesis Example 32. As a result,

| a powder of 12-(4,6-diphenylbenzo[h]quinazolin-2-yl)-7,7-dimethyl-7,12-dihydrobenzofuro[3,2-g]indeno[1,2-b]indole | 3.5 g (yield 38%) | was obtained.

The resulting N-aromatic substituted nitrogen-containing heterocyclic compound is the indenoindole compound (2-10) represented by the following structural formula.

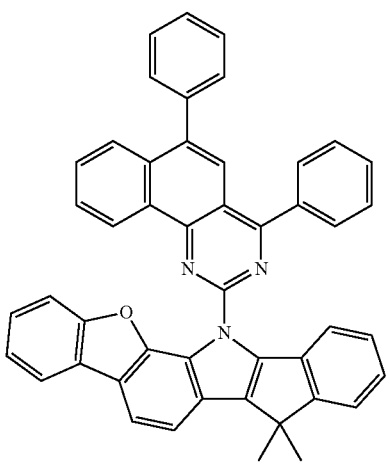

(2-10)

Synthesis Example 34

Synthesis of N-aromatic Substituted Nitrogen-containing Heterocyclic Compound (2-11);

the reaction was conducted under the same conditions as in Synthesis Example 24, except that 13,13-dimethyl-8,13-dihydrobenzofuro[3,2-e]indeno[1,2-b]indole was used instead of 7,7-dimethyl-7,12-dihydrobenzo[4,5]thieno[3,2-g]indeno[1,2-b]indole used in in Synthesis Example 24. As a result,

| a powder of 13,13-dimethyl-8-(4-phenylquinazolin-2-yl)-8,13-dihydrobenzofuro[3,2-e]indeno[1,2-b]indole | 3.0 g (yield 38%) |

The resulting N-aromatic substituted nitrogen-containing heterocyclic compound is the indenoindole compound (2-11) represented by the following structural formula.

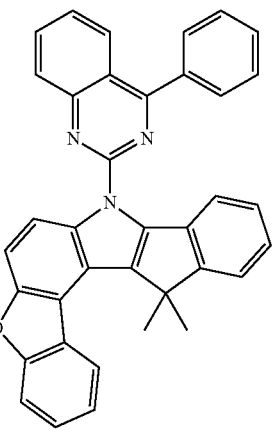

(2-11)

Synthesis Example 35

Synthesis of N-aromatic Substituted Nitrogen-containing Heterocyclic Compound (2-12);

the reaction was conducted under the same conditions as in Synthesis Example 34, except that 2-chloro-4,6-diphenylquinazoline was used instead of 2-chloro-4-phenylquinazoline used in Synthesis Example 34. As a result,

| a powder of 13,13-dimethyl-8-(4,6-diphenylquinazolin-2-yl)-8,13-dihydrobenzofuro[3,2-e]indeno[1,2-b]indole | 3.2 g (yield 38%) | was obtained.

The resulting N-aromatic substituted nitrogen-containing heterocyclic compound is the indenoindole compound (2-12) represented by the following structural formula.

(2-12)

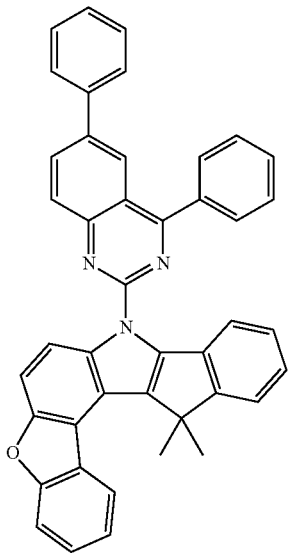

Synthesis Example 36

Synthesis of N-aromatic Substituted Nitrogen-containing Heterocyclic Compound (3-1);

the reaction was conducted under the same conditions as in Synthesis Example 35, except that 7,7-dimethyl-7,13-dihydroindeno[2',1':4,5]thieno[2,3-a]carbazole was used instead of 13,13-dimethyl-8,13-dihydrobenzofuro[3,2-e]indeno[1,2-b]indole used in in Synthesis Example 35. As a result,

| | |
|---|---|
| a powder of 13-(4,6-diphenylguinazolin-2-yl)-7,7-dimethyl-7,13-dihydroindeno[2',1':4,5]thieno[2,3-a]carbazole | 7.0 g (yield 38%) |

The resulting N-aromatic substituted nitrogen-containing heterocyclic compound is the carbazole compound (3-1) represented by the following structural formula.

(3-1)

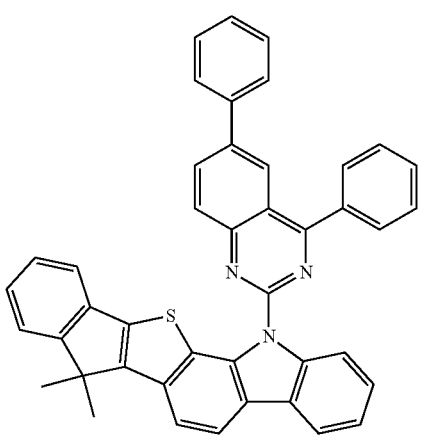

Synthesis Example 37

Synthesis of N-aromatic Substituted Nitrogen-containing Heterocyclic Compound (3-2);

the reaction was conducted under the same conditions as in Synthesis Example 36, except that 4-(biphenyl-4-yl)-2-chloroquinazoline was used instead of 2-chloro-4,6-diphenylquinazoline used in Synthesis Example 36. As a result,

| | |
|---|---|
| a powder of 13-[4-(biphenyl-4-yl)-quinazolin-2-yl]-7,7-dimethyl-7,13-dihydroindeno[2',1':4,5]thieno[2,3-a]carbazole | 6.7 g (yield 37%) | was obtained.

The resulting N-aromatic substituted nitrogen-containing heterocyclic compound is the carbazole compound (3-2) represented by the following structural formula.

(3-2)

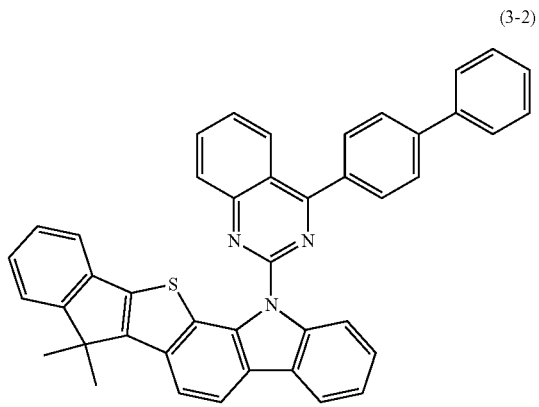 [SMILES: CC1(C)c2ccccc2-c2sc3c(ccc4c5ccccc5n(-c5nc(-c6ccc(-c7ccccc7)cc6)c6ccccc6n5)c43)c21]

Synthesis Example 38

Synthesis of N-aromatic Substituted Nitrogen-containing Heterocyclic Compound (3-3);

the reaction was conducted under the same conditions as in Synthesis Example 36, except that 2-chloro-4-(phenyl-$d_5$)quinazoline was used instead of 2-chloro-4,6-diphenylquinazoline used in Synthesis Example 36. As a result,

| | |
|---|---|
| a powder of 7,7-dimethyl-13-[4-(phenyl-d5)-quinazolin-2-yl]-7,13-dihydroindeno[2',1':4,5]thieno[2,3-a]carbazole | 8.4 g (yield 32%) | was obtained.

The resulting N-aromatic substituted nitrogen-containing heterocyclic compound is the carbazole compound (3-3) represented by the following structural formula.

(3-3)

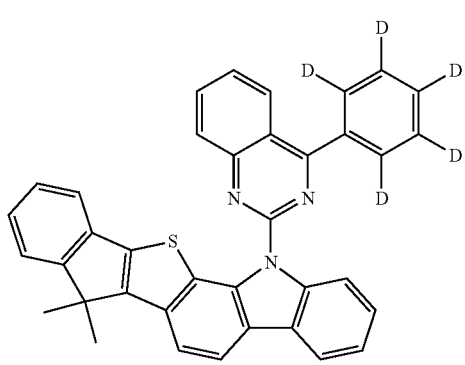

Synthesis Example 39

Synthesis of N-aromatic Substituted Nitrogen-containing Heterocyclic Compound (3-4);

the reaction was conducted under the same conditions as in Synthesis Example 36, except that 2-(4-bromophenyl)-4-phenylquinazoline was used instead of 2-chloro-4,6-diphenylquinazoline used in Synthesis Example 36. As a result,

| | |
|---|---|
| a powder of 7,7-dimethyl-13-[4-(4-phenylquinazolin-2-yl)phenyl]-7,13-dihydroindeno[2',1':4,5]thieno[2,3-a]carbazole | 5.2 g (yield 28%) | was obtained.

The resulting N-aromatic substituted nitrogen-containing heterocyclic compound is the carbazole compound (3-4) represented by the following structural formula.

(3-4)

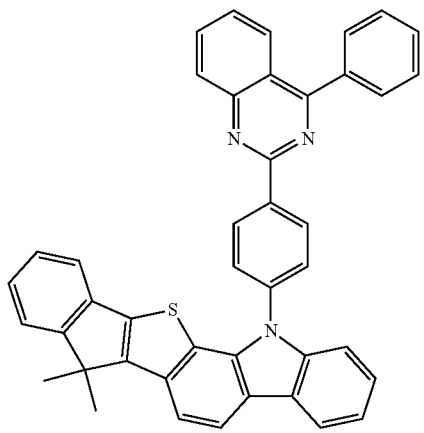

Synthesis Example 40

Synthesis of N-aromatic Substituted Nitrogen-containing Heterocyclic Compound (3-5);

the reaction was conducted under the same conditions as in Synthesis Example 36, except that 2-(3-bromophenyl)-4-phenylquinazoline was used instead of 2-chloro-4,6-diphenylquinazoline used in Synthesis Example 36. As a result,

| | |
|---|---|
| a powder of 7,7-dimethyl-13-[3-(4-phenylquinazolin-2-yl)phenyl]-7,13-dihydroindeno[2',1':4,5]thieno[2,3-a]carbazole | 8.4 g (yield 32%) | was obtained.

The resulting N-aromatic substituted nitrogen-containing heterocyclic compound is the carbazole compound (3-5) represented by the following structural formula.

(3-5)

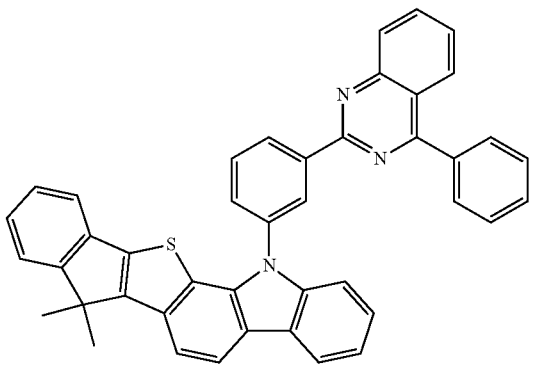

Synthesis Example 41

Synthesis of N-aromatic Substituted Nitrogen-containing Heterocyclic Compound (3-6);

the reaction was conducted under the same conditions as in Synthesis Example 36, except that 2-chloro-4-phenyl-benzo[h]quinazoline was used instead of 2-chloro-4,6-diphenylquinazoline used in Synthesis Example 36. As a result,

| | |
|---|---|
| a powder of 7,7-dimethyl-13-(4-phenylbenzo[h]quinazolin-2-yl)-7,13-dihydroindeno[2',1':4,5]thieno[2,3-a]carbazole | 8.4 g (yield 32%) | was obtained.

The resulting N-aromatic substituted nitrogen-containing heterocyclic compound is the carbazole compound (3-6) represented by the following structural formula.

(3-6)

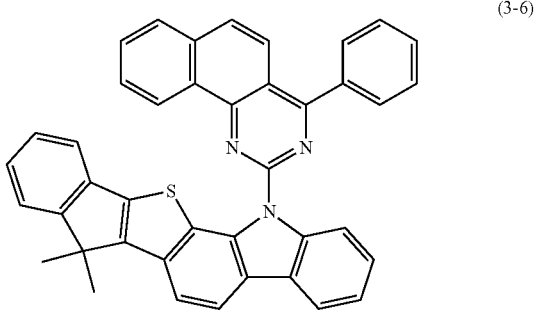 [SMILES: CC1(C)c2ccccc2-c2sc3c(ccc4c5ccccc5n(-c5nc(-c6ccccc6)c6ccc7ccccc7c6n5)c43)c21]

Synthesis Example 42

Synthesis of N-aromatic Substituted Nitrogen-containing Heterocyclic Compound (3-7);

the reaction was conducted under the same conditions as in Synthesis Example 41, except that 8,8-dimethyl-5,8-dihydroindeno[2',1':4,5]thieno[3,2-c]carbazole was used instead of 7,7-dimethyl-7,13-dihydroindeno[2',1':4,5]thieno[2,3-a]carbazole used in Synthesis Example 41. As a result,

| a powder of 8,8-dimethyl-5-(4-phenylbenzo[h]quinazolin-2-yl)-5,8-dihydroindeno[2',1':4,5]thieno[3,2-c]carbazole | 9.3 g (yield 35%) |
|---|---| was obtained.

The resulting N-aromatic substituted nitrogen-containing heterocyclic compound is the carbazole compound (3-7) represented by the following structural formula.

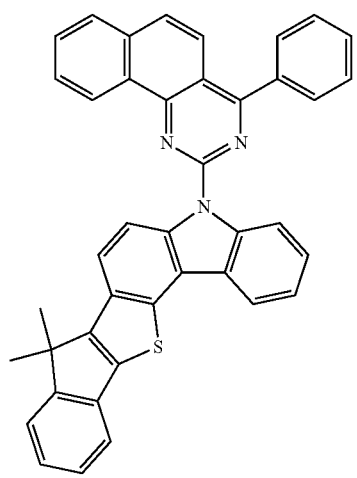

(3-7)

Synthesis Example 43

Synthesis of N-aromatic Substituted Nitrogen-containing Heterocyclic Compound (3-8);

the reaction was conducted under the same conditions as in Synthesis Example 24, except that 7,7-dimethyl-7,13-dihydroindeno[2',1':4,5]furo[2,3-a]carbazole was used instead of 7,7-dimethyl-7,12-dihydrobenzo[4,5]thieno[3,2-g]indeno[1,2-b]indole was used in Synthesis Example 24. As a result,

| a powder of 7,7-dimethyl-13-(4-phenylquinazolin-2-yl)-7,13-dihydroindeno[2',1':4',5]furo[2,3-a]carbazol | 6.2 g (yield 32%) |
|---|---| was obtained.

The resulting N-aromatic substituted nitrogen-containing heterocyclic compound is the carbazole compound (3-8) represented by the following structural formula.

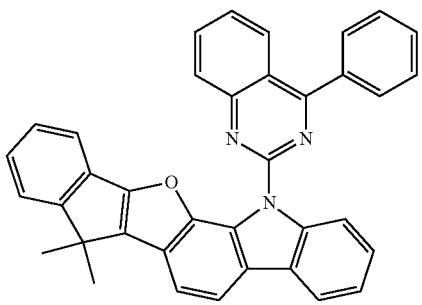

(3-8)

Synthesis Example 44

Synthesis of N-aromatic Substituted Nitrogen-containing Heterocyclic Compound (3-9);

the reaction was conducted under the same conditions as in Synthesis Example 43, except that 2-chloro-4-phenylbenzo[h]quinazoline was used instead of 2-chloro-4-phenylquinazoline used in Synthesis Example 43. As a result,

| a powder of 7,7-dimethyl-13-(4-phenylbenzo[h]quinazolin-2-yl)-7,13-dihydroindeno[2',1':4,5]furo[2,3-a]carbazole | 8.6 g (yield 30%) |
|---|---| was obtained.

The resulting N-aromatic substituted nitrogen-containing heterocyclic compound is the carbazole compound (3-9) represented by the following structural formula.

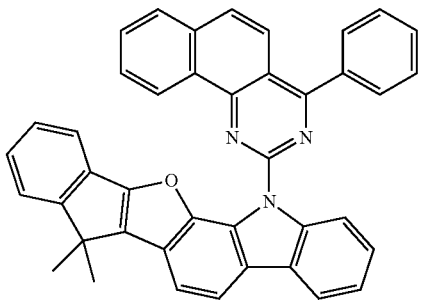

(3-9)

Synthesis Example 45

Synthesis of N-aromatic Substituted Nitrogen-containing Heterocyclic Compound (3-10);

the reaction was conducted under the same conditions as in Synthesis Example 43, except that 2-chloro-4,6-diphenylquinazoline was used instead of 2-chloro-4-phenylquinazoline used in Synthesis Example 43. As a result,

| a powder of 13-(4,6-diphenylquinazolin-2-yl)-7,7-dimethyl-7,13-dihydroindeno[2'1':4,5]furo[2,3-a]carbazole | 7.2 g (yield 29%) |
|---|---| was obtained.

The resulting N-aromatic substituted nitrogen-containing heterocyclic compound is the carbazole compound (3-10) represented by the following structural formula.

(3-10)

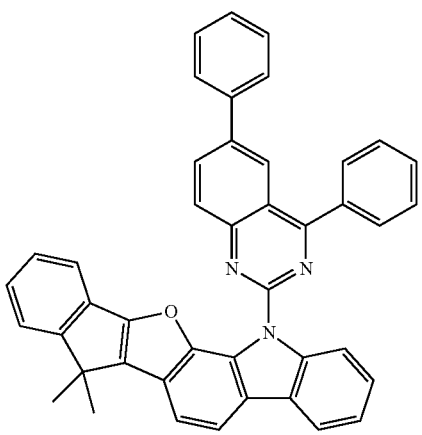

Synthesis Example 46

Synthesis of N-aromatic Substituted Nitrogen-containing Heterocyclic Compound (3-11);
the reaction was conducted under the same conditions as in Synthesis Example 24, except that
7,7-diphenyl-7,13-dihydroindeno[2',1':4,5]thieno[2,3-a]carbazole was used instead of 7,7-dimethyl-7,12-dihydrobenzo[4,5]thieno[3,2-g]indeno[1,2-b]indole used in Synthesis Example 24. As a result,

| a powder of 7,7-diphenyl-13-(4-phenylquinazolin-2-yl)-7,13-dihydroindeno[2',1':4,5]thieno[2,3-a]carbazole (Compound 3-11) | 6.7 g (yield 37%) | was obtained.
The resulting N-aromatic substituted nitrogen-containing heterocyclic compound is the carbazole compound (3-11) represented by the following structural formula.

(3-11)

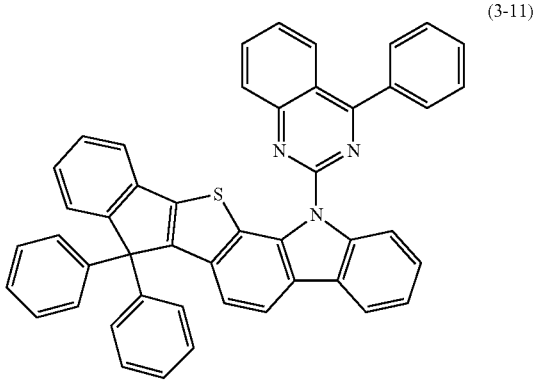 [SMILES: c1ccc(-c2nc(-n3c4ccccc4c4ccc5c6c(sc5c43)-c3ccccc3C6(c3ccccc3)c3ccccc3)nc3ccccc23)cc1]

Synthesis Example 47

Synthesis of N-aromatic Substituted Nitrogen-containing Heterocyclic Compound (3-12);
the reaction was conducted under the same conditions as in Synthesis Example 24, except that
9,9-dimethyl-9,15-dihydrobenzo[a]indeno[2',1':4,5]thieno[3,2-i]carbazole was used instead of 7,7-dimethyl-7,12-dihydrobenzo[4,5]thieno[3,2-g]indeno[1,2-b]indole used in Synthesis Example 24. As a result,

| a powder of 9,9-dimethyl-15-(4-phenylguinazolin-2-yl)-9,15-dihydrobenzo[a]indeno[2',1':4,5]thieno[3,2-i]carbazole | 4.8 g (yield 42%) | was obtained.
The resulting N-aromatic substituted nitrogen-containing heterocyclic compound is the carbazole compound (3-12) represented by the following structural formula.

(3-12)

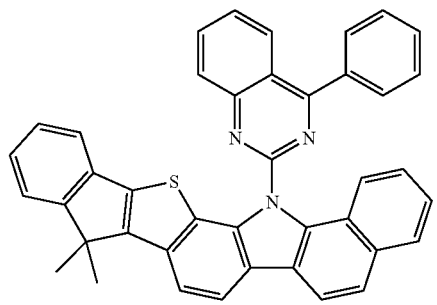

Synthesis Example 48

Synthesis of N-aromatic Substituted Nitrogen-containing Heterocyclic Compound (3-13);
the reaction was conducted under the same conditions as in Synthesis Example 24, except that
7-phenyl-7,13-dihydroindolo[2',3':4,5]thieno[2,3-a]carbazole was used instead of 7,7-dimethyl-7,12-dihydrobenzo[4,5]thieno[3,2-g]indeno[1,2-b]indole used in Synthesis Example 24. As a result,

| a powder of 7-phenyl-13-(4-phenylquinazolin-2-yl)-7,13-dihydroindolo[2',3':4,5]thieno[2,3-a]carbazole | 4.3 g (yield 43%) | was obtained.
The resulting N-aromatic substituted nitrogen-containing heterocyclic compound is the carbazole compound (3-13) represented by the following structural formula.

(3-13)

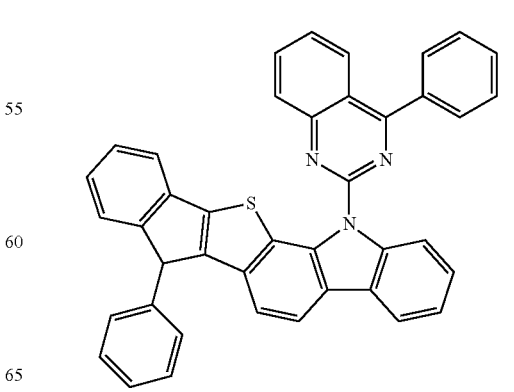

Synthesis Example 49

Synthesis of N-aromatic Substituted Nitrogen-containing Heterocyclic Compound (3-14);

the reaction was conducted under the same conditions as in Synthesis Example 24, except that 12,12-dimethyl-1,12-dihydroindeno[1',2':4,5]thieno[2,3-a]carbazole was used instead of 7,7-dimethyl-7,12-dihydrobenzo[4,5]thieno[3,2-g]indeno[1,2-b]indole used in Synthesis Example 24. As a result,

| | |
|---|---|
| a powder of 12,12-dimethyl-1-(4-phenylquinazolin-2-yl)-1,12-dihydroindeno[1',2':4,5]thieno[2,3-a]carbazole | 6.3 g (yield 44%) | was obtained.

The resulting N-aromatic substituted nitrogen-containing heterocyclic compound is the carbazole compound (3-14) represented by the following structural formula.

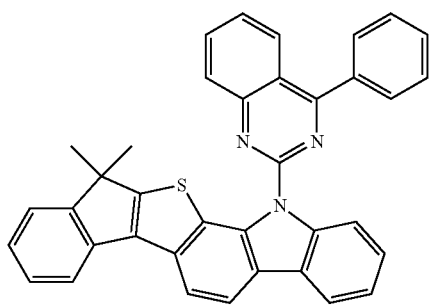

(3-14)

Synthesis Example 50

Synthesis of N-aromatic Substituted Nitrogen-containing Heterocyclic Compound (3-15);

the reaction was conducted under the same conditions as in Synthesis Example 36, except that 2-bromonaphthalene was used instead of 2-chloro-4,6-diphenylquinazoline used in Synthesis Example 36. As a result,

| | |
|---|---|
| a powder of 7,7-dimethyl-13-(naphthalen-2-yl)-7,13-dihydroindeno[2',1':4,5]thieno[2,3-a]carbazole | 5.4 g (yield 47%) | was obtained.

The resulting N-aromatic substituted nitrogen-containing heterocyclic compound is the carbazole compound (3-15) represented by the following structural formula.

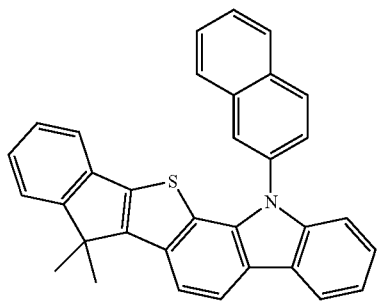

(3-15)

Example 1

The organic EL device with the structure shown in FIG. 1 was fabricated by performing vapor deposition according to the following procedure.

First, an ITO-attached glass substrate in which an ITO electrode (transparent anode 2) with a thickness of 150 nm was formed on a glass substrate (transparent substrate 1) was prepared.

The glass substrate 1 was ultrasonically cleaned for 20 min in isopropyl alcohol and then dried for 10 min on a hot plate heated to 200° C. UV ozone treatment was then performed for 15 min, the ITO-attached glass substrate was attached inside a vacuum vapor deposition device, and the device was depressurized to 0.001 Pa or less.

Compound (HIM-1) of the structural formula indicated below was then formed as the hole injection layer 3 to a thickness of 5 nm so as to cover the transparent anode 2.

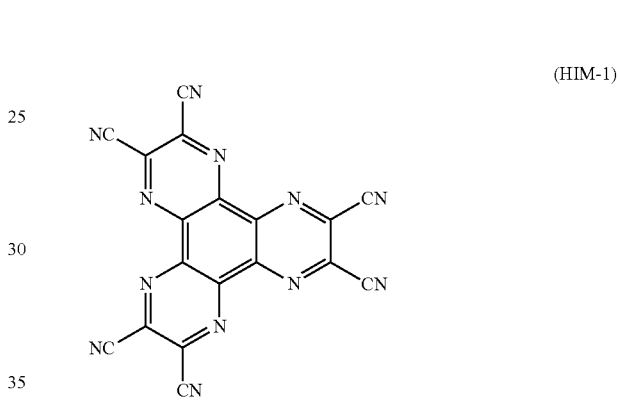

(HIM-1)

A di(triarylamine) compound (5-1) having two triarylamine skeletons in a molecule with the structural formula indicated below was formed as the first hole transport layer 4 to a thickness of 60 nm on the hole injection layer 3.

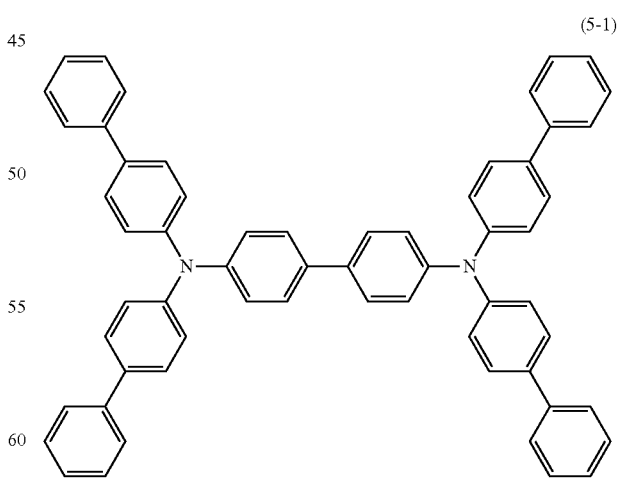

(5-1)

The arylamine compound (1-1) synthesized in Synthesis Example 1 was formed as the second hole transport layer 5 to a thickness of 5 nm on the first hole transport layer 4 formed in the above-described manner.

(1-1)

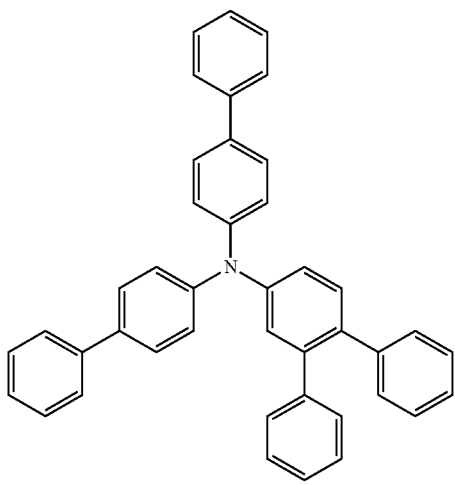

Compound (EMD-1) of the structural formula indicated below and the indenoindole compound (2-2) of the structural formula indicated below that was synthesized in Synthesis Example 25 were formed as the luminous layer 6 to a thickness of 20 nm on the second hole transport layer 5 by binary vapor deposition at vapor deposition rates such that the vapor deposition rate ratio of EMD-1 to Compound (2-2) was 5:95.

(EMD-1)

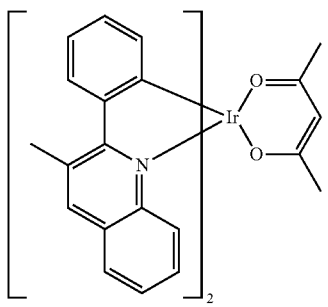

(2-2)

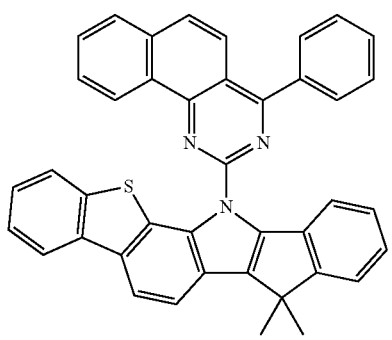

The anthracene derivative (4a-1) of the structural formula indicated below and Compound (ETM-1) of the structural formula indicated below were formed as the electron transport layer 7 to a thickness of 30 nm on the luminous layer 6 by binary vapor deposition at vapor deposition rates such that the vapor deposition rate ratio of Compound (4a-1) to ETM-1 was 50:50.

(4a-1)

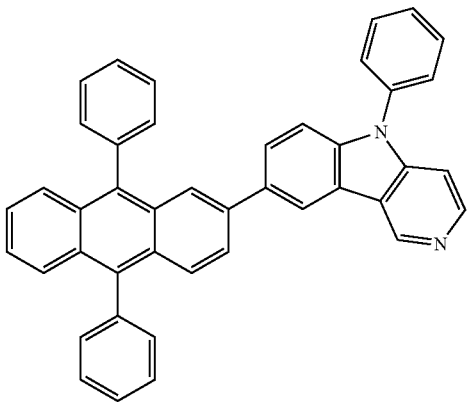

(ETM-1)

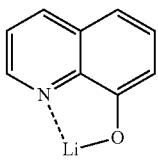

Lithium fluoride was formed as the electron injection layer 8 to a thickness of 1 nm on the electron transport layer 7.

Finally, aluminum was vapor deposited to a film thickness of 100 nm to form the cathode 9.

Characteristics of the organic EL device fabricated in the above-described manner were measured at normal temperature in the atmosphere.

The materials used to form the first hole transport layer, second hole transport layer, luminous layer, and electron transport layer in the fabricated organic EL device are shown in Table 1. The measurement results on light emission characteristics and device life which were obtained when a direct current voltage was applied to the organic EL device are shown in Table 2.

The device life was measured as a time till the emission luminance attenuated to 6790 cd/m$^2$ (corresponds to 97% when the initial luminance is 100%; 97% attenuation) when a constant-current drive was performed at an emission luminance at the emission start time (initial luminance) of 7000 cd/m$^2$.

Example 2

An organic EL device was fabricated in the same manner as in Example 1, except that the second hole transport layer 5 with a thickness of 5 nm was formed using the following arylamine compound (1-9) synthesized in Synthesis Example 2, and light emission characteristics and life of the device were measured.

(1-9)

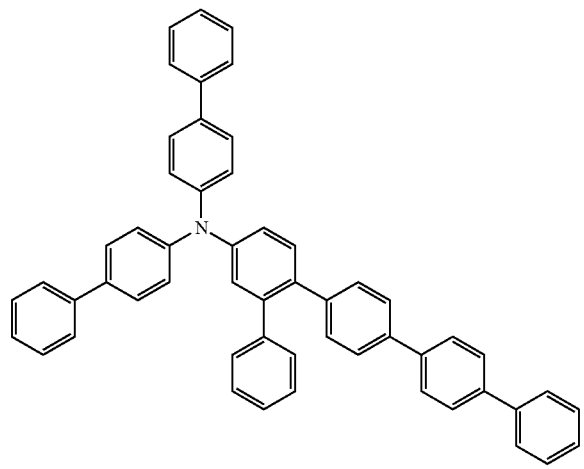

The materials used to form the first hole transport layer, second hole transport layer, luminous layer, and electron transport layer in the fabricated organic EL device are shown in Table 1. The measurement results on light emission characteristics and device life are shown in Table 2.

Example 3

An organic EL device was fabricated in the same manner as in Example 1, except that the second hole transport layer 5 with a thickness of 5 nm was formed using the following arylamine compound (1-20) synthesized in Synthesis Example 3, and light emission characteristics and life of the device were measured.

(1-20)

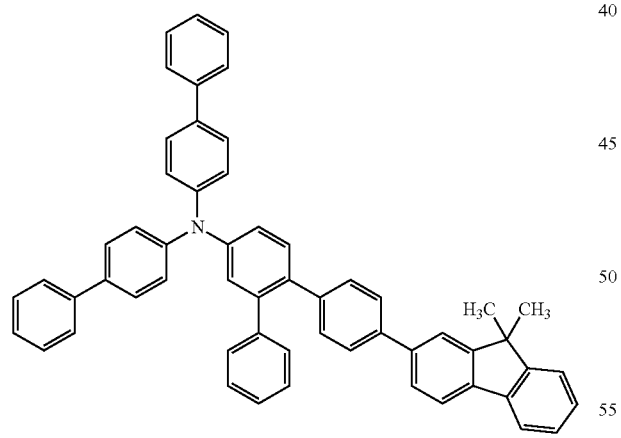

The materials used to form the first hole transport layer, second hole transport layer, luminous layer, and electron transport layer in the fabricated organic EL device are shown in Table 1. The measurement results on light emission characteristics and device life are shown in Table 2.

Example 4

An organic EL device was fabricated in the same manner as in Example 1, except that the second hole transport layer 5 with a thickness of 5 nm was formed using the following arylamine compound (1-29) synthesized in Synthesis Example 4, and light emission characteristics and life of the device were measured.

(1-29)

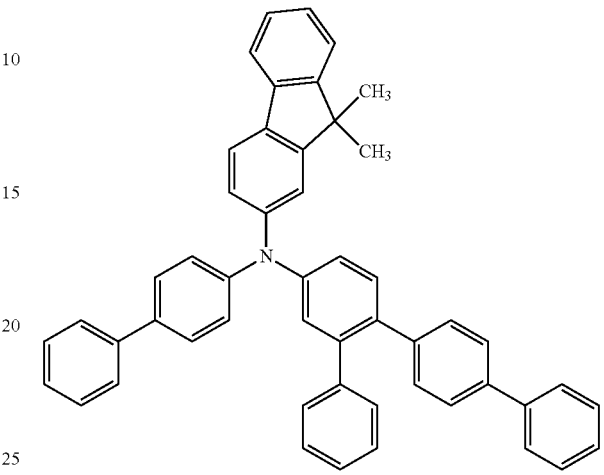

The materials used to form the first hole transport layer, second hole transport layer, luminous layer, and electron transport layer in the fabricated organic EL device are shown in Table 1. The measurement results on light emission characteristics and device life are shown in Table 2.

Example 5

An organic EL device was fabricated in the same manner as in Example 1, except that the second hole transport layer 5 with a thickness of 5 nm was formed using the following arylamine compound (1-55) synthesized in Synthesis Example 5, and light emission characteristics and life of the device were measured.

(1-55)

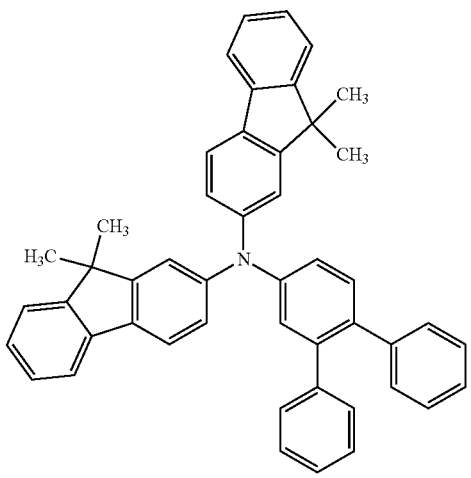

The materials used to form the first hole transport layer, second hole transport layer, luminous layer, and electron transport layer in the fabricated organic EL device are shown in Table 1. The measurement results on light emission characteristics and device life are shown in Table 2.

Example 6

An organic EL device was fabricated in the same manner as in Example 1, except that the second hole transport layer 5 with a thickness of 5 nm was formed using the following arylamine compound (1-87) synthesized in Synthesis Example 8, and light emission characteristics and life of the device were measured.

(1-87)

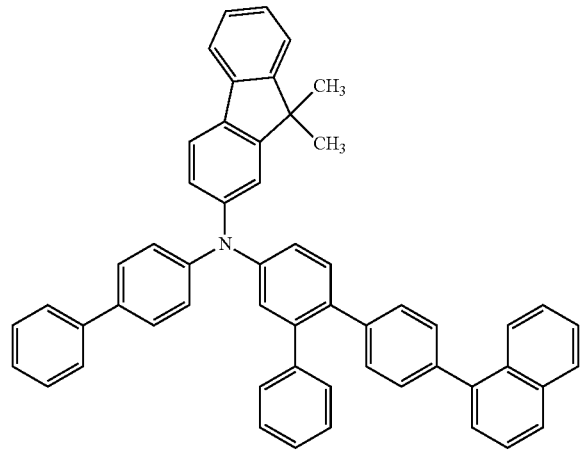

The materials used to form the first hole transport layer, second hole transport layer, luminous layer, and electron transport layer in the fabricated organic EL device are shown in Table 1. The measurement results on light emission characteristics and device life are shown in Table 2.

Example 7

An organic EL device was fabricated in the same manner as in Example 1, except that the second hole transport layer 5 with a thickness of 5 nm was formed using the following arylamine compound (1-92) synthesized in Synthesis Example 10, and light emission characteristics and life of the device were measured.

(1-92)

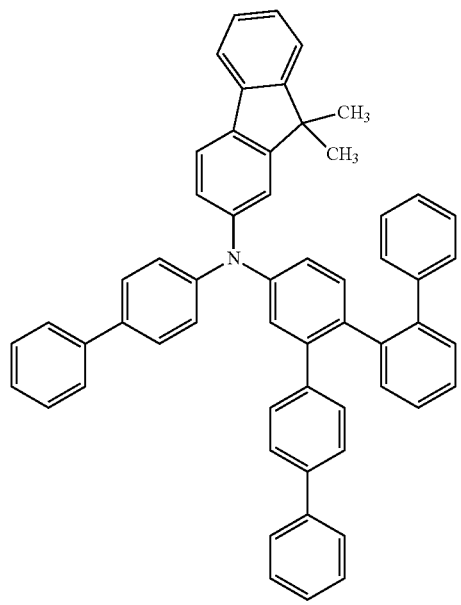

The materials used to form the first hole transport layer, second hole transport layer, luminous layer, and electron transport layer in the fabricated organic EL device are shown in Table 1. The measurement results on light emission characteristics and device life are shown in Table 2.

Example 8

An organic EL device was fabricated in the same manner as in Example 1, except that the carbazole compound (3-16) represented by the structural formula indicated below was used instead of the indenoindole compound (2-2) and the luminous layer 6 with a thickness of 20 nm was formed by performing binary vapor deposition of the carbazole compound (3-16) and Compound (EMD-1), which was used in Example 1, at vapor deposition rates such that the vapor deposition rate ratio of (EMD-1) to Compound (3-16) was 5:95, and light emission characteristics and life of the device were measured.

(3-16)

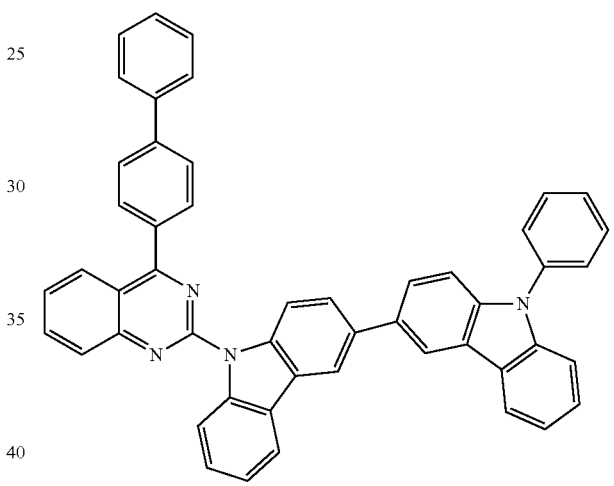

The materials used to form the first hole transport layer, second hole transport layer, luminous layer, and electron transport layer in the fabricated organic EL device are shown in Table 1. The measurement results on light emission characteristics and device life are shown in Table 2.

Example 9

An organic EL device was fabricated in the same manner as in Example 8, except that the second hole transport layer 5 with a thickness of 5 nm was formed using the arylamine compound (1-9) synthesized in Synthesis Example 2, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Example 10

An organic EL device was fabricated in the same manner as in Example 8, except that the second hole transport layer 5 with a thickness of 5 nm was formed using the arylamine compound (1-20) synthesized in Synthesis Example 3, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Example 11

An organic EL device was fabricated in the same manner as in Example 8, except that the second hole transport layer 5 with a thickness of 5 nm was formed using the arylamine compound (1-29) synthesized in Synthesis Example 4, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Example 12

An organic EL device was fabricated in the same manner as in Example 8, except that the second hole transport layer 5 with a thickness of 5 nm was formed using the arylamine compound (1-55) synthesized in Synthesis Example 5, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Example 13

An organic EL device was fabricated in the same manner as in Example 8, except that the second hole transport layer 5 with a thickness of 5 nm was formed using the arylamine compound (1-87) synthesized in Synthesis Example 8, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Example 14

An organic EL device was fabricated in the same manner as in Example 8, except that the second hole transport layer 5 with a thickness of 5 nm was formed using the arylamine compound (1-92) synthesized in Synthesis Example 10, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Comparative Example 1

An organic EL device was fabricated in the same manner as in Example 1, except that the second hole transport layer 5 with a thickness of 5 nm was formed using the di(triarylamine) compound (5-1) represented by the structural formula indicated below instead of Compound (1-1) synthesized in Synthesis Example 1, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Comparative Example 2

An organic EL device was fabricated in the same manner as in Example 1, except that the second hole transport layer 5 with a thickness of 5 nm was formed using Compound (HTM-1) represented by the structural formula indicated below instead of Compound (1-1) synthesized in Synthesis Example 1, and light emission characteristics and life of the device were measured.

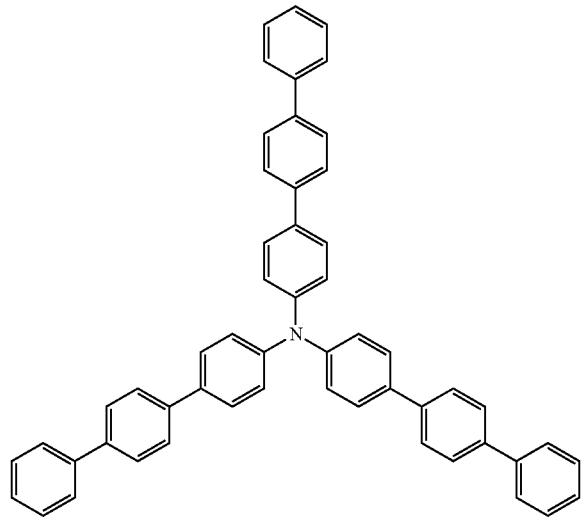

(HTM-1)

The materials used to form the first hole transport layer, second hole transport layer, luminous layer, and electron transport layer in the fabricated organic EL device are shown in Table 1. The measurement results on light emission characteristics and device life are shown in Table 2.

Comparative Example 3

An organic EL device was fabricated in the same manner as in Example 8, except that the second hole transport layer 5 with a thickness of 5 nm was formed using Compound (HTM-1) represented by the structural formula indicated above instead of Compound (1-1) synthesized in Synthesis Example 1, and light emission characteristics and life of the device were measured.

The materials used to form the first hole transport layer, second hole transport layer, luminous layer, and electron transport layer in the fabricated organic EL device are shown in Table 1. The measurement results on light emission characteristics and device life are shown in Table 2.

Comparative Example 4

An organic EL device was fabricated in the same manner as in Example 8, except that the first hole transport layer 4 with a thickness of 60 nm was formed using the di(arylamine) compound (5'-2) having two triphenylamine structures in a molecule represented by the structural formula indicated below blow instead of Compound (5-1) having the structural formula indicated above, and the second hole transport layer 5 with a thickness of 5 nm was formed using the arylamine compound (5'-2) represented by the structural formula indicated below instead of the arylamine compound (1-1) synthesized in Synthesis Example 1.

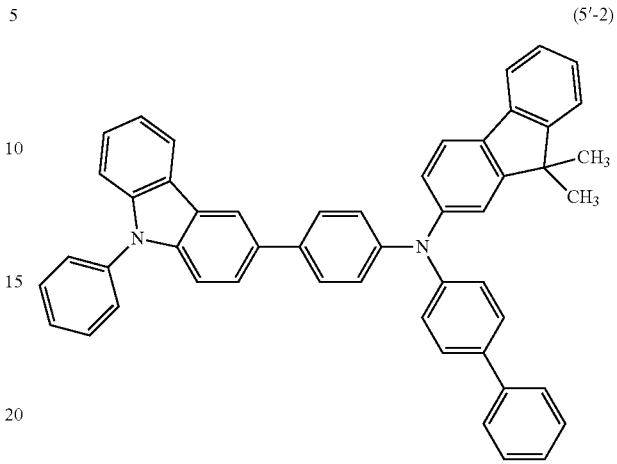

(5'-2)

The materials used to form the first hole transport layer, second hole transport layer, luminous layer, and electron transport layer in the fabricated organic EL device are shown in Table 1. The measurement results on light emission characteristics and device life are shown in Table 2.

TABLE 1

|  | First hole transport layer | Second hole transport layer | Luminous layer | Electron transport layer |
| --- | --- | --- | --- | --- |
| Example 1 | Compound 5-1 | Compound 1-1 | EMD-1/Compound 2-2 | Compound 4a-1/ETM-1 |
| Example 2 | Compound 5-1 | Compound 1-9 | EMD-1/Compound 2-2 | Compound 4a-1/ETM-1 |
| Example 3 | Compound 5-1 | Compound 1-20 | EMD-1/Compound 2-2 | Compound 4a-1/ETM-1 |
| Example 4 | Compound 5-1 | Compound 1-29 | EMD-1/Compound 2-2 | Compound 4a-1/ETM-1 |
| Example 5 | Compound 5-1 | Compound 1-55 | EMD-1/Compound 2-2 | Compound 4a-1/ETM-1 |
| Example 6 | Compound 5-1 | Compound 1-87 | EMD-1/Compound 2-2 | Compound 4a-1/ETM-1 |
| Example 7 | Compound 5-1 | Compound 1-92 | EMD-1/Compound 2-2 | Compound 4a-1/ETM-1 |
| Example 8 | Compound 5-1 | Compound 1-1 | EMD-1/Compound 3-16 | Compound 4a-1/ETM-1 |
| Example 9 | Compound 5-1 | Compound 1-9 | EMD-1/Compound 3-16 | Compound 4a-1/ETM-1 |
| Example 10 | Compound 5-1 | Compound 1-20 | EMD-1/Compound 3-16 | Compound 4a-1/ETM-1 |
| Example 11 | Compound 5-1 | Compound 1-29 | EMD-1/Compound 3-16 | Compound 4a-1/ETM-1 |
| Example 12 | Compound 5-1 | Compound 1-55 | EMD-1/Compound 3-16 | Compound 4a-1/ETM-1 |
| Example 13 | Compound 5-1 | Compound 1-87 | EMD-1/Compound 3-16 | Compound 4a-1/ETM-1 |
| Example 14 | Compound 5-1 | Compound 1-92 | EMD-1/Compound 3-16 | Compound 4a-1/ETM-1 |
| Comp. Ex. 1 | Compound 5-1 | Compound 5-1 | EMD-1/Compound 2-2 | Compound 4a-1/ETM-1 |
| Comp. Ex. 2 | Compound 5-1 | HTM-1 | EMD-1/Compound 2-2 | Compound 4a-1/ETM-1 |
| Comp. Ex. 3 | Compound 5-1 | HTM-1 | EMD-1/Compound 3-16 | Compound 4a-1/ETM-1 |
| Comp. Ex. 4 | Compound 5'-2 | Compound 5'-2 | EMD-1/Compound 3-16 | Compound 4a-1/ETM-1 |

TABLE 2

|  | Voltage [V] (@10 mA/cm$^2$) | Luminance [cd/m$^2$] (@10 mA/cm$^2$) | Luminous efficiency [cd/A] (@10 mA/cm$^2$) | Power efficiency [lm/W] (@10 mA/cm$^2$) | Device life, 97% attenuation (h) |
| --- | --- | --- | --- | --- | --- |
| Example 1 | 4.21 | 2755 | 27.58 | 20.58 | 201 |
| Example 2 | 4.23 | 2699 | 27.01 | 20.30 | 241 |
| Example 3 | 4.16 | 2800 | 28.03 | 21.02 | 166 |
| Example 4 | 4.05 | 2754 | 27.57 | 21.54 | 175 |
| Example 5 | 4.00 | 2632 | 26.35 | 20.67 | 159 |
| Example 6 | 4.10 | 2807 | 28.10 | 21.53 | 199 |
| Example 7 | 4.04 | 2820 | 28.23 | 21.95 | 155 |
| Example 8 | 4.11 | 2640 | 26.44 | 20.32 | 270 |
| Example 9 | 4.15 | 2606 | 26.09 | 20.10 | 339 |
| Example 10 | 4.08 | 2702 | 27.05 | 20.85 | 292 |

TABLE 2-continued

|  | Voltage [V] (@10 mA/cm²) | Luminance [cd/m²] (@10 mA/cm²) | Luminous efficiency [cd/A] (@10 mA/cm²) | Power efficiency [lm/W] (@10 mA/cm²) | Device life, 97% attenuation (h) |
|---|---|---|---|---|---|
| Example 11 | 3.94 | 2693 | 26.96 | 21.53 | 289 |
| Example 12 | 3.90 | 2527 | 25.30 | 20.42 | 233 |
| Example 13 | 3.99 | 2745 | 27.48 | 21.64 | 260 |
| Example 14 | 3.97 | 2774 | 27.77 | 21.98 | 246 |
| Comp. Ex. 1 | 3.90 | 2050 | 20.53 | 16.87 | 57 |
| Comp. Ex. 2 | 4.33 | 2598 | 26.01 | 18.82 | 61 |
| Comp. Ex. 3 | 4.55 | 2517 | 25.19 | 17.77 | 46 |
| Comp. Ex. 4 | 3.79 | 2033 | 20.34 | 16.86 | 32 |

As follows from the abovementioned test results, comparing Examples 1 to 7 with Comparative Examples 1 and 2 which had the same combination of materials of the luminous layer 6, in the organic EL devices of Examples 1 to 7, the luminous efficiency at the time a current with a current density of 10 mA/cm² was flowing was 26.35 to 28.23 cd/A which was higher than 20.53 to 26.01 cd/A in the organic EL devices of Comparative Examples 1 and 2.

Further, the power efficiency in the organic EL devices of Examples 1 to 7 was 20.30 to 21.95 lm/W which was higher than 16.87 to 18.82 lm/W in the organic EL devices of Comparative Examples 1 and 2.

It is also clear that the device life (9796 attenuation) in the organic EL devices of Examples 1 to 7 was 155 to 270 h which was much longer than 57 to 61 h in the organic EL devices of Comparative Examples 1 and 2.

Further, comparing Examples 8 to 14 with Comparative Examples 3 and 4 which had the same combination of materials of the luminous layer 6, in the organic EL devices of Examples 8 to 14, the luminous efficiency at the time a current with a current density of 10 mA/cm² was flowing was 25.30 to 27.77 cd/A which was higher than 20.34 to 25.19 cd/A in the organic EL devices of Comparative Examples 3 and 4.

Further, the power efficiency in the organic EL devices of Examples 8 to 14 was 20.10 to 21.98 lm/W which was higher than 16.86 to 17.77 lm/W in the organic EL devices of Comparative Examples 3 and 4.

It is also clear that the device life (97% attenuation) in the organic EL devices of Examples 8 to 14 was 233 to 339 h which was much longer than 32 to 46 h in the organic EL devices of Comparative Examples 3 and 4.

INDUSTRIAL APPLICABILITY

The organic EL device of the present invention in which a specific arylamine compound and a specific N-aromatic substituted nitrogen-containing heterocyclic compound are used as device materials has increased luminous efficiency and greatly improved durability and can be expected to be put to uses such as domestic electrical appliances and illumination.

DESCRIPTION OF REFERENCE NUMERALS

1 Glass substrate
2 Transparent anode
3 Hole injection layer
4 First hole transport layer
5 Second hole transport layer
6 Luminous layer
7 Electron transport layer
8 Electron injection layer
9 Cathode

The invention claimed is:
1. An organic electroluminescence device having an anode, a hole transport layer, a luminous layer, an electron transport layer, and a cathode in the order of description, wherein the hole transport layer includes an arylamine compound represented by the following formula (1):

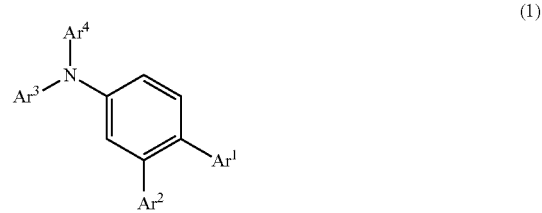

(1)

wherein
Ar¹ represents an unsubstituted phenyl group, a phenyl group substituted with a naphthyl group or a fluorenyl group, an unsubstituted biphenylyl group, an unsubstituted terphenylyl group, an unsubstituted naphthyl group, or an unsubstituted spirofluorenyl group;
Ar² represents an unsubstituted phenyl group or an unsubstituted biphenylyl group;
Ar³ and Ar⁴ each represents an unsubstituted phenyl group, a phenyl group substituted with a naphthyl group or a fluorenyl group, an unsubstituted biphenylyl group, an unsubstituted fluorenyl group, a fluorenyl group substituted with an alkyl group or a phenyl group, an unsubstituted phenanthrenyl group, or an unsubstituted spirofluorenyl group;
the luminous layer includes an N-aromatic substituted nitrogen-containing heterocyclic compound selected from A) an indenoindole compound represented by one of the following formulae (2a) to (2c):

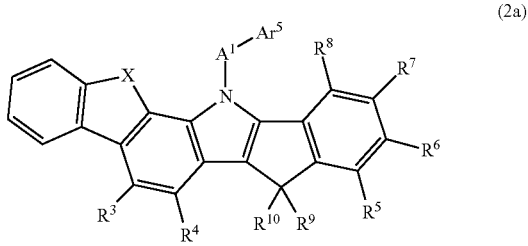

(2a)

-continued (2b)

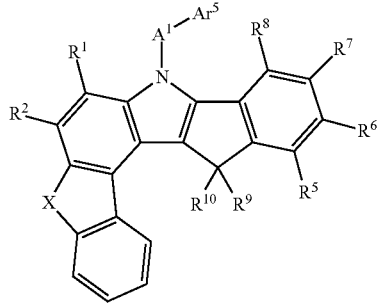

(2c)

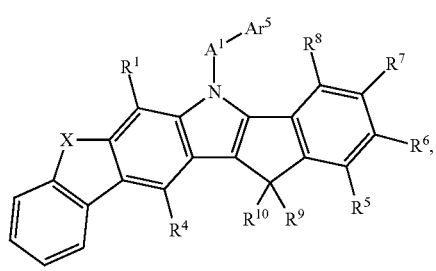

in which

Ar¹ represents a divalent aromatic hydrocarbon group, a divalent aromatic heterocyclic group, or a single bond;

Ar⁵ represents a monovalent aromatic hydrocarbon group or a monovalent aromatic heterocyclic group;

$R^1$ to $R^8$ each represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a di-aromatic substituted amino group;

$R^1$ to $R^8$ may be bonded to each other via a single bond, an optionally substituted methylene group, an oxygen atom, or a sulfur atom to form a ring; further, some of $R^1$ to $R^4$ or some of $R^5$ to $R^8$ may be detached from the benzene ring, and the remaining groups of $R^1$ to $R^4$ or the remaining groups of $R^5$ to $R^8$ may be bonded to vacancies in the benzene ring generated by the detachment via an optionally substituted methylene group, an oxygen atom, a sulfur atom, or a monoarylamino group to form a ring;

$R^9$ and $R^{10}$ are each an alkyl group having 1 to 6 carbon atoms, a monovalent aromatic hydrocarbon group, or a monovalent aromatic heterocyclic group and may be bonded to each other via a single bond, an optionally substituted methylene group, an oxygen atom, or a sulfur atom to form a ring; and X is a divalent linking group and represents an optionally substituted methylene group, an oxygen atom, a sulfur atom, or a monoarylamino group;

and B) a carbazole compound represented by one of the following formulas (3a-1) to (3a-4), (3b-1), and (3-16):

(3a-1)

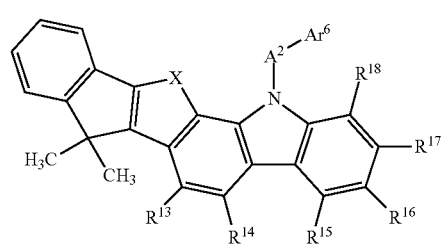

(3a-2)

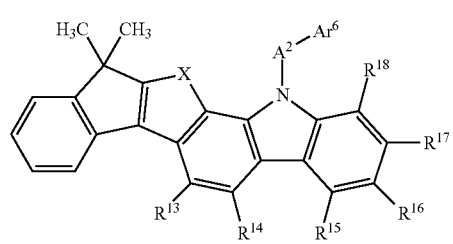

(3a-3)

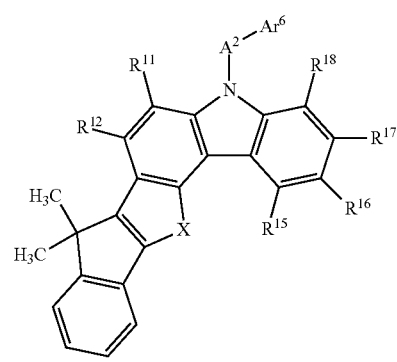

(3a-4)

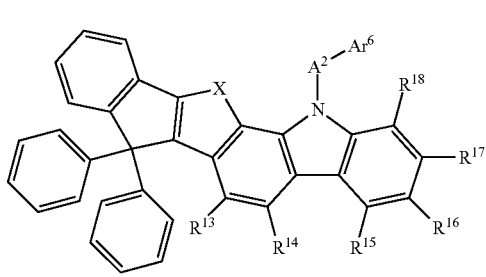

(3b-1)

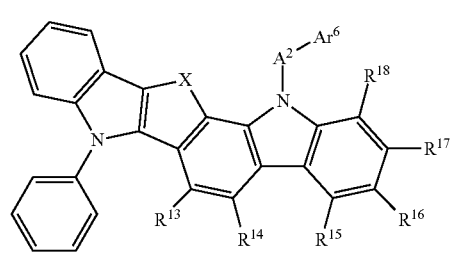

-continued (3-16)

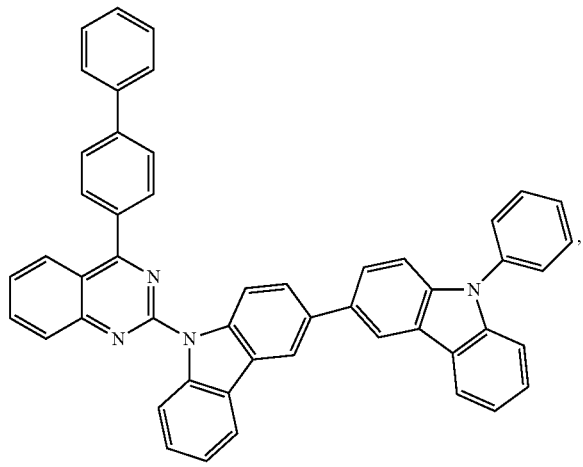

in which

A² represents a divalent aromatic hydrocarbon group, a divalent aromatic heterocyclic group, or a single bond;

Ar⁶ represents a monovalent aromatic hydrocarbon group or a monovalent aromatic heterocyclic group;

$R^{11}$ to $R^{18}$ each represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a di-aromatic substituted amino group; and these $R^{11}$ to $R^{18}$ may be bonded to each other via a single bond, an optionally substituted methylene group, an oxygen atom, or a sulfur atom to form a ring; further, some of $R^{11}$ to $R^{14}$ or some of $R^{15}$ to $R^{18}$ may be detached from the benzene ring, and the remaining groups of $R^{11}$ to $R^{14}$ or the remaining groups of $R^{15}$ to $R^{18}$ may be bonded to vacancies in the benzene ring generated by the detachment via an optionally substituted methylene group, an oxygen atom, a sulfur atom, or a monoarylamino group to form a ring;

wherein the hole transport layer has a two-layer structure including a first hole transport layer and a second hole transport layer, and the second hole transport layer is positioned on a side of the luminous layer and includes the arylamine compound represented by formula (1).

2. The organic electroluminescence device according to claim 1, wherein the arylamine compound is represented by the following formula (1a):

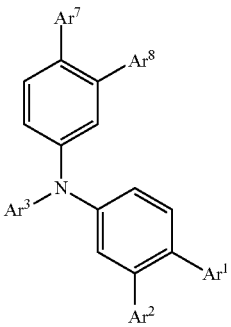

(1a)

wherein

A¹ to A³ are as defined in the formula (1); and

Ar⁷ and A⁸ each represents a monovalent aromatic hydrocarbon group or a monovalent aromatic heterocyclic group.

3. The organic electroluminescence device according to claim 2, wherein the arylamine compound is represented by the following formula (1b):

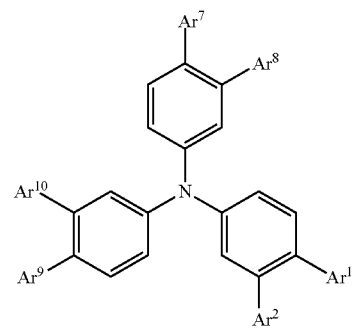

(1b)

wherein

Ar¹, Ar², Ar⁷, and Ar⁸ are as defined in the formula (1) or the formula (1a); and Ar⁹ and Ar¹⁰ each represents a monovalent aromatic hydrocarbon group or a monovalent aromatic heterocyclic group.

4. The organic electroluminescence device according to claim 1, wherein the electron transport layer includes an anthracene derivative represented by the following formula (4):

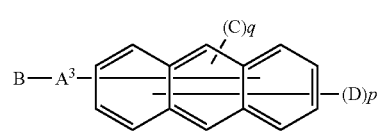

(4)

wherein

A³ represents a divalent aromatic hydrocarbon group, a divalent aromatic heterocyclic group, or a single bond;

B represents a monovalent aromatic heterocyclic group;

C represents a monovalent aromatic hydrocarbon group or a monovalent aromatic heterocyclic group;

D represents a hydrogen atom, a deuterium atom, a fluorine atom, a chlorine atom, a cyano group, an alkyl group having 1 to 6 carbon atoms, a monovalent aromatic hydrocarbon group, or a monovalent aromatic heterocyclic group; and in p and q, p is an integer of 7 or 8 and q is an integer of 1 or 2 provided that a sum of p and q is 9.

5. The organic electroluminescence device according to claim 4, wherein the anthracene derivative is represented by the following formula (4a):

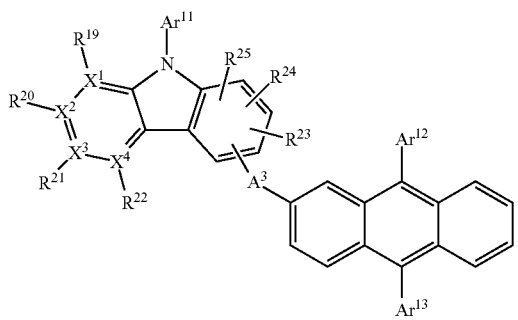

(4a)

wherein $A^3$ is as defined in the general formula (4);

$Ar^{11}$, $Ar^{12}$, and $Ar^{13}$ each represents a monovalent aromatic hydrocarbon group or a monovalent aromatic heterocyclic group;

$R^{19}$ to $R^{25}$ is each a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, or an aryloxy group and may be bonded to each other via a single bond, an optionally substituted methylene group, an oxygen atom, or a sulfur atom to form a ring; and $X^1$, $X^2$, $X^3$, and $X^4$ each represents a carbon atom or a nitrogen atom, provided that only any one thereof is a nitrogen atom, and none of $R^{19}$ to $R^{25}$, including a hydrogen atom, is bonded to the nitrogen atom.

6. The organic electroluminescence device according to claim 4, wherein the anthracene derivative is represented by the following formula (4b):

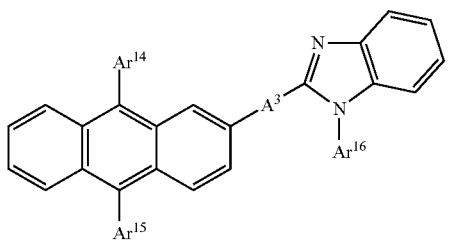

(4b)

wherein $A^3$ is as defined in the formula (4); and $Ar^{14}$, $Ar^{15}$, and $Ar^{16}$ each represents a monovalent aromatic hydrocarbon group or a monovalent aromatic heterocyclic group.

7. The organic electroluminescence device according to claim 4, wherein the anthracene derivative is represented by the following formula (4c):

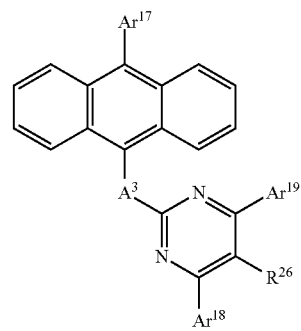

(4c)

wherein $A^3$ is as defined in the formula (4);

$Ar^{17}$, $Ar^{18}$, and $Ar^{19}$ each represents a monovalent aromatic hydrocarbon group or a monovalent aromatic heterocyclic group; and $R^{26}$ represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, or an aryloxy group.

8. The organic electroluminescence device according to claim 1, wherein the luminous layer includes a red luminous material.

9. The organic electroluminescence device according to claim 8, wherein the luminous layer includes a phosphorescence luminous material.

10. The organic electroluminescence device according to claim 9, wherein the phosphorescence luminous material is a metal complex including iridium or platinum.

11. An organic electroluminescence device having an anode, a hole transport layer, a luminous layer, an electron transport layer, and a cathode in the order of description, wherein the hole transport layer includes an arylamine compound represented by the following formula (1), and the luminous layer includes an N-aromatic substituted nitrogen-containing heterocyclic compound:

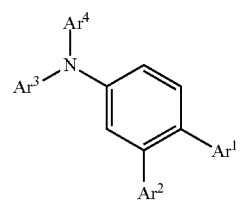

(1)

wherein $Ar^1$ to $Ar^4$ each represent a monovalent aromatic hydrocarbon group or a monovalent aromatic heterocyclic group, wherein the arylamine compound is represented by the following formula (1b):

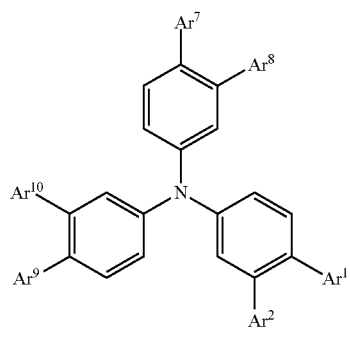
(1b)
wherein
$Ar^1$, $Ar^2$, $Ar^7$, and $Ar^8$ are as defined in the formula (1) or $Ar^7$ and $Ar^8$ each represent a monovalent aromatic hydrocarbon group or a monovalent aromatic heterocyclic group; and
$Ar^9$ and $Ar^{10}$ each represent a monovalent aromatic hydrocarbon group or a monovalent aromatic heterocyclic group.
* * * * *